US011925685B2

(12) United States Patent
Weiner et al.

(10) Patent No.: US 11,925,685 B2
(45) Date of Patent: Mar. 12, 2024

(54) DNA ANTIBODY CONSTRUCTS ENCODING ANTI-ZIKV ENVELOPE ANTIBODIES

(71) Applicants: David Weiner, Merion, PA (US); Karuppiah Muthumani, Cherry Hill, NJ (US); Jian Yan, Wallingford, PA (US)

(72) Inventors: David Weiner, Merion, PA (US); Karuppiah Muthumani, Cherry Hill, NJ (US); Jian Yan, Wallingford, PA (US)

(73) Assignees: The Trustees of the University of Pennsylvania, Philadelphia, PA (US); Inovio Pharmaceuticals, Inc., Plymouth Meeting, PA (US); The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 16/334,441

(22) PCT Filed: Sep. 19, 2017

(86) PCT No.: PCT/US2017/052203

§ 371 (c)(1),
(2) Date: Mar. 19, 2019

(87) PCT Pub. No.: WO2018/053478

PCT Pub. Date: Mar. 22, 2018

(65) Prior Publication Data

US 2019/0209674 A1 Jul. 11, 2019

Related U.S. Application Data

(60) Provisional application No. 62/417,093, filed on Nov. 3, 2016, provisional application No. 62/396,750, filed on Sep. 19, 2016.

(51) Int. Cl.
*A61K 39/12* (2006.01)
*A61K 31/7088* (2006.01)
(Continued)

(52) U.S. Cl.
CPC .......... *A61K 39/42* (2013.01); *A61K 31/7088* (2013.01); *A61K 39/12* (2013.01);
(Continued)

(58) Field of Classification Search
CPC .................................................. C07K 16/1081
See application file for complete search history.

(56) References Cited

U.S. PATENT DOCUMENTS

2010/0297664 A1 11/2010 Wadhwa
2016/0017367 A1 1/2016 Despres
2016/0039916 A1 2/2016 Jiang

FOREIGN PATENT DOCUMENTS

WO 2010057159 5/2010
WO 2014093894 6/2014
(Continued)

OTHER PUBLICATIONS

Fitch, W. M., 2000, Homology, a personal view on some of the problems, TIG 16(5):227-231.*
(Continued)

*Primary Examiner* — Jeffrey S Parkin
(74) *Attorney, Agent, or Firm* — Riverside Law LLP

(57) ABSTRACT

Disclosed herein is a composition comprising a recombinant nucleic acid sequence that encodes an antibody to a Zika viral antigen, and functional fragments thereof. The invention also relates to a composition comprising the combination of a first composition that elicits an immune response in a mammal against zika virus and a second composition comprising a recombinant nucleic acid sequence encoding an antibody, a fragment thereof, a variant thereof, or a
(Continued)

combination thereof. In some instances, the nucleic acid molecule comprises a nucleotide sequence encoding an anti-ZIKV-Envelope (anti-ZIKV E) Protein antibody.

14 Claims, 47 Drawing Sheets

Specification includes a Sequence Listing.

(51) Int. Cl.

| | |
|---|---|
| ***A61K 39/42*** | (2006.01) |
| ***A61P 31/14*** | (2006.01) |
| ***C07K 14/18*** | (2006.01) |
| ***C07K 16/10*** | (2006.01) |
| ***C12N 7/00*** | (2006.01) |
| *A61K 39/00* | (2006.01) |

(52) U.S. Cl.

CPC .............. *A61P 31/14* (2018.01); *C07K 14/18* (2013.01); *C07K 16/10* (2013.01); *C07K 16/1081* (2013.01); *C12N 7/00* (2013.01); *A61K 2039/505* (2013.01); *A61K 2039/53* (2013.01); *C07K 2317/56* (2013.01); *C12N 2770/24134* (2013.01); *C12N 2770/24171* (2013.01); *Y02A 50/30* (2018.01)

(56) References Cited

FOREIGN PATENT DOCUMENTS

| | | |
|---|---|---|
| WO | 2015089492 | 6/2015 |
| WO | 2016089862 | 6/2016 |

OTHER PUBLICATIONS

TheiBen, G., Feb. 2002, Secret life of genes, Nature 415:741.*
Xiang, J., et al., 1999, Light-chain framework region residue Tyr71 of chimeric B72.3 antibody plays an important role in influencing the TAG72 antigen binding, Prot. Engineer. 12(5):417-421.*
Chen, C., et al., Sep. 1992, Generation and analysis of random point mutations in an antibody CDR2 sequence: Many mutated antibodies lose their ability to bind antigen, J. Exp. Med. 176:855-866.*
Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*
Winkler, K., et al., 2000, Changing the antigen binding specificity by single point mutations of an anti-p24 (HIV-1) antibody, J. Immunol. 165:4505-4514.*
Stettler, K., et al., Jul. 14, 2016, Specificity, cross-rectivity, and function of antibodies elicited by Zika virus infection, Science 353(6301):823-826.*
Stettler, K., et al., Jul. 14, 2016, Specificity, cross-rectivity, and function of antibodies elicited by Zika virus infection, Science 353(6301):823-826 (supplementary material, pp. 1-39).*
Flingai, S., et al., Jul. 2015, Protection against dengue disease by synthetic nucleic acid antibody prophylaxi/immunotherapy, Scientific Reports 5, 12616; doi: 10.1038/srep12626 (pp. 1-9).*
Shan, C., et al., Jul. 2018, Zika Virus Vaccine: Progress and Challenges, Cell Host Microbe 24:12-17.*
Heinz, F. X., and K. Stiasny, Mar. 2017, The Antigenic Structure of Zika Virus and Its Relation to Other Flaviviruses: Implications for Infection and Immunoprophylaxis, Microbiol. Mol. Biol. Rev. 81(1):e00055-16, pp. 1-27.*
Estevez-Herrera, J., et al., Mar. 2021, Zika Virus Pathogenesis: A Battle for Immune Evasion, Vaccines 9, 294,9030294, pp. 1-30.*
Liu, M. A., et al., Nov. 2006, DNA vaccines: Recent developments and future possibilities, Human Gene Therapy 17:1051-1061.*
Iavarone, C., et al., 2017, Mechanism of action of mRNA-based vaccines, Exp. Rev. Vaccines 16(9):871-881.*
Abbink et al., 2016, "Protective efficacy of multiple vaccine platforms against Zika virus challenge in rhesus monkeys," Science 353:1192-32.
Hutnick et al., 2012, "Intradermal DNA vaccination enhanced by low-current electroporation improves antigen expression and induces robust cellular and humoral immune responses," Hum gene Ther 23:943-50.
Larocca et al.: "Vaccine protection against Zika virus from Brazil", Nature, vol. 536, No. 7617, Aug. 1, 2016 (Aug. 1, 2016), pp. 474-478.
Lazear et al., 2016, "A Mouse Model of Zika Virus Pathogenesis," Cell Host Microbe 19:720-30.
Muthumani et al., "Rapid and Long-Term Immunity Elicited by DNA-Encoded Antibody Prophylaxis and DNA Vaccination Against Chikungunya Virus" Journal of Infectious Diseases. JID, vol. 214, No. 3, Mar. 21, 2016 (Mar. 21, 2016), pp. 369-378.
Muthumani et al., 2015, "A synthetic consensus anti-spike protein DNA vaccine induces protective immunity against Middle East respiratory syndrome coronavirus in nonhuman primates," Sci Trans Med 7:301ra132.
Roa et al., 2016, "Zika virus outbreak: reproductive health and rights in Latin America," Lancet 387:843.
Rossi et al., 2016, "Characterization of a Novel Murine Model to Study Zika Virus," Am J Trop Med Hyg, 94 (6):1362-1369.
Rouvinski et al., 2015, "Recognition determinants of broadly neutralizing human antibodies against dengue viruses," Nature 520:109-13.
Samarasekera et al., 2016, "Concern over Zika virus grips the world," Lancet 387:521-4.
Swanstrom et al., "Dengue Virus Envelope Dimer Epitope Monoclonal Antibodies Isolated from Dengue Patients Are Protective against Zika Virus", mBio, (Jul. 19, 2016), vol. 7, No. 4, pp. 1-8, XP055436611.
Trimble et al., 2016, "Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial," Lancet 386:2078-88.
Weaver et al., 2016, "Zika virus: History, emergence, biology, and prospects for control," Antiviral Res 130:69-80.
Zhao et al., "Structural Basis of Zika Virus-Specific Antibody Protection," Cell, Aug. 1, 2016; 166(4):1016-1027.

* cited by examiner

VH identity

| | 8A9F9_H | 1D4G7_H | 8D10F4_H | 3F12E9_H | 1C2A6_H |
|---|---|---|---|---|---|
| 8A9F9_H | 100 | 43.3 | 99.1 | 80.9 | 100 |
| 1D4G7_H | 43.3 | 100 | 43.3 | 44.9 | 43.3 |
| 8D10F4_H | 99.1 | 43.3 | 100 | 80 | 99.1 |
| 3F12E9_H | 80.9 | 44.9 | 80 | 100 | 80.9 |
| 1C2A6_H | 100 | 43.3 | 99.1 | 80.9 | 100 |

VL identity’

| | 8A9F9_L | 1D4G7_L | 8D10F4_L | 3F12E9_L | 1C2A6_L |
|---|---|---|---|---|---|
| 8A9F9_L | 100 | 64.3 | 96.4 | 76.8 | 98.2 |
| 1D4G7_L | 64.3 | 100 | 65.2 | 58.9 | 63.4 |
| 8D10F4_L | 96.4 | 65.2 | 100 | 75 | 95.5 |
| 3F12E9_L | 76.8 | 58.9 | 75 | 100 | 77.7 |
| 1C2A6_L | 98.2 | 63.4 | 95.5 | 77.7 | 100 |

Model RMSD

| RMSD | 8D10F4 | 1C2A6 | 8A9F9 | 3F12E9 | 1D4G7 |
|---|---|---|---|---|---|
| 8D10F4 | | 227 | 227 | 226 | 219 |
| 1C2A6 | 0.302 | | 227 | 226 | 219 |
| 8A9F9 | 0.385 | 0.347 | | 226 | 219 |
| 3F12E9 | 0.723 | 0.752 | 0.722 | | 219 |
| 1D4G7 | 1.364 | 1.388 | 1.351 | 1.434 | |

\# residues compared

RMSD (Å)

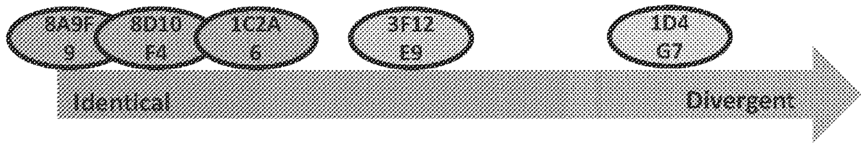

- The VH and VL chains in 1C2A6, 8D10F4 and 8A9F9 are identical or nearly identical.
- 1C2A6, 8D10F4 and 8A9F9 are likely to bind the same epitope in the same manner. There may be affinity differences, as with any antibody changes.
- 1D4G7 and 3F12E9 represent more divergent Fv’s than 1C2A6, 8D10F4 and 8A9F9.
- 3F12E9 is more similar to the set of three mAbs cited above than it is to 1D4G7. It may bind similarly.
- Backbone variation according to RMSD measurement shows the same pattern as sequence identity.

Figure 6

- All Fv models are superimposed in ribbon format to emphasize overall fold.
- The large VH CDR3 of 1D4G7 is clearly visible, as are several other fold differences in other CDR and in framework regions.
- Despite the sequence divergence of 3F12E9, it is still closer in overall sequence and conformation to 1C2A6, 8D10F4 and 8A9F9 than to 1D4G7.

- 1D4G7 lacks a cleft between the VH and VL domains due to its large CDR3 loop.
- Sequence similarities translate to structural similarities, so overall CDR conformations and molecular shapes are conserved according to previously demonstrated clustering.

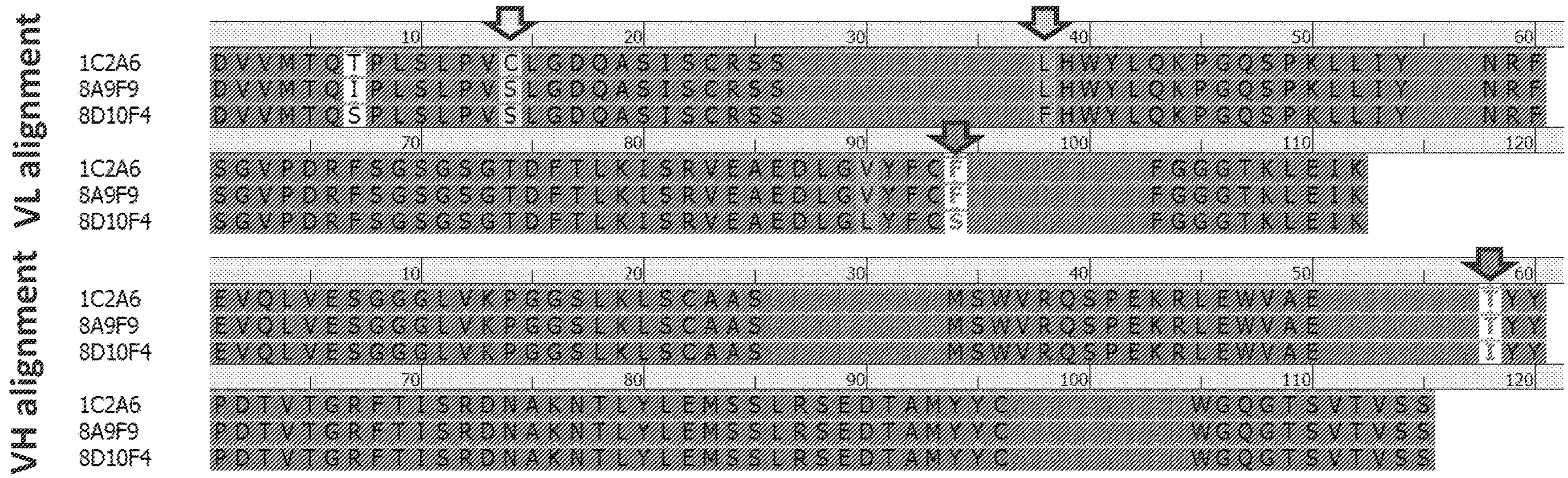

- 1C2A6 has a free CYS residue distal to the CDRs exposed on the surface (yellow arrow).
- Another potentially relevant difference occurs in VH FR2 region (orange arrow). This residue is not directly involved in CDR conformation but does influence local residue packing.
- Two changes occur within the IMGT-defined CDR regions (red arrows). The VL changes (F, F, S) directly impact the VL-VH interface.

Figure 9

- A free CYS leaves a highly modifiable chemical group exposed on the molecule surface.

- As this mAb is nearly identical to two others (the CYS being unique to 1C2A6), if the other two mAbs show similar neutralizing activity it may be better to go with a mAb that does not have a free CYS.

| Protein | Developability Index (Fv) | Molecular Charge | Total Pi Interactions | Total Hydrogen Bonds | Ligand Contact Surface Area | Ligand Polar Contact Surface Area | Ligand Nonpolar Contact Surface Area | Receptor Contact Surface Area | Receptor Polar Contact Surface Area | Receptor Nonpolar Contact Surface Area |
|---|---|---|---|---|---|---|---|---|---|---|
| **8D10F4** | 57.447 | 2.52 | 6 | 4 | 211.61 | 85.863 | 125.75 | 205 | 82.854 | 122.15 |
| **1C2A6** | 57.237 | 2.73 | 9 | 2 | 186.67 | 73.108 | 113.56 | 182.2 | 69.19 | 113.01 |
| **8A9F9** | 60.132 | 2.94 | 9 | 2 | 186.67 | 73.108 | 113.56 | 182.2 | 69.19 | 113.01 |
| **3F12E9** | 60.661 | 6.71 | 10 | 5 | 224.98 | 72.912 | 152.06 | 223.97 | 72.732 | 151.23 |
| **1D4G7** | 70.578 | 0.84 | 10 | 6 | 323.22 | 116.31 | 206.91 | 331.6 | 172.51 | 159.09 |

- Developability index is highest for 1D4G7, very likely due to the long CDR3 loop which contains multiple nonpolar residues. Based on past experience, though, this alone does not appear to be an issue.
- F→S variation in the interface/CDR region of 8D10F4 is responsible for the reduced number of predicted pi interactions compared to 1C2A6 and 8A9F9.
- Additional features such as potential post-translational modifications can be assessed. These may be less relevant but can be run.

Figure 11

MDWTWILFLVAAATRVHSGIIGLLLTTAMAAEITRRGSAYYM
YLDRNDAGEAISFPTTLGMNKCYIQIMDLGHMCDATMSYECP
MLDEGVEPDDVDCWCNTTSTWVVYGTCHHKKGEARRSRRAVT
LPSHSTRKLQTRSQTWLESREYTKHLIRVENWIFRNPGFALA
AAAIAWLLGSSTSQKVIYLVMILLIAPAYSIRCIGVSNRDFV
EGMSGGTWVDVVLEHGGCVTVMAQDKPTVDIELVTTTVSNMA
EVRSYCYEASISDMASDSRCPTQGEAYLDKQSDTQYVCKRTL
VDRGWGNGCGLFGKGSLVTCAKFTCSKKMTGKSIQPENLEYR
IMLSVHGSQHSGMIVNDIGHETDENRAKVEVTPNSPRAEATL
GGFGSLGLDCEPRTGLDFSDLYYLTMNNKHWLVHKEWFHDIP
LPWHAGADTGTPHWNNKEALVEFKDAHAKRQTVVVLGSQEGA
VHTALAGALEAEMDGAKGRLFSGHLKCRLKMDKLRLKGVSYS
LCTAAFTFTKVPAETLHGTVTVEVQYAGTDGPCKVPAQMAVD
MQTLTPVGRLITANPVITESTENSKMMLELDPPFGDSYIVIG
VGDKKITHHWHRSGSTIGKAFEATVRGAKRMAVLGDTAWDFG
SVGGVFNSLGKGIHQIFGAAFKSLFGGMSWFSQILIGTLLVW
LGLNTKNGSISLTCLALGGVMIFLSTAVSA

SEQ ID No. 23

Figure 15

DNA ANTIBODY CONSTRUCTS ENCODING ANTI-ZIKV ENVELOPE ANTIBODIES

CROSS-REFERENCE TO RELATED APPLICATIONS

This application is a U.S. national phase application filed under 35 U.S.C. § 371 claiming priority to International Patent Application No. PCT/US17/52203, filed Sep. 19, 2017, which is entitled to priority to U.S. Provisional Application No. 62/396,750, filed Sep. 19, 2016 and U.S. Provisional Application No. 62/417,093, filed Nov. 3, 2016, the contents of each of which are incorporated by reference herein in their entireties.

TECHNICAL FIELD

The present invention relates to a recombinant nucleic acid sequence that encodes an antibody to a Zika viral antigen, and functional fragments thereof. The invention also relates to a combination of zika vaccines with a composition comprising a recombinant nucleic acid sequence for generating one or more synthetic antibodies, and functional fragments thereof, in vivo. The compositions of the invention provide improved methods for inducing immune responses, and for prophylactically and/or therapeutically immunizing individuals against zika virus.

BACKGROUND

Zika disease is caused by infection with the Zika virus and can be transmitted to humans through the bite of infected mosquitoes or sexually transmitted between humans. Zika infection have been linked to severe birth defects. Currently, therapeutic antibodies are approved for treatment of multiple diseases. Unfortunately, manufacture and delivery of purified antibodies is cost-prohibitive. Furthermore, antibody therapies must be re-administered weekly-to-monthly—a challenging consideration in ensuring effective treatment to prevent or reduce the risk of a patient developing Zika.

Thus, there is need in the art for improved therapeutics that prevent and/or treat Zika infection. The current invention satisfies this need.

SUMMARY

One aspect of the present invention provides a composition comprising a recombinant nucleic acid sequence that encodes an antibody to a Zika viral antigen, and functional fragments thereof.

One aspect of the present invention provides a combination of a composition that elicits an immune response in a mammal against zika virus with a composition comprising a recombinant nucleic acid sequence encoding an antibody, a fragment thereof, a variant thereof, or a combination thereof. The composition can be administered to a subject in need thereof to facilitate in vivo expression and formation of a synthetic antibody. In one embodiment, the nucleic acid molecule comprises a nucleotide sequence encoding an anti-ZIKV-Envelope (anti-ZIKV E) Protein antibody.

One aspect of the present invention provides nucleic acid constructs capable of expressing a polypeptide that elicits an immune response in a mammal against zika virus. The nucleic acid constructs are comprised of an encoding nucleotide sequence and a promoter operably linked to the encoding nucleotide sequence. The encoding nucleotide sequence expresses the polypeptide, wherein the polypeptide includes consensus zika antigens, including pre-membrane-envelope (prM+Env or prME). The promoter regulates expression of the polypeptide in the mammal.

Another aspect of the present invention provides nucleic acid molecules that are capable of generating in a mammal an immune response against a zika virus. In one embodiment, the nucleic acid molecules comprise nucleic acid sequences capable of expressing a consensus zika antigen in the mammal and a pharmaceutically acceptable excipient. In one embodiment, the nucleic acid molecule comprise a promoter operably linked to a coding sequence that encodes the consensus zika antigen. In one embodiment, the consensus zika antigen is comprised of consensus prME.

Another aspect of the present invention provides methods of eliciting an immune response against zika virus in a mammal, comprising delivering a nucleic acid molecule to tissue of the mammal, the nucleic acid molecule comprising a nucleic acid sequence capable of expressing a consensus antigen of the zika virus in a cell of the mammal to elicit an immune response in the mammal, and electroporating cells of the tissue to permit entry of the nucleic acid molecule into the cells.

The present invention is directed to a nucleic acid molecule encoding one or more synthetic antibodies, wherein the nucleic acid molecule comprises at least one selected from the group consisting of a) a nucleotide sequence encoding an anti-ZIKV envelope (E) protein synthetic antibody; and b) a nucleotide sequence encoding a fragment of an anti-ZIKV envelope (E) synthetic antibody.

In one embodiment, the nucleic acid molecule comprises a nucleotide sequence encoding a cleavage domain.

In one embodiment, the nucleic acid molecule comprises a nucleotide sequence encoding one or more of a variable heavy chain region and a variable light chain region of an anti-ZIKV E antibody.

In one embodiment, the nucleic acid molecule comprises a nucleotide sequence encoding one or more sequences at least 90% homologous to one or more of SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:21, and SEQ ID NO:22.

In one embodiment, the nucleic acid molecule comprises a nucleotide sequence encoding a variable heavy chain region and a variable light chain region of an anti-ZIKV E antibody. In one embodiment, the nucleic acid molecule comprises a nucleotide sequence encoding one or more sequences at least 90% homologous to one or more of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:21, and SEQ ID NO:22.

In one embodiment, the nucleic acid molecule comprises a nucleotide sequence encoding a polypeptide comprising a variable heavy chain region; an IRES element; and a variable light chain region. In one embodiment, the IRES element is one of a viral IRES or an eukaryotic IRES.

In one embodiment, the nucleic acid molecule comprises:

a) a nucleotide sequence having at least about 95% identity over an entire length of the nucleic acid sequence to a nucleic acid sequence encoding a sequence selected from the group consisting of SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:21, and SEQ ID NO:22;

In one embodiment, the nucleotide sequence encodes a leader sequence. In one embodiment, the nucleic acid molecule comprises an expression vector.

The invention further provides a composition comprising any of the nucleic acid molecules described herein.

In one embodiment, the composition comprises a pharmaceutically acceptable excipient.

The invention further relates to a method of preventing or treating a disease in a subject, the method comprising administering to the subject a nucleic acid molecule or a composition as described herein.

In one embodiment, the disease is a Zika virus infection.

In one embodiment, the method further comprises administering an antibiotic agent to the subject. In one embodiment, an antibiotic is administered less than 10 days after administration of the nucleic acid molecule or composition.

In one embodiment, the method further comprises administering an antibiotic agent to the subject. In one embodiment, an antibiotic is administered less than 10 days after administration of the nucleic acid molecule or composition.

BRIEF DESCRIPTION OF THE DRAWINGS

FIG. 6 depicts ZIKA mAb VH and VL alignments and identity and RMSD matrices.

FIG. 9 depicts mAB 1C2A6, 8D10F4, and 8A9F9 VH and VL alignments. The sequence for 1C2A6 VL is amino acids 20-131 of SEQ ID NO:8. The sequence for 8A9F9 VL is amino acids 20-131 of SEQ ID NO:4. The sequence for 8D10F4 VL is amino acids 20- 131 of SEQ ID NO:6. The sequence for 1C2A6 VH is amino acids 20-134 of SEQ ID NO:7. The sequence for 8A9F9 VH is amino acids 20-134 of SEQ ID NO:3. The sequence for 8D10F4 VH is amino acids 20-134 of SEQ ID NO:16.

FIG. 11 depicts a summary of Fv biophysical features for 8D10F4, 1C2A6, 8A9F9, 3F12E9, and 1D4G7.

FIG. 15 displays an annotated amino acid sequence for a zika antigen—leader sequence+prME.

FIG. 16 shows genetic distance between isolates, and FIG. 17 displays a genetic tree.

FIG. 20A showing nonspecific binding to anti-sera in the cell lysates; FIG. 20B showing specific binding to anti-pan-flavivirus in the cell lysates.

FIG. 22 of individual mice. FIG. 23 group averages. Mean responses in each group one week after the third immunization.

FIG. 27A depicts a consensus sequence of Zika prM (precursor membrane) and E (envelope) genes (ZIKV-prME) was generated using prM and E sequences from various ZIKA isolated between 1952 and 2015 that caused infection in humans. FIG. 27B depicts the ZIKA-prME consensus sequence was cloned into the pVax1 vector after additional modifications and optimizations were made to improve its in vivo expression including the addition of a highly efficient immunoglobulin E (IgE) leader peptide sequence. FIG. 27C displays the endonuclease restriction digest and gene sequencing were used to validate the final vaccine plasmid. FIGS. 27D and 27E depict the expression of the ZIKA-prME protein off the plasmid was confirmed by performing Western analysis and indirect immunofluorescence assay from vaccine-transfected 293T cells at 48 hours post84 transfection.

FIG. 28A through FIG. 28C, depicts experimental results demonstrating the characterization of cellular immune responses in mice following vaccination with the ZIKV-prME DNA vaccine. FIG. 28A depicts ELISpot analysis measuring IFN-γ secretion in splenocytes. C57/BL6 mice (n=5/group) were immunized intramuscularly three times with 25 μg of either pVax1 or the ZIKV-prME DNA vaccine followed by in vivo EP. IFN-γ generation, as an indication of cellular immune response induction, was measured by IFN-γ ELISPOT. Splenocytes harvested 7 days after the third immunization were incubated in the presence of one of six peptide pools spanning the entire prM and envelope proteins. Results are shown in stacked bar graphs. The data represent the average numbers of SFU (spot forming units) per million splenocytes with values representing the mean responses in each group (n=4)±SEM. FIG. 28B depicts the epitope composition of the ZIKV-prME-specific IFN-γ response as determined by stimulation with matrix peptide pools one week after the third immunization. Values represent mean responses in each group (n=4)±SEM. Experiments were performed independently at least three times with similar results. FIG. 28C depicts immunization with ZIKV-prME induces higher number of IFN-γ and TNF-α secreting cells when stimulated by ZIKV peptides. One week after the last immunization with the ZIKV-prME vaccine, splenocytes were cultured in the presence of pooled ZIKV peptides (5 μM) or tissue culture medium only. Frequencies of ZIKV peptide-specific IFN-γ and TNF-α secreting cells were measured by fluorescence-activated cell sorting (FACS) assay. Single function gates were set based on negative control (unstimulated) samples and were placed consistently across samples. The percentage of the total CD8+ T cell responses are shown. These data are representative of two independent immunization experiments.

FIG. 29A depicts ELISpot analysis of serum collected from MR766-immunized mice. FIG. 29B depicts ELISpot analysis of serum collected from Brazil-immunized mice. Anti-ZIKV Env antibody levels in the serum were measured by ELISA (C&D). FIG. 29C depicts Anti-ZIKV Env antibody levels in the serum measured by ELISA in MR766-immunized mice. FIG. 29D depicts Anti-ZIKV Env antibody levels in the serum measured by ELISA in Brazil-immunized mice.

FIG. 30A depicts results from 1 of 2 independent experiments are presented. Similar results were obtained in the second experiment. FIG. 30B depicts the differences in the anti-ZIKV endpoint titers produced in response to the ZIKV-prME immunogen were analyzed in sera from immunized animals after each boost. FIG. 30C depicts western blot analysis of ZIKV-envelope antigen expression. The recombinant ZIKV-Env protein at various concentration were electrophoresed on a 12.5% SDS polyacrylamide gel and analyzed by Western blot analysis with sera from pVax1 or ZIKV-prME immunized mice, as indicated. Expression of the ZIKV-Env protein is indicated by the arrowheads. FIG. 30D depicts an immunofluorescence analysis of Vero cells infected with either ZIKV-MR766 or mock infected following incubation with sera from ZIKV-prME or pVax1 immunized mice. FIG. 30E depicts samples from the pZIKV-prME immunized mice were tested by plaque-reduction neutralization (PRNT) assay for their ability to neutralize ZIKV infectivity in vitro. PRNT50 was defined as the serum dilution factor that could inhibit 50% of the input virus. Values in parentheses indicate the PRNT50. Control plasmid pZIKV-Capsid and pVax1 sera were used as negative controls.

FIG. 31A through FIG. 31E, depicts experimental results demonstrating induction of ZIKV specific cellular immune responses following ZIKV=prME DNA vaccination of NHPs. FIG. 31A depicts rhesus macaques were immunized intradermally (ID) with 2 mg of ZIKV-prME plasmid at weeks 0 and 4 administered as 1 mg at each of two sites, with immunization immediately followed by intradermal EP. PBMCs were isolated pre-immunization and at week 6 and were used for the ELISPOT assay to detect IFN-γ-secreting cells in response to stimulation with ZIKV-prME peptides. The number of IFN-γ producing cells obtained per million PBMCs against six peptide pools encompassing the entire prME protein is indicated on the y-axis for the vaccination groups. Values represent mean responses in each group (n=5)±SEM. FIG. 31B depicts the detection of ZIKV-prME-specific antibody responses following DNA vaccination. Anti-ZIKV IgG antibodies were measured pre-immunization and at week 6 by ELISA. FIG. 31C depicts end-point ELISA titers for anti ZIKV-envelope antibodies are shown following the first and second immunizations. FIG. 31D depicts western blot analysis using week 6 pooled monkey sera demonstrated binding to recombinant envelope protein. FIG. 31E depicts immunofluorescence analysis of Vero cells infected with ZIKV MR766 at 10 PFU. Cells were probed 24 hrs following infection with wk 6 pooled monkey sera at 1:100 and then detected with secondary anti-human IgG-AF488.

FIG. 32A through FIG. 32C, depicts experimental results demonstrating plaque-reduction neutralization activity of serum from Rhesus Macaques immunized with ZIKV-prME. Rhesus Macaques were immunized as described in Materials and Methods. FIG. 32A depicts pre-immunization and week 6 immune sera from individual monkeys were tested by plaque reduction neutralization (PRNT) assay for their ability to neutralize ZIKV infectivity in vitro. PRNT50 was defined as the serum dilution factor that could inhibit 50% of the input virus. Calculated IC50 values are listed for each monkey. FIGS. 21B and 21C depict the cytopathic effect of ZIKV MR766 and PR209 in Vero, SK-N-SH, and U87MG cells. FIG. 32B depicts Vero cells were mock infected or infected with the MR766 or PR209 viruses. FIG. 32C depicts SK-N-SH and U87MG cells were mock or infected with MR766 at an MOT of 0.001 PFU/cell in the presence of pooled NHP sera immunized with ZIKV-prME vaccine (Wk 6). The induction of syncytium formation (CPE) and prME protein expression were analyzed 48 hours post infection by indirect immunofluorescence assay (IFA) using the immunized NHP sera. Pictures were taken at 4× objective.

FIG. 33A depicts IFN α, β receptor knockout mice (four to six) were immunized intramuscularly three times with 25 μg of pZIKV-prME or pVax1 plasmid at 2-week intervals. Splenocytes were collected two weeks after the last immunization and incubated with prME peptides and the number of IFN-γ-producing cells were measured by ELISPOT. FIG.

33B depicts serum antibody specific for ZIKV Env protein in immunized animals was measured by ELISA at various days post immunization. FIG. 33C depicts the endpoint titer 0, 1, 2, 3, 4 and 5 weeks after immunization.

FIG. 34A depicts mice were immunized once and challenged with 106 PFU of ZIKV-PR209, 2 weeks later. FIG. 34B depicts mice were immunized twice at 2 week intervals and challenged with 106 PFU of ZIKV-PR209 7 days after the second immunization. FIG. 34C depicts mice were immunized twice at 2 week intervals and challenged with 2×106 PFU of ZIKV PR209, 7 days after the second immunization. The survival curves were constructed using data from two separate experiments. FIG. 34D depicts weight change for animals immunized 2× is depicted; the data reflect the results from two independent experiments with 10 to 15 mice per group per experiment. FIG. 34E depicts clinical scores for animals in FIG. 34B. FIG. 34F depicts clinical scores for animals in FIG. 34C. The designation for the clinical scores is as follows: 1-no disease, 2-decreased mobility; 3-hunched posture and decreased mobility; 4-hindlimb knuckle walking (partial paralysis), 5-paralysis of one hind limb and 6-paralysis of both hind limbs.

FIG. 35A depicts a diagrammatic representation of the ZIKV-prME DNA vaccine indicating the cloning of rME into the pVax1 mammalian expression vector. A consensus design strategy was adopted for the ZIKV-prME consensus sequence. Codon-optimised synthetic genes of the prME construct included a synthetic IgE leader sequence. The optimised gene construct was inserted into the BamHl and Xhol sites of a modified pVax1 vector under the control of the CMV promoter. FIG. 35B depicts a model building of the ZIKV-E proteins demonstrates overlap of the vaccine target with potentially relevant epitope regions. Several changes made for vaccine design purpose are located in domains II and III (located within dashed lines of inset, middle left). Vaccine-specific residue changes in these regions are shown in violet CPK format on a ribbon backbone representation of an E (envelope) protein dimer (each chain in light and dark green, respectively). Regions corresponding to the defined EDE are indicated in cyan, and the fusion loop is indicated in blue. Residue Ile156 (T156I) of the vaccine E protein, modelled as exposed on the surface of the 150 loop, is part of an N-linked glycosylation motif NXS/T in several other ZIKV strains as well as in multiple dengue virus strains. FIG. 35C depicts expression analysis by SDS-PAGE of ZIKV-prME protein expression in 293T cells using western blot analysis. The 293T cells were transfected with the ZIKV-prME plasmid and the cell lysates and supernatants were analysed for expression of the vaccine construct with pan-flavivirus immunised sera. Protein molecular weight markers (kDa); cell lysate and supernatant from ZIKV-prME transfected cells and rZIKV-E positive control were loaded as indicated. FIG. 35D depicts expression analysis by SDS-PAGE of ZIKV-prME protein expression in 293T cells using western blot analysis. The 293T cells were transfected with the ZIKV-prME plasmid and the cell lysates and supernatants were analysed for expression of the vaccine construct with ZIKV-prME immunised sera. Protein molecular weight markers (kDa); cell lysate and supernatant from ZIKV-prME transfected cells and rZIKV-E positive control were loaded as indicated. FIG. 35E depicts Immunofluorescence assay (IFA) analysis for ZIKV-prME protein expression in 293T cells. The cells were transfected with 5 μg of the ZIKVprME plasmid. Twenty-four hours post transfection, immunofluorescence labelling was performed with the addition of sera (1:100) from ZIKV-prME immunised mice followed by the addition of the secondary anti-mouse IgG-AF488 antibody for detection. Staining with sera from ZIKV-prME and pVax1 immunised mice is shown. DAPI panels show control staining of cell nuclei. Overlay panels are combinations of antimouse IgG-AF488 and DAPI staining patterns. DAPI, 4',6-diamidino-2-phenylindole; ZIKV-prME, precursor membrane and envelope of Zika virus.

FIG. 36A depicts a timeline of vaccine immunizations and immune analysis used in the study. FIG. 36B depicts ELISpot analysis measuring IFN-γ secretion in splenocytes in response to ZIKV-prME immunization. C57BL/6 mice (n=4/group) were immunised i.m. three times with 25 μg of either pVax1 or the ZIKV-prME DNA vaccine followed by electroporation. IFN-γ generation, as an indication of induction of cellular immune responses, was measured by an IFN-γ ELISpot assay. The splenocytes harvested 1 week after the third immunization were incubated in the presence of one of the six peptide pools spanning the entire prM and Envelope proteins. Results are shown in stacked bar graphs. The data represent the average numbers of SFU (spot-forming units) per million splenocytes with values representing the mean responses in each±s.e.m. FIG. 36C depicts the epitope composition of the ZIKVprME-specific IFN-γ response as determined by stimulation with matrix peptide pools 1 week after the third immunization. The values represent mean responses in each group±s.e.m. The experiments were performed independently at least three times with similar results. FIG. 36D depicts flow cytometric analysis of T-cell responses. Immunization with ZIKV-prME induces higher number of IFN-γ and TNF-α secreting cells when stimulated by ZIKV peptides. One week after the last immunization with the ZIKV-prME vaccine, splenocytes were cultured in the presence of pooled ZIKV peptides (5 μM) or R10 only. Frequencies of ZIKV peptide-specific IFN-γ and TNF-α secreting cells were measured by flow cytometry. Single function gates were set based on negative control (unstimulated) samples and were placed consistently across samples. The percentage of the total $CD8^+$ T-cell responses are shown. These data are representative of two independent immunization experiments. IFN, interferon; TNF, tumour necrosis factor; ZIKV-prME, precursor membrane and envelope of Zika virus.

FIG. 37A depicts ELISA analysis measuring binding antibody production (measured by OD450 values) in immunised mice. The C57BL/6 mice (n=4) were immunised i.m. three times with 25 μg of ZIKV-prME plasmid or pVax1 at 2-week intervals. Binding to rZIKV-E was analysed with sera from animals at different time points (days 21, 35 and 50) post immunization at various dilutions. The data shown are representative of at least three separate experiments. FIG. 37B depicts End point binding titre analysis. Differences in the anti-ZIKV end point titres produced in response to the ZIKV-prME immunogen were analysed in sera from immunised animals after each boost. FIG. 37C depicts Western blot analysis of rZIKV-E specific antibodies induced by ZIKV-prME immunization. The rZIKV-E protein was electrophoresed on a 12.5% SDS polyacrylamide gel and analysed by western blot analysis with pooled sera from ZIKV-prME immunised mice (day 35). Binding to rZIKV-E is indicated by the arrowhead. FIG. 37D depicts immunofluorescence analysis of ZIKV specific antibodies induced by ZIKV-prME immunization. The Vero cells infected with either ZIKV-MR766 or mock infected were stained with pooled sera from ZIKV-prME immunised mice (day 35) followed by an anti-mouse-AF488 secondary antibody for detection. FIG. 37E depicts plaque-reduction neutralization (PRNT) assay analysis of neutralising antibodies induced by ZIKV-prME immunization. The serum samples from the ZIKV-prME immunised mice were tested for their ability to neutralise ZIKV infectivity in vitro. PRNT50 was defined as the serum dilution factor that could inhibit 50% of the input virus. The values in parentheses indicate the PRNT50. Control ZIKV-Cap (DNA vaccine expressing the ZIKV capsid protein) and pVax1 sera were used as negative controls. ZIKV-prME, precursor membrane and envelope of Zika virus.

FIG. 38A depicts ELISpot analysis measuring IFN-γ secretion in peripheral blood mononuclear cells (PBMCs) in response to ZIKV-prME immunization. Rhesus macaques were immunised intradermally with 2 mg of ZIKV-prME plasmid at weeks 0 and 4 administered as 1 mg at each of two sites, with immunization immediately followed by intradermal electroporation. PBMCs were isolated pre-immunization and at week 6 and were used for the ELISPOT assay to detect IFN-γ-secreting cells in response to stimulation with ZIKV-prME peptides as described in the 'Materials and Methods' section. The number of IFN-γ producing cells obtained per million PBMCs against six peptide pools encompassing the entire prME protein is shown. The values represent mean responses in each group (n=5)±s.e.m. FIG. 38B depicts the detection of ZIKV-prME-specific antibody responses following DNA vaccination. Anti-ZIKV IgG antibodies were measured pre-immunization and at week 6 by ELISA. FIG. 38C depicts end point ELISA titres for anti ZIKV-envelope antibodies are shown following the first and second immunizations. FIG. 38D depicts western blot analysis using week 6 RM immune sera demonstrated binding to recombinant envelope protein. FIG. 38E depicts PRNT activity of serum from RM immunised with ZIKV-prME. Preimmunization and week 6 immune sera from individual monkeys were tested by plaque-reduction neutralization (PRNT) assay for their ability to neutralise ZIKV infectivity in vitro. PRNT50 was defined as the serum dilution factor that could inhibit 50% of the input virus. Calculated (PRNT50) values are listed for each monkey. IFN, interferon; ZIKV-prME, precursor membrane and envelope of Zika virus.

FIG. 39A depicts survival of IFNAR$^{-/-}$ mice after ZIKV infection. Mice were immunised twice with 25 μg of the ZIKV-prME DNA vaccine at 2-week intervals and challenged with ZIKV-PR209 virus 1 week after the second immunization with $1\times10^6$ plaque-forming units FIG. 39B depicts survival of IFNAR$^{-/-}$ mice after ZIKV infection. Mice were immunised twice with 25 μg of the ZIKV-prME DNA vaccine at 2-week intervals and challenged with ZIKV-PR209 virus 1 week after the second immunization with $2\times10^6$ plaque-forming units FIG. 39C depicts the weight change of animals immunized with $1\times10^6$ plaque-forming units. FIG. 39D depicts the weight change of animals immunized with $2\times10^6$ plaque-forming units. FIG. 39E depicts the clinical scores of animals immunized with $1\times10^6$ plaque-forming units. FIG. 39F depicts the clinical scores of animals immunized with $2\times10^6$ plaque-forming units. The designation for the clinical scores is as follows: 1: no disease, 2: decreased mobility; 3: hunched posture and decreased mobility; 4: hind limb knuckle walking (partial paralysis); 5: paralysis of one hind limb; and 6: paralysis of both hind limbs. The data reflect the results from two independent experiments with 10 mice per group per experiment. ZIKV-prME, precursor membrane and envelope of Zika virus.

FIG. 40B depicts brain sections from pVax1 and ZIKV-prME vaccinated groups were collected 7-8 days after challenge and stained with H&E (haematoxylin and eosin) for histology. The sections taken from representative, unprotected pVax1 control animals shows pathology. (i): nuclear fragments within neuropils of the cerebral cortex (inset shows higher magnification and arrows to highlight nuclear fragments); (ii): perivascular cuffing of vessels within the cortex, lymphocyte infiltration and degenerating cells; (iii): perivascular cuffing, cellular degeneration and nuclear fragments within the cerebral cortex; and (iv): degenerating neurons within the hippocampus (arrows). An example of normal tissue from ZIKV-prME vaccinated mice appeared to be within normal limits (v and vi). FIG. 40C depicts levels of ZIKV RNA in the plasma samples from mice following vaccination and viral challenge at the indicated day post infection. The results are indicated as the genome equivalents per millilitre of plasma. FIG. 40D depicts levels of ZIKV-RNA in the brain tissues were analysed at day 28 post infection. The results are indicated as the genome equivalent per gram of tissue. ZIKV-prME, precursor membrane and envelope of Zika virus.

FIG. 41A and FIG. 41B, depicts experimental results demonstrating protection of mice lacking the type I interferon α, β receptor following passive transfer of anti-ZIKV immune sera following ZIKV challenge. Pooled NHP anti-ZIKV immune sera, titred for anti-ZIKA virus IgG, was administered i.p. (150 μl/mouse) to mice 1 day after s.c. challenge with a ZIKA virus ($10^6$ plaque-forming units per mouse). As a control, normal monkey sera and phosphate-buffered saline (PBS) were administered (150 μl/mouse) to age-matched mice as controls. FIG. 41A depicts the mouse weight change during the course of infection and treatment. Each point represents the mean and standard error of the calculated percent pre-challenge (day 0) weight for each mouse. FIG. 41B depicts the survival of mice following administration of the NHP immune sera. ZIKV-prME, precursor membrane and envelope of Zika virus.

FIG. 42A through FIG. 42D, depicts experimental results demonstrating the characterization of immune responses of ZIKV-prME-MR766 or ZIKV-prME Brazil vaccine in C57BL/6 mice. FIG. 42A depicts ELISpot and ELISA analysis measuring cellular and antibody responses after vaccination with either ZIKV-prME-MR766 and ZIKV-prME-Brazil DNA vaccines. C57BL/6 mice (n=4/group) were immunized intramuscularly three times with 25 μg of ZIKV-prME-MR766 followed by in vivo EP. IFN-γ generation, as an indication of cellular immune response induction, was measured by IFN-γ ELISpot. Splenocytes harvested one week after the third immunization were incubated in the presence of one of six peptide pools spanning the entire prM and E proteins. Results are shown in stacked bar graphs. The data represent the average numbers of SFU (spot forming units) per million splenocytes with values representing the mean responses in each ±SEM. FIG. 42B depicts ELISpot and ELISA analysis measuring cellular and antibody responses after vaccination with either ZIKV-prME-MR766 and ZIKV-prME-Brazil DNA vaccines. C57BL/6 mice (n=4/group) were immunized intramuscularly three times with 25 μg of ZIKV prME-Brazil followed by in vivo EP. IFN-γ generation, as an indication of cellular immune response induction, was measured by IFN-γ ELISpot. Splenocytes harvested one week after the third immunization were incubated in the presence of one of six peptide pools spanning the entire prM and E proteins. Results are shown in stacked bar graphs. The data represent the average numbers of SFU (spot forming units) per million splenocytes with values representing the mean responses in each ±SEM. FIG. 42C depicts ELISA analysis measuring binding antibody production in immunized C57BL/6 mice. Binding to rZIKV-E was analyzed with sera from mice at day 35 post immunization at various dilutions. FIG. 42D depicts ELISA analysis measuring binding antibody production in immunized C57BL/6 mice. Binding to rZIKV-E was analyzed with sera from mice at day 35 post immunization at various dilutions.

FIG. 43A through FIG. 43D, depicts experimental results demonstrating the expression, purification, and characterization of ZIKV-Envelope protein. FIG. 43A depicts the cloning plasmid for rZIKV E expression. FIG. 43B depicts the characterization of the recombinant ZIKV-E (rZIKV-E) protein by SDS-PAGE and Western blot analysis. Lane 1-BSA control; Lane 2-lysates from *E. coli* cultures transformed with pET-28a vector plasmid, was purified by nickel metal affinity resin columns and separated by SDS-PAGE after IPTG induction. Lane 3, 37 recombinant ZV-E purified protein was analyzed by Western blot with anti-His tag antibody. Lane M, Protein molecular weight marker. FIG. 43C depicts the purified rZIKV-E protein was evaluated for its antigenicity. ELISA plates were coated with rZIKV-E and then incubated with various dilutions of immune sera from the mice immunized with ZIKV-prME vaccine or Pan-flavivirus antibody as positive control. Bound IgG was detected by the addition of peroxidase-conjugated anti-mouse antibody followed by tetramethylbenzidine substrate as described in Experimental Example. FIG. 43D depicts western blot detection of purified rZIKV-E protein with immune sera from ZIKV prME immunized mice. Various concentrations of purified rZIKV-E protein were loaded onto an SDS-PAGE gel as described. A dilution of 1:100 immune sera, and goat anti-mouse at 1:15,000 were used for 1 hour at room temperature. After washing, the membranes were imaged on the Odyssey infrared imager. Odyssey protein molecular weight standards were used. The arrows indicate the position of rZIKV-E protein.

FIG. 44A through FIG. 44C, depicts experimental results demonstrating the characterization of immune responses ZIKA-prME in IFNAR$^{-/-}$ mice. ELISpot and ELISA analysis measuring cellular and antibody responses to ZIKV-prME in IFNAR$^{-/-}$ mice. Mice (n=4/group) were immunized intramuscularly three times with 25 μg of ZIKV-prME followed by in vivo EP. FIG. 44A depicts IFN-γ generation, as an indication of cellular immune response induction, was measured by IFN-γ ELISPOT. FIG. 44B depicts ELISA analysis measuring binding antibody production in immunized IFNAR$^{-/-}$ mice. Binding to rZIKV-E was analyzed with sera from mice at various time points post immunization. FIG. 44C depicts endpoint titer analysis of anti-ZIKV antibodies produced in immunized IFNAR$^{-/-}$ mice.

FIG. 45A through FIG. 45D, depicts experimental results demonstrating the neutralization activity of immune sera from Rhesus Macaques immunized against ZIKV-prME. SK-N-SH and U87MG cells were mock infected or infected with MR766 at an MOI of 0.01 PFU/cell in the presence of pooled NHP sera immunized with ZIKV-prME vaccine (Wk 6). Zika viral infectivity were analyzed 4 days post infection by indirect immunofluorescence assay (IFA) using sera from ZIKV-prME vaccinated NHPs. FIG. 45A depicts photographs of stained tissue sample slices taken with a 20× objective demonstrating inhibition of infection by ZIKV viruses MR766 and PR209 in Vero, SK-N-SH and U87MG FIG. 45B depicts photographs of stained tissue sample slices taken with a 20× objective demonstrating inhibition of infection by ZIKV viruses SK-N-SH and U87MG in Vero, SK-N-SH and U87MG FIG. 45C depicts a bar graph shows the percentage of infected (GFP positive cells) demonstrating the inhibition of infection by ZIKV viruses MR766 and PR209 in Vero, SK-N-SH and U87MG FIG. 45D depicts a bar graph showing the percentage of infected (GFP positive cells) demonstrating the inhibition of infection by ZIKV viruses SK-N-SH and U87MG in Vero, SK-N-SH and U87MG FIG. 46, comprising FIG. 46A depicts Kaplan-Meier survival curves of IFNAR$^{-/-}$ mice inoculated via intracranial with $10^6$ pfu ZIKV-PR209 virus. FIG. 46B depicts Kaplan-Meier survival curves of IFNAR$^{-/-}$ mice inoculated via intravenously with $10^6$ pfu ZIKV-PR209 virus. FIG. 46C depicts Kaplan-Meier survival curves of IFNAR$^{-/-}$ mice inoculated via intraperitoneial with $10^6$ pfu ZIKV-PR209 virus. FIG. 46D depicts Kaplan-Meier survival curves of IFNAR$^{-/-}$ mice inoculated via subcutaneously with $10^6$ pfu ZIKV-PR209 virus.

DETAILED DESCRIPTION

Figure 1:
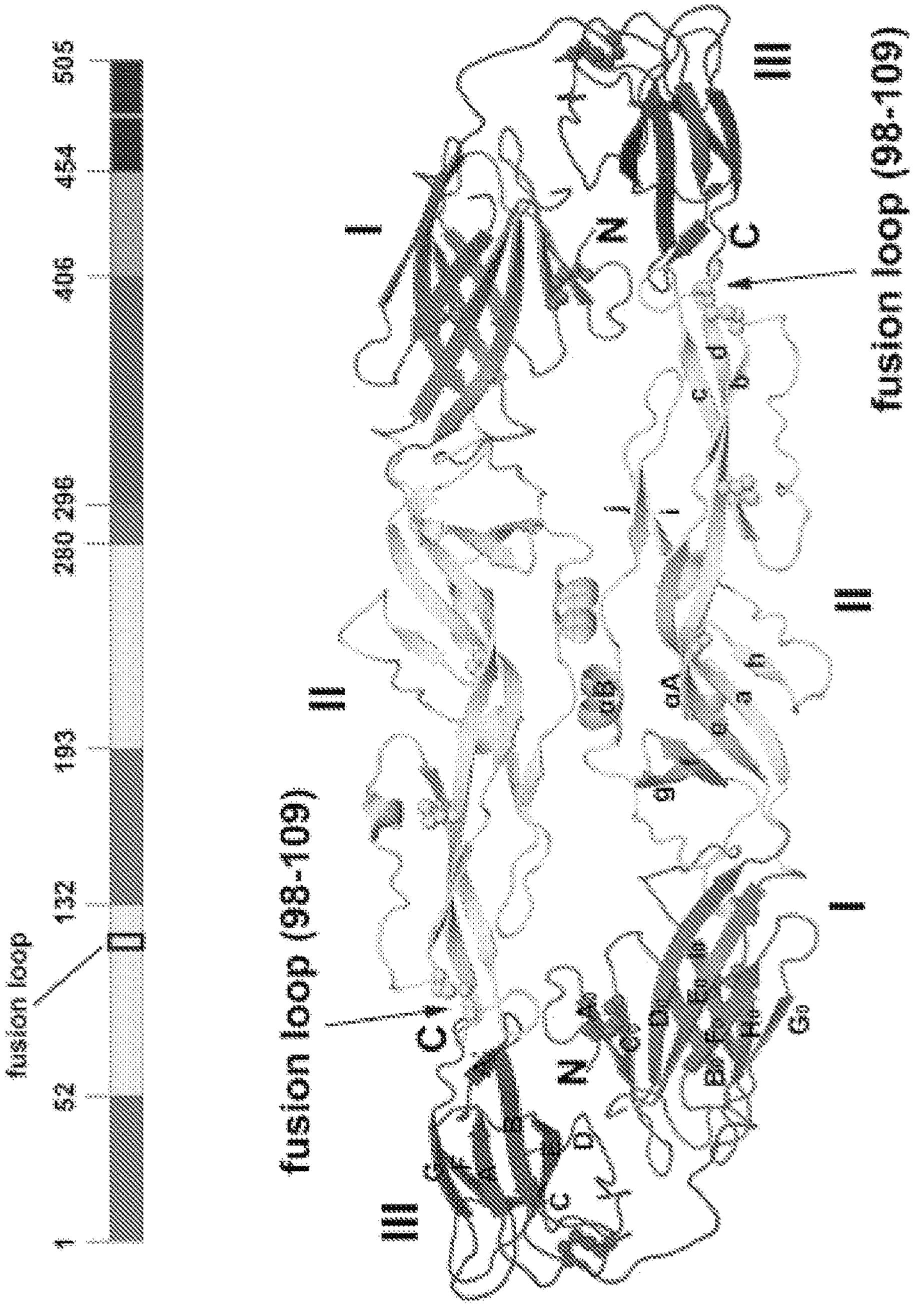
FIG. 1 depicts the structure of the ZIKV-E protein.

The present invention relates to a composition comprising a recombinant nucleic acid sequence that encodes an antibody to a Zika viral antigen, and functional fragments thereof. The composition can be administered to a subject in need thereof to facilitate in vivo expression and formation of a synthetic antibody.

The invention also relates to a combination of a first composition that elicits an immune response in a mammal against zika virus and a second composition comprising a recombinant nucleic acid sequence encoding an antibody, a fragment thereof, a variant thereof, or a combination thereof.

Another aspect of the present invention provides an immunogenic composition comprising one or more nucleic acid molecules comprising one or more nucleic acid sequences capable of generating in a mammal an immune response against a zika virus. In one embodiment, the nucleic acid molecules comprise one or more nucleic acid sequences capable of expressing a consensus zika antigen in the mammal and a pharmaceutically acceptable excipient. In one embodiment, the nucleic acid molecule comprises a promoter operably linked to a coding sequence that encodes the consensus zika antigen. In one embodiment, the consensus zika antigen comprises consensus prME, NS1, capsid, or a fusion of one or more of aforementioned antigens. In one embodiment, the nucleic acid molecule comprises an optimized nucleic acid sequence encoding a consensus zika antigen comprising an amino acid sequence at least 90% homologous to SEQ ID NO: 23, SEQ ID NO: 25, SEQ ID NO: 27, SEQ ID NO: 29, and SEQ ID NO:39.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Composition

One aspect of the present invention provides a combination of a composition that elicits an immune response in a mammal against zika virus with a composition comprising a recombinant nucleic acid sequence encoding an antibody, a fragment thereof, a variant thereof, or a combination thereof. The composition can be administered to a subject in need thereof to facilitate in vivo expression and formation of a synthetic antibody. In one embodiment, the nucleic acid molecule comprises a nucleotide sequence encoding an anti-ZIKV-Envelope (anti-ZIKV E) Protein antibody.

The present invention relates to a combination of a first composition that elicits an immune response in a mammal against zika virus and a second composition comprising a recombinant nucleic acid sequence encoding an antibody, a fragment thereof, a variant thereof, or a combination thereof.

Zika Vaccine

Another aspect of the present invention provides an immunogenic composition comprising one or more nucleic acid molecules that are capable of generating in a mammal an immune response against a zika virus. The present invention also provides isolated nucleic acid molecules that are capable of generating in a mammal an immune response against a zika virus. In one embodiment, the nucleic acid molecules comprise one or more nucleic acid sequences capable of expressing a consensus zika antigen in the mammal and a pharmaceutically acceptable excipient. In one embodiment, the nucleic acid molecules comprise a promoter operably linked to a coding sequence that encodes the consensus zika antigen. In one embodiment, the consensus zika antigen is comprised of consensus prME, NS1, capsid, or a fusion of one or more of aforementioned antigens. In one embodiment, the nucleic acid molecule comprises a optimized nucleic acid sequence encoding a consensus zika antigen comprising an amino acid sequence at least 90% homologous to SEQ ID NO: 23, SEQ ID NO: 25, SEQ ID NO: 27, SEQ ID NO: 29, SEQ ID NO: 31, SEQ ID NO: 33, and SEQ ID NO: 39.

| SEQ ID NO | Description (with respect to Zika vaccine) |
|---|---|
| 23 | consensus Zika IgE Leader-prME protein |
| 24 | consensus Zika IgE Leader-prME (construct 1) DNA |
| 25 | consensus Zika IgE Leader-prME (construct 1) protein |
| 26 | consensus Zika IgE Leader-NS1 DNA |
| 27 | consensus Zika IgE Leader-NS1 protein |
| 28 | consensus Zika IgE Leader-capsid DNA |

-continued

| SEQ ID NO | Description (with respect to Zika vaccine) |
|---|---|
| 29 | consensus Zika IgE Leader-capsid protein |
| 30 | Zika IgE Leader-prME MR766 DNA |
| 31 | Zika IgE Leader-prME MR766 protein |
| 32 | Zika IgE Leader-prME Brazil DNA |
| 33 | Zika IgE Leader-prME Brazil protein |
| 34 | consensus Zika IgE Leader-NS1 DNA (pGX7211) |
| 35 | consensus Zika IgE Leader-capsid DNA (pGX7212) |
| 36 | Zika IgE Leader-prME Brazil DNA (pGX7213) |
| 37 | Zika IgE Leader-prME MR766 DNA (pGX7214) |
| 38 | Zika PreEnv (MR766) w/out capsid DNA (pGX7210) |
| 39 | Zika PreEnv (MR766) w/out capsid Protein (pGX7210) |

In some embodiments, the nucleic acid sequences herein can have removed from the 5' end the IgE leader sequence, and the protein sequences herein can have removed from the N-terminus the IgE leader sequence.

In one embodiment, nucleic acid molecule can encode a peptide having the amino acid sequence set forth in SEQ ID NO: 23, SEQ ID NO: 25, SEQ ID NO: 27, SEQ ID NO: 29, SEQ ID NO: 31, SEQ ID NO: 33, or SEQ ID NO: 39. In one embodiment, the nucleic acid molecule comprises the nucleotide sequence set forth in SEQ ID NO: 24, SEQ ID NO: 26, SEQ ID NO: 28, SEQ ID NO: 30, SEQ ID NO: 32, SEQ ID NO:34, SEQ ID NO:35, SEQ ID NO:36, SEQ ID NO:37, or SEQ ID NO:38. In some embodiments, the sequence can be the nucleotide sequence having at least about 90%, 91%, 92%, 93%, 94%, 95%, 96%, 97%, 98%, 99% or 100% identity over an entire length of the nucleotide sequence set forth in SEQ ID NO: 24, SEQ ID NO: 26, SEQ ID NO: 28, SEQ ID NO: 30, SEQ ID NO: 32, SEQ ID NO:34, SEQ ID NO:35, SEQ ID NO:36, SEQ ID NO:37, or SEQ ID NO:38. In other embodiments, sequence can be the nucleotide sequence that encodes the amino acid sequence having at least about 90%, 91%, 92%, 93%, 94%, 95%, 96%, 97%, 98%, 99%, or 100% identity over an entire length of the amino acid sequence set forth in SEQ ID NO: 23, SEQ ID NO: 25, SEQ ID NO: 27, SEQ ID NO: 29, SEQ ID NO: 31, SEQ ID NO: 33, or SEQ ID NO: 39.

In some embodiments, the nucleic acid molecule comprises an RNA sequence that is a transcript from a DNA sequence having at least about 96%, 97%, 98%, 99% or 100% identity over an entire length of the nucleic acid sequence set forth in the SEQ ID NO: 24, SEQ ID NO: 26, SEQ ID NO: 28, SEQ ID NO: 30, SEQ ID NO: 32, SEQ ID NO:34, SEQ ID NO:35, SEQ ID NO:36, SEQ ID NO:37, or SEQ ID NO:38. In some embodiments, the nucleic acid molecule comprises an RNA sequence that encodes an amino acid sequence having at least about 96%, 97%, 98%, 99% or 100% identity over an entire length of the amino acid sequence set forth in SEQ ID NO: 23, SEQ ID NO: 25, SEQ ID NO: 27, SEQ ID NO: 29, SEQ ID NO: 31, SEQ ID NO: 33, or SEQ ID NO: 39.

The consensus-Zika antigen can be a peptide having the amino acid sequence set forth in SEQ ID NO: 23, SEQ ID NO: 25, SEQ ID NO: 27, SEQ ID NO: 29, SEQ ID NO: 31, SEQ ID NO: 33, or SEQ ID NO: 39. In some embodiments, the antigen can have an amino acid sequence having at least about 90%, 91%, 92%, 93%, 94%, 95%, 96%, 97%, 98%, 99%, or 100% identity over an entire length of the amino acid sequence set forth in SEQ ID NO: 23, SEQ ID NO: 25, SEQ ID NO: 27, SEQ ID NO: 29, SEQ ID NO: 31, SEQ ID NO: 33, or SEQ ID NO: 39.

Immunogenic fragments of proteins with amino acid sequences homologous to immunogenic fragments of SEQ ID NO: 23, SEQ ID NO: 25, SEQ ID NO: 27, SEQ ID NO: 29, SEQ ID NO: 31, SEQ ID NO: 33, or SEQ ID NO: 39, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO: 23, SEQ ID NO: 25, SEQ ID NO: 27, SEQ ID NO: 29, SEQ ID NO: 31, SEQ ID NO: 33, or SEQ ID NO: 39. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of a nucleic acid molecule encodes at least one immunodominant or sub-immunodominant epitope of a full length optimized consensus zika antigen.

Some embodiments relate to immunogenic fragments of SEQ ID NO: 23, SEQ ID NO: 25, SEQ ID NO: 27, SEQ ID NO: 29, SEQ ID NO: 31, SEQ ID NO: 33, or SEQ ID NO: 39 comprising at least 60%, at least 65%, at least 70%, at least 75%, at least 80%, at least 85%, at least 90%, at least 95%, at least 96%, at least 97%, at least 98% or at least 99% of the full length of SEQ ID NO: 23, SEQ ID NO: 25, SEQ ID NO: 27, SEQ ID NO: 29, SEQ ID NO: 31, SEQ ID NO: 33, or SEQ ID NO: 39. Immunogenic fragments can be at least 96%, at least 97% at least 98% or at least 99% homologous to fragments of SEQ ID NO: 23, SEQ ID NO: 25, SEQ ID NO: 27, SEQ ID NO: 29, SEQ ID NO: 31, SEQ ID NO: 33, or SEQ ID NO: 39. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO: 24, SEQ ID NO: 26, SEQ ID NO: 28, SEQ ID NO: 30, SEQ ID NO: 32, SEQ ID NO:34, SEQ ID NO:35, SEQ ID NO:36, SEQ ID NO:37, or SEQ ID NO:38.

In some embodiments, the nucleic acid molecule includes a sequence that encodes for a zika antigen minus an IgE leader sequence on the N-terminal end of the coding sequence. In some embodiments, the DNA nucleic acid molecule further comprises an IgE leader sequence attached to an N-terminal end of the coding sequence and operably linked to the promoter.

The nucleic acid molecule can further include a polyadenylation sequence attached to the C-terminal end of the coding sequence. In one embodiment, the nucleic acid molecule is codon optimized.

In some embodiments, the pharmaceutically acceptable excipient is an adjuvant. Preferably, the adjuvant is selected from the group consisting of: IL-12 and IL-15. In some embodiments, the pharmaceutically acceptable excipient is a transfection facilitating agent. Preferably, the transfection facilitating agent is a polyanion, polycation, or lipid, and more preferably poly-L-glutamate. Preferably, the poly-L-glutamate is at a concentration less than 6 mg/ml. In one embodiment, the nucleic acid molecule is a DNA plasmid. In one embodiment, the DNA plasmid has a concentration of total DNA plasmid of 1 mg/ml or greater.

In some embodiments, the nucleic acid molecule comprises a plurality of unique nucleic acid molecules, wherein each of the plurality of unique nucleic acid molecules encode a polypeptide comprising a consensus prME protein, consensus prME (construct 1), consensus NS1 DNA, or consensus capsid protein.

The nucleic acid molecules can include a DNA plasmid comprising a nucleic acid sequence encoding an amino acid sequence including, but not limited to, SEQ ID NO:23, SEQ ID NO:25, SEQ ID NO:27, SEQ ID NO: 29, SEQ ID NO: 31, and SEQ ID NO: 33.

In one embodiment, the nucleic acid molecule can include a nucleic acid molecule comprising a nucleotide sequence including but is not limited to SEQ ID NO: 24, SEQ ID NO: 26, SEQ ID NO: 28, SEQ ID NO: 30, SEQ ID NO: 32, SEQ ID NO:34, SEQ ID NO:35, SEQ ID NO:36, SEQ ID NO:37, and SEQ ID NO:38.

In one embodiment, the nucleic acid molecule comprises a optimized nucleic acid sequence. The optimized sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The zika antigen encoded by the optimized sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The zika antigen encoded by the optimized sequence can be designed to elicit stronger cellular and/or humoral immune responses than a corresponding native antigen.

In some embodiments of the present invention, the nucleic acid molecule vaccines can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

In some embodiments, methods of eliciting an immune response in mammals against a consensus zika antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus zika antigen, described above. The one or more of CTACK protein, TECK protein, MEC protein and functional fragments thereof may be administered prior to, simultaneously with or after administration of the nucleic acid molecules provided herein. In some embodiments, an isolated nucleic acid molecule that encodes one or more proteins of selected from the group consisting of: CTACK, TECK, MEC and functional fragments thereof is administered to the mammal.

The immunogenic composition can induce an immune response in the subject administered the composition. The induced immune response can be specific for a native antigen. The induced immune response can be reactive with a native antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a native antigen. The induced humoral immune response can be reactive with the native antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized zika antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a native antigen related to the optimized consensus-encoded antigen. The neutralizing antibodies can be reactive with the native antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the native antigen genetically related to the optimized consensus antigen. These IgG antibodies can be reactive with the native antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized zika antigen.

The immunogenic composition can induce a cellular immune response in the subject administered the immunogenic composition. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a $CD8^+$ T cell response. The elicited $CD8^+$ T cell response can be reactive with the native antigen genetically related to the optimized consensus antigen. The elicited $CD8^+$ T cell response can be polyfunctional. The induced cellular immune response can include eliciting a $CD8^+$ T cell response, in which the $CD8^+$ T cells produce interferon-gamma (IFN-γ), tumor necrosis factor alpha (TNF-α), interleukin-2 (IL-2), or a combination of IFN-γ and TNF-α.

The induced cellular immune response can include an increased $CD8^+$ T cell response associated with the subject administered the immunogenic composition as compared to the subject not administered the immunogenic composition. The $CD8^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The $CD8^+$ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized zika antigen.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized zika antigen.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized zika antigen.

The cellular immune response induced by the immunogenic composition can include eliciting a $CD4^+$ T cell response. The elicited $CD4^+$ T cell response can be reactive with the native antigen genetically related to the optimized consensus antigen. The elicited $CD4^+$ T cell response can be polyfunctional. The induced cellular immune response can include eliciting a $CD4^+$ T cell response, in which the $CD4^+$ T cells produce IFN-γ, TNF-α, IL-2, or a combination of IFN-γ and TNF-α.

The induced cellular immune response can include an increased frequency of $CD4^+$ T cells that produce IFN-γ. The frequency of $CD4^+IFN\text{-}\gamma^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized zika antigen.

The induced cellular immune response can include an increased frequency of $CD4^+$ T cells that produce TNF-α. The frequency of $CD4^+TNF\text{-}\alpha^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized zika antigen.

The induced cellular immune response can include an increased frequency of $CD4^+$ T cells that produce both IFN-γ and TNF-α. The frequency of $CD4^+IFN-\gamma^+$ $TNF-\alpha^+$ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized zika antigen.

Synthetic Antibody

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-ZIKV-Envelope (anti-ZIKV E) Protein antibody.

In one embodiment, the nucleotide sequence encoding an anti-ZIKV antibody comprises one or more codon optimized nucleic acid sequences encoding an amino acid sequence as set forth in one or more of SEQ ID NO:1-22. In one embodiment, the nucleotide sequence encoding an anti-ZIKV antibody comprises one or more codon optimized nucleic acid sequences encoding an amino acid sequence at least 90% homologous to one or more of SEQ ID NO:1-22. In one embodiment, the nucleotide sequence encoding an anti-ZIKV antibody comprises one or more codon optimized nucleic acid sequences encoding an immunogenic fragment of an amino acid as set forth in one or more of SEQ ID NO:1-22. In one embodiment, the nucleotide sequence encoding an anti-ZIKV antibody comprises one or more codon optimized nucleic acid sequences encoding an immunogenic fragment of an amino acid sequence at least 90% homologous to one or more of SEQ ID NO:1-22.

In one embodiment, the nucleotide sequence encoding an anti-ZIKV antibody comprises one or more RNA sequence transcribed from one or more DNA sequences encoding an amino acid sequence as set forth in one or more of SEQ ID NO:1-22. In one embodiment, the nucleotide sequence encoding an anti-ZIKV antibody comprises one or more RNA sequence transcribed from one or more DNA sequences encoding an amino acid sequence at least 90% homologous to one or more of SEQ ID NO:1-22. In one embodiment, the nucleotide sequence encoding an anti-ZIKV antibody comprises one or more RNA sequence transcribed from one or more DNA sequences encoding an immunogenic fragment of an amino acid sequence as set forth in one or more of SEQ ID NO:1-22. In one embodiment, the nucleotide sequence encoding an anti-ZIKV antibody comprises one or more RNA sequence transcribed from one or more DNA sequences encoding an immunogenic fragment of an amino acid sequence at least 90% homologous to one or more of SEQ ID NO:1-22.

In one embodiment, the nucleotide sequence encoding an anti-ZIKV E antibody comprises one or more codon optimized nucleic acid sequences encoding the variable VH and VL regions of SEQ ID NO:1 and SEQ ID NO:2 respectively. In one embodiment, an anti-ZIKV E antibody comprises a nucleic acid sequence encoding an amino acid sequence as set forth in SEQ ID NO: 11 or SEQ ID NO: 12.

In one embodiment, the nucleotide sequence encoding an anti-ZIKV E antibody comprises one or more codon optimized nucleic acid sequences encoding the variable VH and VL regions of SEQ ID NO:3 and SEQ ID NO:4 respectively. In one embodiment, an anti-ZIKV E antibody comprises a nucleic acid sequence encoding an amino acid sequence as set forth in SEQ ID NO: 13 or SEQ ID NO: 14.

In one embodiment, the nucleotide sequence encoding an anti-ZIKV E antibody comprises one or more codon optimized nucleic acid sequences encoding the variable VH and VL regions of SEQ ID NO:5 and SEQ ID NO:6 respectively. In one embodiment, an anti-ZIKV E antibody comprises a nucleic acid sequence encoding an amino acid sequence as set forth in SEQ ID NO: 15 or SEQ ID NO: 16.

In one embodiment, the nucleotide sequence encoding an anti-ZIKV E antibody comprises one or more codon optimized nucleic acid sequences encoding the variable VH and VL regions of SEQ ID NO:7 and SEQ ID NO:8 respectively. In one embodiment, an anti-ZIKV E antibody comprises a nucleic acid sequence encoding an amino acid sequence as set forth in SEQ ID NO: 21 or SEQ ID NO: 22.

In one embodiment, the nucleotide sequence encoding an anti-ZIKV E antibody comprises one or more codon optimized nucleic acid sequences encoding the variable VH and VL regions of SEQ ID NO:9 and SEQ ID NO:10 respectively. In one embodiment, an anti-ZIKV E antibody comprises a nucleic acid sequence encoding an amino acid sequence as set forth in SEQ ID NO: 17 or SEQ ID NO: 18.

The composition of the invention can treat, prevent and/or protect against any disease, disorder, or condition associated with Zika infection. In certain embodiments, the composition can treat, prevent, and or/protect against viral infection. In certain embodiments, the composition can treat, prevent, and or/protect against birth defects. In certain embodiments, the composition can treat, prevent, and or/protect against microcephaly.

The synthetic antibody can treat, prevent, and/or protect against disease in the subject administered the composition. The synthetic antibody can treat, prevent, and/or protect against disease in an unconceived child, an unborn child, an embryo or a fetus of the subject administered the composition. The synthetic antibody, by binding the antigen, can treat, prevent, and/or protect against disease in the subject or an unconceived child, an unborn child, an embryo or a fetus of the subject administered the composition. The synthetic antibody can promote survival of the disease in the subject or an unconceived child, an unborn child, an embryo or a fetus of the subject administered the composition. The synthetic antibody can provide at least about 50%, 55%, 60%, 65%, 70%, 75%, 80%, 85%, 90%, 95%, or 100% survival of the disease in the subject an unconceived child, an unborn child, an embryo or a fetus of the subject administered the composition. In other embodiments, the synthetic antibody can provide at least about 65%, 66%, 67%, 68%, 69%, 70%, 71%, 72%, 73%, 74%, 75%, 76%, 77%, 78%, 79%, or 80% survival of the disease in the subject or an unconceived child, an unborn child, an embryo or a fetus of the subject administered the composition.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human (3-globin polyadenylation signal. The SV40 polyadenylation signal may be a polyadenylation signal from a pCEP4 plasmid (Invitrogen, San Diego, Calif.).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NOs: 24, 26, 28, 30 or 32. In another embodiment, the nucleotide sequence comprises an RNA sequence transcribed by a DNA sequence encoding a polypeptide sequence of SEQ ID NOs:1-23, 25, 27, 29, 31, or 33, or a variant thereof or a fragment thereof. Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be pcrNP. pcrNP and pcrMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, copending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. Antibody

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

b. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

5. Antigen

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with Zika infection. In one embodiment, the antigen can be a Zika envelope protein.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

a. Viral Antigens

The viral antigen can be a viral antigen or fragment or variant thereof. The virus can be a disease causing virus. The virus can be the Zika virus.

The antigen may be a Zika viral antigen, or fragment thereof, or variant thereof. The Zika antigen can be from a factor that allows the virus to replicate, infect or survive. Factors that allow a Zika virus to replicate or survive include, but are not limited to structural proteins and non-structural proteins. Such a protein can be an envelope protein.

In one embodiment, an envelope protein is ZIKV E protein.

6. Excipients and Other Components of the Composition

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. Method of Generating the Synthetic Antibody

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. Method of Identifying or Screening for the Antibody

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. Method of Delivery of the Composition

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. Method of Treatment

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing a *Borrelia* spp infection. In one embodiment, the method treats, protects against, and/or prevents Lyme disease.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. Use in Combination with Antibiotics

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

The present invention has multiple aspects, illustrated by the following non-limiting examples.

12. Generation of Synthetic Antibodies In Vitro and Ex Vivo

In one embodiment, the synthetic antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

13. Examples

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The studies presented herein demonstrate the generation of functional anti-Zika "DNA monoclonal antibodies" (DMAb) via intramuscular electroporation of plasmid DNA. Codon-optimized variable region DNA sequences from anti-Zika monoclonal antibodies were synthesized onto a human IgG1 constant domain. Plasmid DNA encoding antibody was delivered to C3H mice mice. This study supports DMAb as an alternative to existing biologic therapies.

Figure 2:
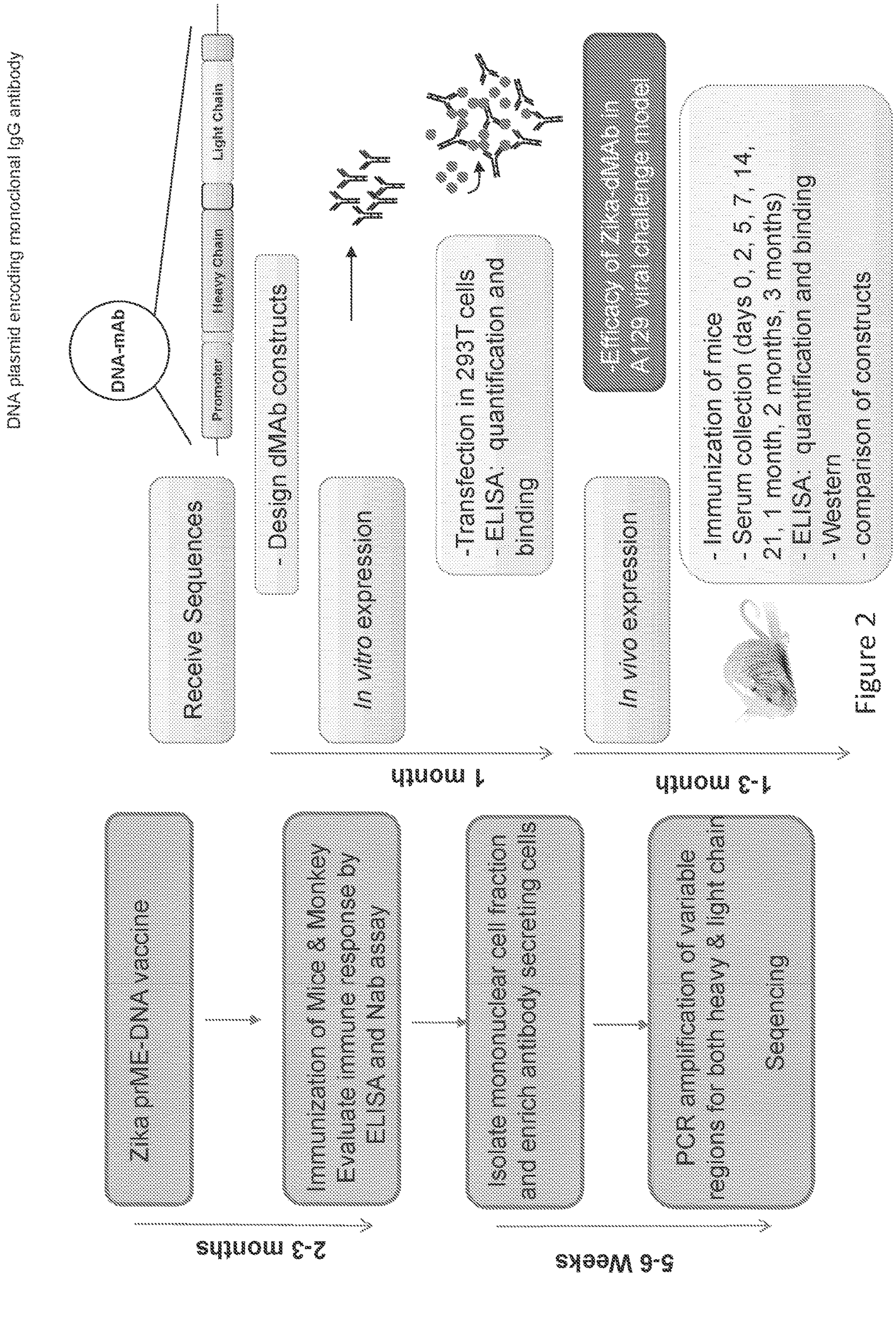
FIG. 2 depicts the workflow for development and characterization of Zika dMABs.
Figure 3:
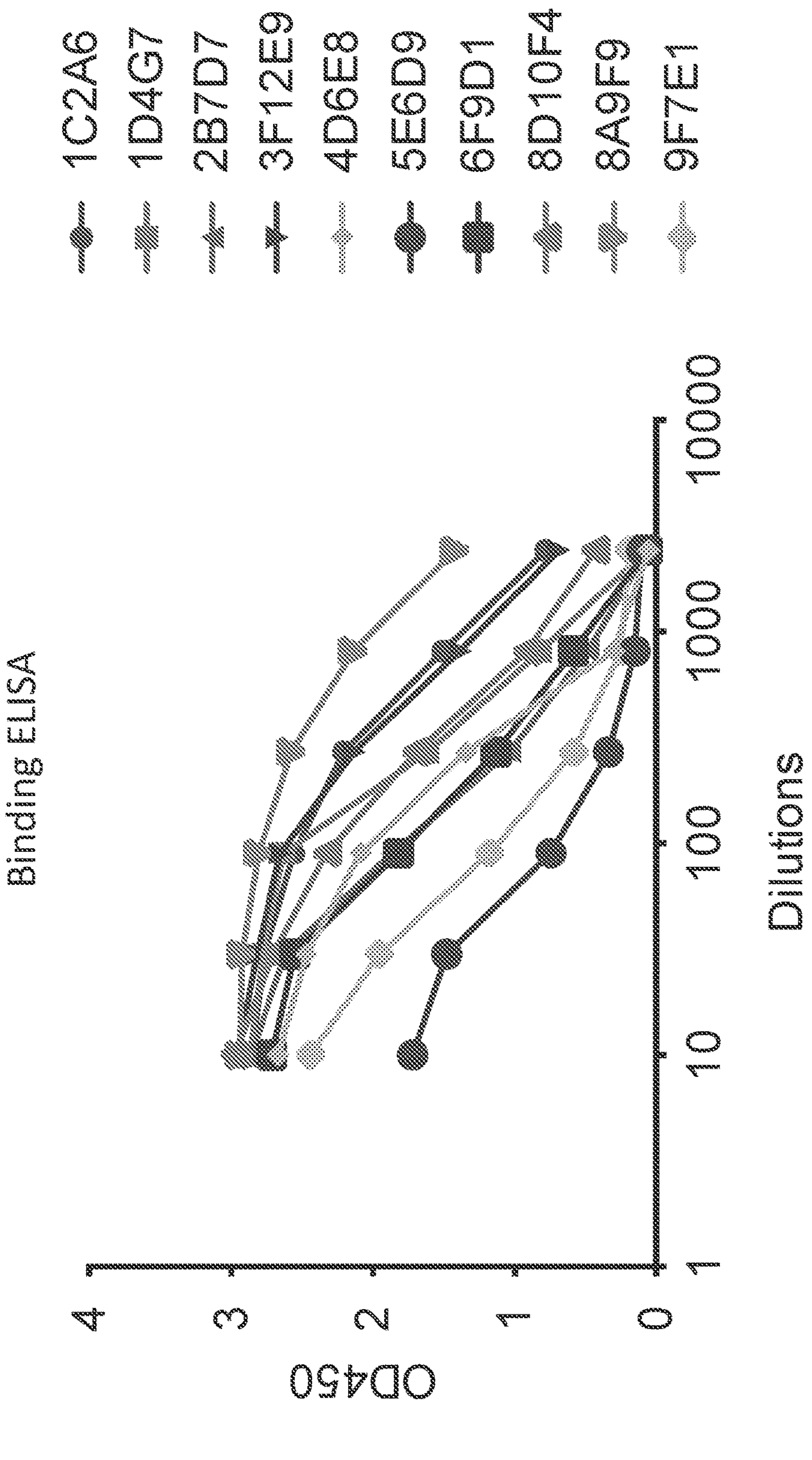
FIG. 3 depicts the binding ELISA for ZIKV-Env specific monoclonal antibodies.
Figure 4:
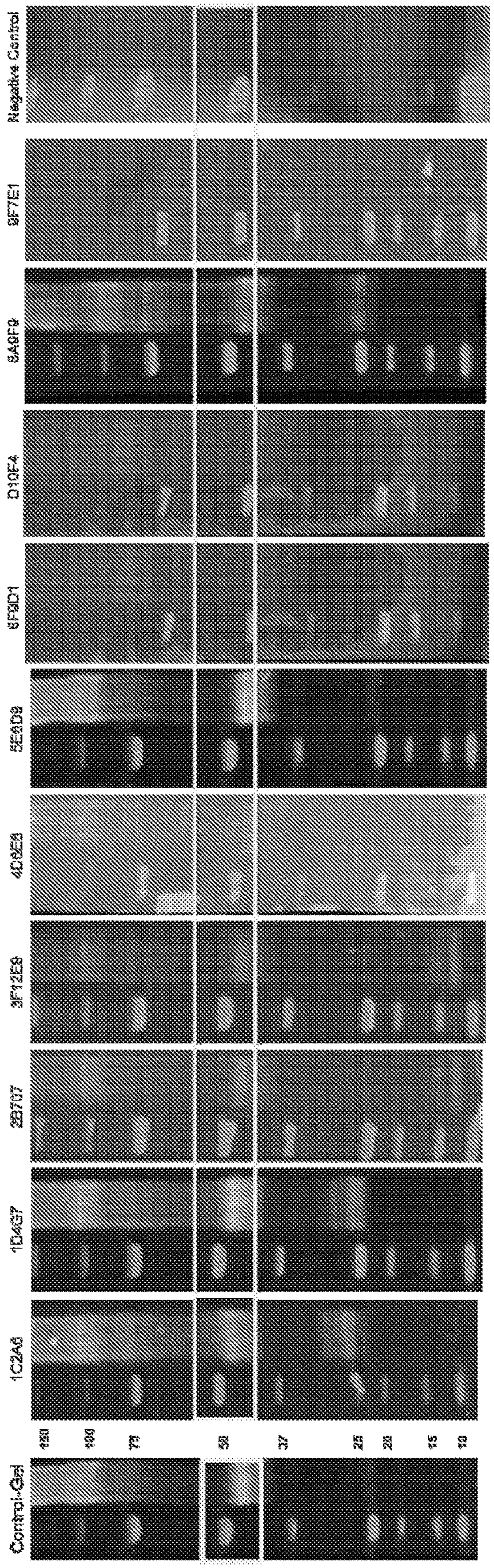
FIG. 4 depicts a western blot of ZV Env and ZV mAB. 2 μg of rZV envelope protein loaded; 1:250 dilution was used for ZV monoclonal antibody.
Figure 5:
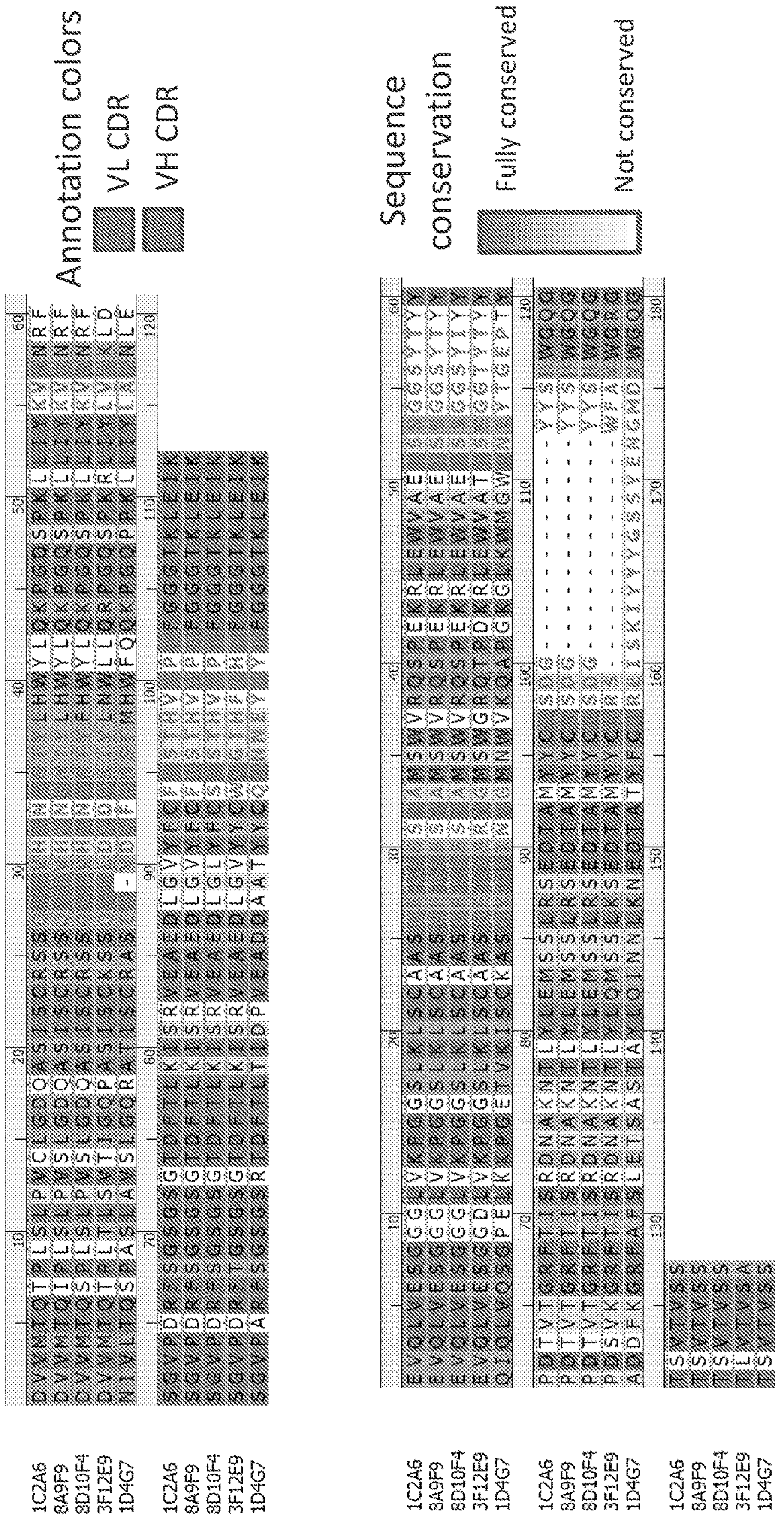
FIG. 5 depicts ZIKA mAb VH and VL alignments.The sequence for 1C2A6 VL is amino acids 20-131 of SEQ ID NO:8. The sequence for 8A9F9 VL is amino acids 20-131 of SEQ ID NO:4. The sequence for 8D10F4 VL is amino acids 20-131 of SEQ ID NO:6. The sequence for 3F12E9 VL is amino acids 21-132 of SEQ ID NO:2. The sequence for 1D4G7 VL is amino acids 21-131 of SEQ ID NO:10. The sequence for 1C2A6 VH is amino acids 20-134 of SEQ ID NO:7. The sequence for 8A9F9 VH is amino acids 20-134 of SEQ ID NO:3. The sequence for 8D10F4 VH is amino acids 20-134 of SEQ ID NO:16. The sequence for 3F12E9 VH is amino acids 20-133 of SEQ ID NO:1. The sequence for 1D4G7 VH is amino acids 20-146 of SEQ ID NO:9.
Figure 7:
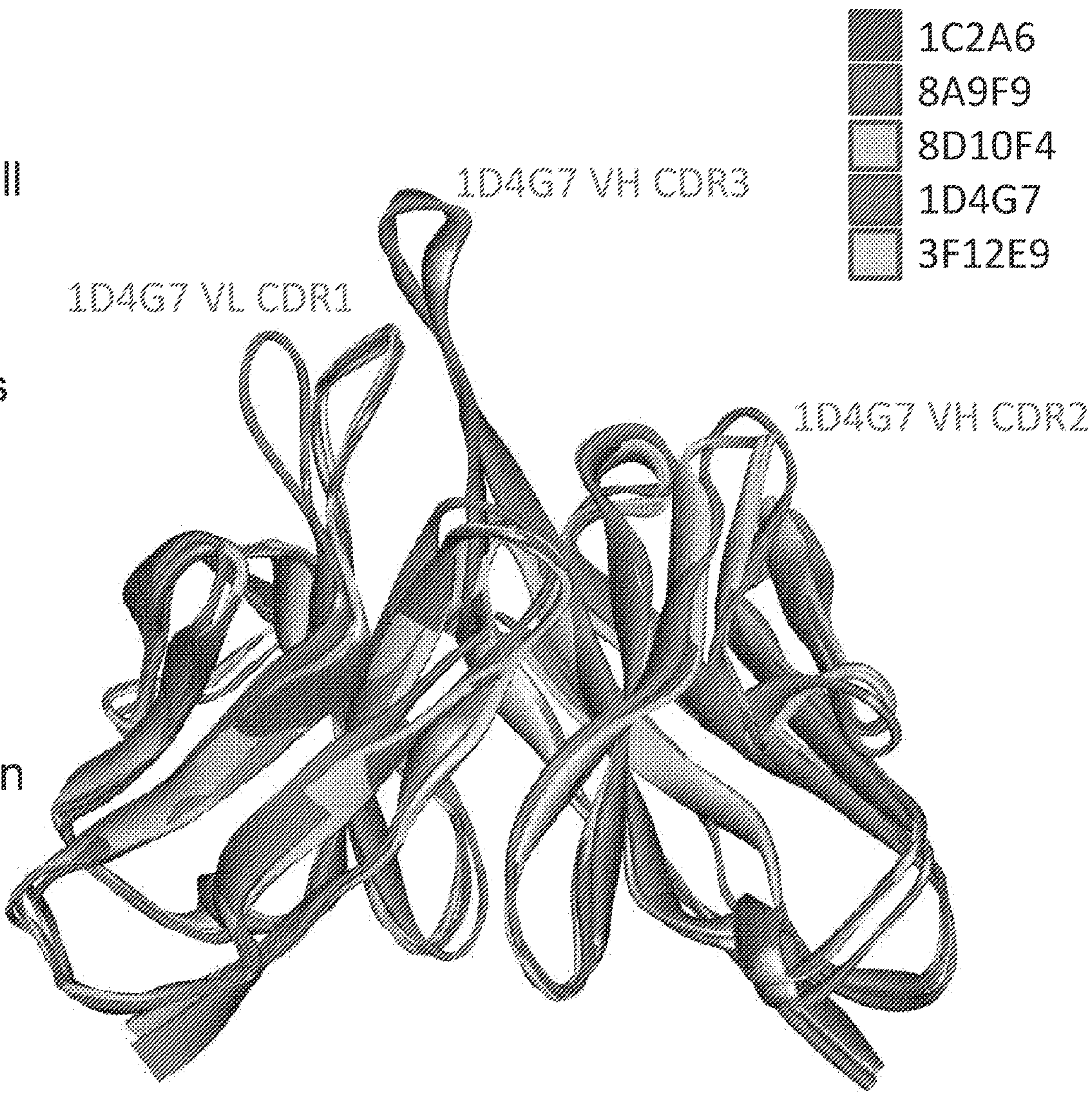
FIG. 7 depicts mAb model superpositions.
Figure 10:
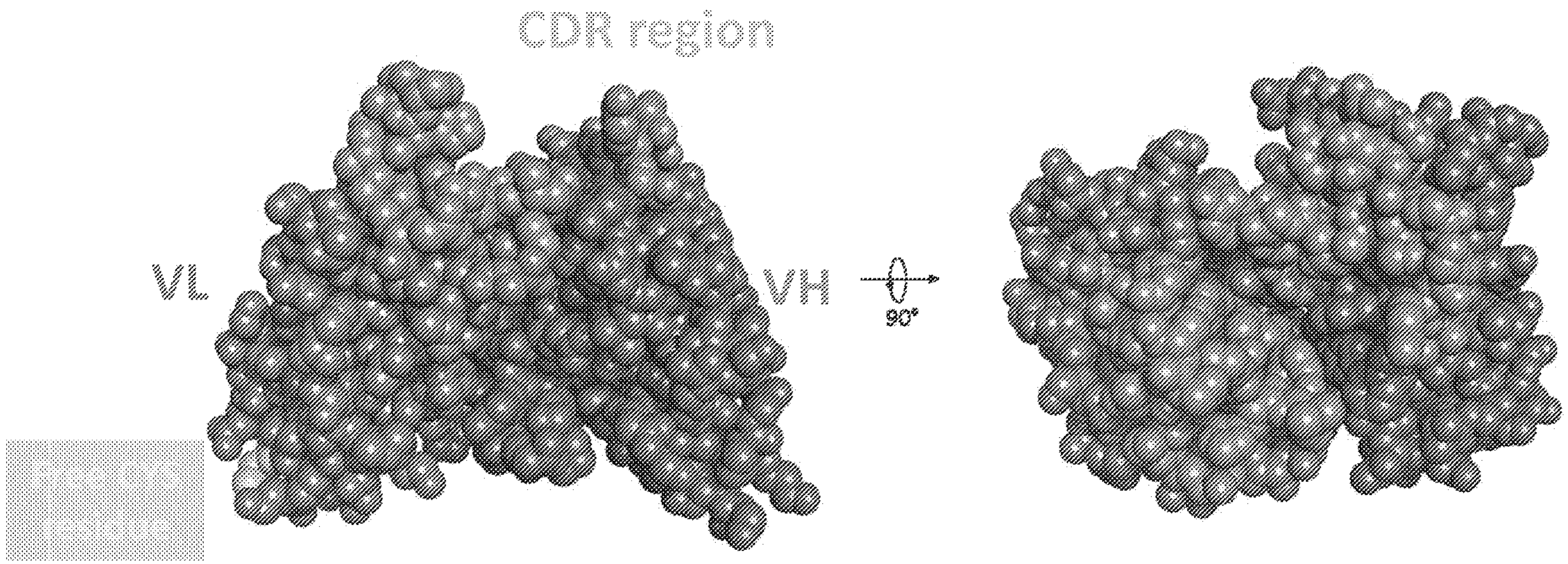
FIG. 10 depicts a model of 1C2A6 Fv.
Figure 12:
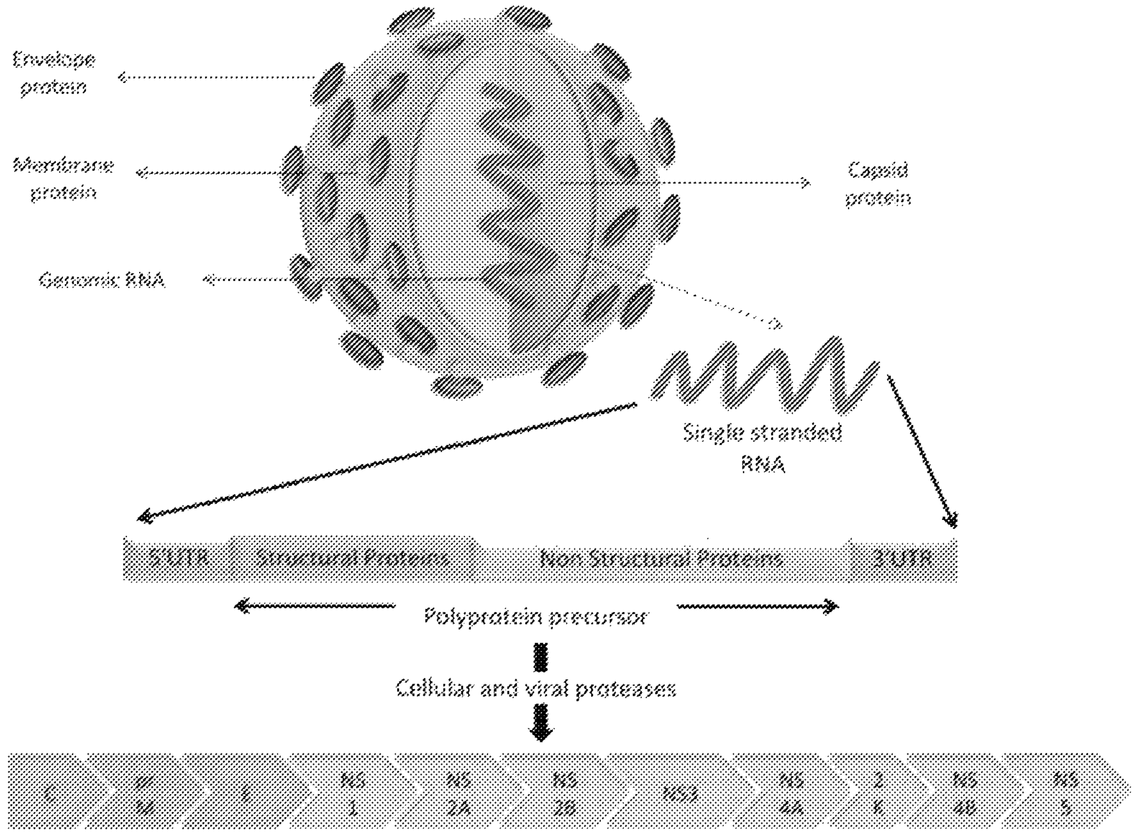
FIG. 12 displays an illustration of a zika virus particle, the zika RNA genome, and its translated genes.

The ZIKV-Env (ZIKV-E) protein is a 505 amino acid protein having a fusion loop (FIG. 1). The antibodies aginst the ZIKV-E protein are expressed in vivo through DNA monoclonal antibodies (dMABs) which express a heavy and light chain (FIG. 2). ZIKV-Env specific monoclonal antibodies, 1C2A6, 1D4G7, 2B7D7, 3F12E9, 4D6E8, 5E6D9, 6F9D1, 9D10F4, 8A9F9, and 9F7E1, each bind ZIKV-Env in vitro (FIGS. 3-4). The monoclonal antibodies show varying degrees of sequence homology among both the $V_H$ and $V_L$ chains (FIG. 5-7). The large VH CDR3 of 1D4G7 is clearly visible, as are several other fold differences in other CDR and in framework regions. Despite the sequence divergence of 3F12E9, it is still closer in overall sequence and conformation to 1C2A6, 8D10F4 and 8A9F9 than to 1D4G7. (FIG. 7). 1D4G7 lacks a cleft between the VH and VL domains due to its large CDR3 loop. Sequence similarities translate to structural similarities, so overall CDR conformations and molecular shapes are conserved according to previously demonstrated clustering. (FIG. 8). 1C2A6 has a free CYS residue distal to the CDRs exposed on the surface Another potentially relevant difference occurs in VH FR2 region. This residue is not directly involved in CDR conformation but does influence local residue packing. Two changes occur within the IMGT-defined CDR regions. The VL changes (F, F, S) directly impact the VL-VH interface. (FIG. 9). A free CYS leaves a highly modifiable chemical group exposed on the molecule surface. (FIG. 10). Developability index is highest for 1D4G7, very likely due to the long CDR3 loop which contains multiple nonpolar residues. Based on past experience, though, this alone does not appear to be an issue (FIG. 11). Based on the high degrees of similarity, 1C2A6, 8D10F4 and 8A9F9 are likely to bind the same epitope in the same basic mode. Small differences between the three sequences include an exposed free CYS residue on 1C2A6 and a reduced number of predicted pi interactions at the VH-VL interface of 8D10F4. 3F12E9 has similarity to 1C2A6, 8D10F4 and 8A9F9 in the CDR regions, but also several important differences. mAb 1D4G7 is likely to bind in a different mode or to a completely different epitope than the other mAbs mentioned above.

Example 2

Zika Vaccine Approach

Figure 13:
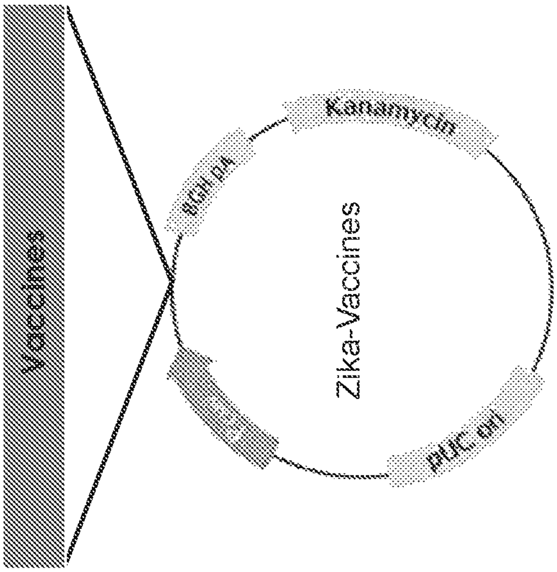
FIG. 13 displays a plasmid map for a zika vaccine, showing the site of the location for the insert (expression cassette) that encodes the zika antigens.
Figure 14:
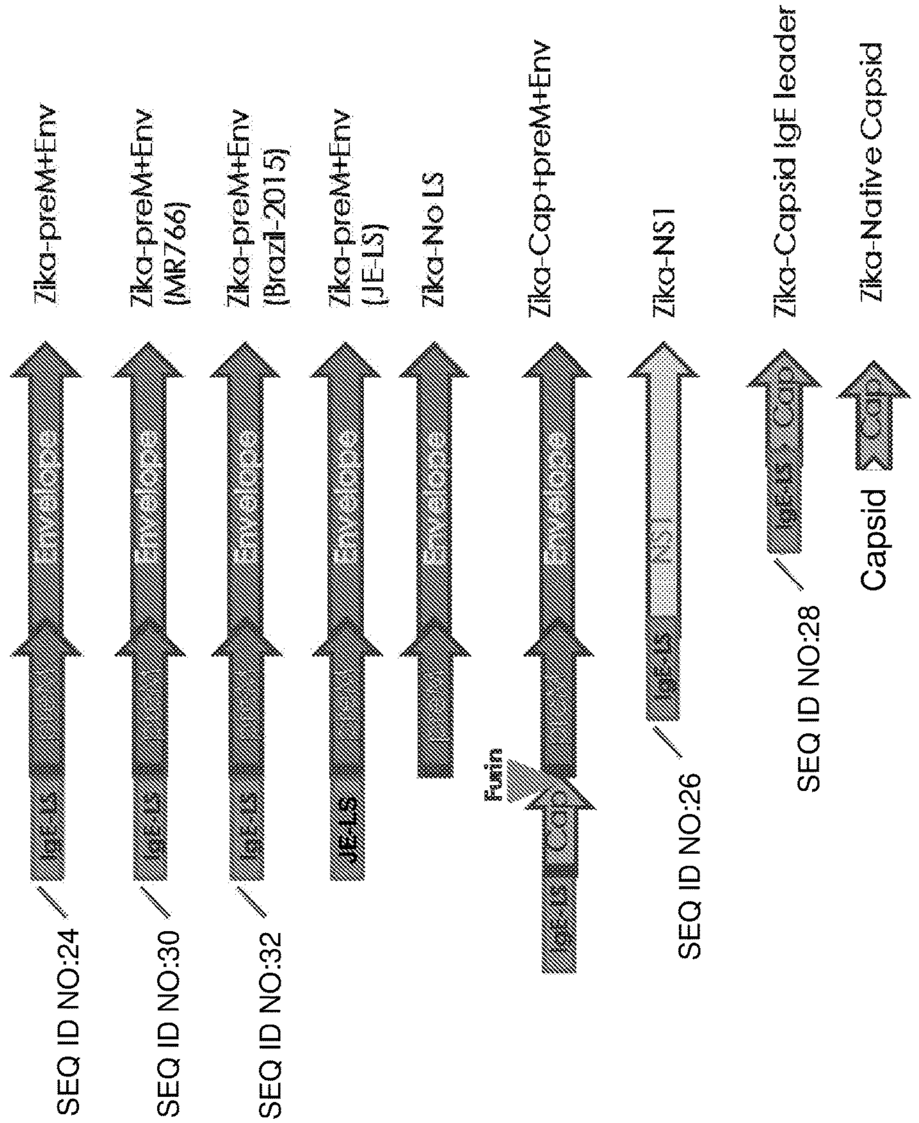
FIG. 14 displays drawings that show the linear structure of various zika antigen designs.

As shown in FIG. 13, a zika antigen expression construct was generated with the backbone shown therein. An expression cassette was inserted behind a CMV promoter and with a trailing polyadenylation tail. The cassette can include encoding sequences for the antigens shown in FIG. 14, including prME, NS1, and capsid.

Phylogenetic Analysis and Vaccine Design of Zika prME

Figure 16:
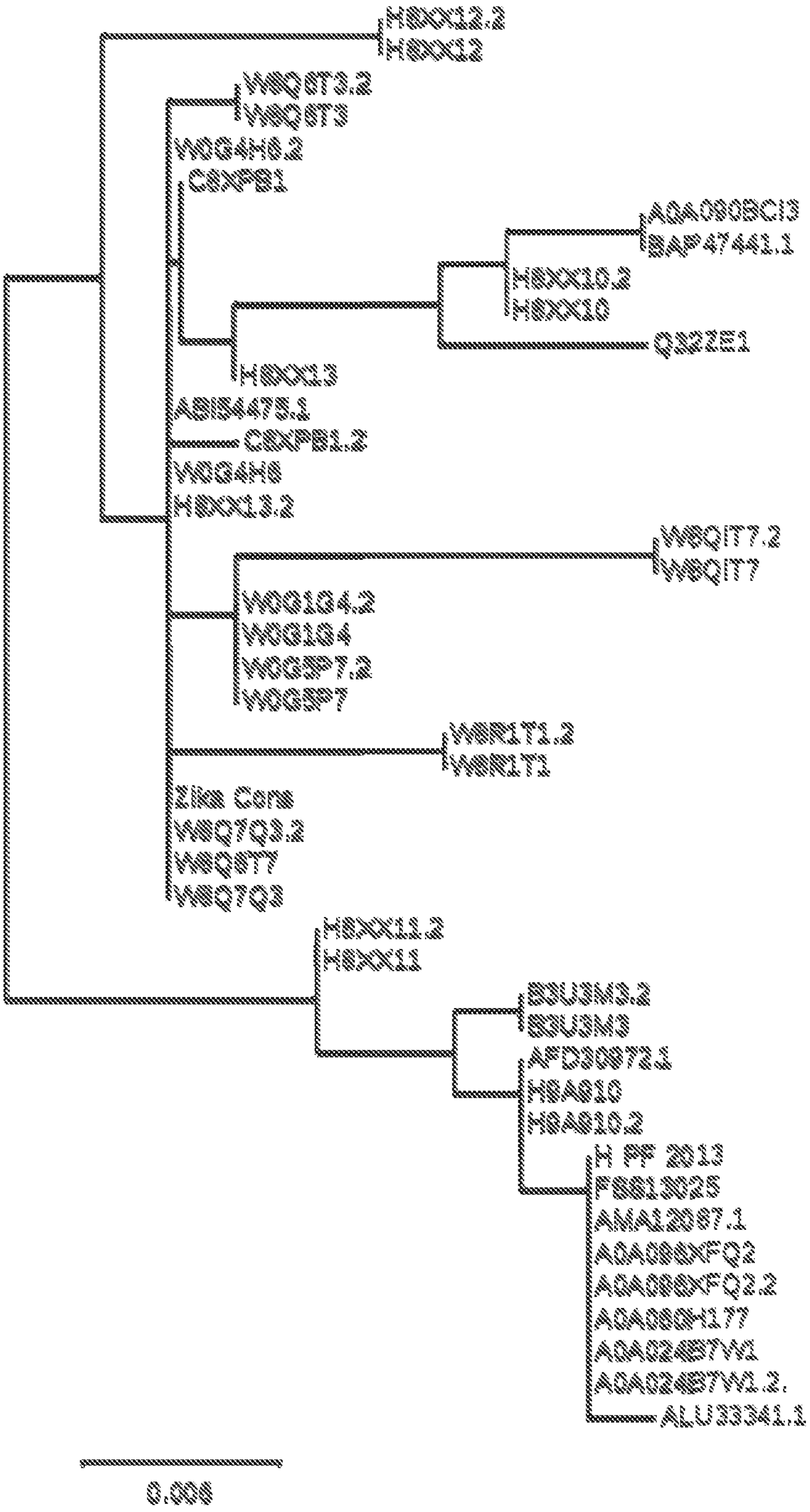
FIGS. 16 and 17 display the genetic relationship between various zika virus strains.
Figure 17:
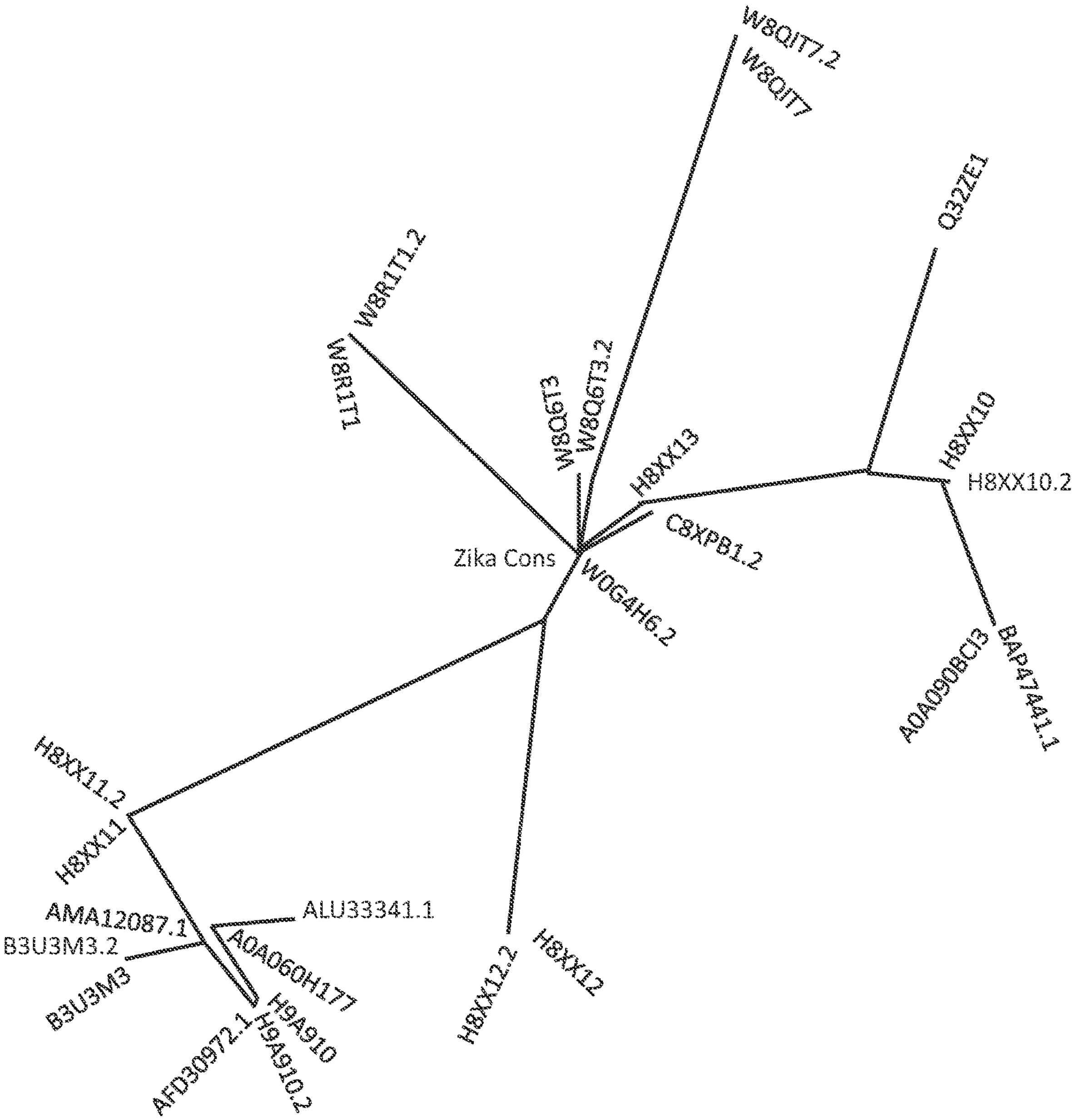
Figure 18:
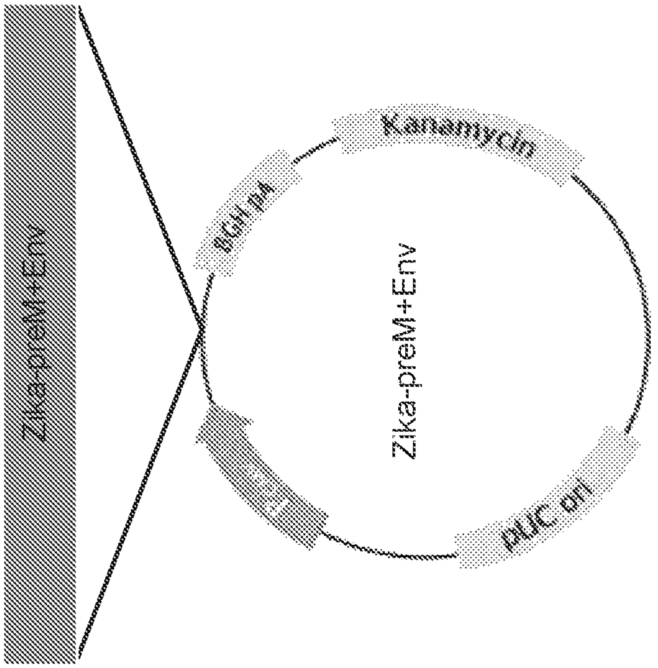
FIG. 18 displays a plasmid map for a zika vaccine, showing the site of the location for the insert (expression cassette) that encodes zika-prM+Env.
Figure 19:
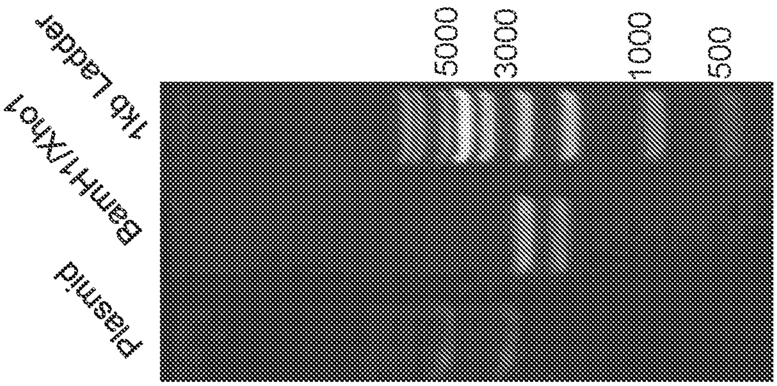
FIG. 19 displays a gel electrophoresis image that shows the presence of expression cassette.

A phylogenetic analysis was made as shown in FIGS. 16 and 17. The star shows the location of the consensus prME sequence SEQ ID NO:3. This consensus prME is shown inserted into the cloning site in the expression vector according to that in FIG. 18.

Figures 20A, 20B:
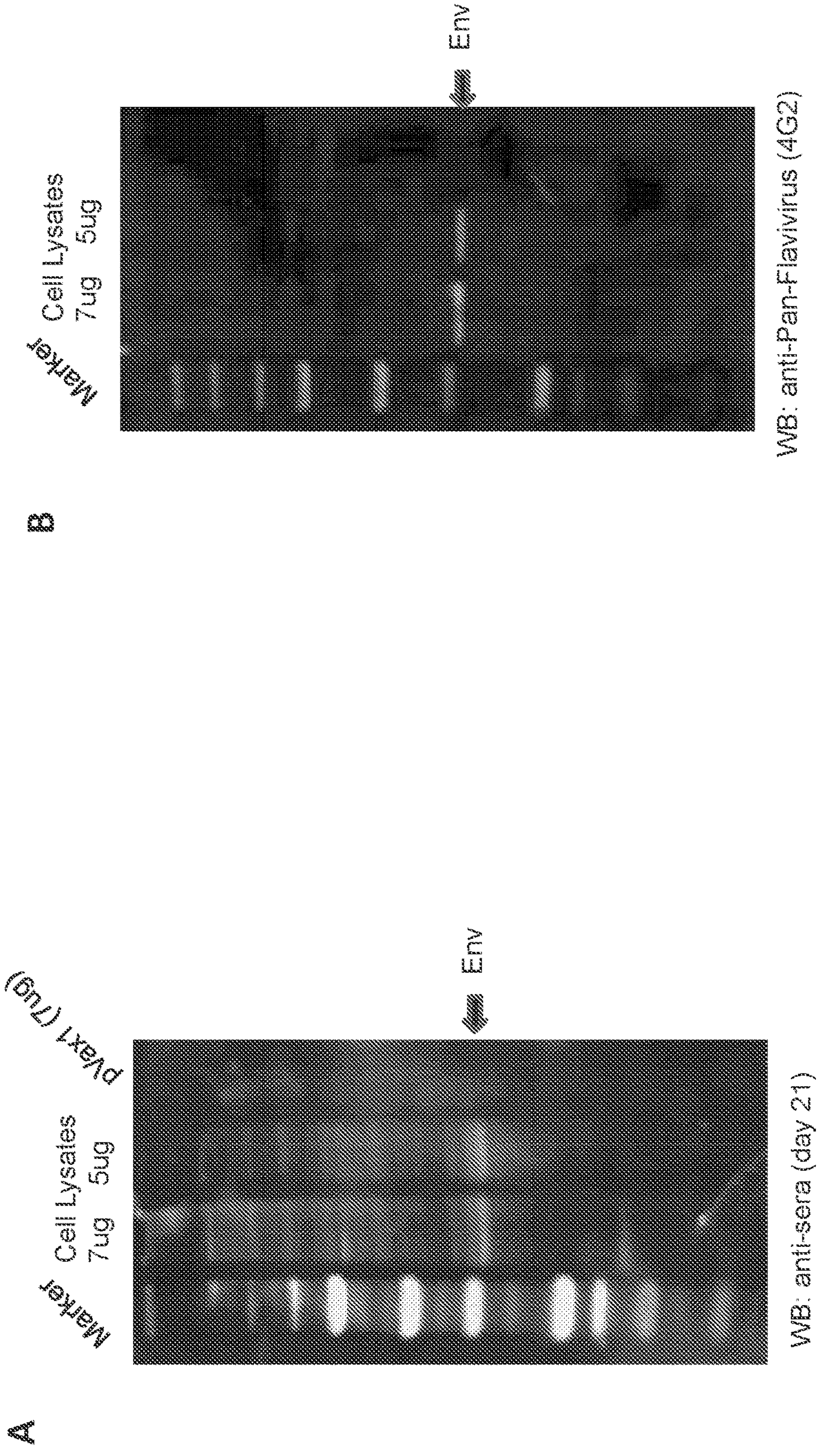
FIGS. 20A and 20B displays western blot gels that show zika-envelope protein.

The expressed protein was characterized by Western blot analysis as shown in FIGS. 20A and 20B, which shows specific binding to anti-flavivirus antibodies.

Figures 21A, 21B:
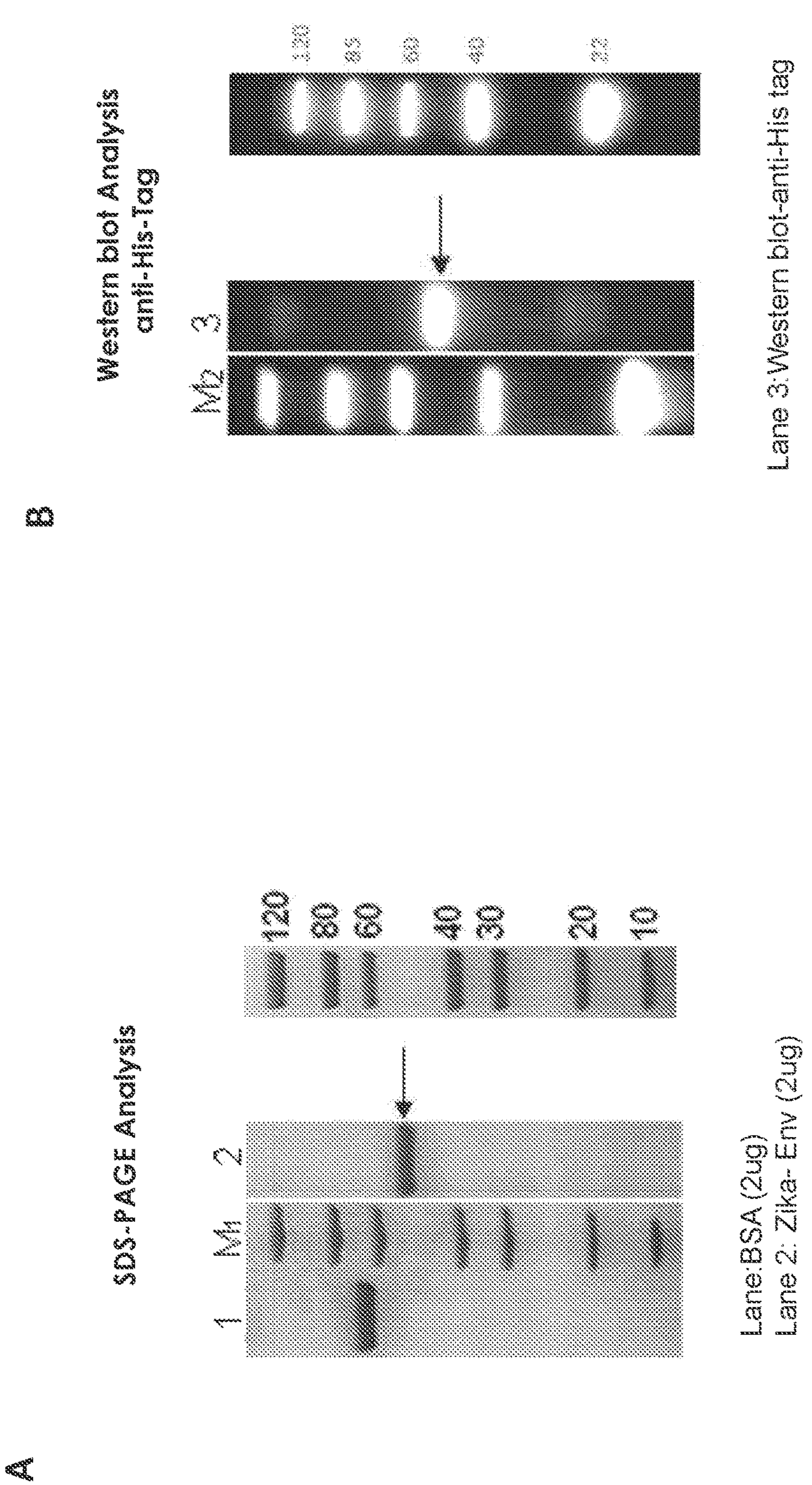
FIG. 21A displays an SDS-PAGE gel that shows purification of zika-envelope protein.
FIG. 21B displays a western blot gel that shows purification of zika-envelope protein.

The protein was then purified, as shown in FIGS. 21A and 21B.

Mouse Immunization

Animals—Balb/C mice (group of 8)

Plasmids—Zika-prME (encoding sequence including SEQ ID NO:2)

Devices—3P electroporation device (Inovio Pharmaceuticals, Plymouth Meeting, Pa.)

Immunization Schedule:

Mice were immunized a total of 3 times with DNA: once (prime) at day 0, and boost at days 14, & 28. Immune analysis was performed one week post DNA 3rd immunization.

Injection method—intramuscular

Bleeding Schedule—Pre-bleed and at day 14, 28 & 35

Bleed Method—retro orbital

Groups &Animals—10 animals/group×3 Groups=30

1) pVax1

2) pVax-1 Zika preME (SEQ ID NO:2)

Cellular Immune Responses Elicited by Zika prME Vaccine

Figure 22:
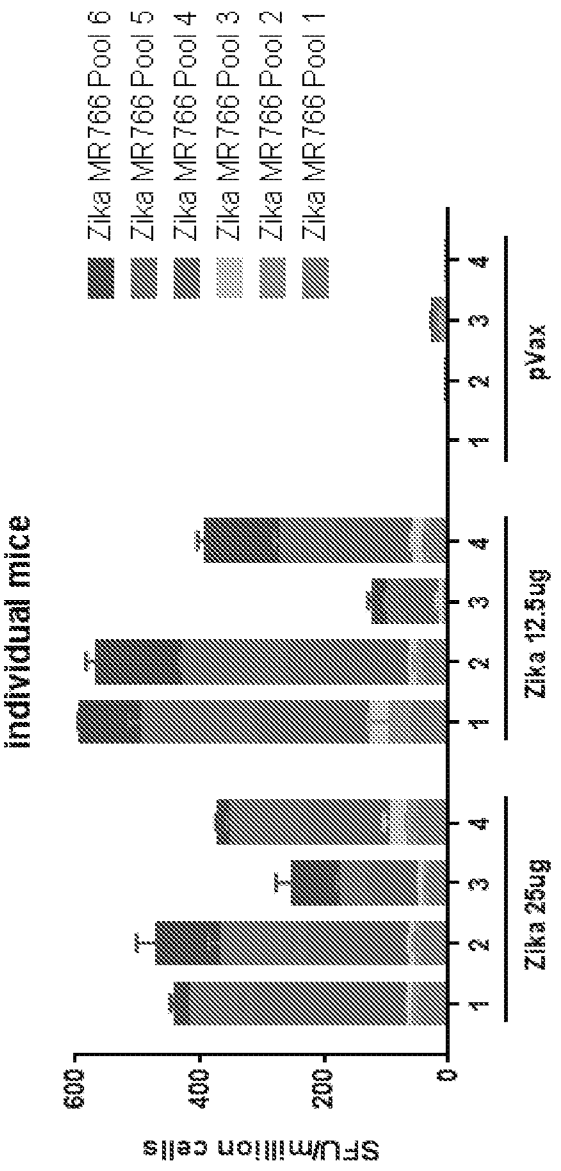
FIGS. 22 and 23 display bar graphs showing spike-specific CD8 T-lymphocyte responses assessed by IFN-gamma ELISpot assay against peptide pools covering preM+envelope antigen.
Figure 23:
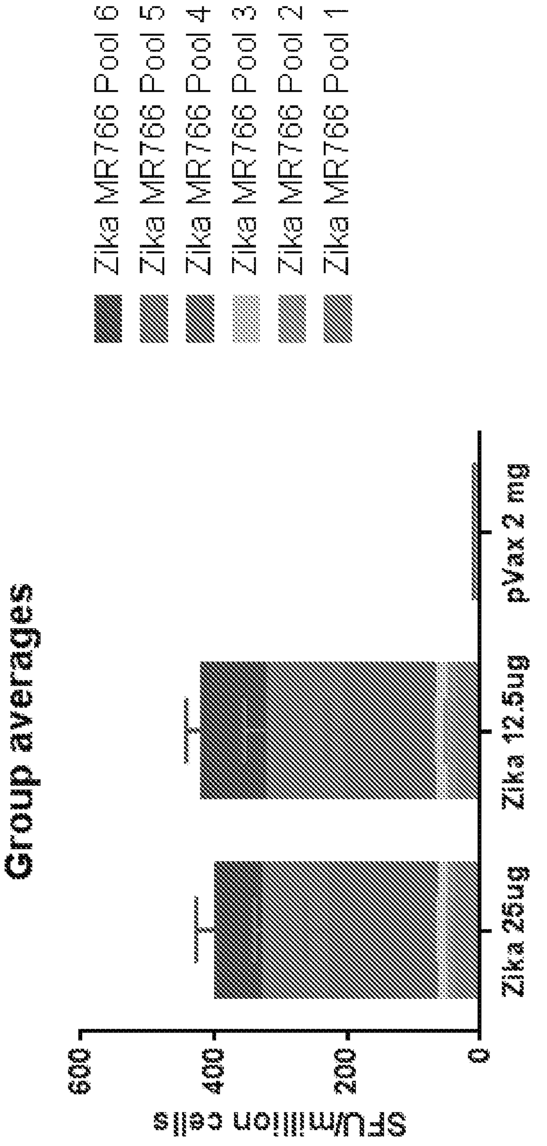

Spike-specific CD8 T-lymphocyte responses were assessed by IFN-g ELISpot assay against peptide pools covering prME antigen. See FIGS. 22 and 23. Mean responses in each group are one week after the third immunization. Error bars indicate standard errors. Responses to pVax control are shown.

Induction of Antibodies in Mice

Figures 24A, 24B:
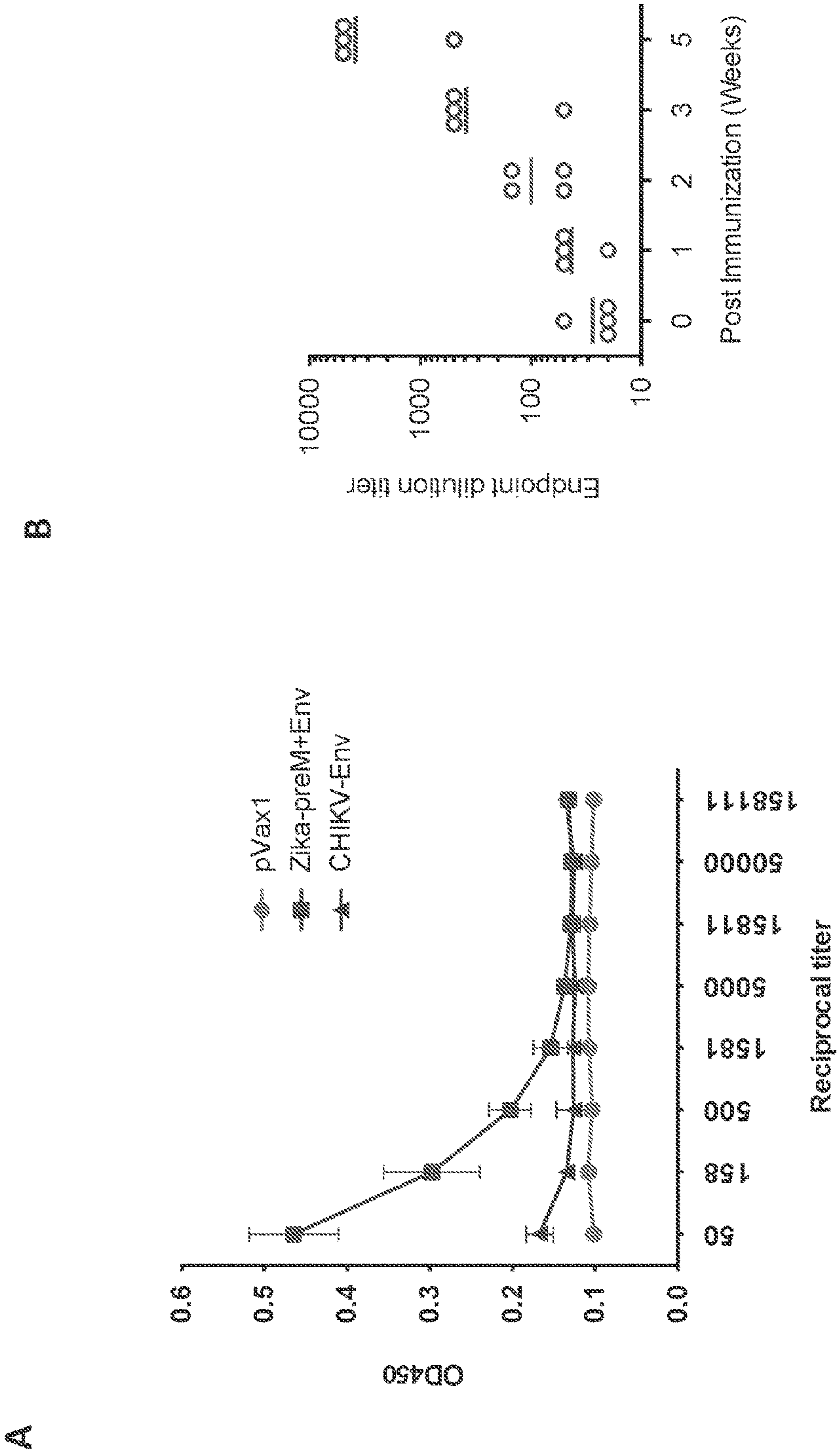
FIGS. 24A and 24B display a graph that represents binding ELISA of samples, showing zika prM+Env vaccination of mice elicits a positive antibody response which reacts with zika-envelope antigen.
Figures 25A, 25B:
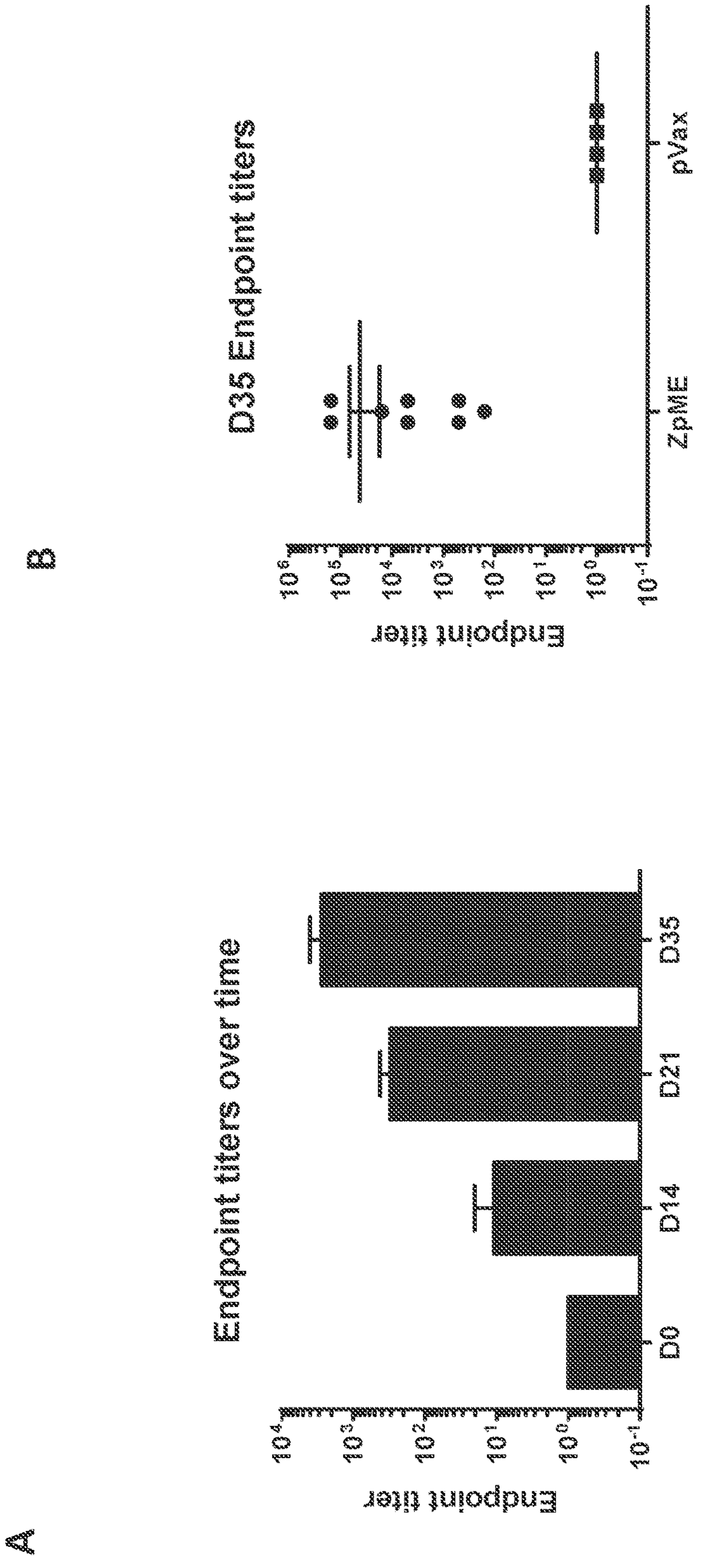
FIGS. 25A and 25B displays graphs that show that ZC-prME immunogen elicits a considerable antibody response which reacts specifically with Zika-Envelope antigen. The cross reactivity of the ZpME sera against Dengue 1, 2, 3, and 4 antigen Envs were negative, while against Zika Env showed strong binding.
Figures 26A, 26B, 26C, 26D, 26E:
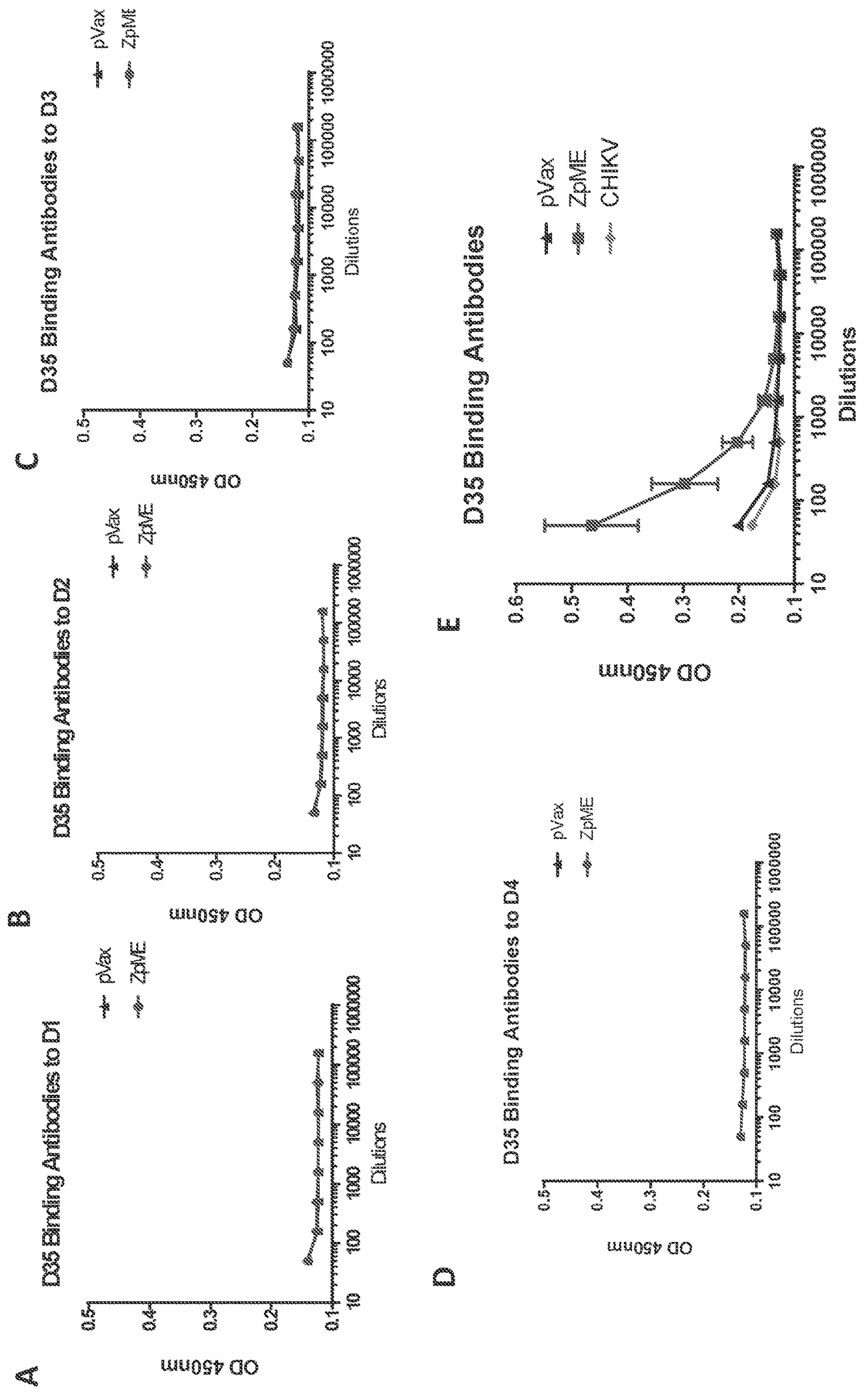
FIGS. 26A through 26E display an analysis indicating that ZC-prME vaccine generated sera does not cross-react with Dengue 1-4 recombinant Env's. Analysis supports that anti-CHIKV vaccine induced sera does not bind to Zika Env, also.

Zika prME vaccination of mice elicited a positive antibody response which reacts with Zika-Envelope antigen. See FIGS. 24 and 25.

Zika prME vaccine were found to be immunogenic in mice based on binding to recombinant protein E antigen. Seroconversion was observed in immunized animals by Western blot analysis and ELISA.

Example 3

Described herein is a novel synthetic DNA consensus-based vaccine targeting the pre-membrane+envelope proteins of Zika virus. Following construct expression confirmation, mice and non-human primates were immunized, through electroporation, showing the induction of both cellular and humoral immunity with neutralization activity in vaccinated animals. In IFN-α/β $R^{-/-}$ mice, either a single or two-injection immunization was 100% protective against weight loss or death in this lethal challenge model. This represents the first Zika viral vaccine approved for human trials.

The materials and methods are now described.

Cells, Virus, and Animals

Human embryonic kidney (HEK) 293T (American Type Culture Collection (ATCC) #CRL-N268, Manassas, Va.) and Vero CCL-81 (ATCC #CCL-81) cells were maintained in Dulbecco's modified Eagle's medium (DMEM; Gibco-Invitrogen) supplemented with 10% Fetal Bovine Serum (FBS) and 1% Penicillin and Streptomycin and passaged upon confluence. Neuronal tumor cell lines SK-N-SH (ATCC HTB-11) and U87MG (ATCC HTB-14) were maintained in Eagle Minimum Essential Medium (MEM; Corning-cellgro) supplemented with 10% Fetal Bovine Serum (FBS) and 1% Penicillin and Streptomycin and passaged upon confluence. Both Zika virus strains MR766 (a kind gift from Dr. Susan Weiss) and PR209 (Bioqual, MD) were amplified in Vero cells and stocks were titered by standard plaque assay on Vero cells.

C57/BL6 and $IFNAR^{-/-}$ mice and rhesus macaques procedures were carried out under ketamine anesthesia. The animals were housed in adjoining individual primate cages allowing social interactions, under controlled conditions of humidity, temperature, and light (12-hour light/12-hour dark cycles). Food and water were available ad libitum. The animals were monitored twice daily and fed commercial monkey chow, treats, and fruits twice daily.

DNA Vaccine construct and synthesis

The Zika-prM+Env plasmid DNA construct encodes full-length precursor of membrane (prM) and Envelope (E) proteins. A consensus strategy was used and the consensus sequences were determined by the alignment of current Zika prM+E protein sequences. The vaccine insert was genetically optimized (i.e. codon and RNA optimization) for enhanced expression in humans and an IgE leader sequence was added to facilitate expression. The construct was synthesized commercially (Genscript, NJ), and then sub cloned into a modified pVax1 expression vector under the control of the cytomegalovirus immediate-early promoter as described before (Muthumani et al., 2015, Sci Trans Med 7:301ra132). The final construct is named ZIKV-prME vaccine and the control plasmid backbone is pVax1. In addition, a number of other matched DNA constructs encoding the prM and Env genes from MR766 and a 2016 Brazilin outbreak strain were also designed, for further evaluation. Large-scale amplifications of DNA constructs were carried out by Inovio, (Plymouth Meeting, Pa.) and purified plasmid DNA was formulated in water for immunizations. The size of the DNA inserts was confirmed via agarose gel electrophoresis. Phylogenetic analysis was performed by multiple-alignment with ClustalW using MEGA version 5 software (Muthumani et al., 2015, Sci Trans Med 7:301ra132).

DNA Immunizations and Electroporation

Mouse immunogenicity studies: Female C57BL/6 mice (6 to 8 weeks old) and $IFNAR^{-/-}$ mice (5 to 7 weeks old) were immunized (n=4) with 25m of DNA in a total volume of 20 or 30 μl of water delivered into the tibialis anterior muscle with in vivo EP delivery. In vivo EP was delivered, with the CELLECTRA adaptive constant current EP device (Inovio Pharmaceuticals, PA), at the same site immediately following immunization. A three-pronged CELLECTRA minimally invasive device was inserted ~2 mm into the muscle. Square-wave pulses were delivered through a triangular 3-electrode array consisting of 26-gauge solid stainless steel electrodes and two constant current pulses of 0.1 Amps were delivered for 52 microsecond/pulse separated by a 1 second delay. Further protocols for the use of EP have been previously described in detail 17. Mice were immunized three times at two-week intervals and sacrificed 1 week after final immunization. Blood was collected after each immunization for analysis of cellular and humoral immune responses (Muthumani et al., 2015, Sci Trans Med 7:301ra132). Rhesus macaque immunogenicity studies: 5 rhesus macaques were immunized ID at 2 sites twice 4 weeks apart with 2 mg ZIKV-prME vaccine. EP was delivered immediately using the same device described for mouse immunizations.

Challenge Studies in IFNAR$^{-/-}$ Mice

IFNAR$^{-/-}$ mice were split into three groups. The first group of mice were immunized once and challenged with 106 PFU ZIKV PR209 2 weeks after immunization. The second group of mice were immunized twice at two week intervals and challenged with 106 PFU ZIKV PR209 1 week after the second immunization. The third group of mice were immunized twice at two week intervals and challenged with 2×106 PFU ZIKV PR209 1 week after the second immunization. Post challenge, animals were weighed and body temperature measured daily by a subcutaneously located temperature chip. In addition, they were observed for clinical signs of disease twice daily (decreased mobility; hunched posture; hind limb knuckle walking (partial paralysis), paralysis of one hind limb or both hind limbs). Criteria for euthanasia on welfare grounds consisted of 20% weight loss or observation of any abnormal clinical signs.

Western Blot and Immunofluorescence Assays

For in vitro expression studies, transfections were performed using the GeneJammer reagent, following the manufacturer's protocols (Agilent). Briefly, cells were grown to 50% confluence in a 35-mm dish and transfected with 1 ug of Zika prME vaccine. The cells were harvested 2 days after transfection, washed twice with phosphate-buffered. saline (PBS), and lysed with cell lysis buffer (Cell Signaling Technology). Western Blot was used to verify the expression of the Zika preM+Env protein from the harvested cell lysate, as described previously (Muthumani et al., 2015, Sci Trans Med 7:301ra132).

The specificity of the mouse and RM immune serum was confirmed using Western Blot analysis. 3-12% Bis-Tris NuPAGE gels (Life Technologies) were loaded with 5 μg or 1ug of ZIKV Env recombinant protein and the Odyssey protein Molecular Weight Marker (Product #928-40000). Gels were run at 200 V for 50 minutes in MOPS buffer. The proteins were transferred onto nitrocellulose membranes using the iBlot 2 Gel Transfer Device (Life Technologies). The membranes were blocked in PBS Odyssey blocking buffer (LI-COR Biosciences) for 1 hour at room temperature. The anti-Flavivirus group antigen (MAB10216-Clone D1-4G2-4-15) antibody was diluted 1:500 to detect vaccine expression and the immune serum from mice and RM was diluted 1:50 in Odyssey blocking buffer with 0.2% Tween 20 (Bio-Rad) and incubated with the membranes overnight at 4° C. The membranes were washed with PBST and then incubated with the appropriate secondary antibody [Goat anti-mouse IRDye680CW (LICOR) for mouse serum and flavivirus antibody; and Goat anti-human IRDye800CW (LICOR) for RM Sera] at 1:15,000 dilution for mouse sera for 1 hour at room temperature. After washing, the membranes were imaged on the Odyssey infrared imager (LI-COR).

For the immunofluorescence assay, HeLa or Vero cells were grown on coverslips and transfected with 5 μg of Zika preM+Env vaccine. Two days after transfection, the cells were fixed with 4% PFA for 15 min. Non-specific binding was then blocked with Normal Goat Serum diluted in PBS at room temperature for 1 hour. The slides were then washed in PBS for 5 min and subsequently incubated with sera from immunized mice or RM at a 1:100 dilution overnight at 4° C. Slides were washed as described above and incubated with appropriate secondary antibody [Goat anti-mouse IgG-AF488 (Sigma) for mouse serum and Goat anti-human IgG-AF488 for RM serum] at 1:200 dilution at room temperature for 1 hour. After washing, Flouroshield Mounting media with DAPI (Abcam) was added to stain the nuclei of all cells. After which, coverslips were mounted and the slides were observed under a microscope (EVOS Cell Imaging Systems; Life Technologies) (Muthumani et al., 2015, Sci Trans Med 7:301ra132). Additionally, Vero, SK-N-SH, or U87-MB cells were grown on four chamber tissue culture treated glass slides (Falcon cat#354114) and infected with MR766 ZV at an MOI of 0.01 for 4-6 days and then stained as described.

Splenocyte and PBMC Isolation

Single-cell suspensions of splenocytes were prepared from all mice. Briefly, spleens from mice were collected individually in 5 ml of RPMI 1640 supplemented with 10% FBS (R10), then processed with a Stomacher 80 paddle blender (A.J. Seward and Co. Ltd.) for 30 s on high speed. Processed spleen samples were filtered through 45-mm nylon filters and then centrifuged at 1500 rpm for 10 min at 4° C. Cell pellets were resuspended in 5 ml of ACK (ammonium-chloride-potassium) lysis buffer (Life Technologies) for 5 min at room temperature, and PBS was then added to stop the reaction. Samples were again centrifuged at 1500 rpm for 10 min at 4° C. Cell pellets were resuspended in R10 at a concentration of 1×107 cells/ml and then passed through a 45-mm nylon filter before use in ELISpot assay and flow cytometric analysis (Muthumani et al., 2015, Sci Trans Med 7:301ra132). For RM, blood (20 ml at each time point) was collected in EDTA tubes, and peripheral blood mononuclear cells (PBMCs) were isolated using a standard Ficoll-Hypaque procedure with Accuspin tubes (Sigma-Aldrich, St. Louis, Mo.).

ELISpot Assay

Briefly, 96-well ELISpot plates (Millipore) were coated with anti-mouse IFN-γ capture Ab (R&D Systems) and incubated overnight at 4° C. The following day, plates were washed with PBS and blocked for 2 h with PBST+1% BSA. Two hundred thousand splenocytes from the pZV-prM+Env-immunized mice were added to each well and incubated overnight at 37° C. in 5% CO2 in the presence of media alone (negative control), media with PMA/Ionomycin (positive control), or media with peptide pools (1 μg/ml) consisting of 15-mers overlapping by 9 amino acids and spanning the length of the Zika envelope protein (Genscript). After 24 h, the cells were washed and then incubated overnight at 4° C. with biotinylated anti-mouse IFN-γ Ab (R&D Systems). Streptavidin-alkaline phosphatase (R&D Systems) was added to each well after washing and then incubated for 2 h at room temperature. The plate was washed, and then 5-bromo-4-chloro-3'-indolylphosphate p-toluidine salt and nitro blue tetrazolium chloride (chromogen color reagent; R&D Systems) was added. Lastly, the plates were rinsed with distilled water, dried at room temperature, and spot forming units were quantified by an automated ELISpot reader (CTL Limited), and the raw values were normalized to SFU per million splenocytes. For RM samples, the ELISPOTPRO for monkey IFN-γ kit (MABTECH) was used as described by the manufacturer, two hundred thousand PBMC's were stimulated with peptide pools, and plates were washed and spots were developed and counted as described before (Muthumani et al., 2015, Sci Trans Med 7:301ra132; Mallilankaraman et al., 12011, PLoS Negl Trop Dis 5:e928).

Humoral Immune Response: Antibody-Binding ELISA

An enzyme-linked immunosorbent assay (ELISA) was used to determine the titers of mouse and RM sera as previously described (Muthumani et al., 2015, Sci Trans Med 7:301ra132). Briefly, 1 μg/ml of purified Zika Envelope protein was used to coat 96-well microtiter plates (Nalgene Nunc International, Naperville, Ill.) at 4° C. overnight. After blocking with 10% FBS in PBS for at least an hour, plates were washed 4 times with 0.05% PBST (Tween20 in PBS). Serum samples from immunized mice and RMs were serially diluted in 1% FBS, 0.2% PBST, added to the plates, then incubated for 1h at room temperature. Plates were again washed 4 times in 0.05% PBST then incubated with HRP-conjugated anti-mouse IgG (Sigma) at 1:35000 dilution for mouse sera for 1h at room temperature. For RM sera, anti-monkey IgG HRP (Southern Biotech) was used at 1:5000 dilutions for 1h at room temperature. Bound enzyme was detected by adding SIGMAFAST™ OPD (o-Phenylenediamine dihydrochloride) tablets according to the manufacturer's instructions (Sigma Aldrich). The reaction was stopped after 15 minutes with the addition of 1N H2SO4. Plates were then read at an optical density of 450 nm. All mouse serum and RM serum samples were assayed in duplicate. Endpoint titers were determined using the method described by Frey et al (Frey et al., 1998, J Immunol Methods 221:35-41).

Neutralization ($PRNT_{50}$) Assay

The plaque-reduction neutralization test (PRNT) involving MR766 and Vero cells was described previously (Sun et al., 2006, J Infect Dis 193:1658-65). Briefly, the mouse or RM sera was serially diluted in serum free DMEM (1:10 to 1:1280) and incubated with an equal volume of MR766 Zika virus (100 pfu) at 37° C. for two hours. Mixtures were added to confluent layers of Vero cells and left at 37° C. for adsorption for two hours. An 2×DMEM media:soft-agar (1:1) overlay was added over cells and plate was incubated 5 days at 37° C. Agar overlay was removed from wells and cells were fixed with 4% paraformaldehyde, washed with 1×PBS, stained with crystal violet solution, washed with 1×PBS, and plates left to dry. Plaques in assays done in 24 well plates were counted manually. Plaques in assays done in 96 well plates were scanned with an automated Immunospot reader (CTL Limited), and plaques in sample wells as well as plaques in negative control (DMEM only) and positive control (100 pfu MR766 Zika virus only) were counted using the automated software provided with the ELISpot Reader. Percent plaque reduction was calculated as follows: % reduction=100×[1-(average number of plaques for each dilution/average number of plaques in positive control wells)]. GraphPad Prism software was used to perform non-linear regression analysis of % plaque reduction vs. a log transformation of each individual serum dilution to facilitate linear interpolation of actual 50% PRNT titers at peak post vaccination response. The medians and interquartile ranges at 50% neutralization were calculated for each neutralization target overall and by vaccine treatment group; the geometric mean titers were also calculated. Titers represent the reciprocal of the highest dilution resulting in a 50% reduction in the number of plaques.

Flow Cytometry and Intracellular Cytokine Staining (ICS) Assay

Splenocytes were added to a 96-well plate (2×106/well) and were stimulated with ZikapreM and Envelope pooled peptides for 5 hours at 37° C./5% $CO_2$ in the presence of Protein Transport Inhibitor Cocktail (Brefeldin A and Monensin) (eBioscience). The Cell Stimulation Cocktail (plus protein transport inhibitors) (phorbol 12-myristate 13-acetate (PMA), ionomycin, brefeldin A and monensin) (eBioscience) was used as a positive control and R10 media as negative control. All cells were then stained for surface and intracellular proteins as described by the manufacturer's instructions (BD, San Diego, Calif.). Briefly, the cells were washed in FACS buffer (PBS containing 0.1% sodium azide and 1% FCS) before surface staining with flourochrome-conjugated antibodies. Cells were washed with FACS buffer, fixed and permeabilized using the BD Cytofix/Ctyoperm™ (BD, San Diego, Calif., USA) according to the manufacturer's protocol followed by intracellular staining. The following antibodies were used for surface staining: LIVE/DEAD Fixable Violet Dead Cell stain kit (Invitrogen), CD19 (V450; clone 1D3; BD Biosciences) CD4 (FITC; clone RM4-5; ebioscience), CD8 (APC-Cy7; clone 53-6.7; BD Biosciences); CD44 (BV711; clone IM7; Biolegend). For intracellular staining the following antibodies were used: IFN-γ (APC; clone XMG1.2; Biolegend), TNF-α (PE; clone MP6-XT22; ebioscience), CD3 (PerCP/Cy5.5; clone 145-2C11; Biolegend); IL-2 (PeCy7; clone JES6-5F14; ebioscience). All data was collected using a LSRII flow cytometer (BD Biosciences) and analyzed using FlowJo software (Tree Star, Ashland, Oreg.).

Statistical Analysis

Graphpad, Prism 4 (Graphpad software, Inc. San Diego, Calif.) was utilized for statistical analysis. Log 10 transformations were applied to end point binding ELISA titers and whole virus PRNT50 titers The results of these experiments are now described.

Construction of the ZIKV-prME Consensus DNA Vaccine

Figures 27A, 27B, 27C, 27D, 27E:
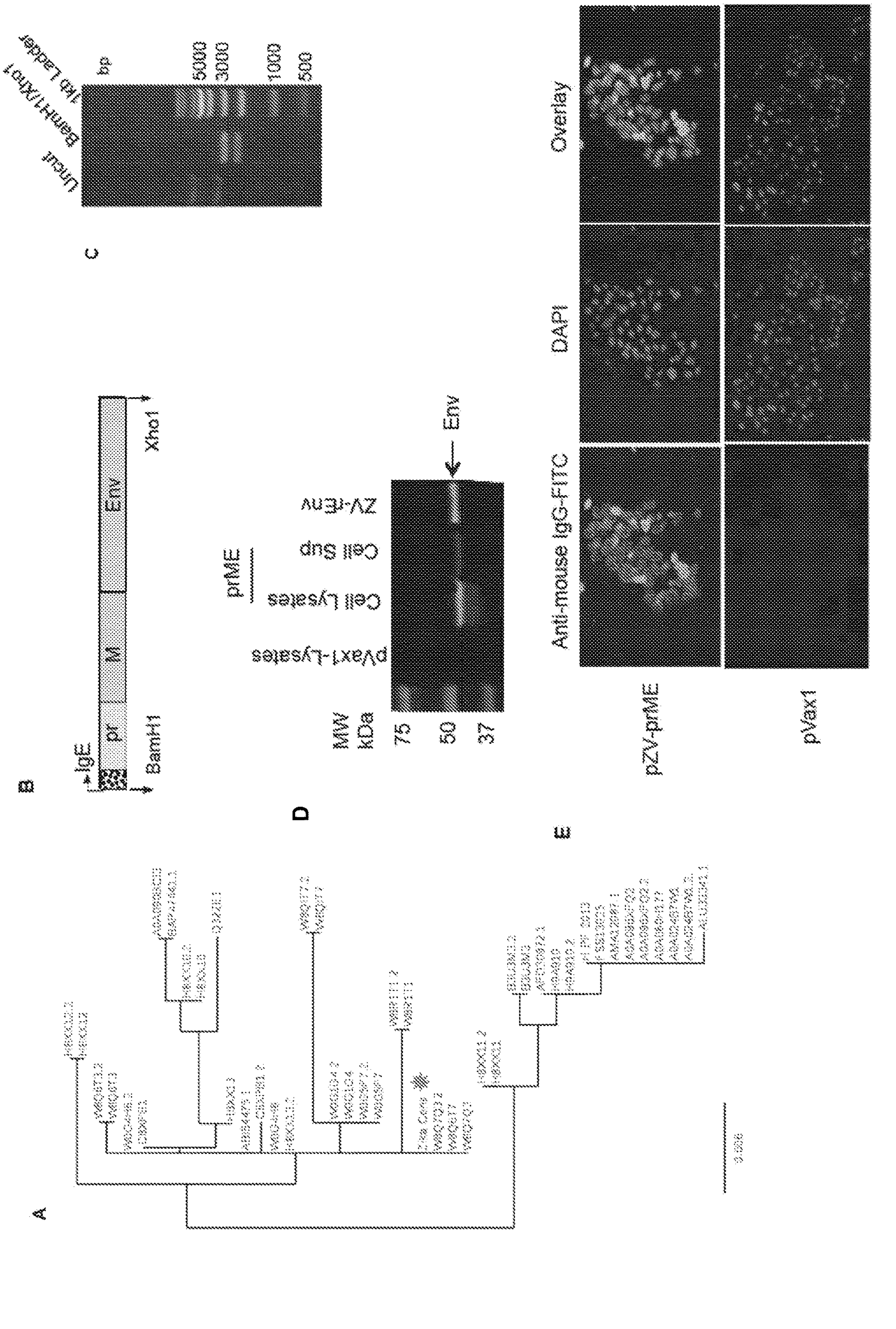
FIGS. 27A through FIG. 27E display the identification, cloning, and expression, of the the ZIKA-prME consensus sequence.

A consensus sequence of Zika prM (precursor membrane) and E (envelope) genes (ZIKV-prME) was generated using prM and E sequences from various ZIKA isolated between 1952 and 2015 that caused infection in humans (FIG. 27A). The ZIKA-prME consensus sequence was cloned into the pVax1 vector after additional modifications and optimizations were made to improve its in vivo expression including the addition of a highly efficient immunoglobulin E (IgE) leader peptide sequence (FIG. 27B). Endonuclease restriction digest and gene sequencing were used to validate the final vaccine plasmid (FIG. 27C). Expression of the ZIKA-prME protein off the plasmid was confirmed by performing Western analysis and indirect immunofluorescence assay from vaccine-transfected 293T cells at 48 hours post 84 transfection (FIGS. 27D and 27E).

Figure 28:
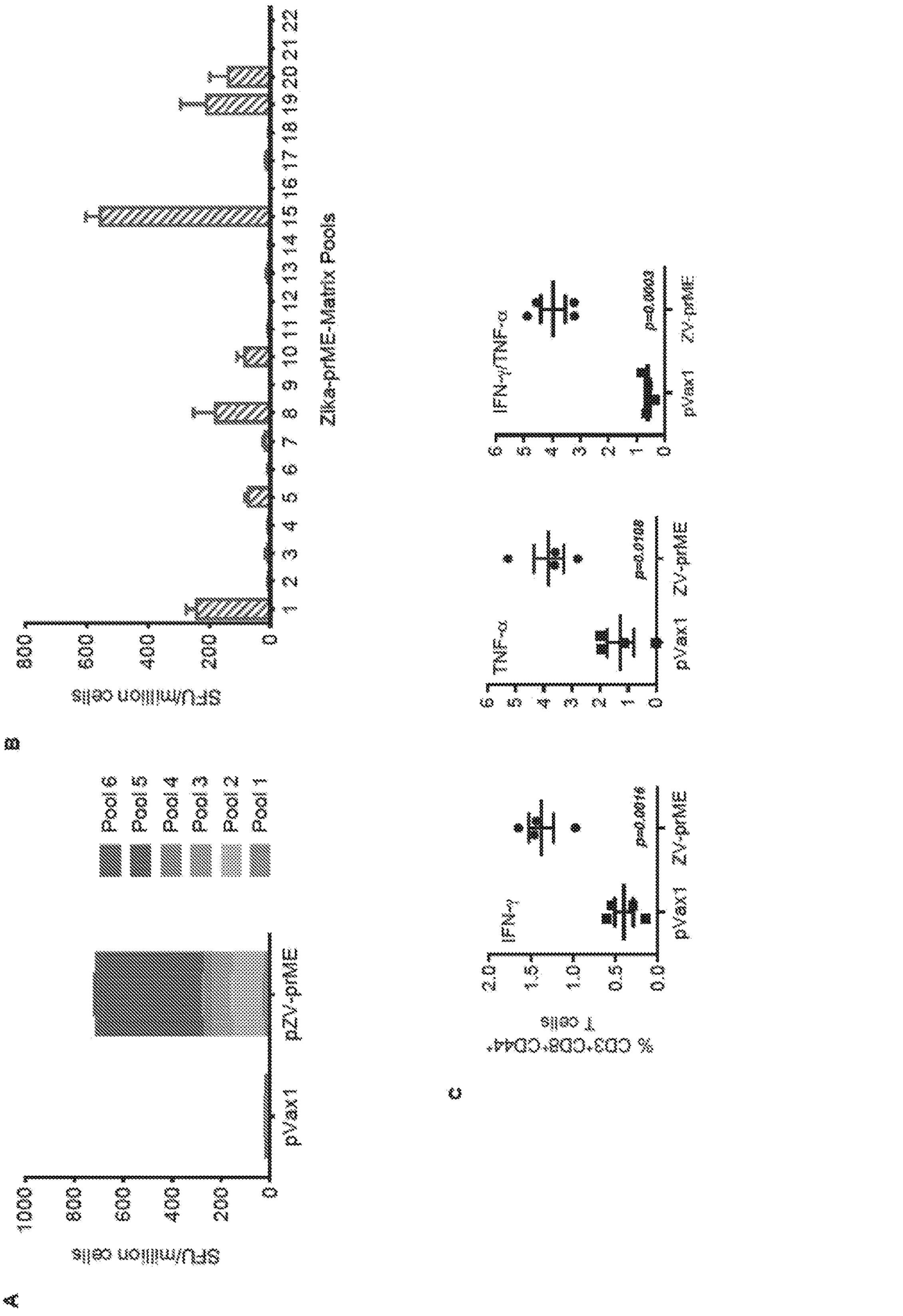
FIG. 28, comprising

Zika-pME DNA Vaccine Induces Antigen-Specific T Cell or Functional Humoral Responses in Mice The ability of the ZIKA-prME plasmid vaccine to induce cellular immune responses was evaluated. Groups of five C57/BL6 mice were immunized with either control plasmid backbone (pVax1) or the ZIKA-prME plasmid vaccine three times at 2-week intervals by intramuscular injection followed by electroporation (EP) at the 92 site of delivery as described (Muthumani et al., 2015, Sci Trans Med 7:301ra132). Animals were sacrificed one week after their third injection and bulk splenocytes harvested from each animal were evaluated in standard enzyme-linked immunospot assays for their ability to secrete interferon-γ after ex-vivo exposure to peptide pools encompassing ZIKA-Env. The assay results show that splenocytes from ZIKA-prME immunized mice produced clear cellular immune response after stimulation with multiple ZIKA-Env peptide pools (FIG. 28A). The region(s) of ZIKA-Env that elicited the strongest cellular response(s) were evaluated by mapping analysis ELISpot in a matrix format using 22 peptide pools consisting of 15-mers (overlapping by 11 amino acids) spanning the entire ZIKA-prME protein. As seen in FIG. 28B, several pools induced elevated T cell responses, but peptide pool 15 induced the highest SFU per 106 responses. The mapping data revealed one dominant prME epitopes 'IRCIGVSNRDFVEGM' for the sequences. The dominant peptides listed were confirmed to contain one H2-Db restricted epitope by using Immune Epitope Database analysis resource IDEP consensus tool, suggesting effective processing of this antigen.

Figure 29:
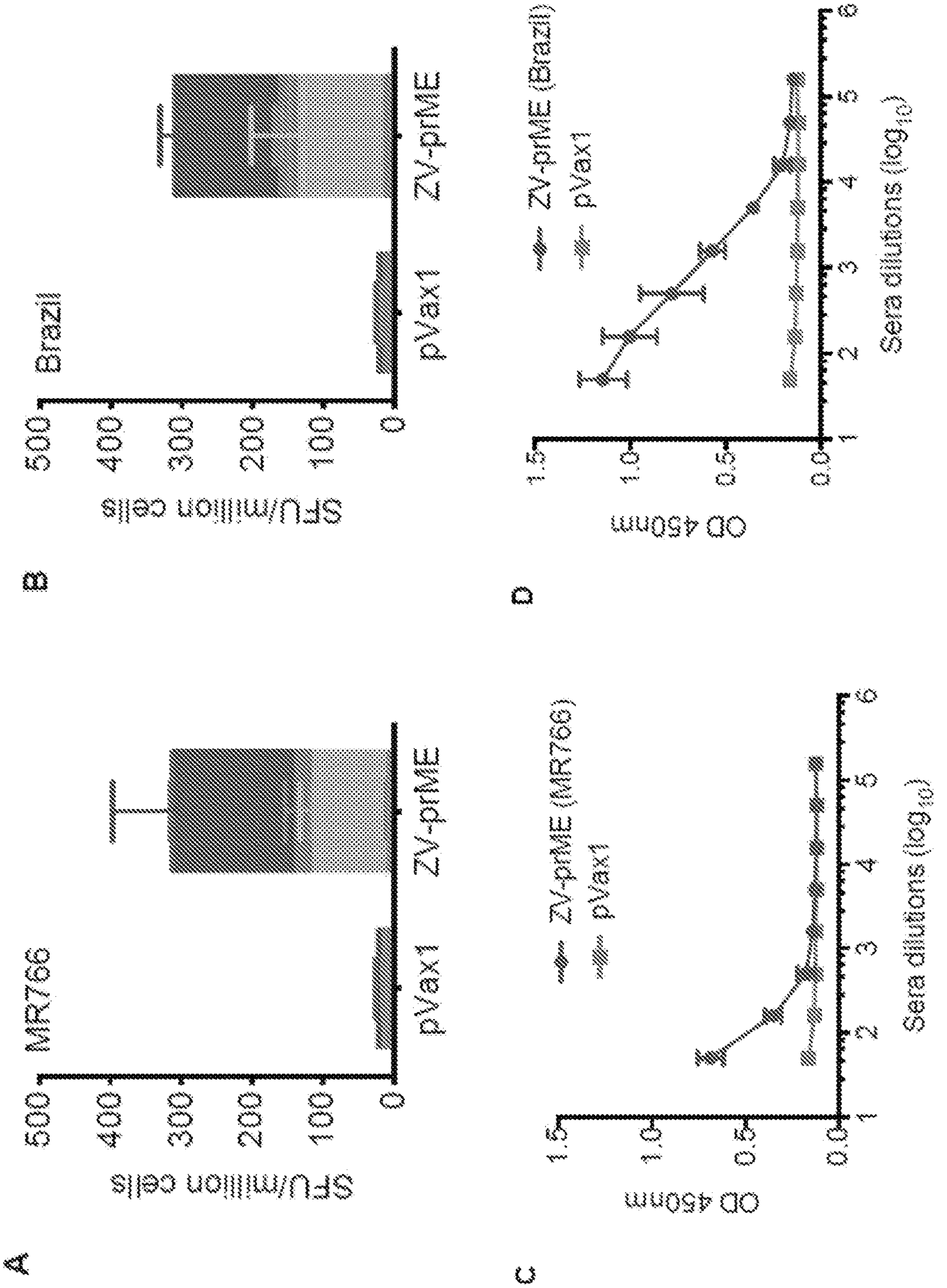
FIG. 29, comprising FIG. 29A through FIG. 29D depicts the profile of IFN-γ production by splenocytes and antibody levels in serum collected from pZIKV-prME (MR766) and pZIKV-prME (Brazil)-immunized mice. Six-week-old C57/BL6 mice were immunized as described in Materials and Methods. Serum and splenocytes were collected one week after the 3rd immunization and incubated with ZIKV-specific prME peptides, and the number of IFN-γ SFU per million cells was assayed by ELISPOT.

Further evaluation of the cellular immunogenicity of the ZIKA-prME vaccine entailed the determination of the polyfunctional properties of $CD8^+$ T cells collected one week after the final immunization. The results show that the ZIKA-prME vaccine increased the proportion of bifunctional vaccine-specific T cells expressing tumor necrosis factor-α (TNF-α) and IFN-γ (FIG. 28C). Importantly, ZIKA-prME vaccination exhibited a strong ability to expand T-cell functionality. Further vaccine studies were performed with plasmids 115 encoding the prME sequence of either a recently identified Brazilian ZIKA strain or of the original MR766 ZIKA strain for comparative studies. Induction of cellular immune responses in mice immunized with either plasmid was measured one week after the third injection by IFN-γ ELISpot after stimulating splenocytes with the same ZIKA-preME peptide pools as used in FIG. 28A. The result shows that the T cell responses and antibody responses induced by the novel consensus ZIKA-prME DNA vaccine construct were at least two fold higher than those generated by either of these two non-consensus plasmid vaccines (FIGS. 29A and 29B). Detailed mapping analysis of the cellular responses induced by either the Brazilian or MR766 prME vaccine revealed that both also induced their most significant cellular response to the dominant Env-specific CTL epitope identified in FIG. 28B for the consensus ZIKA-prME plasmid (data not shown). Overall the consensus immunogen appeared consistently more robust in these assays and was studied further.

Figure 30:
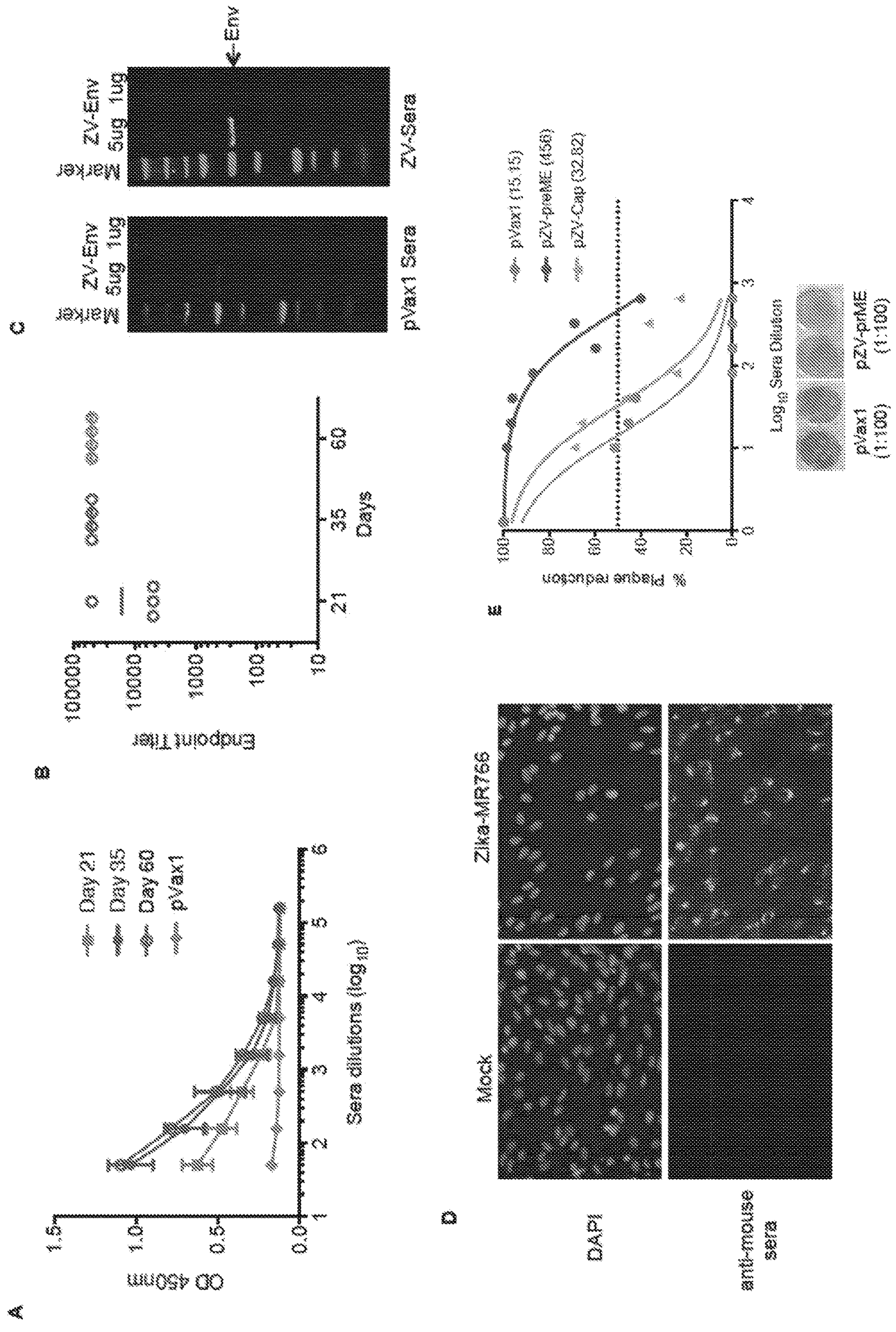
FIG. 30, comprising FIG. 30A through FIG. 30E depicts experimental results demonstrating anti-ZIKV antibody responses are induced by ZIKV-prME plasmid vaccination. C57BL/6 mice were immunized intramuscularly three times with 25 μg of ZIKV-prME plasmid or pVax1 at 2-week intervals. Binding to envelope antigen was analyzed with sera from animals at different time points post immunization at various dilutions. ELISA plates were coated with vaccine matched recombinant ZIKV-envelope protein.

The ability of the consensus ZIKA-prME vaccine to induce humoral immune responses in mice was evaluated. Groups of C57/BL6 mice were immunized three times at 2-week intervals with 25 μg of either empty control plasmid or consensus ZIKAprME vaccine plasmid by i.m. injection followed by EP. Serum was obtained from each injected mice at day 0 (prior to first immunization), day 14 (two weeks after the first immunization), day 21 (one week after the second immunization) and day 35 (one week after the third immunization). Each sera collected was tested by ELISA for ZIKA specific IgG responses using immobilized rZIKA-Env as the capture antigen. A significant increase in anti-ZIKA-specific IgG was observed on day 21 with a further boost in sera IgG levels seen in day 35 sera (FIG. 30A). Day 138 60 sera from vaccinated animals show that the high antibody responses seen in day 35 sera were maintained long-term following the final boost. Most importantly, sera from vaccinated mice contained very high levels of antibody as indicated by the endpoint titers (FIG. 30B). Additional assessment of the specificity of the vaccine-induced antibodies was performed by screening day 35 pooled-sera for its ability to detect rZIKA-E by Western analysis (FIG. 30C) and to stain Zika-infected cells by an immunofluorescent assay (FIG. 30D). Results from both of these analyses confirmed specificity.

Furthermore, ZIKA-specific binding antibody responses were also assessed in mice immunized with plasmids encoding the prME sequences from a Brazilian strain and the MR766 strain described above. Day 35 sera from sham- or vaccine-immunized mice were analyzed in ELISA for binding to rZIKA-E. This analysis indicates that both plasmids induced significant antibody binding (FIGS. 29C and 29D) and that immunization with the consensus ZIKA-prME DNA vaccine generates a good humoral response with increased affinity to heterologous ZIKA Envelopes.

A plaque reduction neutralization test (PRNT) assay was performed on day 35 pooled-sera from mice immunized three times with either empty pVax1, consensus ZIKA-prME plasmid vaccine, or a consensus ZIKA-capsid plasmid vaccine using a method adapted from a previously described technique for analyzing DV, WNV and other flaviviruses 15. As shown in FIG. 30E, anti-ZIKA reciprocal PRNT50 dilution titers after the third vaccination were significantly higher in mice that 160 received the ZIKA-prME vaccine than in those that received the ZIKA-Capsid DNA vaccine or the control DNA pVax1. Neutralizing antibodies induced by the ZIKA-prME vaccine used in this experiment had a PRNT50 titer=456. Representative photographs of viral plaques are shown in the bottom for 1:100 dilutions of sera.

Figure 31:
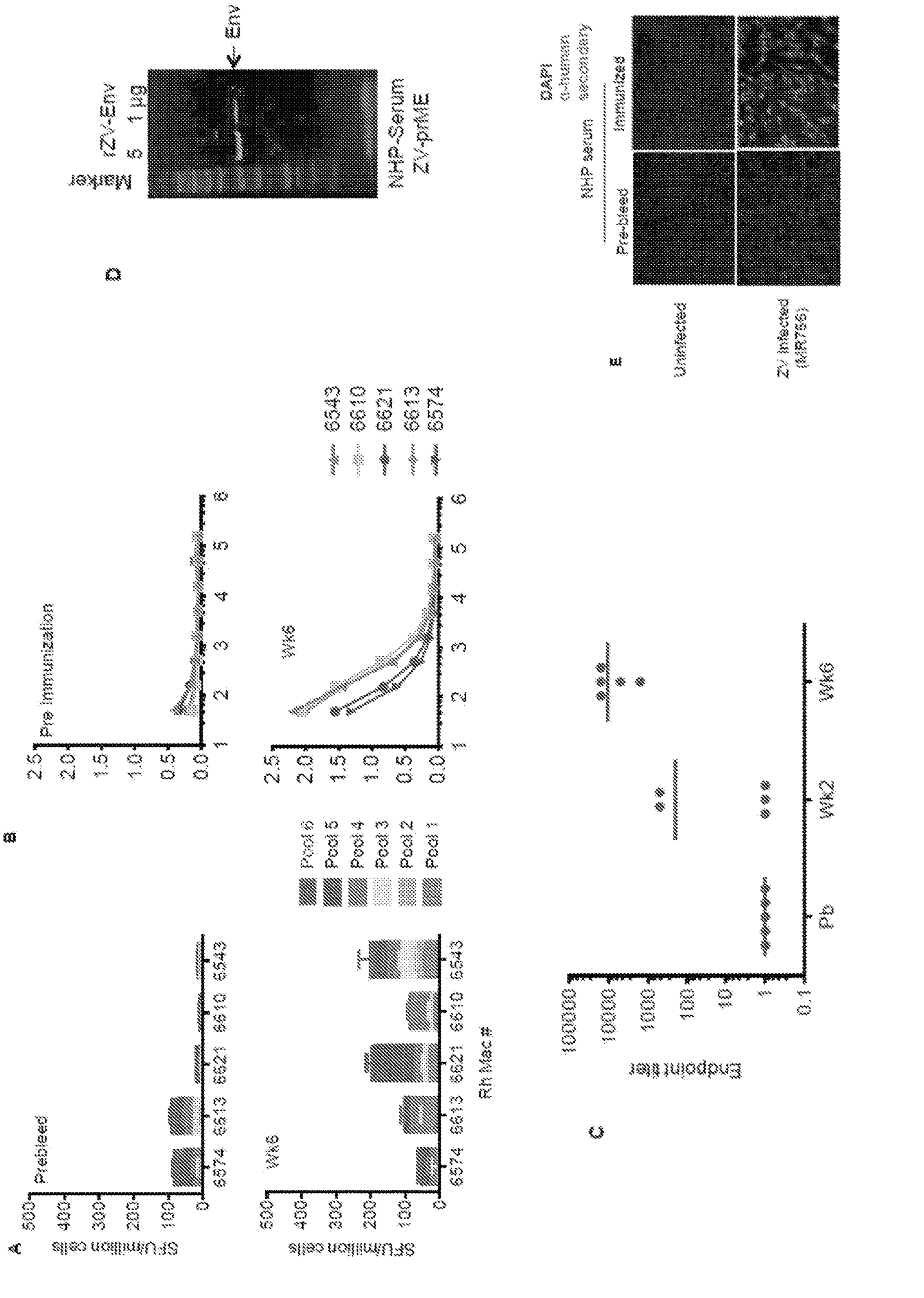
FIG. 31, comprising

Cellular and Humoral Responses Elicited by the ZIKA-prME DNA Vaccine in Non-Human Primates NHPs were immunized by intradermal (ID) immunization followed by electroporation based on previous studies showing that this method may enhance antigen-specific humoral immune responses by DNA vaccines. Rhesus macaque (RM; n=5/group) were administered 2.0 mg of vaccine plasmid ID with EP, and sera and PBMCs were collected from RM at day 0 (pre-immunization prior to first immunization), week 2 (2 weeks post first immunization), week 6 (2 weeks post second immunization). To measure vaccine-induced cellular immune responses, ELISpot analysis was performed on Wk6 PBMCs ex vivo stimulated with the ZIKA-E peptide pools used in FIG. 28A. The results show that the ZIKA prME immunization boosted anti-Zika T cell responses in all RM and broadened their antigen recognition compared to responses in pre-immune sera (FIG. 31A).

Figure 32:
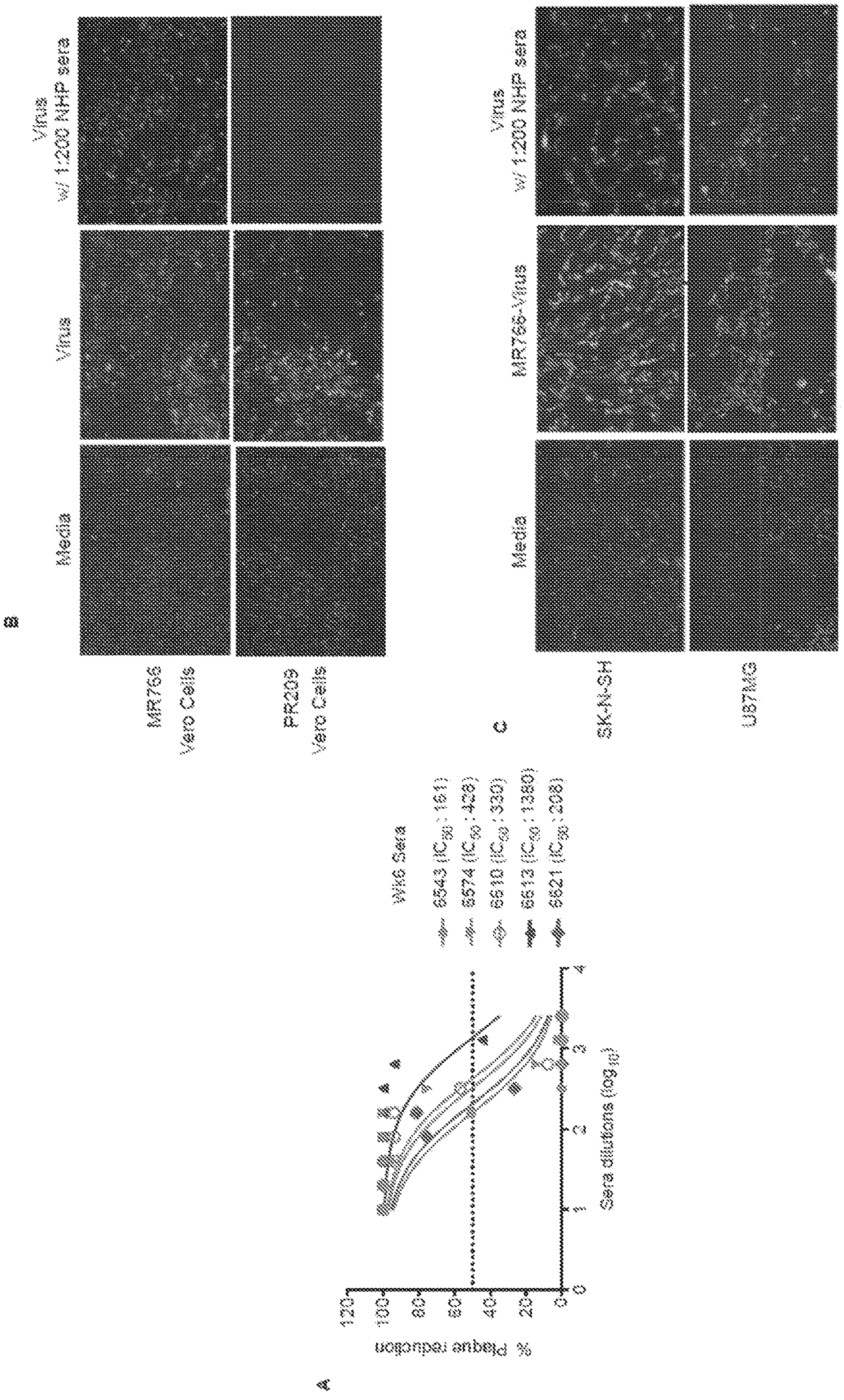
FIG. 32, comprising

Specific anti-Zika virus antibody responses in sera 181 from ID+EP vaccinated RM were assessed by ELISA. Following primary vaccination, ZIKA-Env-specific binding antibodies were detectable in RM two weeks after the first immunization with further boosting with a subsequent immunization (FIG. 31B). Sera from vaccinated RM from the same post-immunization time point were diluted to study end points titers and assayed again the rZIKA-Env (FIG. 31C). ELISA results were confirmed by Western analysis using pooled RM sera from the vaccinated group (FIG. 31D). Further, sera from immunized RM were also able to recognize ZIKA-MR766-infected Vero cells in an immunoflourescence assay (FIG. 31E). Next, it was attempted to detect the neutralization antibody (nAb) response in the sera from ZIKA-immunized RM. The PRNT50 (inverse of the serum dilution at which 50% of the control ZIKA infection was inhibited) was used to test for NAb activity and was performed on each individual immunized animal. Samples with an antibody titer<10, which were the limit of the detection of the assay, were assigned for each group of animals. Interestingly, ZIKA-prME immunized monkey had titers range from 161 to 1380 (average 501±224) (FIG. 32A).

The ability of the NHP immune sera to block infection in ZIKA infected neuroblastoma cells (SK-N-SH cells) and neural progenitor cells (U-87MG) of importance. Cell lines with MR766 or PR209 with control or vaccine sera and analyzed for infection at 24 hours. Sera from vaccinated RM inhibited either virus in both cell lines post infection (multiplicity of infection of 1.0) (FIGS. 21B and 21C). These data support the effectiveness of sera from ZIKA-prME DNA vaccinated RM to inhibit ZIKA infection.

Figure 33:
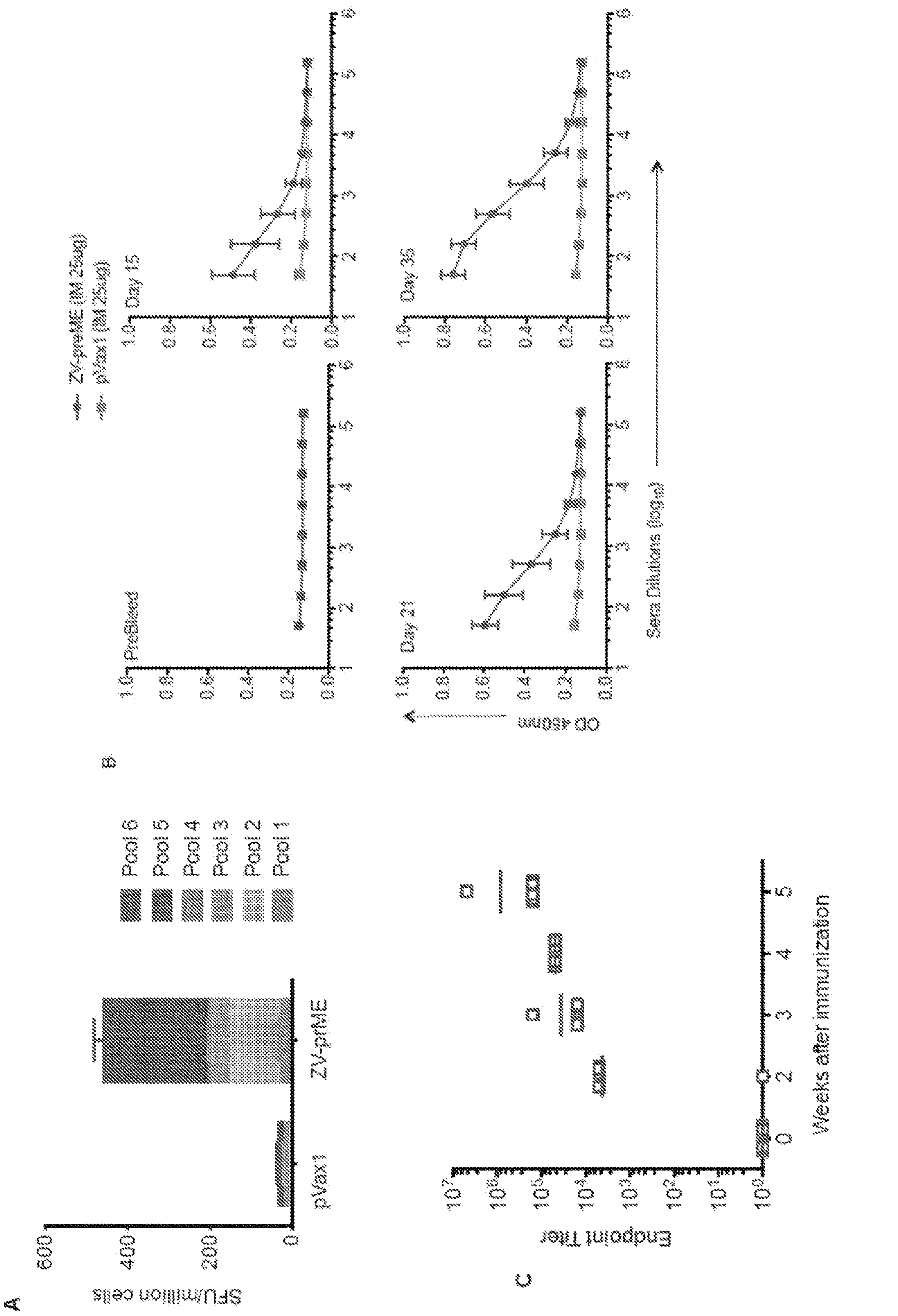
FIG. 33, comprising FIG. 33A through FIG. 33C depicts experimental results demonstrating Profile of IFN-γ and antibody production by spleen cells isolated from pZIKV prME in mice lacking the type I interferon α, β receptor.

ZIKA-Specific Functional Immune Responses and Protection Against Zika Virus in Mice Lacking the Receptor for Type I Interferon (IFNAR), Immunized with the ZIKAprME DNA Vaccine Mechanisms of ZIKA-induced disease and immunity are poorly defined, and the protective versus the hypothetical pathogenic nature of the immune response to ZIKA infection is as yet unclear. Most strains of mice are resistant to ZIKA infection, however, mice lacking IFN-α/β receptor (IFNAR) were found to be susceptible to infection and disease, most succumbing within 6-7 days of challenge 16. The ability of the consensus ZIKA-prME plasmid vaccine to induce cellular and humoral immune responses in this mouse strain was investigated. Groups of IFNAR mice were immunized 3 times at 2-week intervals with empty control plasmid or with the consensus ZIKA-prME plasmid by EP. Serum was collected from immunized mice at days 0, 14, 21, and 35 and splenocytes were harvested from mice one week following the final immunization. Splenocytes from vaccine-immunized IFNAR mice produced a clear cellular immune response as indicated by levels of SFU per 106 cells in an ELISpot assay (FIG. 33A). Results from ELISAs using rZIKA-Env as a capture antigen show that animals had detectable anti-ZIKA serum IgG by day 14 and these levels were boosted at subsequent collection times (FIG. 33B). Sera from vaccinated mice contained significant levels of antibody as indicated by the endpoint titers (FIG. 33B). The results indicate that IFNAR mice immunized with the consensus ZIKA-prME vaccine are capable anti-ZIKA cellular and humoral immune responses supporting further study for vaccine protection in this potential challenge model.

In exploratory studies, IFNAR mice were challenged with 1×106 PFU of the PR209 isolate, administered subcutaneously (s.c.); intraperitoneal (i.v); intracranial (i.c.) and intravenously (i.v). After challenge, all animals were monitored for clinical signs including routine body weight, recording body temperature measurement well as other signs of a moribund condition such as hind limb weakness and paralysis. No change in the general appearance of the mice was observed during the first 2 days after inoculation. However, after the third day, all four routes of infection showed reduced activity, decreased mobility, hunched posture; accompanied by hind limb weakness and water intake and obvious weight loss. Animals regardless of challenge site succumbed to the infection between day 6 and day 8 and this challenge dose was utilized in subsequent studies.

Figure 34:
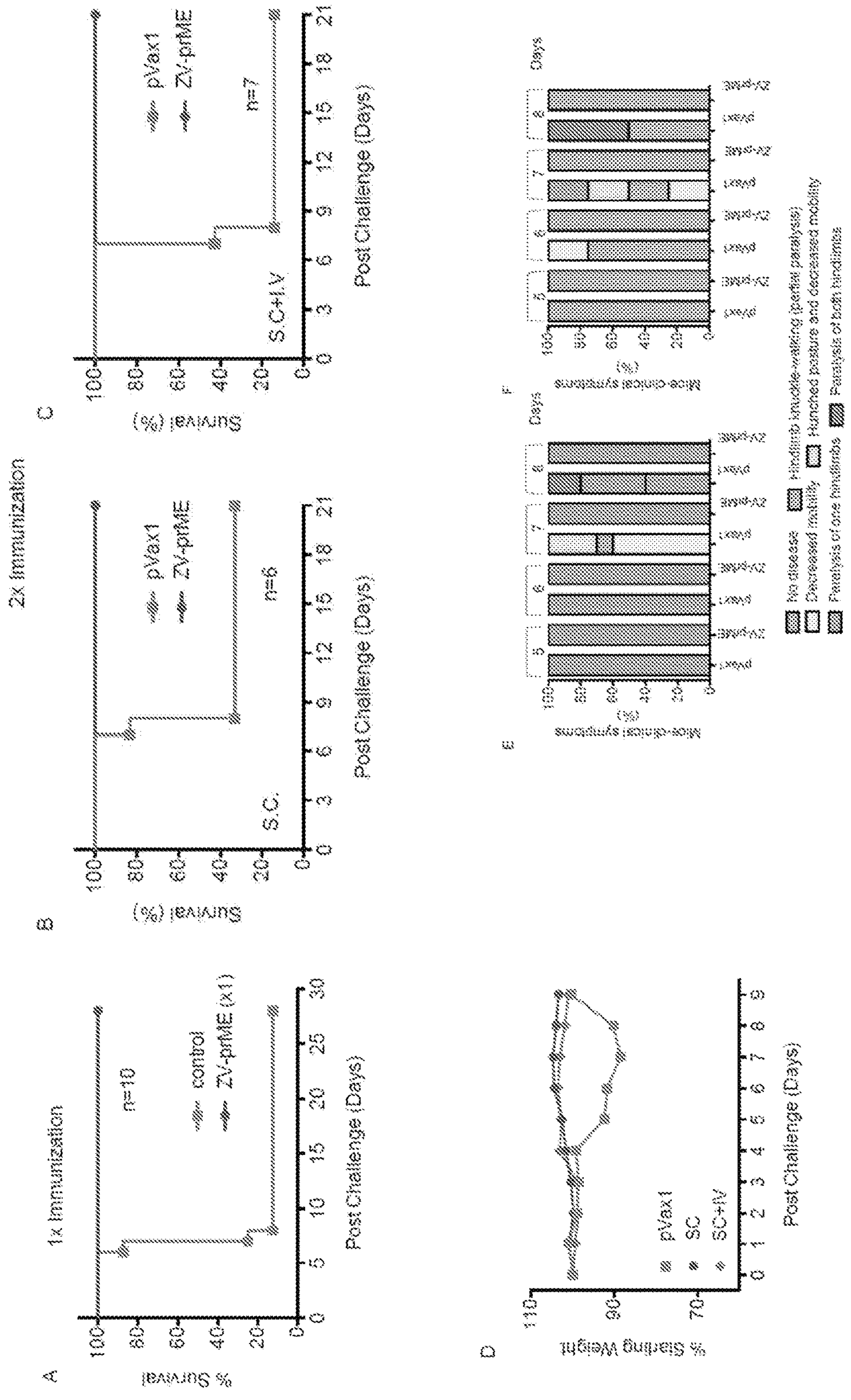
FIG. 34, comprising FIG. 34A through FIG. 34F depicts experimental results demonstrating survival data for immunized mice lacking the type I interferon α, β receptor following Zika virus infection. Survival of IFN-α/β receptor knockout mice after Zika infection.

Two groups of vaccinated animals (10 per group) or two sets of pVax1 immunized controls, were vaccinated 1× on day 0 and 1× on day 14 and challenged on day 21 with either 1×106 PFU or 2×106 PFU of PR209 (FIGS. 23B and 23C). 100% of the vaccinated animals survived while only 30% of the 1×106 PFU or 10% of the 2×106 PFU challenged controls survived. Next, a group of animals was immunized 1× and challenged them on Day 14 post immunization. 100% of these animals survived, while 10% of the control animals survived. All mice vaccinated with ZIKA-prME once and then challenged with Zika virus were protected from the lethal challenge (FIG. 34A). In all challenges, vaccinated animals also did not exhibit symptoms of disease and were protected from weight loss (FIG. 34D). Infection of control mice with Zika virus produced a marked decrease in body weight often combined to decreased mobility, hunched posture, hind limb knuckle-walking and/or paralysis both hind limbs with significant mortality (FIGS. 23E and 23F). Taken together, these data illustrate that ZV-prME DNA vaccine mediated immune responses that protect mice against Zika challenge.

In the present studies, humoral and cellular responses using prME as antigen produced from a DNA-based vaccine plus electroporation were documented in rodents and non-human primates. The optimized enhanced DNA vaccine technology by EP delivery approach was effective at stimulating robust and broad immune responses and a single immunization induced immunity that was protective from disease and mortality in IFNAR mice. This study supports the concept that protective immunity can be generated using a flexible and rapidly clinically implementable DNA vaccination strategy against this serious emerging viral infection.

Example 4

In Vivo Protection Against ZIKV Infection and Pathogenesis Through Passive Antibody Transfer and Active Immunization with a prMEnv DNA Vaccine In this study, novel, synthetic, DNA vaccine targeting the pre-membrane+envelope proteins (prMEnv) of ZIKV generated and evaluated for in vivo efficacy. Following initial in vitro development and evaluation studies of the plasmid construct, mice and non-human primates were immunised with this prMEnv DNA-based immunogen through electroporation-mediated enhanced DNA delivery. Vaccinated animals were found to generate antigen-specific cellular and humoral immunity and neutralization activity. In mice lacking receptors for interferon (IFN)-α/β (designated $IFNAR^{-/-}$) immunization with this DNA vaccine induced, following in vivo viral challenge, 100% protection against infection-associated weight loss or death in addition to preventing viral pathology in brain tissue. In addition, passive transfer of non-human primate anti-ZIKV immune serum protected $IFNAR^{-/-}$ mice against subsequent viral challenge. This initial study of this ZIKV vaccine in a pathogenic mouse model supports the importance of immune responses targeting prME in ZIKV infection and suggests that additional research on this vaccine approach may have relevance for ZIKV control in humans.

The materials and methods are now described.

Cells, Virus and Animals

Human embryonic kidney 293T (American Type Culture Collection (ATCC) #CRL-N268, Manassas, Va., USA) and Vero CCL-81 (ATCC #CCL-81) cells were maintained in DMEM (Dulbecco's modified Eagle's medium; Gibco-Q3 Invitrogen) supplemented with 10% fetal bovine serum (FBS) and 1% penicillin and streptomycin and passaged upon confluence. Both ZIKV virus strains MR766 (a kind gift from Dr Susan Weiss) and PR209 (Bioqual, MD) were amplified in Vero cells and stocks were titred by standard plaque assay on Vero cells. Five- to six-week-old female C57BL/6 (The Jackson Laboratory) and $IFNAR^{-/-}$ (MMRRC repository—The Jackson Laboratory) mice were housed and treated/vaccinated in a temperature-controlled, light-cycled facility in accordance with the National Institutes of Health, Wistar and the Public Health Agency of Canada IACUC (Institutional Animal Care and Use Committee) guidelines.

The RMs were housed and treated/vaccinated at Bioqual, MD, USA. This study was carried out in strict accordance with the recommendations described in the Guide for the Care and Use of Laboratory Animals of the NIH, the Office of Animal Welfare, and the U.S. Department of Agriculture. All animal immunization work was approved by the Bioqual Animal Care and Use Committee (IACUC). Bioqual is accredited by the American Association for Accreditation of Laboratory Animal Care. All the procedures were carried out under ketamine anaesthesia by trained personnel under the supervision of veterinary staff, and all the efforts were made to protect the welfare of the animals and to minimise animal suffering in accordance with the 'Weatherall report for the use of non-human primates' recommendations. The animals were housed in adjoining individual primate cages allowing social interactions, under controlled conditions of humidity, temperature and light (12 h light/12 h dark cycles). Food and water were available ad libitum. The animals were monitored twice daily and fed commercial monkey chow, treats and fruits twice daily by trained personnel.

Construction of ZIKV-prME DNA Vaccine

The ZIKV-prME plasmid DNA constructs encodes full-length precursor of membrane (prM) plus envelope (E) and Capsid proteins were synthesised. A consensus strategy was used and the consensus sequences were determined by the alignment of current ZIKV prME protein sequences. The vaccine insert was genetically optimised (i.e., codon and RNA optimisation) for enhanced expression in humans and an IgE leader sequence was added to facilitate expression. The construct was synthesised commercially (Genscript, NJ, USA), and then subcloned into a modified pVax1 expression vector under the control of the cytomegalovirus immediate-early promoter as described before (Muthumani et al., 2016, Sci Transl Med 7:301ra132). The final construct is named ZIKV-prME vaccine and the control plasmid backbone is pVax1. In addition, a number of other matched DNA constructs encoding the prM and E genes from MR766 (DQ859059.1) and a 2016 Brazilin (AMA12084.1) outbreak strain were also designed, for further evaluation. Large-scale amplifications of DNA constructs were carried out by Inovio Pharmaceuticals Inc. (Plymouth Meeting, Pa., USA) and purified plasmid DNA was formulated in water for immunizations. The size of the DNA inserts was confirmed via agarose gel electrophoresis. Phylogenetic analysis was performed by multiple alignment with ClustalW using MEGA version 5 software (Muthumani et al., 2016, Sci Transl Med 7:301ra132).

DNA Immunizations and Electroporation-Mediated Delivery Enhancement

Female C57BL/6 mice (6-8 weeks old) and IFNAR$^{-/-}$ mice (5-6 weeks old) were immunised with 25 μg of DNA in a total volume of 20 or 30 μl of water delivered into the tibialis anterior muscle with in vivo electroporation delivery. In vivo electroporation was delivered with the CELLECTRA adaptive constant current electroporation device (Inovio Pharmaceuticals) at the same site immediately following DNA injection. A three-pronged CELLECTRA minimally invasive device was inserted ~2 mm into the muscle. Square-wave pulses were delivered through a triangular three electrode array consisting of 26-gauge solid stainless steel electrodes and two constant current pulses of 0.1 Amps were delivered for 52 μs/pulse separated by a 1 s delay. Further protocols for the use of electroporation have been previously described in detail (Flingai et al., 2015, Sci Rep 5:12616). The mice were immunised three times at 2-week intervals and killed 1 week after the final immunization. The blood was collected after each immunization for the analysis of cellular and humoral immune responses (Muthumani et al., 2016, Sci Transl Med 7:301ra132). Rhesus macaque immunogenicity studies: five rhesus macaques were immunised intradermally at two sites two times at 5-week intervals with 2 mg ZIKV-prME vaccine. Electroporation was delivered immediately using the same device described for mouse immunizations.

Western Blot Analysis

For in vitro expression studies, transfections were performed using the GeneJammer reagent, following the manufacturer's protocols (Agilent). Briefly, the cells were grown to 50% confluence in a 35 mm dish and transfected with 1 μg of ZIKV-prME vaccine. The cells were collected 2 days after transfection, washed twice with PBS and lysed with cell lysis buffer (Cell Signaling Technology). Western Blot was used to verify the expression of the ZIKV-prME protein from the harvested cell lysate and the immune specificity of the mouse and RM serum through the use of either anti-Flavivirus or immune sera from the ZIKV-prME vaccinated mice, as described previously (Muthumani et al., 2016, Sci Transl Med 7:301ra132). In brief, 3-12% Bis-Tris NuPAGE gels (Life Technolo-gies) were loaded with 5 μg or 1 μg of ZIKV envelope recombinant protein (rZIKV-E); transfected cell lysates or supernatant and the Odyssey protein Molecular Weight Marker (Product #928-40000). The gels were run at 200 V for 50 min in MOPS buffer. The proteins were transferred onto nitrocellulose membranes using the iBlot 2 Gel Transfer Device (Life Technologies). The membranes were blocked in PBS Odyssey blocking buffer (LI-COR Biosciences) for 1 h at room temperature. To detect vaccine expression, the anti-Flavivirus group antigen (MAB10216-Clone D1-4G2-4-15) antibody was diluted 1:500 and the immune serum from mice and RM was diluted 1:50 in Odyssey blocking buffer with 0.2% Tween 20 (Bio-Rad) and incubated with the membranes overnight at 4° C. The membranes were washed with PBST and then incubated with the appropriate secondary antibody (goat anti-mouse IRDye680CW; LI-COR Biosciences) for mouse serum and flavivirus antibody; and goat anti-human IRDye800CW (LI-COR Biosciences) for RM sera at 1:15,000 dilution for mouse sera for 1 h at room temperature. After washing, the membranes were imaged on the Odyssey infrared imager (LI-COR Biosciences).

Immunofluorescence Assays

For the immunofluorescence assay, the cells were grown on coverslips and transfected with 5 μg of ZIKV-prME vaccine. Two days after transfection, the cells were fixed with 4% paraformaldehyde for 15 min. Nonspecific binding was then blocked with normal goat serum diluted in PBS at room temperature for 1 h. The slides were then washed in PBS for 5 min and subsequently incubated with sera from immunised mice or RM at a 1:100 dilutions overnight at 4° C. The slides were washed as described above and incubated with appropriate secondary antibody (goat anti-mouse IgGAF488; for mouse serum and goat anti-human IgG-AF488 for RM serum; Sigma) at 1:200 dilutions at room temperature for 1 h. After washing, Flouroshield mounting media with DAPI (Abcam) was added to stain the nuclei of all cells. After which, coverslips were mounted and the slides were observed under a microscope (EVOS Cell Imaging Systems; Life Technologies) (Muthumani et al., 2016, Sci Transl Med 7:301ra132). In addition, Vero, SK-N-SH or U87-MB cells were grown on four-chamber tissue culture treated glass slides and infected at MOI of 0.01 with ZIKV-MR766 or PR209 that were preincubated with/without RM immune sera (1:200), and stained at 4 days post ZIKV infection using pan flavirus antibody as described (Rossi et al., 2016, J Rop Med Hyg 94:1362-9).

Histopathology Analysis

For histopathology, formalin-fixed, paraffin-embedded brain tissue was sectioned into 5 μm thick sagittal sections, placed on Superfrost microscope slides (Fisher Scientific) and backed at 37° C. overnight. The sections were deparaffinised using two changes of xylene and rehydrated by immersing in 100%, 90% and then 70% ethanol. The sections were stained for nuclear structures using Harris haematoxylin (Surgipath) for 2 min followed by differentiation in 1% acid alcohol (Surgipath) and treatment with Scott's tap water for 2 min. Subsequently, the sections were counterstained for cytoplasmic structures using eosin (Surgipath) for 2 min. The slides were dehydrated with 70%, 90% and 100% ethanol, cleared in xylene and mounted using Permount (Fisher Scientific).

Splenocyte and PBMC Isolation

Single-cell suspensions of splenocytes were prepared from all the mice. Briefly, the spleens from mice were collected individually in 5 ml of RPMI 1640 supplemented with 10% FBS (R10), then processed with a Stomacher 80 paddle blender (A.J. Seward and Co. Ltd.) for 30 s on high speed. The processed spleen samples were filtered through 45 mm nylon filters and then centrifuged at 1,500 g for 10 min at 4° C. The cell pellets were resuspended in 5 ml of ACK (ammonium-chloride-potassium) lysis buffer (Life Technologies) for 5 min at room temperature, and PBS was then added to stop the reaction. The samples were again centrifuged at 1,500 g for 10 min at 4° C. The cell pellets were resuspended in R10 and then passed through a 45 mm nylon filter before use in ELISpot assay and flow cytometric analysis (Muthumani et al., 2016, Sci Transl Med 7:301ra132). For RM, blood (20 ml at each time point) was collected in EDTA tubes and the PBMCs were isolated using a standard Ficoll-hypaque procedure with Accuspin tubes (Sigma-Aldrich, St. Louis, Mo., USA). Five millitres of blood was also collected into sera tubes at each time point for sera isolation.

Flow Cytometry and Intracellular Cytokine Staining Assay

The splenocytes were added to a 96-well plate ($2\times10^6$/well) and were stimulated with ZIKV-prME pooled peptides for 5 h at 37° C./5% CO2 in the presence of Protein Transport Inhibitor Cocktail (brefeldin A and monensin; eBioscience). The cell stimulation cocktail (plus protein transport inhibitors; PMA (phorbol 12-myristate 13-acetate), ionomycin, brefeldin A and monensin; eBioscience) was used as a positive control and R10 media as the negative control. All the cells were then stained for surface and intracellular proteins as described by the manufacturer's instructions (BD Biosciences, San Diego, Calif., USA). Briefly, the cells were washed in FACS buffer (PBS containing 0.1% sodium azide and 1% FBS) before surface staining with flourochrome-conjugated antibodies. The cells were washed with FACS buffer, fixed and permeabilised using the BD Cytofix/Ctyoperm™ (BD Biosciences) according to the manufacturer's protocol followed by intracellular staining. The following antibodies were used for surface staining: LIVE/DEAD Fixable Violet Dead Cell stain kit (Invitrogen), CD19 (V450; clone 1D3; BD Biosciences) CD4 (FITC; clone RM4-5; eBioscience), CD8 (APC-Cy7; clone 53-6.7; BD Biosciences); CD44 (BV711; clone IM7; BioLegend). For intracellular staining, the following antibodies were used: IFN-γ (APC; clone XMG1.2; BioLegend), TNF-α (PE; clone MP6-XT22; eBioscience), CD3 (PerCP/Cy5.5; clone 145-2C11; BioLegend); IL-2 (PeCy7; clone JES6-SH4; eBioscience). All the data were collected using a LSRII flow cytometer (BD Biosciences) and analysed using FlowJo software (Tree Star, Ashland, Oreg., USA).

ELISpot Assay

Briefly, 96-well ELISpot plates (Millipore) were coated with anti-mouse IFN-γ capture Ab (R&D Systems) and incubated overnight at 4° C. The following day, the plates were washed with PBS and blocked for 2 h with PBST+1% BSA. Two hundred thousand splenocytes from immunised mice were added to each well and incubated overnight at 37° C. in 5% CO2 in the presence of media alone (negative control), media with PMA/ionomycin (positive control) or media with peptide pools (1 μg/ml) consisting of 15-mers overlapping by nine amino acids and spanning the length of the ZIKV prME protein (Genscript). After 24 h, the cells were washed and then incubated overnight at 4° C. with biotinylated anti-mouse IFN-γ Ab (R&D Systems). Streptavidin-alkaline phosphatase (R&D Systems) was added to each well after washing and then incubated for 2 h at room temperature. The plate was washed, and then 5-bromo-4-chloro-3'-indolylphosphate p-toluidine salt and nitro blue tetrazolium chloride (chromogen colour reagent; R&D Systems) was added. Last, the plates were rinsed with distilled water, dried at room temperature and SFU were quantified by an automated ELISpot reader (CTL Limited), and the raw values were normalised to SFU per million splenocytes. For RM samples, the ELISPOT$^{PRO}$ for monkey IFN-γ kit (MABTECH) was used as described by the manufacturer; two hundred thousand PBMCs were stimulated with peptide pools; and the plates were washed and spots were developed and counted as described before (Muthumani et al., 2016, Sci Transl Med 7:301ra132).

Humoral Immune Response: Antibody-Binding ELISA

An ELISA was used to determine the titres of mouse and RM sera as previously described (Muthumani et al., 2016, Sci Transl Med 7:301ra132). Briefly, 1 μg of purified rZIKV-E protein was used to coat 96-well microtiter plates (Nalgene Nunc International, Naperville, Ill., USA) at 4° C. overnight. After blocking with 10% FBS in PBS for at least an hour, the plates were washed four times with 0.05% PBST (Tween20 in PBS). Serum samples from immunised mice and RMs were serially diluted in 1% FBS, added to the plates, then incubated for 1 h at room temperature. The plates were again washed four times in 0.05% PBST, then incubated with HRP-conjugated anti-mouse IgG (Sigma) at a 1:35,000 dilution for mouse sera for 1 h at room temperature. For RM sera, anti monkey IgG HRP (Southern Biotech) was used at a 1:5,000 dilutions for 1 h at room temperature. The bound enzyme was detected by adding SIGMAFAST OPD (o-phenylenediamine dihydrochloride) substrate solution according to the manufacturer's instructions (Sigma-Aldrich). The reaction was stopped after 15 min with the addition of 1 N $H_2SO_4$. The optical density at 450 nm was read on a Synergy plate reader. All the mouse and RM serum samples were assayed in duplicate. End point titres were determined using the method described previously (Frey et al., 1998, J Immunol Methods 21:35-41).

Neutralization ($PRNT_{50}$) Assay

The PRNT involving MR766 and Vero cells was described previously (Sun et al., 2006, J Infect Dis 193: 1658-65). Briefly, heat-inactivated mouse or RM sera were serially diluted in serumfree DMEM (1:10 to 1:1280) and incubated with an equal volume of ZIKV MR766 (100 PFU) at 37° C. for 2 h. The mixtures were added to the confluent layers of Vero cells and left at 37° C. for adsorption for 2 h. A 2×DMEM media:soft-agar (1:1) overlay was added over cells and the plate was incubated for 5 days at 37° C. The agar overlay was removed and the cells were fixed with 4% paraformaldehyde, washed with 1×PBS, stained with crystal violet solution, washed with 1×PBS and the plates were left to dry. The plaques in assays done in 24-well plates were scanned with an automated Immunospot reader (CTL Limited), and the plaques in sample wells and in negative control (DMEM only) and positive control (100 PFU MR766 ZIKV virus only) wells were counted using the automated software provided with the ELISpot reader. The percentage plaque reduction was calculated as follows: % reduction=100×{1−(average number of plaques for each dilution/average number of plaques in positive control wells)}. GraphPad Prism software was used to perform nonlinear regression analysis of % plaque reduction versus a log transformation of each individual serum dilution to facilitate linear interpolation of actual 50% PRNT titres at peak post vaccination response. The medians and interquartile ranges at 50% neutralization were calculated for each neutralization target overall and by vaccine treatment group; the geometric mean titres were also calculated. The titres represent the reciprocal of the highest dilution resulting in a 50% reduction in the number of plaques.

ZIKV Challenge Studies in IFNAR$^{-/-}$ Mice

For the ZIKA challenge studies, IFNAR$^{-/-}$ mice (n=10/group) were immunised once or twice with the ZIKA-prME vaccine or pVax1. The mice were with either $1\times10^6$ PFU or $2\times10^6$ PFU ZIKV-PR209 virus on day 15 (single immunization group) or day 21 one week after the second immunization (two immunization groups). Also, additional groups of IFNAR$^{-/-}$ mice (n=10/group) were immunised once and challenged with $2\times10^6$ PFU ZIKV-PR209 virus on day 15. Post challenge, the animals were weighed and body temperature was measured daily by a subcutaneously located temperature chip. In addition, they were observed for clinical signs of disease twice daily (decreased mobility; hunched posture; hind-limb knuckle walking (partial paralysis), paralysis of one hind limb or both hind limbs) and the blood was drawn for viral load determination. The criteria for killing on welfare grounds consisted of 20% weight loss or paralysis in one or both hind limbs.

Real-Time RT-PCR Assay for Measurement of ZIKV Load

The brains from treated mice were immersed in RNAlater (Ambion) 4° C. for 1 week, then stored at −80° C. The brain tissue was then weighed and homogenised in 600 μl RLT buffer in a 2 ml cryovial using a TissueLyser (Qiagen) with a stainless steel bead for 6 min at 30 cycles/s. Viral RNA was also isolated from blood with the RNeasy Plus mini kit (Qiagen). A ZIKV specific real-time RT-PCR assay was utilised for the detection of viral RNA from subject animals. RNA was reverse transcribed and amplified using the primers ZIKV 835 and ZIKV 911c and probe ZIKV 860FAM with the TaqMan Fast Virus 1-Step Master Mix (Applied Biosystems). A standard curve was generated in parallel for each plate and used for the quantification of viral genome copy numbers. The StepOnePlus Real-Time PCR System (ABI) software version 2.3 was used to calculate the cycle threshold (Ct) values, and a Ct value≤38 for at least one of the replicates was considered positive, as previously described (Lanciotti et al., 2008, Emerg Infect Dis 14:1232-9). Pre-bleeds were negative in this assay.

Statistical Analysis

Differences in fold increases in antibody titres were compared using Mann-Whitney analysis. Statistical analysis was performed using Graphpad, Prism 4 (Graphpad software, Inc. San Diego, Calif., USA). For all the analyses, $P<0.05$ was considered to be significant. $Log_{10}$ transformations were applied to end point binding ELISA titres and whole-virus $PRNT_{50}$ titres.

The results of the experiments are now described.

Construction of the ZIKV-prME Consensus DNA Vaccine

Figure 35:
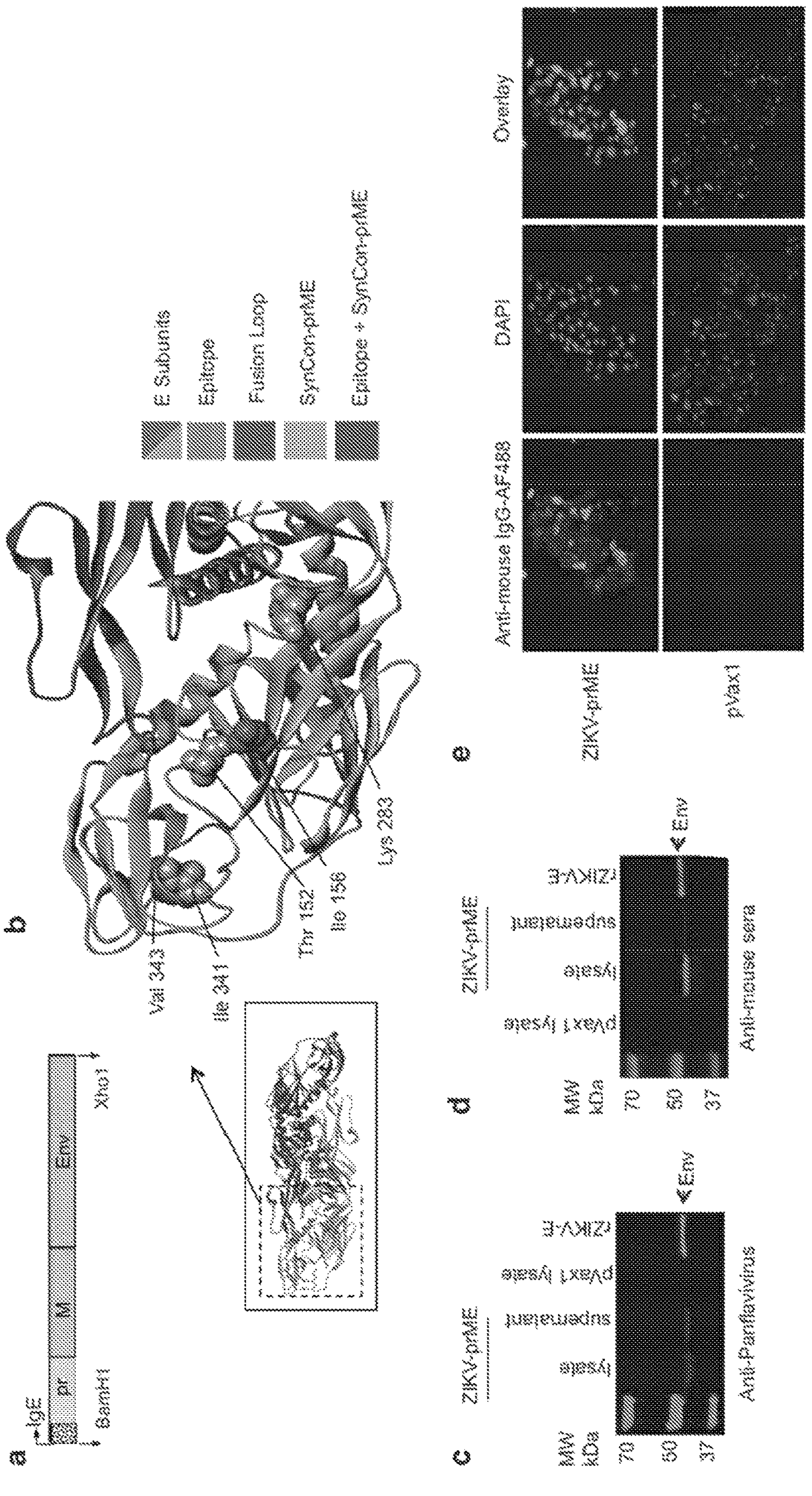
FIG. 35, comprising FIG. 35A through FIG. 35E depicts experimental results demonstrating the construction of the ZIKV-prME consensus DNA vaccine.

A consensus sequence of ZIKV prM (precursor membrane) and Env (envelope) genes (ZIKV-prME) was generated using prM and Env sequences from various ZIKV isolated between the years of 1952 and 2015, which caused infection in humans. The ZIKV-prME consensus sequence was cloned into the pVax1 vector after additional modifications and optimisations were made to improve its in vivo expression including the addition of a highly efficient immunoglobulin E (IgE) leader peptide sequence (FIG. 35A). Optimal alignment of ZIKV-envelope sequences was performed using homology models and visualisation on Discovery Studio 4.5. Reference models included PDB 5JHM and PDB 5IZ7. Aligned residues corresponding to specific regions on the prME antigen were labelled in the models for visualisation purposes (FIG. 35B). The optimised consensus vaccine selections are in general conservative or semi-conservative relative to multiple ZIKV strains analysed in this study. Structural studies of EDE-specific neutralising antibodies have revealed that these recognition determinants can be found at a serotype-invariant site at the envelope-dimer interface, which includes the exposed main chain of the fusion loop and two conserved glycan chains (N67- and N153-linked glycans) (Rouvinski et al., 2015, Nature 520: 109-13). These two glycosylation sites are not highly conserved in other flaviviruses. Moreover, ZIKV does not possess the N67-linked glycosylation site, and the N154-linked glycosylation site (equivalent to the N153-linked glycosylation site in dengue) is absent in some of the isolated ZIKV strains. As part of the consensus design, therefore the construct was designed leaving out this glycosylation site. Lack of glycosylation at this site has been correlated with improved binding of EDE1 type broadly neutralising antibodies (bnAbs) to ZIKV-envelope protein (Rouvinski et al., 2015, Nature 520:109-13).

Subsequent to construction, expression of the ZIKV-prME protein from the plasmid was confirmed by western blot analysis and an indirect immunofluorescence assay. The protein extracts prepared from the cells transiently transfected with ZIKV-prME were analysed for expression by western blot using panflavivirus antibody (FIG. 35C) and sera collected from ZIKV-prME immunised mice (FIG. 35D). ZIKV-prME expression was further detected by IFA by the staining of 293T cells transfected with ZIKV-prME plasmid at 48 h post transfection with anti-ZIKV-prME specific antibodies (FIG. 35E).

ZIKV-prMEnv DNA Vaccine Induces Antigen-Specific T Cells in C57BL/6 Mice

Figure 36:
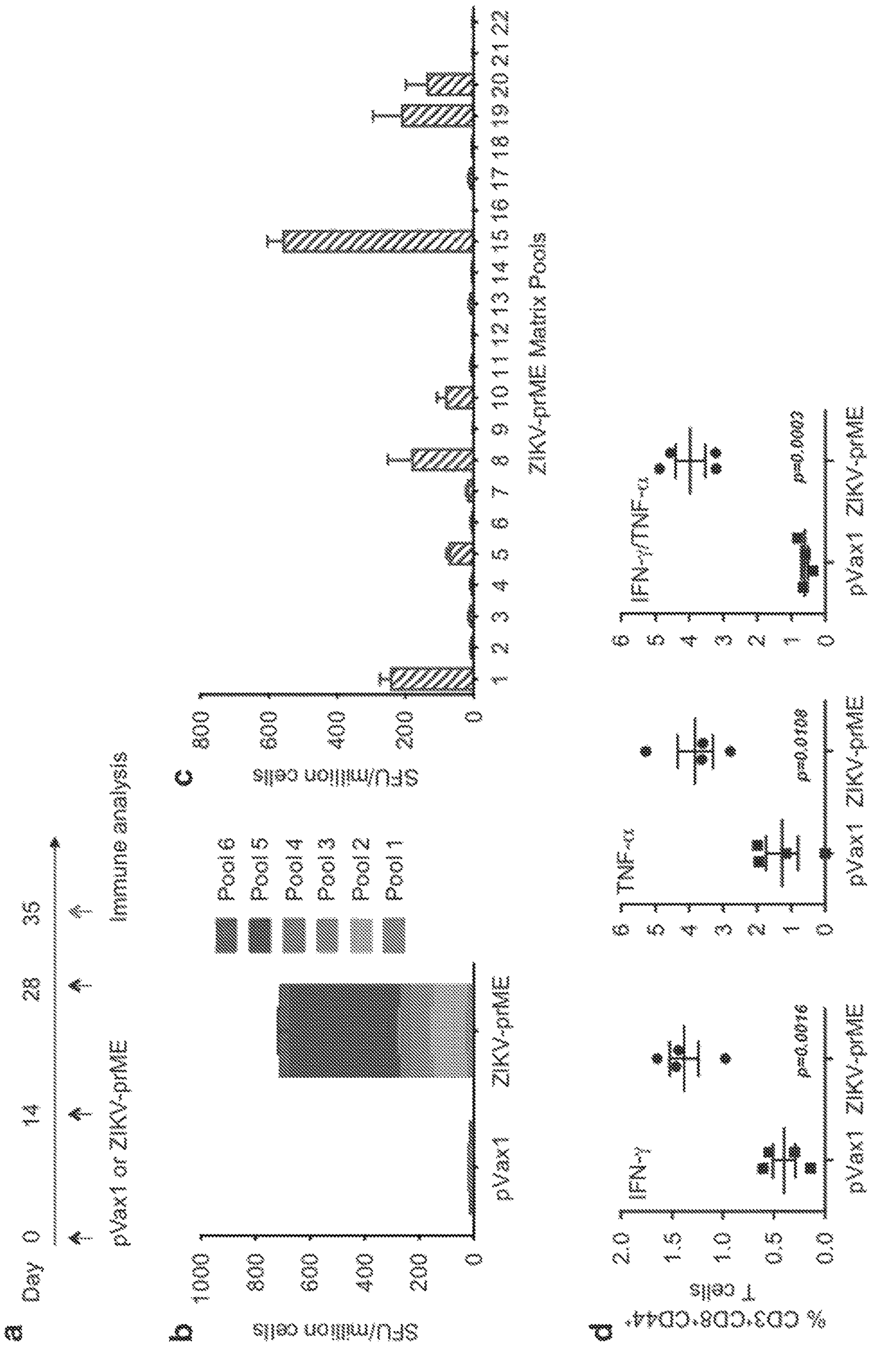
FIG. 36, comprising FIG. 36A through FIG. 36D depicts experimental results demonstrating the characterization of cellular immune responses in mice following vaccination with the ZIKV-prME DNA vaccine.

The ability of the ZIKV-prMEnv plasmid vaccine to induce cellular immune responses was evaluated. Groups of four female C57BL/6 mice were immunised with either the control plasmid backbone (pVax1) or the ZIKV-prME plasmid vaccine three times at 2 week intervals through intramuscular (i.m.) injection followed by electroporation at the site of delivery (FIG. 36A). The animals were killed 1 week after their third injection and bulk splenocytes harvested from each animal were evaluated in ELISpot assays for their ability to secrete interferon-γ (IFN-γ) after ex vivo exposure to peptide pools encompassing ZIKV-prME is included. The assay results show that splenocytes from ZIKV-prME immunised mice produced a cellular immune response after stimulation with multiple ZIKV-E peptide pools (FIG. 36B). The region(s) of ZIKVEnv, which elicited the strongest cellular response(s) were evaluated by ELISpot assay in a matrix format using 22 peptide pools consisting of 15-mers (overlapping by 11 amino acids) spanning the entire ZIKV-prME protein. Several pools demonstrated elevated T cell responses, with peptide pool 15 exhibiting the highest number of spot-forming units (SFU) (FIG. 36C). This matrix mapping analysis revealed a dominant prME epitope, 'IRCIGVSNR DFVEGM' (aa167-181). This peptide was confirmed to contain a H2-Db restricted epitope through analysis utilising the Immune Epitope Database Analysis Resource tool (http://tools.iedb.org), which supports that in this haplotype the antigen is effectively processed.

Further evaluation of the cellular immunogenicity of the ZIKV-prMEnv vaccine entailed the determination of the polyfunctional properties of $CD8^+$ T cells collected 1 week after the final immunization. The results show that the ZIKV-prMEnv vaccination increased the proportion of bifunctional vaccine-specific T cells expressing TNF-α (tumour necrosis factor-a) and IFN-γ. Importantly, ZIKV-prMEnv vaccination exhibited a strong ability to expand T cell functionality (FIG. 36D).

Figure 42:
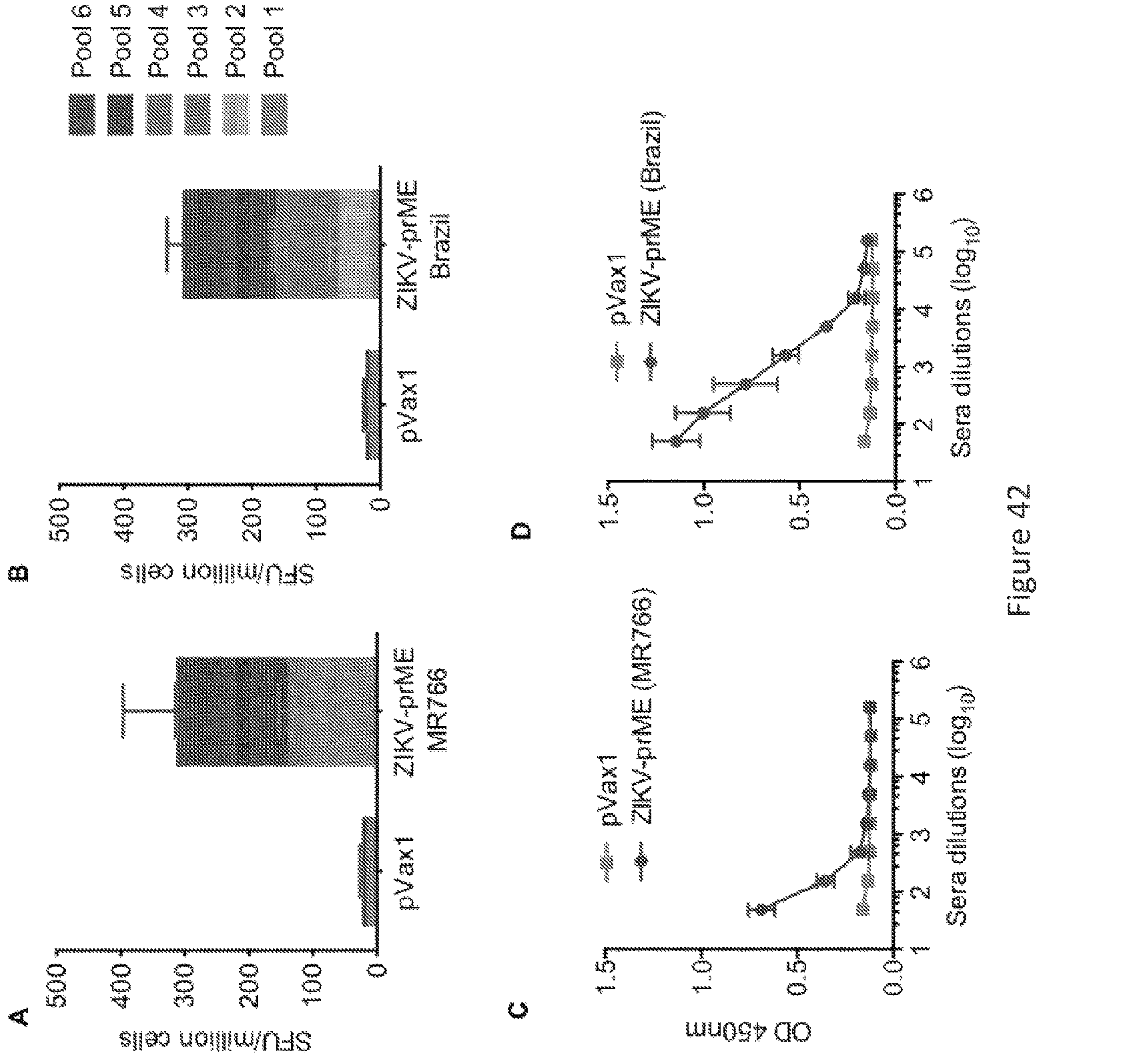
FIG. 42, comprising

In addition, comparative immune studies were performed with optimised plasmids encoding the prMEnv sequence of either a recently identified Brazilian ZIKV strain or of the original MR766 ZIKV strain. Induction of cellular immune responses in mice immunised with either plasmid was measured 1 week after the third vaccination through IFN-γ ELISpot analysis after stimulating splenocytes with the ZIKV-prMEnv peptide pools. The results illustrate that the T-cell responses induced by the consensus ZIKVprME DNA vaccine construct were consistently higher than those generated by either of these two non-consensus plasmid vaccines (FIGS. 42A and 42B). Detailed mapping analysis of the cellular responses induced by either the Brazilian or MR766 prME vaccines revealed that both vaccines induced significant cellular response against the dominant Env-specific CTL epitope as identified in FIGS. 36B and 36C for the consensus ZIKV-prMEnv plasmid (data not shown). The consensus immunogen consistently induced more robust responses in these T-cell assays at the same dose and was evaluated further in additional assays.

Generation of a ZIKV Recombinant Envelope Protein

Figure 43:
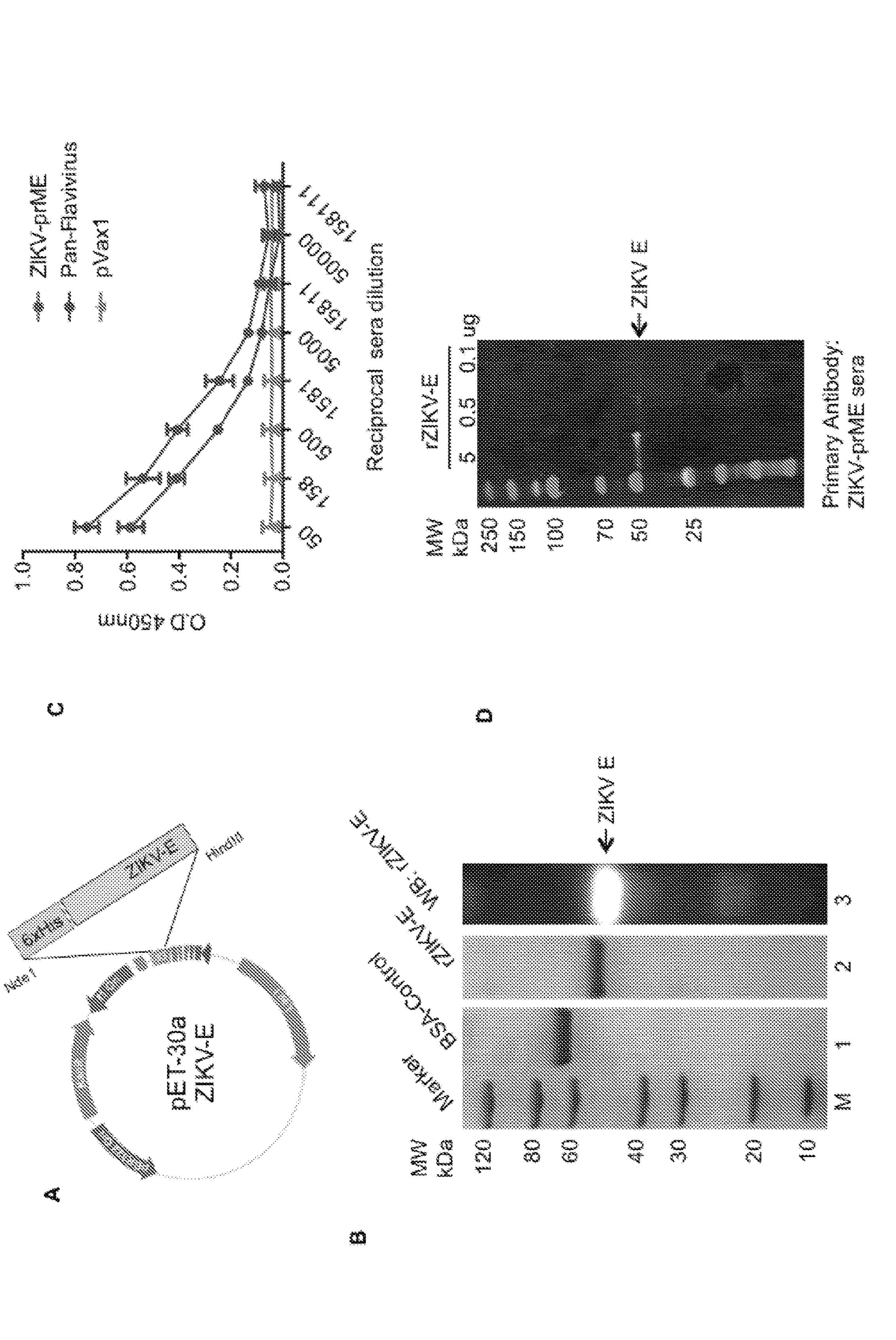
FIG. 43, comprising

At the onset of these studies, there were no available commercial reagents to evaluate specific anti-ZIKV immune responses. Therefore, by necessity, recombinant ZIKV-envelope protein (rZIKV-E) was generated to support the assays performed in this study. To generate this reagent, a consensus ZIKV-Envelope sequence based on the ZIKV-prME vaccine consensus antigen was cloned into a pET30a *Escherichia coli* expression vector (FIG. 43A). The rZIKV-E antigen was produced in *E. coli* cultures, purified using nickel column chromatography and analysed using SDS-PAGE, which showed overexpressed proteins of the predicted size in lysate from rZIKV-E transfected bacteria that could be detected by western analysis using an anti-His tag antibody (FIG. 43B). The sera from mice immunised with the ZIKV-prME vaccine bound to rZIKV-Env that was used as a capture antigen in an ELISA (enzyme-linked immunosorbent assay; FIG. 43C). A commercial antibody (designated panflavivirus) that reacts to the envelope protein of multiple flaviviruses, also bound to rZIKV-E. Western analysis demonstrated that immune sera from ZIKV-prMEnv immunised mice specifically recognised rZIKV-E (FIG. 43D). These data indicate that the generated rZIKV-E reacted specifically with immune sera from ZIKV-prMEnv vaccinated mice, thus this recombinant protein was used for further immunogenicity studies.

Figure 37:
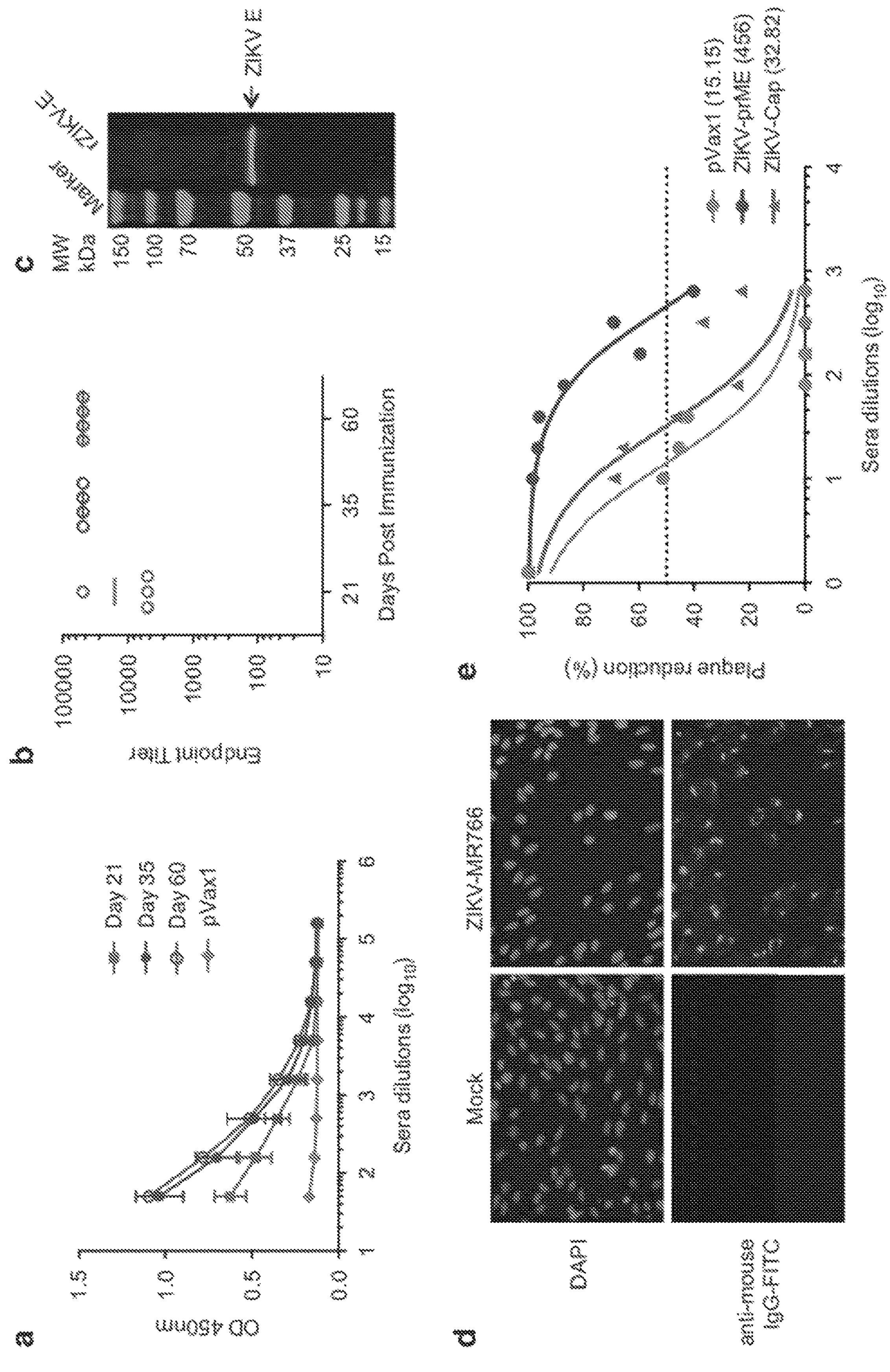
FIG. 37, comprising FIG. 37A through FIG. 37E depicts experimental results demonstrating that anti-ZIKV antibody responses are induced by ZIKV-prME vaccination.

Induction of Functional Humoral Responses in C57BL/6 Mice by the ZIKV-prME DNA Vaccine The ability of the consensus ZIKV-prMEnv vaccine to induce humoral immune responses in mice was evaluated. Groups of four C57BL/6 mice were immunised intramuscularly (i.m.) through electroporation-mediated delivery three times at 2-week intervals with 25 μg of either the empty control pVax1 or the consensus ZIKV-prMEnv vaccine plasmids. The sera were obtained from each immunised mouse and were tested by ELISA for ZIKV-specific IgG responses using immobilised rZIKV-E as the capture antigen. A significant increase in anti-ZIKV-specific IgG was observed on day 21 with a further boost in the sera IgG levels noted on day 35 (FIG. 37A). Day 60 sera from vaccinated animals show that elevated ZIKV-specific antibody responses were maintained long term following the final boost. Most importantly, the sera from vaccinated mice contained very high levels of rZIKV-E-specific antibodies as indicated by the end point titres (FIG. 37B). Additional assessment of the specificity of the vaccine-induced antibodies was performed by screening pooled sera from ZIKVprMEnv plasmid inoculated mice for its ability to detect rZIKV-E (envelope) by western analysis (FIG. 37C) and to stain ZIKV (MR766 strain)-infected cells by an immunofluorescence assay (FIG. 37D). The results from both these analyses confirmed specificity of the vaccine-induced humoral responses.

Furthermore, ZIKV-specific binding antibody responses were also assessed in mice immunised with plasmids encoding the prMEnv sequences from a Brazilian strain and the MR766 strain described above. Day 35 (1 week after third immunization) sera from pVax1− and both non-consensus vaccine-immunised mice were analysed by ELISA for binding to rZIKV-E. This analysis indicates that both MR766 and Brazil vaccine plasmids induced significant antibody binding, and that immunization with the consensus ZIKV-prME DNA vaccine generates an effective humoral response against rZIKV-E (FIGS. 43C and 43D).

A plaque reduction neutraliszation test (PRNT) assay was performed on pooled day 35 sera from mice immunised (3×) with either the control pVax1 plasmid, the consensus ZIKV-prMEnv plasmid vaccine or a consensus ZIKV-C (capsid) plasmid vaccine. The PRNT assay used was a method adapted from a previously described technique for analysing dengue virus, West Nile virus and other flaviviruses (Davis et al., 2001, J Virol 75:4040-7). As shown in FIG. 37E, ZIKV-prME vaccination yielded significant neutralization response with anti-ZIKV reciprocal PRNT50 dilution titres (inverse of the serum dilution at which 50% of the control ZIKV infection was inhibited) of 456±5, whereas mice vaccinated with the ZIKV-Cap DNA vaccine demonstrated titres (33±6) that were only minimally over pVax1 control plasmid vaccinated animals (titre=15±2).

Figure 44:
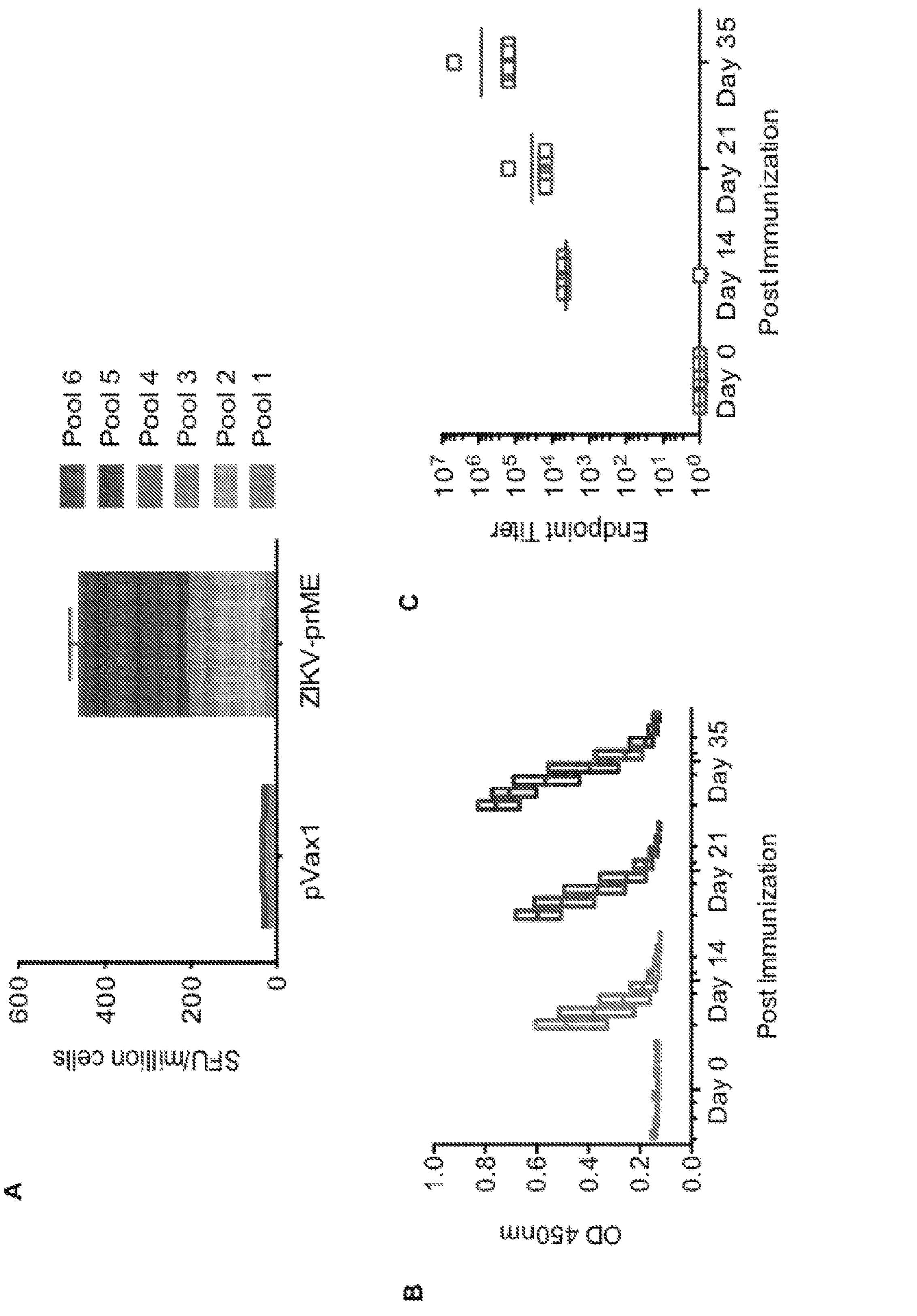
FIG. 44, comprising

Immune Responses and Protection Against ZIKV in Mice Lacking the Type I Interferon Receptor ($IFNAR^{-/-}$) Following Immunization with the ZIKV-prME DNA Vaccine Mechanisms of ZIKV-induced disease and immunity are poorly defined, and the protective versus the hypothetical pathogenic nature of the immune response to ZIKV infection is as yet unclear (Rossi et al., 2016, J Rop Med Hyg 94:1362-9). Most strains of mice are resistant to ZIKV infection, however, mice lacking IFN-α/β receptor ($IFNAR^{-/-}$) were found to be susceptible to infection and disease with most succumbing within 6-7 days post challenge (Lazear et al., 2016, Cell Host Microbe 19:720-30). The ability of the consensus ZIKV-prME plasmid vaccine to induce cellular and humoral immune responses in this mouse strain was investigated. Five to six week old female $IFNAR^{-/-}$ mice (n=4) were immunised i.m., with electroporation-mediated delivery, three times at 2-week intervals with either the control pVax1 plasmid or ZIKV prME vaccine plasmid vaccine. The serum was collected from immunised mice at days 0, 14, 21, and 35, and splenocytes were harvested from mice 1 week following the final immunization (day 35). The splenocytes from vaccine-immunised mice produced a clear cellular immune response as indicated by levels of SFU per $10^6$ cells in an ELISpot assay (FIG. 44A). The results from ELISA analysis, using rZIKV-E as a capture antigen, show detectable anti-ZIKV serum IgG by day 14 (titres of 1:1,000) and these levels were boosted with subsequent vaccinations with binding antibody titres reaching at least 1:100,000 (FIGS. 44B and 44C). By comparison, the $PRNT_{50}$ titre for the day 35 postimmunization samples was 1:60 (data not shown). The results indicate that $IFNAR^{-/-}$ mice immunised with the consensus ZIKV-prMEnv vaccine are capable of generating anti-ZIKV cellular and humoral immune responses supporting further study in this model of putative vaccine effects in a pathogenic challenge.

Figure 38:
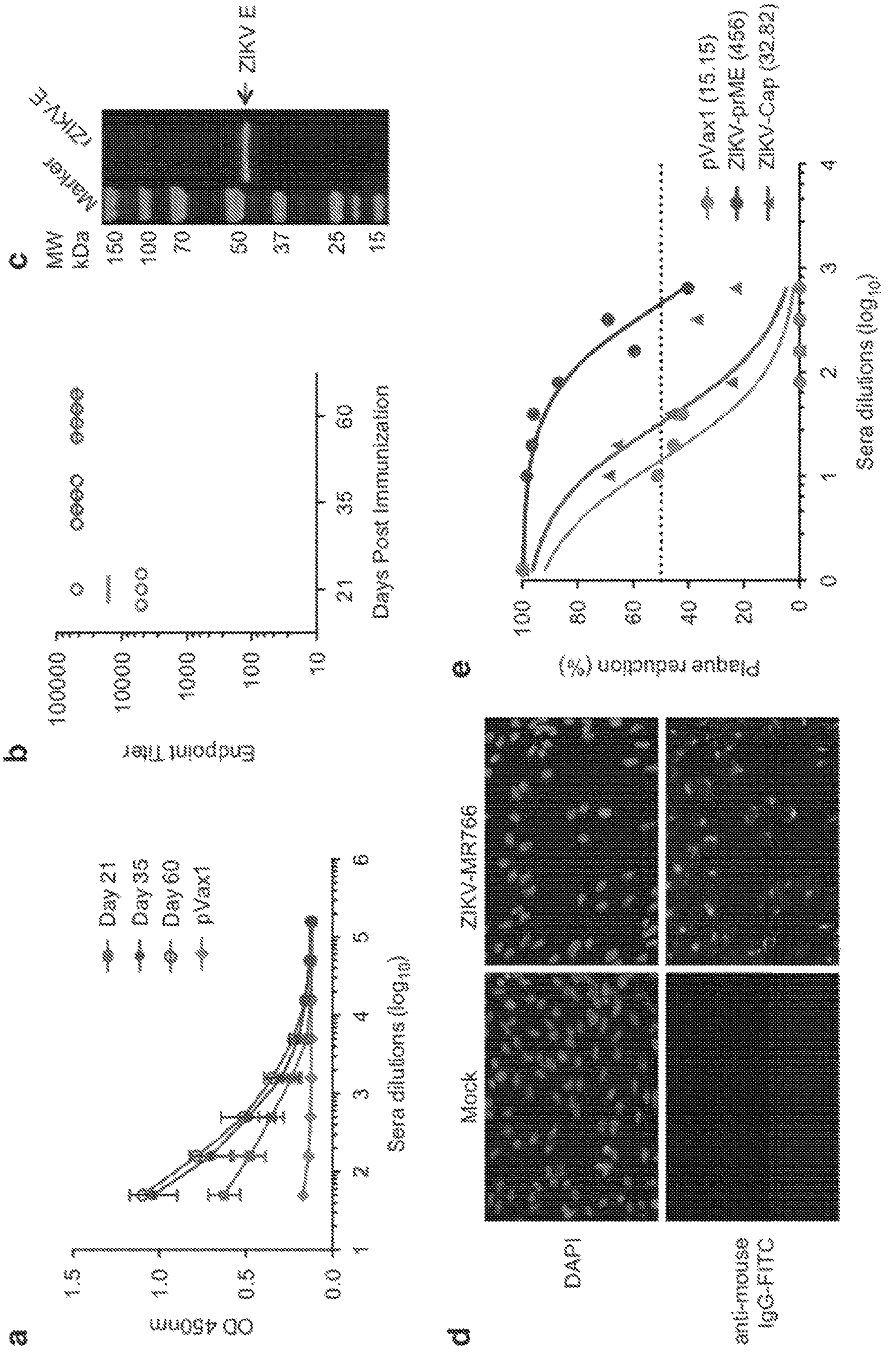
FIG. 38, comprising FIG. 38A through FIG. 38E depicts experimental results demonstrating Induction of ZIKV specific cellular immune responses following ZIKV-prME vaccination of non-human primates (NHPs).

ZIKV-Specific Functional Cellular and Humoral Responses Elicited by the ZIKV-prMEnv DNA Vaccine in Non-Human Primates NHPs were immunised by intradermal immunization using intradermal electroporation, based on recent studies showing potent immune responses in a lower voltage intradermal format (Hutnick et al., 2012, Hum gene Ther 23:943-50; Broderick et al., Mol Ther Nucleic Acids 1:e11). Rhesus macaques (RM; n=5/group) were administered 2.0 mg of vaccine plasmid intradermally with electroporation, with each animal vaccinated twice 4 weeks apart. The sera and peripheral blood mononuclear cells (PBMCs) were collected at day 0 (pre-immunization) and week 6 (2 weeks post second immunization). ELISpot analysis of pre-immunization and week 6 PBMCs ex vivo stimulated with the ZIKV-prMEnv peptide pools showed that ZIKV-prMEnv immunization induced robust anti-ZIKV T cell responses in RM (FIG. 38A).

Specific anti-ZIKV antibody responses in sera from vaccinated RM were assessed by ELISA. At week 6, rZIKV-Env-specific binding antibodies were detectable in animals vaccinated with ZIKVprMEnv (FIG. 27B). End point titres were determined for each animal at week 2 (after 1 immunization) and week 6 (after 2 immunizations; FIG. 38C). The ELISA results were confirmed by western blot analysis using RM sera from the individual vaccinated animals (FIG. 38D). The neutralization activity of the antibodies generated in RM at week 6 was evaluated by a PRNT50 assay. All the vaccinated monkeys had significant neutralization activity with anti-ZIKV reciprocal $PRNT_{50}$ dilution titres ranging from 161 to 1380 (average 501±224 standard error of the mean; FIG. 38E). PRNT titres did not directly correlate with ELISA titre (data not shown).

Figure 45:
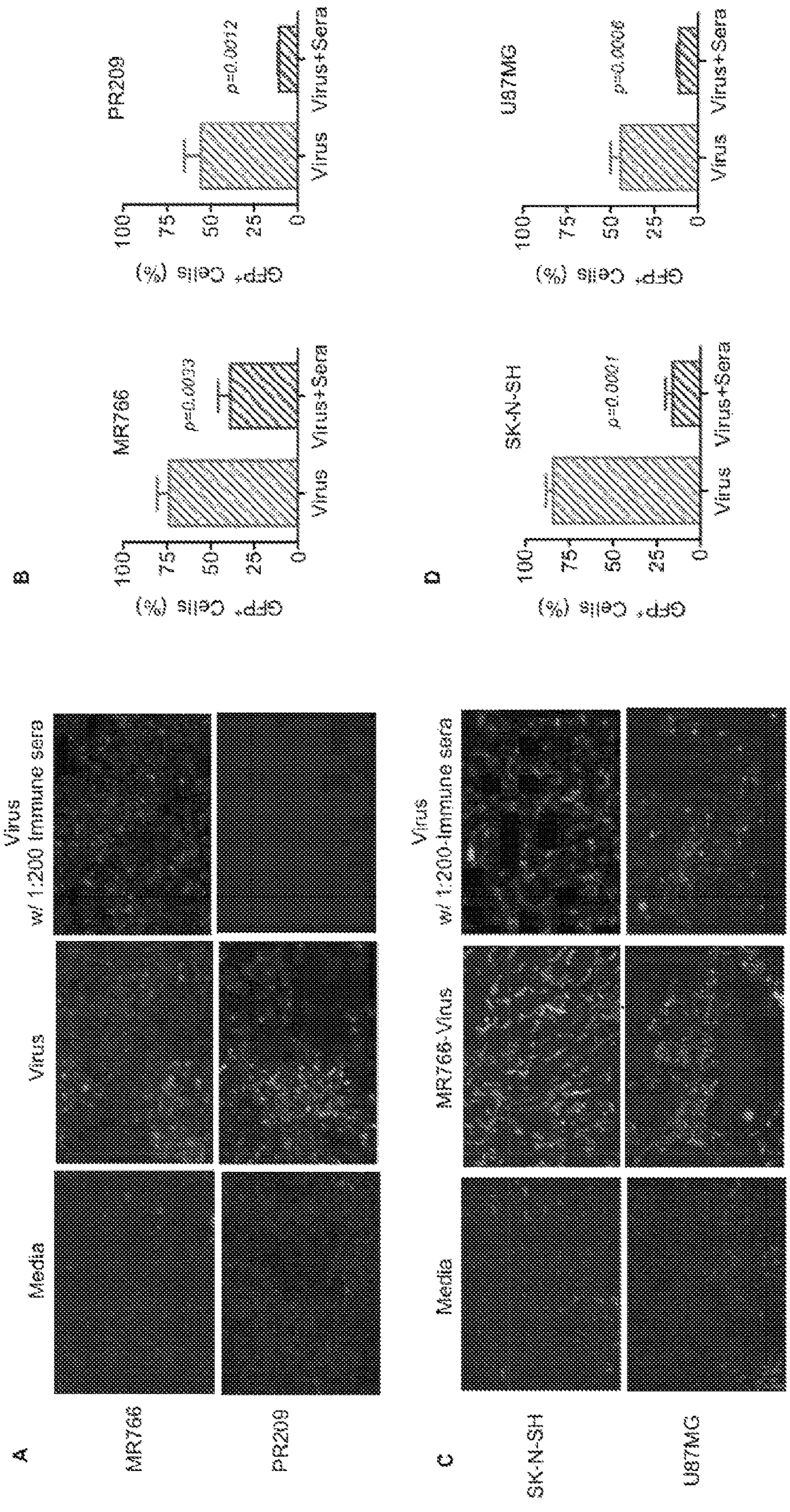
FIG. 45, comprising
Figure 46:
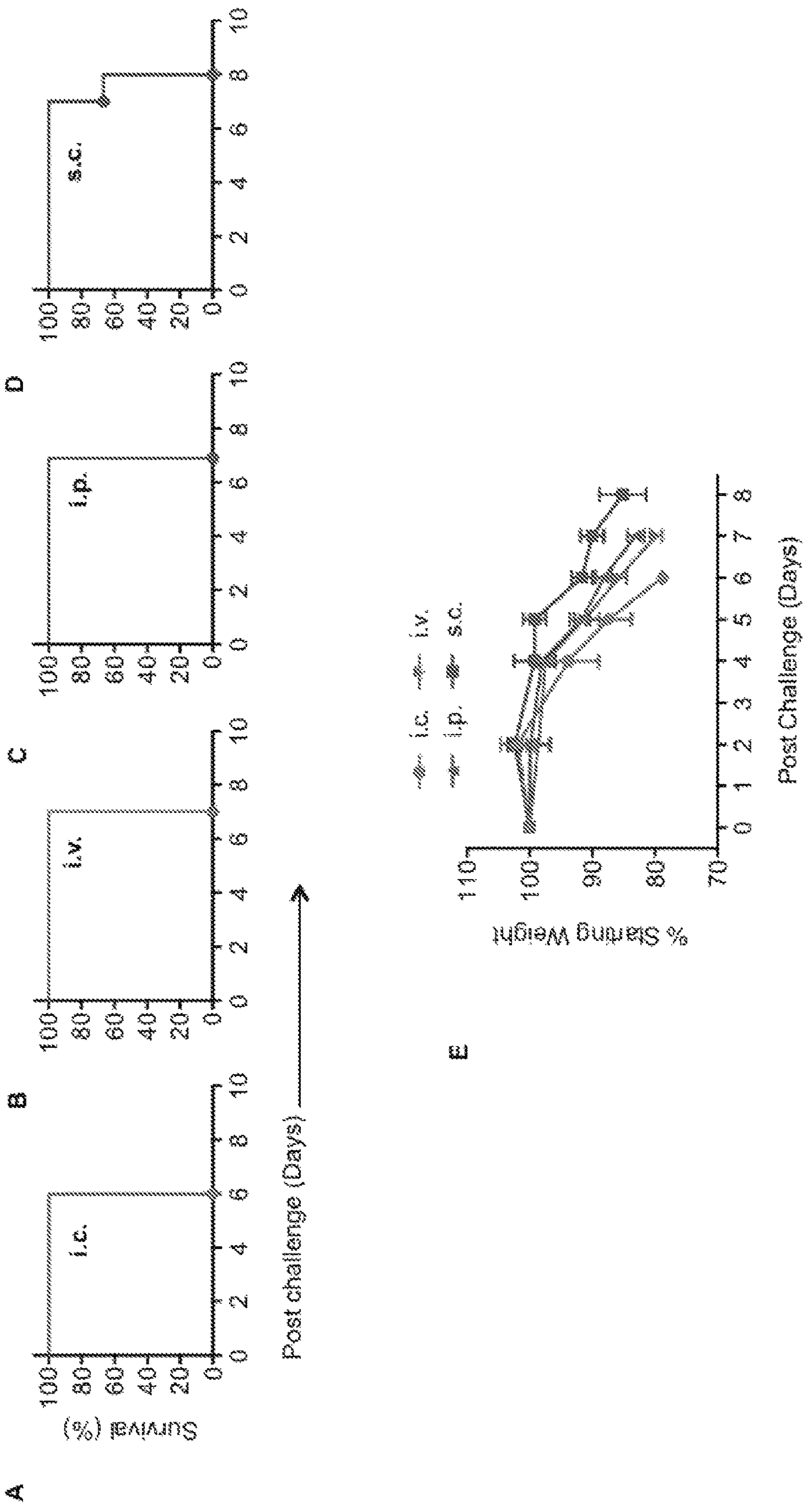
FIG. 46A through FIG. 46D, depicts experimental results demonstrating ZIKV is virulent to IFNAR$^{-/-}$ mice. These data confirm that ZIKV is virulent in IFNAR$^{-/-}$ resulting in morbidity and mortality.
FIG. 46E depicts the mouse weight change during the course of infection for all the routes.
Figure 47:
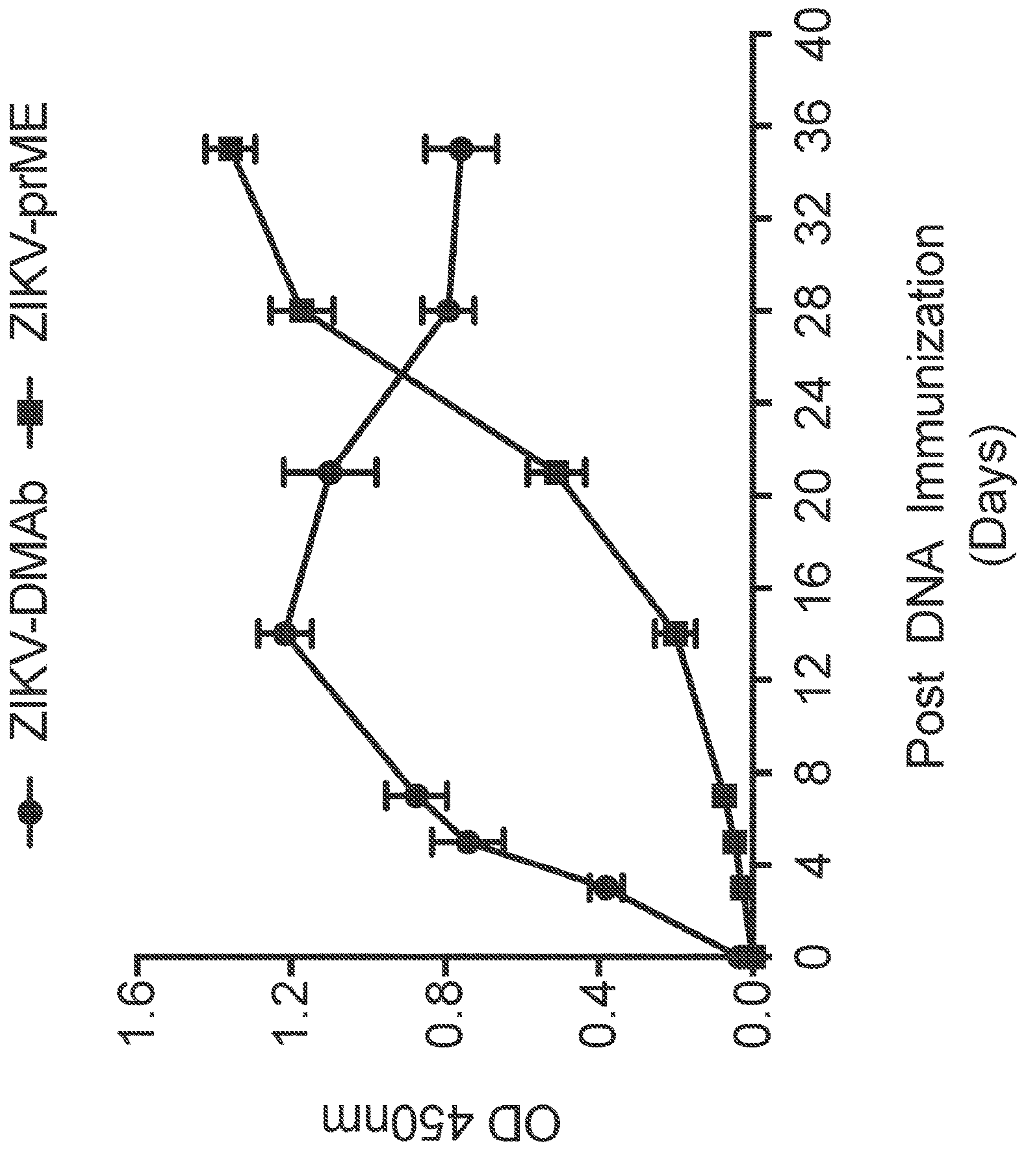
FIG. 47 depicts experimental results demonstrating the induction of persistent and systemic anti-Zika virus-Env antibodies. Anti-ZIKV antibody responses are induced by ZIKV-prME+ZV-DMAb immunization. A129 mice (n=4) were immunized i.m. three times with 25 μg of ZIKV-prME plasmid at 2-week intervals or one time with ZIKV-DMAb. Binding to recombinant ZIKV-Envelope was analyzed with sera from animals at different time points as indicated. Induction of persistent and systemic anti-ZIKV Env antibodies following a single ZV-IgG (human anti-ZIKV) injection and ZIKV-prME immunization (mouse anti-ZIKV Envelope). The data shown are representative of at least two separate experiments and mean OD450 values are shown ±SD.

The ability of the NHP vaccine immune sera to block ZIKV infection of Vero cells, neuroblastoma (SK-N-SH) or neural progenitor (U-87MG) cells in vitro was examined by IFA. ZIKV Q2 strains (MR766 or PR209) were pre-incubated in sera or dilution of NHP-immune sera and added to monolayers of each cell type. Four days post infection, ZIKV-positive cells were identified by IFA using pan flavirus antibody (FIGS. 45A-45C) and quantified the ZIKV-positive cells (FIGS. 45B-45D). The sera from ZIKA-prME vaccinated RM inhibited the ZIKV infection in each cell type.

Protection Against ZIKV Infection and Disease in $IFNAR^{-/-}$ Mice Following ZIKV-prME Immunization In exploratory studies, 5-6-week-old $IFNAR^{(-/-)}$ mice (n=10) were challenged with $1\times10^6$ plaque-forming units (PFU) of the ZIKV-PR209 isolate, administered by either subcutaneous (s.c.); intraperitoneal (i.p.); intracranial; or intravenous (i.v.) routes. After the challenge, all the animals were monitored for clinical signs of infection, which included routine measurement of body weight as well as inspection for other signs of a moribund condition such as hind limb weakness and paralysis. No change in the general appearance of the mice was observed during the first 4 days after inoculation. However, after the fourth day, the mice in each of the groups demonstrated reduced overall activity, decreased mobility and a hunched posture often accompanied by hind-limb weakness, decreased water intake and obvious weight loss. The animals succumbed to the infection between day 6 and day 8 regardless of the route of viral challenge (FIG. 46A-46E). On the basis of these data, the subsequent studies to evaluate ZIKV-prME-mediated protection in this model used the s.c. route for challenge.

Figure 39:
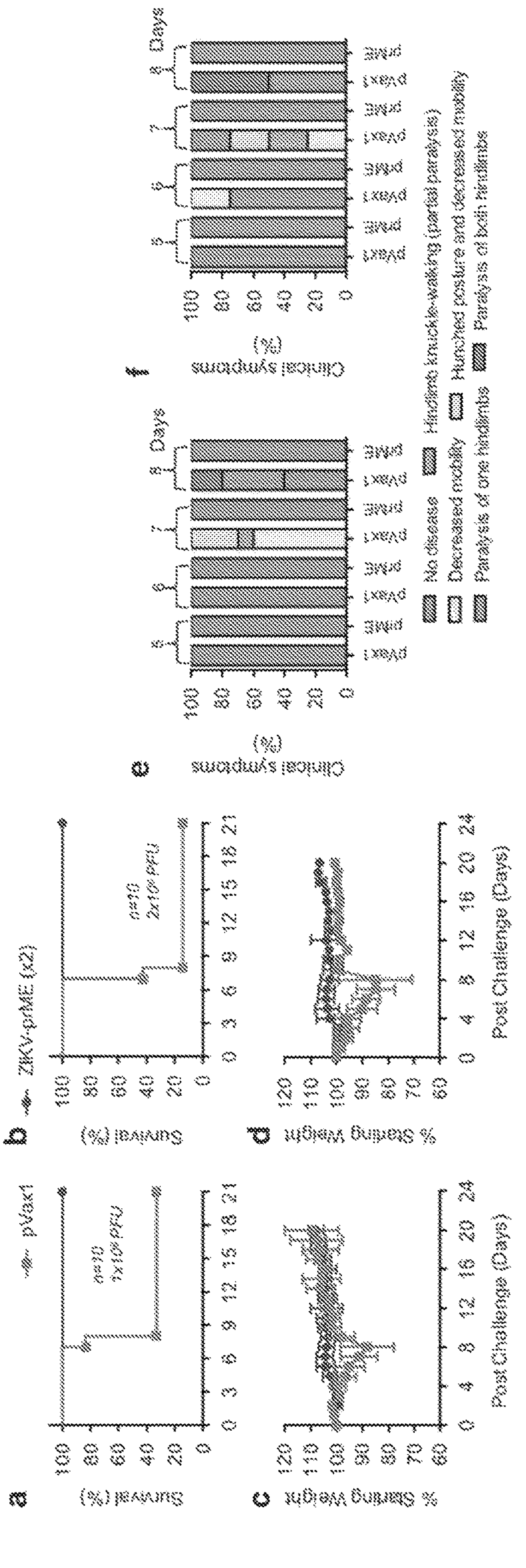
FIG. 39, comprising FIG. 39A through FIG. 39F depicts experimental results demonstrating survival data for immunised mice lacking the type I interferon α, β receptor following ZIKV infection.

The protective efficacy of the ZIKV-prMEnv vaccine was next evaluated in this $IFNAR^{-/-}$ mice model. Two groups of mice (n=10) were immunised (25 μg of vaccine) by the i.m. route, through electroporation-mediated delivery with the ZIKV-prME vaccine. Also, two groups of 10 mice were immunised by the i.m. route through electroporation-mediated delivery with the control pVax1 vector. The immunizations were performed two times, two weeks apart, and all the animals were challenged on day 21 (1 week post second immunization). One set of control and vaccinated mice received $1\times10^6$ PFU of ZIKV-PR209 by the s.c. route and the other set of each group were challenged with a total of $2\times10^6$ PFU ZIKV-PR209 by the s.c. route. At 3 weeks post challenge, 100% of all ZIKV-prME vaccinated animals survived, whereas only 30% of the single- or 10% of double-dose challenged controls survived (FIGS. 39A and 39B). In all the challenges, the vaccinated animals were without signs of disease including no evidence of weight loss (FIGS. 39C and 39D). The infection of control mice with ZIKV-PR209 virus produced a marked decrease in body weight along with decreased mobility, hunched posture, hindlimb knuckle walking and/or paralysis of one or both hind limbs (FIGS. 39E and 39F).

Figure 40:
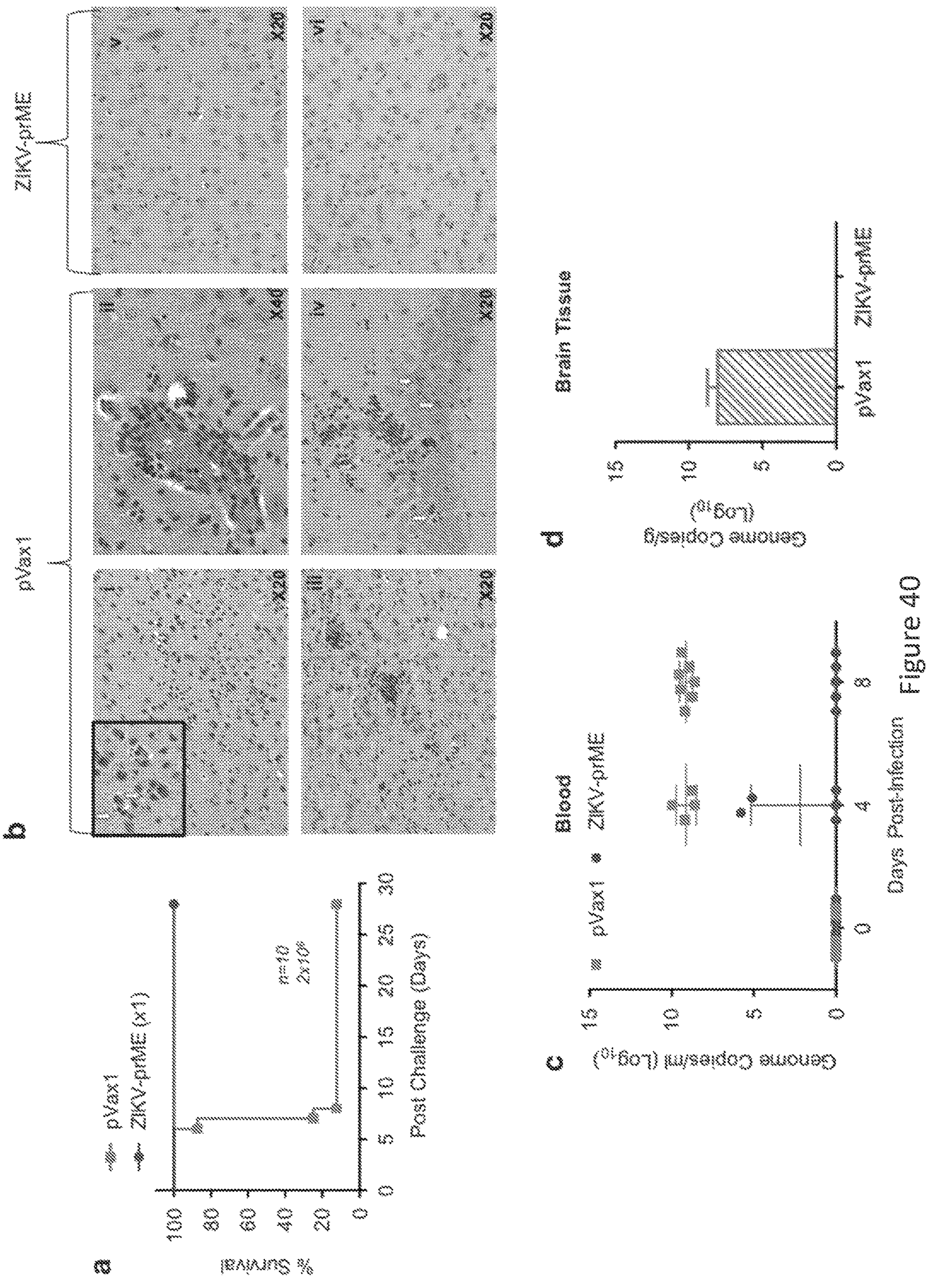
FIG. 40, comprising FIG. 40A through FIG. 40*d* depicts experimental results demonstrating single immunization with the ZIKV-prME vaccine provided protection against ZIKV challenge in mice lacking the type I interferon α, β receptor. The mice were immunised once and challenged with $2\times10^6$ plaque-forming units of ZIKV-PR209, 2 weeks after the single immunization. The survival curves depict 10 mice per group per experiment FIG. 40A demonstrates that the ZIKV-prME vaccine prevented ZIKA-induced neurological abnormalities in the mouse brain

The potential ability of a single immunization with the ZIKVprME DNA vaccine to protect $IFNAR^{-/-}$ mice from ZIKV challenge was evaluated. Groups of 10 mice were immunised i.m. with electroporation once with either control plasmid or ZIKV-prME vaccine and challenged 2 weeks later with a double total dose of $2\times10^6$PFU ZIKV-PR209 administration. Three weeks post challenge, 100% of the ZIKV-prME vaccinated animals survived, whereas only 10% of the control animals survived (FIG. 40A). To determine gross histopathological changes, brain tissue was sectioned into 5 μm-thick sagittal sections, stained for nuclear structures and counterstained for cytoplasmic structures using eosin (FIG. 40B). The mice were killed at day 7 or 8 post challenge for the analysis of histology and viral load. The ZIKV infection caused severe brain pathology in the mice. The unvaccinated control (pVax1) mice brain sections showed nuclear fragments within neutrophils (FIG. 40B); perivascular cuffing of vessel within the cortex, lymphocyte infiltration and degenerating cells of the cerebral cortex (FIG. 29B) and degenerating neurons within the hippocampus (FIG. 40B). In contrast, however, the ZIKV prME vaccinated animals presented with normal histopathology in brain tissues (FIG. 40B) supporting that protective antibodies induced by immunization with the synthetic ZIKA-prME vaccine could limit viral-induced disease in the brain. This observation demonstrates the potential for vaccination to protect the brain in this model. Consistent with the amelioration of body weight loss and mobility impairment in vaccinated mice following ZIKV challenge, a significantly lower viral load was noted in the blood (FIG. 40C) and brain (FIG. 40D) of the ZIKV-prME vaccinated animals compared with viral challenged pVax1 vaccinated animals in the high (2×$10^6$ PFU) dose challenge groups. Taken together, these data illustrate that ZIKV-prME DNA vaccine-mediated immune responses can protect mice against ZIKV challenge.

Passive Transfer of Anti-ZIKV Immune Sera Protects Mice Against ZIKV Infection

Figure 41:
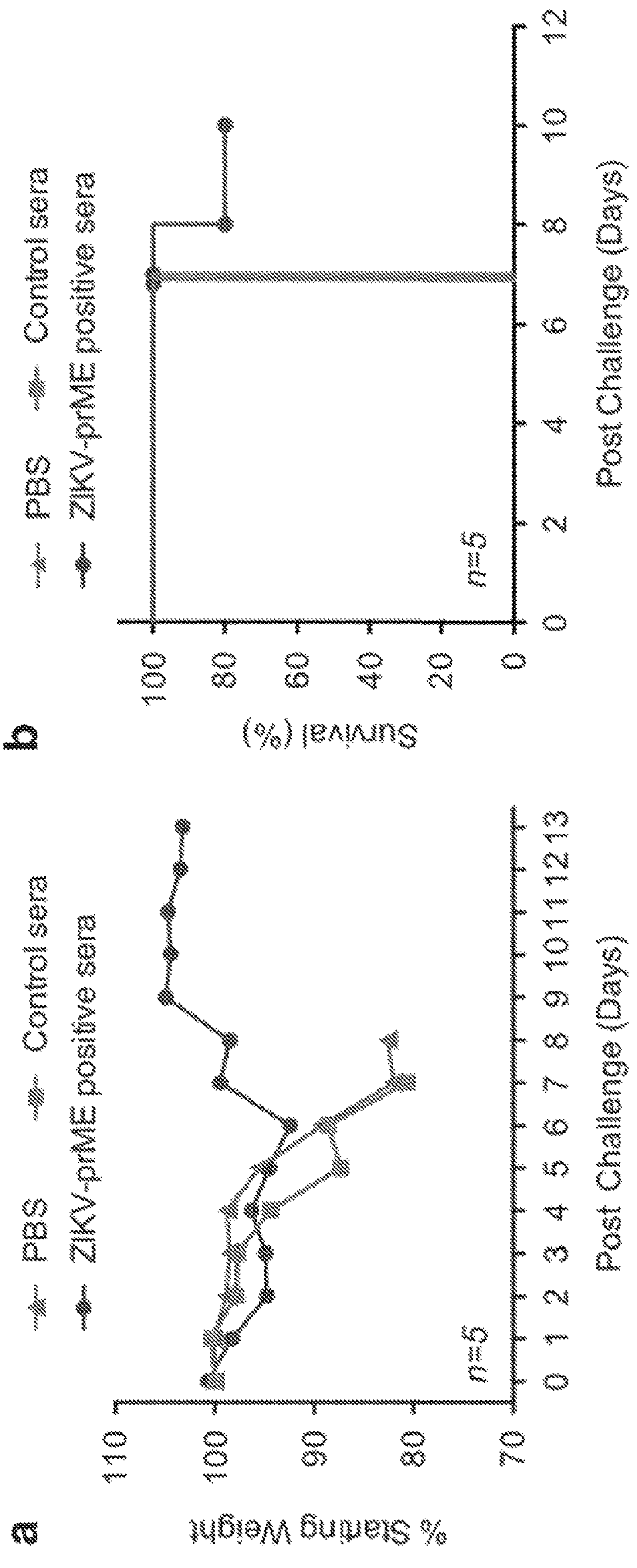
FIG. 41, comprising

Next, whether transfer of immune sera from ZIKVpr-MEnv vaccinated RM would prevent ZIKV-mediated pathogenesis in IFNAR$^{-/-}$ mice was tested. To this end, 150 μg equivalent IgG ($PRNT_{50}$≈1/160) from week 6 RM were adoptively transferred into IFNAR$^{-/-}$ mice 1 day after the ZIKV viral challenge. Two groups of control mice were included, one group receiving pre-immune sera from RM and the other group receiving phosphate-buffered saline (PBS). The mice that received PBS or control sera lost 15 to 25% of their original body weight during the course of infection, and all died 6-8 days post infection. When vaccine immune sera from RMs were transferred to infection-susceptible mice, the animals lost weight on day 3 and 4, but subsequently regained it beginning on day 5 and 80% ultimately survived infectious challenge (FIG. 41A) demonstrating the ability of the NHP sera transfer to confer protection against clinical manifestations of ZIKV infection following viral challenge (FIG. 41B). In repeated experiments performed to evaluate the efficacy of immune serum transfer in protection against challenge with ZIKV, the survival among ZIKV-prME immune sera recipients ranged from 80 to 100%. These studies show that anti-ZIKV vaccine immune sera had the ability to confer significant protection against ZIKV infection in the absence of an acquired adaptive anti-ZIKV immune response.

Vaccination with the ZIKV-prME Consensus Construct

Serious concerns have been raised by the recent spread of ZIKV and its associated pathogenesis in humans. Currently, there are no licensed vaccines or therapeutics for this emerging infectious agent. Very recently, a collection of experimental ZIKV vaccines have been shown to lower viral load post challenge in nonpathogenic animal infection models (Larocca et al., 2016, Nature 536:474-8; Abbink et al., 2016, Science 353:1192-32) These data are encouraging. In this regard, it is important to examine additional novel vaccine approaches targeting ZIKA in additional models. Here a synthetic DNA vaccine, designed to express a novel consensus ZIKV-prM and E antigen, was evaluated for immunogenicity following electroporation-enhanced immunization in mice and non-human primates. It was observed that ZIKV-prME DNA vaccination was immunogenic and generated antigen-specific T cells and binding and neutralising antibodies in both mice and NHPs. Uniquely, the NHPs were immunised with ZIKV-prME through electroporation by the intradermal route, which uses lower voltage and a smaller transfection area than i.m. electroporation, as has been recently described (Trimble et al., 2016, Lancet 386:2078-88) Further study of such approaches may provide advantages in clinical settings.

The ZIKV-prME consensus construct includes a designed change of the potential NXS/T motif, which removes a putative glycosylation site. Deletion of glycosylation at this site has been correlated with improved binding of EDE1 type bnAbs (broadly neutralising antibodies) against ZIKV-E protein (Muthumani et al., 2016, Sci Transl Med 7:301ra132). The antibody responses induced by the consensus ZIKV-prME appear as robust or in some cases superior in magnitude to those elicited by similarly developed ZIKV-prME-MR766 and ZIKV-prME-Brazil vaccines. These constructs were sequence matched with the original ZIKV-MR766 isolate or a recently circulating ZIKV strain from Brazil, respectively. While supportive, further study will provide more insight into the effects of such incorporated designed changes on induced immune responses.

As there are few pathogenic challenge models for ZIKV, the putative protective nature of the immune responses of the ZIKV-prME vaccine in C57BL/6 and IFNAR$^{-/-}$ mice was compared. Both the strains of mice responded with a robust humoral immune response when immunised with ZIKV-prME. The T-cell responses were also induced, but appear to be more robust in wild-type C57BL/6 compared with those induced in the IFNAR$^{-/-}$ animals, supporting a partial defect in innate to adaptive immunity transition as expected owing to the knock-out phenotype in the mouse. However, based on the induction of antigen specific immunity, the model was useful for evaluation of the impact of the vaccine on both infection and pathogenesis. A single vaccination with ZIKV-prME in IFNAR$^{-/-}$ mice was protective against disease and death in this model, including protection of neuro-pathogenesis. Flavivirus-neutralising antibodies directed against the Env antigen are thought to have a key role in protection against disease, an idea supported directly by passive antibody transfer experiments in animal models and indirectly by epidemiological data from prospective studies in geographical areas that are prone to mosquito-borne viral infections (Weaver et al., 2016, Antiviral Res 130:69-80; Roa et al., 2016, Lancet 387:843; Samarasekera et al., 2016, Lancet 387:521-4). Although immunization of IFNAR$^{-/-}$ mice with the ZIKV-prME DNA vaccine as well as serum transfer from immunised NHPs were protective in this murine model, the IFNAR$^{-/-}$ vaccinated as opposed to serum-transferred mice exhibited improved control of weight loss as an indication of control of pathogenesis. Although additional studies are needed, this result potentially suggests a role for the T-cell response in this aspect of protection in this model. In addition, it was observed that control IFNAR$^{-/-}$ mice who recovered from challenge remain viral positive by PCR for at least several weeks, suggesting an additional benefit of vaccination. This study supports the potential of vaccination and, in this case this synthetic DNA vaccination, to impact prevention of disease in a susceptible host.

Example 5

Rapid and Long-Term Immunity Elicited by DNA Encoded Antibody Prophylaxis and DNA Vaccination Against Zika Virus Vaccination is known to exhibit a lag phase before generation of immunity; thus, there is a gap of time during infection before an immune response is in effect. The following provides specific novel approaches that utilize the benefit of vaccines and the native immune response along with a rapid generation of effective immunity using the DNA synthetic antibodies or dMabs.

An antibody-based prophylaxis/therapy entailing the electroporation mediated delivery of synthetic plasmids, encoding biologically active anti-Zika virus envelope mAb (designated dMAb), is designed and evaluated for anti-viral efficacy as well as for the ability to overcome shortcomings inherent with conventional active vaccination by a novel passive immune-based strategy. One intramuscular injection of the ZIKV-dMAb produces antibodies in vivo more rapidly than active vaccination with an ZIKV-DNA vaccine. This dMAb neutralized diverse ZIKV clinical isolates and protected mice from viral challenge. Combinations of both afford rapid as well as long-lived protection.

A DNA based dMAb strategy induces rapid protection against an emerging viral infection, which can be combined with DNA vaccination providing a uniquely both short term and long-term protection against this emerging infectious disease. These studies have implications for pathogen treatment and control strategies.

dMAb IgG Quantification and Binding Assays

ELISA assays are performed with sera from subjects administered an ZIKV-dMAb to quantify expression kinetics and target antigen binding.

Analysis of dMAb Generated IgG

IgG expression of ZIKV infected cells are analyzed by western blot. For immunofluorescence analysis ZIKV infected cells are visually evaluated by confocal microscopy and quantitatively or semi-quantitatively analyzed.

dMAb DNA Plasmid Administration and In Vivo Analysis

Expression kinetics and functionality were evaluated in subjects following injection of control or ZIKV-dMAb. For studies that include the DNA vaccine, the ZIKV-DNA vaccine plasmid is administered.

Challenge Study

Subjects receive electroporation-enhanced injection of ZIKV-dMAb or control plasmids. The ZIKV-DNA vaccine was delivered as described above. After DNA delivery, subjects are challenged with ZIKV. The animals are monitored for survival and signs of infection. Serum samples are collected for cytokine quantification and other immune analysis. Blood samples are collected from after infection and viremia levels are measured.

Neutralizing Antibody Analysis

Anti-ZIKV neutralizing antibody titers from subjects administered ZIKV-dMAb are determined. Neutralization titers may be calculated as the reciprocal of the highest dilution mediating 100% reduction of the cytopathic effects in the cells.

Cytokine Quantitative Analysis

Sera is collected from ZIKV-dMAb, and ZIKV-DNA vaccine injected subjects as well as ZIKV challenged subjects. TNF-$\alpha$, IL-1$\beta$ and IL-6 sera cytokine levels are measured.

Anti-ZIKV dMAbs Design and Confirmation of Expression

The optimized synthetic plasmids constructed from the anti-ZIKV-neutralizing mAb were designed for the IgG and Fab antibodies. Cells are transfected with either the ZIKV-IgG plasmid or the ZIKV-Fab (VL, VH, or combined) plasmids to validate expression in vitro. The ZIKV-Fab and ZIKV-IgG expressed antibodies in the muscle that appeared to be properly assembled and biologically functional in vitro.

In Vivo Expression and Quantification of Anti-ZIKV dMAb

Following confirmation of in vitro expression, the ability of ZIKV-Fab or ZIKV-IgG to produce anti-ZIKV antibodies in vivo is measured. Both constructs generate mAbs. Subjects are administered either ZIKV-IgG or ZIKV-Fab, and sera antibody levels are evaluated through a binding ELISA. Sera collected after injection from both ZIKV-IgG and ZIKV-Fab bind to ZIKV protein but not to an unrelated control antigen. These data indicate that in vivo produced anti-ZIKV antibodies from ZIKV-IgG or ZIKV-Fab constructs have similar biological characteristics to conventionally produced antigen specific antibodies.

In Vivo Specificity and Broadly Neutralizing Activity in Sera from Anti-ZIKV dMAb Injected Subjects The anti-ZIKV dMAb generated mAbs are tested for binding specificity and anti-ZIKV neutralizing activity. Sera antibodies bind to ZIKV-infected cells. There is a strong specificity of the antibody generated from the anti-ZIKV dMAb plasmid.

Furthermore, the anti-ZIKV neutralizing activity in sera from subjects that received anti-ZIKV dMAb is measured against that in ZIKV strains. Sera from anti-ZIKV dMAb—injected subjects effectively neutralize ZIKV isolates, demonstrating that a single injection can produce significant neutralizing levels of human anti-ZIKV IgG. Thus, antibodies produced in vivo by anti-ZIKV dMAb constructs have relevant biological activity (ie, binding and neutralizing activity against ZIKV).

Anti-ZIKV dMAb Injection Protects Mice from Lethal ZIKV Challenge

To determine whether antibodies generated from anti-ZIKV dMAb provide protection against early exposure to ZIKV, groups of 10 subjects receive of a control or anti-ZIKV dMAb on day 0. Each group subsequently is challenged subcutaneously with virus to mimic natural ZIKV infection. Subject survival and weight changes are subsequently recorded. Anti-ZIKV dMAb plasmids confer protective immunity.

The longevity of immune protection is next evaluated. A second group of subjects are challenged with ZIKV after injection with anti-ZIKV dMAb, or control plasmid on day 0. Subjects are monitored for survival. Anti-ZIKV dMAb provides a more durable degree of immune protection.

Anti-ZIKV dMAb protects subjects from both subcutaneous viral challenge and intranasal viral challenge compared with control-injected subjects, demonstrating that anti-ZIKV dMAbs can protect against systemic and mucosal infection.

An efficacy study comparing the protective efficacy of anti-ZIKV dMAb administration vs a ZIKV-DNA vaccine (ZIKV-DNA) is next performed. A novel consensus-based DNA vaccine was developed by our laboratory and is capable of providing protection against ZIKV challenge. The DNA vaccine also induced both measurable cellular immune responses, as well as potent neutralizing antibody responses. Groups of subjects are administered a single injection of anti-ZIKV dMAb, ZIKV-DNA, or the pVax1, followed by viral challenge. Anti-ZIKV dMAb confers protective immunity more rapidly than the ZIKV-DNA vaccine.

Comparison Between In Vivo Protective Immunity Conferred by Anti-ZIKV dMAb Administration and ZIKV-DNA Vaccination Next, a long-term ZIKV challenge protection study was performed following vaccination with the ZIKV-DNA vaccine or administration of anti-ZIKV dMAb on day 0. ZIKV-DNA confers longer protective immunity than anti-ZIKV dMAb.

Co-Delivery of Anti-ZIKV dMAb and the ZIKV-DNA Vaccine Produces Systemic Humoral Immunity, Cell-Mediated Immunity, and Protection In Vivo One potential issue of combining antibody delivery with vaccination approaches is that the antibodies can neutralize many traditional vaccines and thus are incompatible platforms. The effect of co-administration of anti-ZIKV dMAb and ZIKV-DNA on subject survival in the context of ZIKV challenge was is evaluated. Subjects are administered at day 0 anti-ZIKV dMAb and ZIKV-DNA. Subsequently, some animals are challenged with ZIKV at day 2 and the others at day 35. Survival in these groups is followed as a function of time. Anti-ZIKV dMAb mediates protection from infection, with the survival percentage decreasing to approximately 30% by 4 days after challenge in control (pVax1) animals.

Both IgG (induced by anti-ZIKV dMAb and ZIKV-DNA vaccine are detected. Anti-ZIKV dMAb mediates rapid protection from infection and death after ZIKV challenge.

Figure 8:
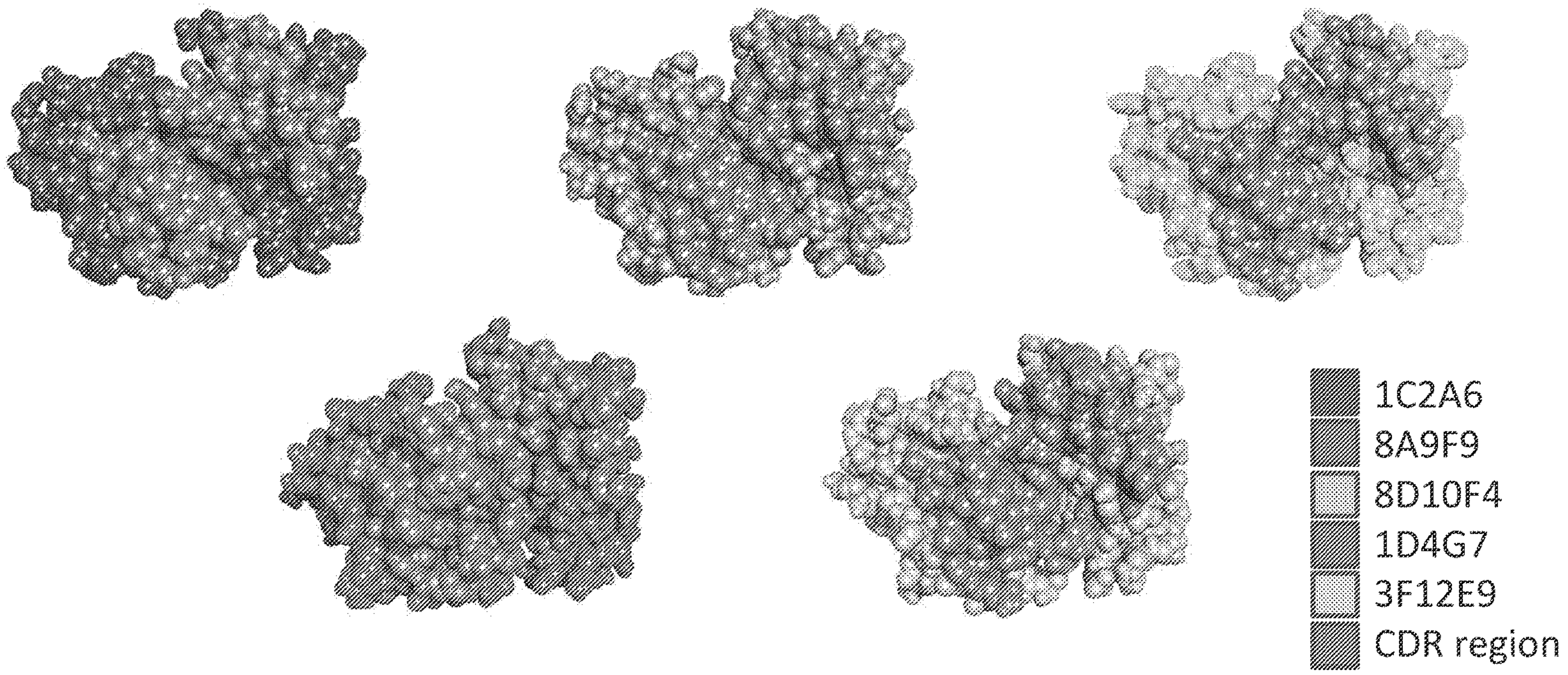
FIG. 8 depicts a comparison of model CDR regions

Furthermore, T-cell responses induced in subjects injected with Anti-ZIKV dMAb, ZIKV-DNA, or anti-ZIKV dMAb plus ZIKV-DNA are evaluated. ZIKV-DNA elicits strong T-cell responses irrespective of co-delivery with anti-ZIKV dMAb, showing the lack of interference of these approaches. Conversely, animals administered only anti-ZIKV dMAb do not develop T-cell responses. Both anti-ZIKV dMAb and ZIKV-DNA vaccine can be administered simultaneously without reciprocal interference, providing immediate and long-lived protection via systemic humoral and cellular immunity (FIG. 8).

Electroporation-Mediated Delivery of Optimized DNA Plasmids for the In Vivo Rapid Production of Biologically Functional mAbs Subjects administered anti-ZIKV dMAbs are fully protected from viral challenge shortly after administration, whereas subjects do not survive infection following a single immunization with ZIKV-DNA vaccine, owing presumably to an insufficient time to mount protective immunity. However, ZIKV-DNA provides complete protection after an immunization regimen followed by challenge at later time points. A similar level of protection occurs in subjects administered a single dose of anti-ZIKV dMAbs, although protection wanes over time. Notably, the co-delivery of anti-ZIKV dMAbs and ZIKV-DNA produces rapid and persistent humoral and cellular immunity, suggesting that a combination approach can have additive or synergistic effects. Importantly, co-delivery of anti-ZIKV dMAbs and ZIKV-DNA are not antagonistic in terms of the development of short- or long-term protective immune responses.

Example 6

Sequences

SEQ ID NO:1 amino acid sequence of ZIKV-3F12E9-VH

SEQ ID NO:2 amino acid sequence of ZIKV-3F12E9-VL

SEQ ID NO:3 amino acid sequence of ZIKV-8A9F9-VH

SEQ ID NO:4 amino acid sequence of ZIKV-8A9F9-VL

SEQ ID NO:5 amino acid sequence of ZIKV-8D10F4-VH

SEQ ID NO:6 amino acid sequence of ZIKV-8D10F4-VL

SEQ ID NO:7 amino acid sequence of ZIKV-IC2A6-VH

SEQ ID NO:8 amino acid sequence of ZIKV-IC2A6-VL

SEQ ID NO:9 amino acid sequence of ZIKV-ID4G7-VH

SEQ ID NO:10 amino acid sequence of ZIKV-ID4G7-VL

SEQ ID NO: 11 Human anti-Zika (3F12E9)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 12 Human anti-Zika (3F12E9)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 13 Human anti-Zika (8A9F9)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 14 Human anti-Zika (8A9F9)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 15 Human anti-Zika (8D10F4)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 16 Human anti-Zika (8D10F4)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 17 Human anti-Zika (1D4G7)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 18 Human anti-Zika (1D4G7)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 19 Human anti-Zika (8A9F9)-IgG1: Human IgG heavy signal peptide-VH-CH1-Hinge Region-CH2 (with LALA variant at 4th and 5th residue)-CH3-custom Furin cleavage site-'GSG' Linker and P2A Peptide-human kappa light chain signal peptide-VL-CL (kappa)

SEQ ID NO: 20 Human anti-Zika (3F12E9)-IgG1: Human IgG heavy signal peptide-VH-CH1-Hinge Region-CH2 (with LALA variant at 4th and 5th residue)-CH3-custom Furin cleavage site-'GSG' Linker and P2A Peptide-human kappa light chain signal peptide-VL-CL (kappa)

SEQ ID NO: 21 Human anti-Zika (IC2A6)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 22 Human anti-Zika (IC2A6)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

SEQ ID NO: 23, consensus Zika IgE Leader-prME protein

SEQ ID NO: 24 consensus Zika IgE Leader-prME (construct 1) DNA

SEQ ID NO:25 consensus Zika IgE Leader-prME (construct 1) protein

SEQ ID NO:26, consensus Zika IgE Leader-NS1 DNA

SEQ ID NO:27, consensus Zika IgE Leader-NS1 protein

SEQ ID NO: 28, consensus Zika IgE Leader-capsid DNA

SEQ ID NO:29, consensus Zika IgE Leader-capsid protein

SEQ ID NO:30, Zika IgE Leader-prME MR766 DNA

SEQ ID NO: 31, Zika IgE Leader-prME MR766 protein

SEQ ID NO: 32, Zika IgE Leader-prME Brazil DNA

SEQ ID NO: 33, Zika IgE Leader-prME Brazil protein

SEQ ID NO:34 consensus Zika IgE Leader-NS1 DNA (pGX7211)

SEQ ID NO:35 consensus Zika IgE Leader-capsid DNA (pGX7212)

SEQ ID NO:36 Zika IgE Leader-prME Brazil DNA (pGX7213)

SEQ ID NO:37 Zika IgE Leader-prME MR766 DNA (pGX7214)

SEQ ID NO:38 Zika PreEnv (MR766) w/out capsid DNA (pGX7210)

SEQ ID NO:39 Zika PreEnv (MR766) w/out capsid Protein (pGX7210)

SEQ ID NO: 40, IgE leader

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding one or more synthetic antibodies, wherein the nucleic acid molecule comprises at least one selected from the group consisting of a) a nucleotide sequence encoding a variable light (VL) chain of an anti-ZIKV envelope (E) protein synthetic antibody, wherein the encoded sequence is selected from the group consisting of SEQ ID NO:2, and an antigen binding fragment thereof that retains all three LCDR regions thereof;

b) a nucleotide sequence encoding a variable heavy (VH) chain of an anti-ZIKV E protein synthetic antibody, wherein the encoded sequence is selected from the group consisting of SEQ ID NO:1, and an antigen binding fragment thereof that retains all three HCDR regions; and c) a nucleotide sequence encoding a combination of a VL chain and VH chain of an anti-ZIKV envelope (E) protein synthetic antibody, wherein the encoded sequence is selected from the group consisting of SEQ ID NO:11, SEQ ID NO:12, SEQ ID NO:20, and an antigen binding fragment thereof that retains at least all three HCDR regions and all three LCDR regions.

2. The nucleic acid molecule of claim 1, further comprising a nucleotide sequence encoding a cleavage domain.

3. The nucleic acid molecule of claim 1, wherein the nucleic acid molecule comprises a nucleotide sequence encoding an anti-ZIKV E antibody.

4. The nucleic acid molecule of claim 1, wherein the anti-ZIKV E antibody comprises an amino acid sequence selected from the group consisting of SEQ ID NO:11, SEQ ID NO:12 and SEQ ID NO:20, or a fragment thereof comprising at least 85% of the full length sequence.

5. The nucleic acid molecule of claim 1, wherein the anti-ZIKV E protein synthetic antibody comprises a variable heavy (VH) chain and a variable light (VL) chain.

6. The nucleic acid molecule of claim 5, wherein anti-ZIKV E protein synthetic antibody VH chain comprises a sequence selected from the group consisting of SEQ ID NO:1, and a fragment thereof comprising at least 85% of the full length sequence.

7. The nucleic acid molecule of claim 5, wherein anti-ZIKV E protein synthetic antibody VL chain comprises a sequence selected from the group consisting of SEQ ID NO:2, and a fragment thereof comprising at least 85% of the full length sequence.

8. The nucleic acid molecule of claim 1, wherein the nucleotide sequence encodes a leader sequence.

9. The nucleic acid molecule of claim 1, wherein the nucleic acid molecule comprises an expression vector.

10. A composition comprising the nucleic acid molecule of claim 1.

11. The composition of claim 10, further comprising a pharmaceutically acceptable excipient.

12. A method of inducing an immune response comprising administering the composition of claim 10 to an individual in need thereof in an amount effective to induce passive immunity in said individual.

13. The method of claim 12, wherein the immune response is persistent.

14. The method of claim 12, wherein the immune response is systemic.

* * * * *

SEQUENCE LISTING

```
<160> NUMBER OF SEQ ID NOS: 40

<210> SEQ ID NO 1
<211> LENGTH: 133
<212> TYPE: PRT
<213> ORGANISM: Artificial Sequence
<220> FEATURE:
<223> OTHER INFORMATION: ZIKV-3F12E9-VH

<400> SEQUENCE: 1

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Arg Tyr Gly Met Ser Trp Gly Arg Gln Thr Pro Asp Lys Arg Leu
    50                  55                  60

Glu Trp Val Ala Thr Ile Ser Ser Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Ser Trp Phe Ala Tyr Trp Gly Arg Gly Thr Leu
        115                 120                 125

Val Thr Val Ser Ala
    130


<210> SEQ ID NO 2
<211> LENGTH: 132
<212> TYPE: PRT
<213> ORGANISM: Artificial Sequence
<220> FEATURE:
<223> OTHER INFORMATION: ZIKV-3F12E9-VL

<400> SEQUENCE: 2

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80
```

-continued

```
Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro His Thr Phe Gly Gly Gly Thr Lys
        115                 120                 125

Leu Glu Ile Lys
    130


<210> SEQ ID NO 3
<211> LENGTH: 134
<212> TYPE: PRT
<213> ORGANISM: Artificial Sequence
<220> FEATURE:
<223> OTHER INFORMATION: ZIKV-8A9F9-VH

<400> SEQUENCE: 3

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Ser Asp Gly Tyr Tyr Ser His Trp Gly Gln Gly Thr
        115                 120                 125

Ser Val Thr Val Ser Ser
    130


<210> SEQ ID NO 4
<211> LENGTH: 131
<212> TYPE: PRT
<213> ORGANISM: Artificial Sequence
<220> FEATURE:
<223> OTHER INFORMATION: ZIKV-8A9F9-VL

<400> SEQUENCE: 4

Met Lys Leu Pro Val Arg Leu Leu Val Leu Met Phe Trp Ile Pro Ala
1               5                   10                  15

Ser Arg Ser Asp Val Val Met Thr Gln Ile Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
```

```
            100                 105                 110

Phe Gln Ser Thr His Val Pro Pro Thr Phe Gly Gly Gly Thr Lys Leu
        115                 120                 125

Glu Ile Lys
    130


<210> SEQ ID NO 5
<211> LENGTH: 82
<212> TYPE: PRT
<213> ORGANISM: Artificial Sequence
<220> FEATURE:
<223> OTHER INFORMATION: ZIKV-8D10F4-VH

<400> SEQUENCE: 5

Met Asn Phe Gly Leu Ser Leu Ile Phe Leu Val Leu Ile Leu Lys Gly
1               5                   10                  15

Val Lys Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Ile Tyr Tyr Pro
65                  70                  75                  80

Asp Thr


<210> SEQ ID NO 6
<211> LENGTH: 131
<212> TYPE: PRT
<213> ORGANISM: Artificial Sequence
<220> FEATURE:
<223> OTHER INFORMATION: ZIKV-8D10F4-VL

<400> SEQUENCE: 6

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Phe His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Ser Gln Ser Thr His Val Pro Pro Thr Phe Gly Gly Gly Thr Lys Leu
        115                 120                 125

Glu Ile Lys
    130


<210> SEQ ID NO 7
<211> LENGTH: 134
<212> TYPE: PRT
<213> ORGANISM: Artificial Sequence
<220> FEATURE:
<223> OTHER INFORMATION: ZIKV-IC2A6-VH
```

<400> SEQUENCE: 7

Met Asn Phe Gly Leu Ser Leu Ile Phe Leu Val Leu Ile Leu Lys Gly
1 5 10 15

Val Gln Cys Glu Val Gln Leu Val Glu Ser Gly Gly Gly Leu Val Lys
20 25 30

Pro Gly Gly Ser Leu Lys Leu Ser Cys Ala Ala Ser Gly Phe Thr Phe
35 40 45

Ser Ser Tyr Ala Met Ser Trp Val Arg Gln Ser Pro Glu Lys Arg Leu
50 55 60

Glu Trp Val Ala Glu Ile Ser Ser Gly Gly Ser Tyr Thr Tyr Tyr Pro
65 70 75 80

Asp Thr Val Thr Gly Arg Phe Thr Ile Ser Arg Asp Asn Ala Lys Asn
85 90 95

Thr Leu Tyr Leu Glu Met Ser Ser Leu Arg Ser Glu Asp Thr Ala Met
100 105 110

Tyr Tyr Cys Ala Ser Asp Gly Tyr Tyr Ser His Trp Gly Gln Gly Thr
115 120 125

Ser Val Thr Val Ser Ser
130

<210> SEQ ID NO 8
<211> LENGTH: 131
<212> TYPE: PRT
<213> ORGANISM: Artificial Sequence
<220> FEATURE:
<223> OTHER INFORMATION: ZIKV-IC2A6-VH

<400> SEQUENCE: 8

Met Lys Leu Pro Val Arg Leu Leu Val Leu Met Phe Trp Ile Pro Ala
1 5 10 15

Ser Ser Ser Asp Val Val Met Thr Gln Thr Pro Leu Ser Leu Pro Val
20 25 30

Cys Leu Gly Asp Gln Ala Ser Ile Ser Cys Arg Ser Ser Gln Ser Leu
35 40 45

Val His Ser Asn Gly Asn Thr Tyr Leu His Trp Tyr Leu Gln Lys Pro
50 55 60

Gly Gln Ser Pro Lys Leu Leu Ile Tyr Lys Val Ser Asn Arg Phe Ser
65 70 75 80

Gly Val Pro Asp Arg Phe Ser Gly Ser Gly Ser Gly Thr Asp Phe Thr
85 90 95

Leu Lys Ile Ser Arg Val Glu Ala Glu Asp Leu Gly Val Tyr Phe Cys
100 105 110

Phe Gln Ser Thr His Val Pro Pro Thr Phe Gly Gly Gly Thr Lys Leu
115 120 125

Glu Ile Lys
130

<210> SEQ ID NO 9
<211> LENGTH: 146
<212> TYPE: PRT
<213> ORGANISM: Artificial Sequence
<220> FEATURE:
<223> OTHER INFORMATION: ZIKV-ID4G7-VH

<400> SEQUENCE: 9

Met Ala Trp Val Trp Thr Leu Leu Phe Leu Met Ala Ala Ala Gln Ser
1 5 10 15

```
Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Glu Ile Ser Lys Ile Tyr Tyr Tyr Gly Ser Ser
        115                 120                 125

Tyr Glu Asn Gly Met Asp Tyr Trp Gly Gln Gly Thr Ser Val Thr Val
    130                 135                 140

Ser Ser
145


<210> SEQ ID NO 10
<211> LENGTH: 131
<212> TYPE: PRT
<213> ORGANISM: Artificial Sequence
<220> FEATURE:
<223> OTHER INFORMATION: ZIKV-ID4G7-VL

<400> SEQUENCE: 10

Met Glu Thr Asp Thr Leu Leu Leu Trp Val Leu Leu Leu Trp Val Pro
1               5                   10                  15

Gly Ser Thr Gly Asn Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Phe Gly Asn Ser Phe Met His Trp Phe Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Ala Thr Tyr Tyr Cys
            100                 105                 110

Gln Gln Asn Asn Glu Tyr Pro Tyr Thr Phe Gly Gly Gly Thr Lys Leu
        115                 120                 125

Glu Ile Lys
    130


<210> SEQ ID NO 11
<211> LENGTH: 728
<212> TYPE: PRT
<213> ORGANISM: Artificial Sequence
<220> FEATURE:
<223> OTHER INFORMATION: Human anti-Zika (3F12E9)-IgG4: Human IgG heavy
      signal peptide-VH-CH1-Hinge Region-CH2-CH3-custom Furin cleavage
      site-'GSG' Linker and P2A Peptide-human kappa light chain signal
      peptide-VL-CL (kappa)

<400> SEQUENCE: 11

Met Asp Trp Thr Trp Arg Ile Leu Phe Leu Val Ala Ala Ala Thr Gly
```

-continued

```
1               5                   10                  15

Thr His Ala Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Arg Tyr Gly Met Ser Trp Gly Arg Gln Thr Pro Asp Lys Arg Leu
    50                  55                  60

Glu Trp Val Ala Thr Ile Ser Ser Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Ser Trp Phe Ala Tyr Trp Gly Arg Gly Thr Leu
        115                 120                 125

Val Thr Val Ser Ala Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
    210                 215                 220

Thr Lys Val Asp Lys Arg Val Ser Pro Asn Met Val Pro His Ala His
225                 230                 235                 240

His Ala Gln Ala Pro Glu Phe Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430
```

```
Gly Asn Val Phe Ser Cys Ser Val Met His Glu Ala Leu His Asn His
        435                 440                 445

Tyr Thr Gln Lys Ser Leu Ser Leu Ser Leu Gly Lys Arg Gly Arg Lys
    450                 455                 460

Arg Arg Ser Gly Ser Gly Ala Thr Asn Phe Ser Leu Leu Lys Gln Ala
465                 470                 475                 480

Gly Asp Val Glu Glu Asn Pro Gly Pro Met Val Leu Gln Thr Gln Val
                485                 490                 495

Phe Ile Ser Leu Leu Leu Trp Ile Ser Gly Ala Tyr Gly Asp Val Val
            500                 505                 510

Met Thr Gln Thr Pro Leu Thr Leu Ser Val Thr Ile Gly Gln Pro Ala
        515                 520                 525

Ser Ile Ser Cys Lys Ser Ser Gln Ser Leu Leu Asp Ser Asp Gly Lys
    530                 535                 540

Thr Tyr Leu Asn Trp Leu Leu Gln Arg Pro Gly Gln Ser Pro Lys Arg
545                 550                 555                 560

Leu Ile Tyr Leu Val Ser Lys Leu Asp Ser Gly Val Pro Asp Arg Phe
                565                 570                 575

Thr Gly Ser Gly Ser Gly Thr Asp Phe Thr Leu Lys Ile Ser Arg Val
            580                 585                 590

Glu Ala Glu Asp Leu Gly Val Tyr Tyr Cys Trp Gln Gly Thr His Phe
        595                 600                 605

Pro His Thr Phe Gly Gly Gly Thr Lys Leu Glu Ile Lys Arg Thr Val
    610                 615                 620

Ala Ala Pro Ser Val Phe Ile Phe Pro Pro Ser Asp Glu Gln Leu Lys
625                 630                 635                 640

Ser Gly Thr Ala Ser Val Val Cys Leu Leu Asn Asn Phe Tyr Pro Arg
                645                 650                 655

Glu Ala Lys Val Gln Trp Lys Val Asp Asn Ala Leu Gln Ser Gly Asn
            660                 665                 670

Ser Gln Glu Ser Val Thr Glu Gln Asp Ser Lys Asp Ser Thr Tyr Ser
        675                 680                 685

Leu Ser Ser Thr Leu Thr Leu Ser Lys Ala Asp Tyr Glu Lys His Lys
    690                 695                 700

Val Tyr Ala Cys Glu Val Thr His Gln Gly Leu Ser Ser Pro Val Thr
705                 710                 715                 720

Lys Ser Phe Asn Arg Gly Glu Cys
                725
```

<210> SEQ ID NO 12
<211> LENGTH: 731
<212> TYPE: PRT
<213> ORGANISM: Artificial Sequence
<220> FEATURE:
<223> OTHER INFORMATION: Human IgG heavy signal peptide-VH-CH1-Hinge Region-CH2-CH3-custom Furin cleavage site-'GSG' Linker and P2A Peptide-human kappa light chain signal peptide-VL-CL (kappa)

<400> SEQUENCE: 12

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45
```

```
Ser Arg Tyr Gly Met Ser Trp Gly Arg Gln Thr Pro Asp Lys Arg Leu
    50                  55                  60

Glu Trp Val Ala Thr Ile Ser Ser Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Ser Trp Phe Ala Tyr Trp Gly Arg Gly Thr Leu
        115                 120                 125

Val Thr Val Ser Ala Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys Arg
    450                 455                 460

Gly Arg Lys Arg Arg Ser Gly Ser Gly Ala Thr Asn Phe Ser Leu Leu
```

-continued

```
465                 470                 475                 480

Lys Gln Ala Gly Asp Val Glu Glu Asn Pro Gly Pro Met Val Leu Gln
                485                 490                 495

Thr Gln Val Phe Ile Ser Leu Leu Leu Trp Ile Ser Gly Ala Tyr Gly
            500                 505                 510

Asp Val Val Met Thr Gln Thr Pro Leu Thr Leu Ser Val Thr Ile Gly
        515                 520                 525

Gln Pro Ala Ser Ile Ser Cys Lys Ser Ser Gln Ser Leu Leu Asp Ser
    530                 535                 540

Asp Gly Lys Thr Tyr Leu Asn Trp Leu Leu Gln Arg Pro Gly Gln Ser
545                 550                 555                 560

Pro Lys Arg Leu Ile Tyr Leu Val Ser Lys Leu Asp Ser Gly Val Pro
                565                 570                 575

Asp Arg Phe Thr Gly Ser Gly Ser Gly Thr Asp Phe Thr Leu Lys Ile
            580                 585                 590

Ser Arg Val Glu Ala Glu Asp Leu Gly Val Tyr Tyr Cys Trp Gln Gly
        595                 600                 605

Thr His Phe Pro His Thr Phe Gly Gly Gly Thr Lys Leu Glu Ile Lys
    610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
            660                 665                 670

Ser Gly Asn Ser Gln Glu Ser Val Thr Glu Gln Asp Ser Lys Asp Ser
        675                 680                 685

Thr Tyr Ser Leu Ser Ser Thr Leu Thr Leu Ser Lys Ala Asp Tyr Glu
    690                 695                 700

Lys His Lys Val Tyr Ala Cys Glu Val Thr His Gln Gly Leu Ser Ser
705                 710                 715                 720

Pro Val Thr Lys Ser Phe Asn Arg Gly Glu Cys
                725                 730


<210> SEQ ID NO 13
<211> LENGTH: 729
<212> TYPE: PRT
<213> ORGANISM: Artificial Sequence
<220> FEATURE:
<223> OTHER INFORMATION: Human IgG heavy signal peptide-VH-CH1-Hinge
      Region-CH2-CH3-custom Furin cleavage site-'GSG' Linker and P2A
      Peptide-human kappa light chain signal peptide-VL-CL (kappa)

<400> SEQUENCE: 13

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95
```

-continued

```
Thr Leu Tyr Leu Glu Met Ser Ser Leu Arg Ser Glu Asp Thr Ala Met
            100                 105                 110

Tyr Tyr Cys Ala Ser Asp Gly Tyr Tyr Ser His Trp Gly Gln Gly Thr
        115                 120                 125

Ser Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Ser Pro Asn Met Val Pro His Ala
225                 230                 235                 240

His His Ala Gln Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
        435                 440                 445

His Tyr Thr Gln Lys Ser Leu Ser Leu Ser Leu Gly Lys Arg Gly Arg
    450                 455                 460

Lys Arg Arg Ser Gly Ser Gly Ala Thr Asn Phe Ser Leu Leu Lys Gln
465                 470                 475                 480

Ala Gly Asp Val Glu Glu Asn Pro Gly Pro Met Val Leu Gln Thr Gln
                485                 490                 495

Val Phe Ile Ser Leu Leu Leu Trp Ile Ser Gly Ala Tyr Gly Asp Val
            500                 505                 510
```

```
Val Met Thr Gln Ile Pro Leu Ser Leu Pro Val Ser Leu Gly Asp Gln
        515                 520                 525

Ala Ser Ile Ser Cys Arg Ser Ser Gln Ser Leu Val His Ser Asn Gly
    530                 535                 540

Asn Thr Tyr Leu His Trp Tyr Leu Gln Lys Pro Gly Gln Ser Pro Lys
545                 550                 555                 560

Leu Leu Ile Tyr Lys Val Ser Asn Arg Phe Ser Gly Val Pro Asp Arg
                565                 570                 575

Phe Ser Gly Ser Gly Ser Gly Thr Asp Phe Thr Leu Lys Ile Ser Arg
            580                 585                 590

Val Glu Ala Glu Asp Leu Gly Val Tyr Phe Cys Phe Gln Ser Thr His
        595                 600                 605

Val Pro Pro Thr Phe Gly Gly Gly Thr Lys Leu Glu Ile Lys Arg Thr
    610                 615                 620

Val Ala Ala Pro Ser Val Phe Ile Phe Pro Pro Ser Asp Glu Gln Leu
625                 630                 635                 640

Lys Ser Gly Thr Ala Ser Val Val Cys Leu Leu Asn Asn Phe Tyr Pro
                645                 650                 655

Arg Glu Ala Lys Val Gln Trp Lys Val Asp Asn Ala Leu Gln Ser Gly
            660                 665                 670

Asn Ser Gln Glu Ser Val Thr Glu Gln Asp Ser Lys Asp Ser Thr Tyr
        675                 680                 685

Ser Leu Ser Ser Thr Leu Thr Leu Ser Lys Ala Asp Tyr Glu Lys His
    690                 695                 700

Lys Val Tyr Ala Cys Glu Val Thr His Gln Gly Leu Ser Ser Pro Val
705                 710                 715                 720

Thr Lys Ser Phe Asn Arg Gly Glu Cys
                725


<210> SEQ ID NO 14
<211> LENGTH: 732
<212> TYPE: PRT
<213> ORGANISM: Artificial Sequence
<220> FEATURE:
<223> OTHER INFORMATION: Human anti-Zika (8A9F9)-IgG1: Human IgG heavy
      signal peptide-VH-CH1-Hinge Region-CH2-CH3-custom Furin cleavage
      site-'GSG' Linker and P2A Peptide-human kappa light chain signal
      peptide-VL-CL (kappa)

<400> SEQUENCE: 14

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Ser Asp Gly Tyr Tyr Ser His Trp Gly Gln Gly Thr
        115                 120                 125
```

-continued

```
Ser Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Arg Gly Arg Lys Arg Arg Ser Gly Ser Gly Ala Thr Asn Phe Ser Leu
465                 470                 475                 480

Leu Lys Gln Ala Gly Asp Val Glu Glu Asn Pro Gly Pro Met Val Leu
                485                 490                 495

Gln Thr Gln Val Phe Ile Ser Leu Leu Leu Trp Ile Ser Gly Ala Tyr
            500                 505                 510

Gly Asp Val Val Met Thr Gln Ile Pro Leu Ser Leu Pro Val Ser Leu
        515                 520                 525

Gly Asp Gln Ala Ser Ile Ser Cys Arg Ser Ser Gln Ser Leu Val His
    530                 535                 540

Ser Asn Gly Asn Thr Tyr Leu His Trp Tyr Leu Gln Lys Pro Gly Gln
```

545 550 555 560

Ser Pro Lys Leu Leu Ile Tyr Lys Val Ser Asn Arg Phe Ser Gly Val
565 570 575

Pro Asp Arg Phe Ser Gly Ser Gly Ser Gly Thr Asp Phe Thr Leu Lys
580 585 590

Ile Ser Arg Val Glu Ala Glu Asp Leu Gly Val Tyr Phe Cys Phe Gln
595 600 605

Ser Thr His Val Pro Pro Thr Phe Gly Gly Gly Thr Lys Leu Glu Ile
610 615 620

Lys Arg Thr Val Ala Ala Pro Ser Val Phe Ile Phe Pro Pro Ser Asp
625 630 635 640

Glu Gln Leu Lys Ser Gly Thr Ala Ser Val Val Cys Leu Leu Asn Asn
645 650 655

Phe Tyr Pro Arg Glu Ala Lys Val Gln Trp Lys Val Asp Asn Ala Leu
660 665 670

Gln Ser Gly Asn Ser Gln Glu Ser Val Thr Glu Gln Asp Ser Lys Asp
675 680 685

Ser Thr Tyr Ser Leu Ser Ser Thr Leu Thr Leu Ser Lys Ala Asp Tyr
690 695 700

Glu Lys His Lys Val Tyr Ala Cys Glu Val Thr His Gln Gly Leu Ser
705 710 715 720

Ser Pro Val Thr Lys Ser Phe Asn Arg Gly Glu Cys
725 730

<210> SEQ ID NO 15
<211> LENGTH: 728
<212> TYPE: PRT
<213> ORGANISM: Artificial Sequence
<220> FEATURE:
<223> OTHER INFORMATION: Human anti-Zika (8D10F4)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

<400> SEQUENCE: 15

Met Asp Trp Thr Trp Arg Ile Leu Phe Leu Val Ala Ala Ala Thr Gly
1 5 10 15

Thr His Ala Glu Val Gln Leu Val Glu Ser Gly Gly Gly Leu Val Lys
20 25 30

Pro Gly Gly Ser Leu Lys Leu Ser Cys Ala Ala Ser Gly Phe Thr Phe
35 40 45

Ser Ser Tyr Ala Met Ser Trp Val Arg Gln Ser Pro Glu Lys Arg Leu
50 55 60

Glu Trp Val Ala Glu Ile Ser Ser Gly Gly Ser Tyr Ile Tyr Tyr Pro
65 70 75 80

Asp Thr Val Thr Gly Arg Phe Thr Ile Ser Arg Asp Asn Ala Lys Asn
85 90 95

Thr Leu Tyr Leu Glu Met Ser Ser Leu Arg Ser Glu Asp Thr Ala Met
100 105 110

Tyr Tyr Cys Ala Ser Asp Gly Tyr Tyr Ser His Trp Gly Gln Gly Thr
115 120 125

Ser Val Thr Val Ser Ser Ala Ser Thr Lys Gly Pro Ser Val Phe Pro
130 135 140

Leu Ala Pro Cys Ser Arg Ser Thr Ser Glu Ser Thr Ala Ala Leu Gly
145 150 155 160

Cys Leu Val Lys Asp Tyr Phe Pro Glu Pro Val Thr Val Ser Trp Asn

-continued

```
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Ser Pro Asn Met Val Pro His Ala
225                 230                 235                 240

His His Ala Gln Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
        435                 440                 445

His Tyr Thr Gln Lys Ser Leu Ser Leu Ser Leu Gly Lys Arg Gly Arg
    450                 455                 460

Lys Arg Arg Ser Gly Ser Gly Ala Thr Asn Phe Ser Leu Leu Lys Gln
465                 470                 475                 480

Ala Gly Asp Val Glu Glu Asn Pro Gly Pro Met Val Leu Gln Thr Gln
                485                 490                 495

Val Phe Ile Ser Leu Leu Leu Trp Ile Ser Gly Ala Tyr Gly Asp Val
            500                 505                 510

Val Met Thr Gln Ser Pro Leu Ser Leu Pro Val Ser Leu Gly Asp Gln
        515                 520                 525

Ala Ser Ile Ser Cys Arg Ser Ser Gln Ser Leu Val His Ser Asn Gly
    530                 535                 540

Asn Thr Tyr Phe His Trp Tyr Leu Gln Lys Pro Gly Gln Ser Pro Lys
545                 550                 555                 560

Leu Leu Ile Tyr Lys Val Ser Asn Arg Phe Ser Gly Val Pro Asp Arg
                565                 570                 575

Phe Ser Gly Ser Gly Ser Gly Thr Asp Phe Thr Leu Lys Ile Ser Arg
            580                 585                 590
```

Val Glu Ala Glu Asp Leu Gly Leu Tyr Phe Cys Ser Gln Ser Thr His
595 600 605

Val Pro Pro Thr Phe Gly Gly Gly Thr Lys Leu Glu Ile Lys Thr Val
610 615 620

Ala Ala Pro Ser Val Phe Ile Phe Pro Pro Ser Asp Glu Gln Leu Lys
625 630 635 640

Ser Gly Thr Ala Ser Val Val Cys Leu Leu Asn Asn Phe Tyr Pro Arg
645 650 655

Glu Ala Lys Val Gln Trp Lys Val Asp Asn Ala Leu Gln Ser Gly Asn
660 665 670

Ser Gln Glu Ser Val Thr Glu Gln Asp Ser Lys Asp Ser Thr Tyr Ser
675 680 685

Leu Ser Ser Thr Leu Thr Leu Ser Lys Ala Asp Tyr Glu Lys His Lys
690 695 700

Val Tyr Ala Cys Glu Val Thr His Gln Gly Leu Ser Ser Pro Val Thr
705 710 715 720

Lys Ser Phe Asn Arg Gly Glu Cys
725

<210> SEQ ID NO 16
<211> LENGTH: 732
<212> TYPE: PRT
<213> ORGANISM: Artificial Sequence
<220> FEATURE:
<223> OTHER INFORMATION: Human anti-Zika (8D10F4)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

<400> SEQUENCE: 16

Met Asp Trp Thr Trp Arg Ile Leu Phe Leu Val Ala Ala Ala Thr Gly
1 5 10 15

Thr His Ala Glu Val Gln Leu Val Glu Ser Gly Gly Gly Leu Val Lys
20 25 30

Pro Gly Gly Ser Leu Lys Leu Ser Cys Ala Ala Ser Gly Phe Thr Phe
35 40 45

Ser Ser Tyr Ala Met Ser Trp Val Arg Gln Ser Pro Glu Lys Arg Leu
50 55 60

Glu Trp Val Ala Glu Ile Ser Ser Gly Gly Ser Tyr Ile Tyr Tyr Pro
65 70 75 80

Asp Thr Val Thr Gly Arg Phe Thr Ile Ser Arg Asp Asn Ala Lys Asn
85 90 95

Thr Leu Tyr Leu Glu Met Ser Ser Leu Arg Ser Glu Asp Thr Ala Met
100 105 110

Tyr Tyr Cys Ala Ser Asp Gly Tyr Tyr Ser His Trp Gly Gln Gly Thr
115 120 125

Ser Val Thr Val Ser Ser Ala Ser Thr Lys Gly Pro Ser Val Phe Pro
130 135 140

Leu Ala Pro Ser Ser Lys Ser Thr Ser Gly Gly Thr Ala Ala Leu Gly
145 150 155 160

Cys Leu Val Lys Asp Tyr Phe Pro Glu Pro Val Thr Val Ser Trp Asn
165 170 175

Ser Gly Ala Leu Thr Ser Gly Val His Thr Phe Pro Ala Val Leu Gln
180 185 190

Ser Ser Gly Leu Tyr Ser Leu Ser Ser Val Val Thr Val Pro Ser Ser
195 200 205

-continued

```
Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Arg Gly Arg Lys Arg Arg Ser Gly Ser Gly Ala Thr Asn Phe Ser Leu
465                 470                 475                 480

Leu Lys Gln Ala Gly Asp Val Glu Glu Asn Pro Gly Pro Met Val Leu
                485                 490                 495

Gln Thr Gln Val Phe Ile Ser Leu Leu Leu Trp Ile Ser Gly Ala Tyr
            500                 505                 510

Gly Asp Val Val Met Thr Gln Ser Pro Leu Ser Leu Pro Val Ser Leu
        515                 520                 525

Gly Asp Gln Ala Ser Ile Ser Cys Arg Ser Ser Gln Ser Leu Val His
    530                 535                 540

Ser Asn Gly Asn Thr Tyr Phe His Trp Tyr Leu Gln Lys Pro Gly Gln
545                 550                 555                 560

Ser Pro Lys Leu Leu Ile Tyr Lys Val Ser Asn Arg Phe Ser Gly Val
                565                 570                 575

Pro Asp Arg Phe Ser Gly Ser Gly Ser Gly Thr Asp Phe Thr Leu Lys
            580                 585                 590

Ile Ser Arg Val Glu Ala Glu Asp Leu Gly Leu Tyr Phe Cys Ser Gln
        595                 600                 605

Ser Thr His Val Pro Pro Thr Phe Gly Gly Gly Thr Lys Leu Glu Ile
    610                 615                 620
```

```
Lys Arg Thr Val Ala Ala Pro Ser Val Phe Ile Phe Pro Pro Ser Asp
625                 630                 635                 640

Glu Gln Leu Lys Ser Gly Thr Ala Ser Val Val Cys Leu Leu Asn Asn
                645                 650                 655

Phe Tyr Pro Arg Glu Ala Lys Val Gln Trp Lys Val Asp Asn Ala Leu
            660                 665                 670

Gln Ser Gly Asn Ser Gln Glu Ser Val Thr Glu Gln Asp Ser Lys Asp
        675                 680                 685

Ser Thr Tyr Ser Leu Ser Ser Thr Leu Thr Leu Ser Lys Ala Asp Tyr
    690                 695                 700

Glu Lys His Lys Val Tyr Ala Cys Glu Val Thr His Gln Gly Leu Ser
705                 710                 715                 720

Ser Pro Val Thr Lys Ser Phe Asn Arg Gly Glu Cys
                725                 730


<210> SEQ ID NO 17
<211> LENGTH: 740
<212> TYPE: PRT
<213> ORGANISM: Artificial Sequence
<220> FEATURE:
<223> OTHER INFORMATION: Human anti-Zika (1D4G7)-IgG4: Human IgG heavy
      signal peptide-VH-CH1-Hinge Region-CH2-CH3-custom Furin cleavage
      site-'GSG' Linker and P2A Peptide-human kappa light chain signal
      peptide-VL-CL (kappa)

<400> SEQUENCE: 17

Met Asp Trp Thr Trp Arg Ile Leu Phe Leu Val Ala Ala Ala Thr Gly
1               5                   10                  15

Thr His Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Glu Ile Ser Lys Ile Tyr Tyr Tyr Gly Ser Ser
        115                 120                 125

Tyr Glu Asn Gly Met Asp Tyr Trp Gly Gln Gly Thr Ser Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Lys Thr Tyr Thr Cys Asn Val Asp His Lys Pro Ser Asn Thr Lys Val
225                 230                 235                 240
```

-continued

```
Asp Lys Arg Val Ser Pro Asn Met Val Pro His Ala His His Ala Gln
                245                 250                 255

Ala Pro Glu Phe Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
    450                 455                 460

Lys Ser Leu Ser Leu Ser Leu Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Val Leu Gln Thr Gln Val Phe Ile Ser
            500                 505                 510

Leu Leu Leu Trp Ile Ser Gly Ala Tyr Gly Asn Ile Val Leu Thr Gln
        515                 520                 525

Ser Pro Ala Ser Leu Ala Val Ser Leu Gly Gln Arg Ala Thr Ile Ser
    530                 535                 540

Cys Arg Ala Ser Glu Ser Val Asp Ser Phe Gly Asn Ser Phe Met His
545                 550                 555                 560

Trp Phe Gln Gln Lys Pro Gly Gln Pro Pro Lys Leu Leu Ile Tyr Leu
                565                 570                 575

Ala Ser Asn Leu Glu Ser Gly Val Pro Ala Arg Phe Ser Gly Ser Gly
            580                 585                 590

Ser Arg Thr Asp Phe Thr Leu Thr Ile Asp Pro Val Glu Ala Asp Asp
        595                 600                 605

Ala Ala Thr Tyr Tyr Cys Gln Gln Asn Asn Glu Tyr Pro Tyr Thr Phe
    610                 615                 620

Gly Gly Gly Thr Lys Leu Glu Ile Lys Arg Thr Val Ala Ala Pro Ser
625                 630                 635                 640

Val Phe Ile Phe Pro Pro Ser Asp Glu Gln Leu Lys Ser Gly Thr Ala
                645                 650                 655

Ser Val Val Cys Leu Leu Asn Asn Phe Tyr Pro Arg Glu Ala Lys Val
```

```
            660                 665                 670

Gln Trp Lys Val Asp Asn Ala Leu Gln Ser Gly Asn Ser Gln Glu Ser
        675                 680                 685

Val Thr Glu Gln Asp Ser Lys Asp Ser Thr Tyr Ser Leu Ser Ser Thr
    690                 695                 700

Leu Thr Leu Ser Lys Ala Asp Tyr Glu Lys His Lys Val Tyr Ala Cys
705                 710                 715                 720

Glu Val Thr His Gln Gly Leu Ser Ser Pro Val Thr Lys Ser Phe Asn
                725                 730                 735

Arg Gly Glu Cys
            740


<210> SEQ ID NO 18
<211> LENGTH: 743
<212> TYPE: PRT
<213> ORGANISM: Artificial Sequence
<220> FEATURE:
<223> OTHER INFORMATION: Human anti-Zika (1D4G7)-IgG1: Human IgG heavy
      signal peptide-VH-CH1-Hinge Region-CH2-CH3-custom Furin cleavage
      site-'GSG' Linker and P2A Peptide-human kappa light chain signal
      peptide-VL-CL (kappa)

<400> SEQUENCE: 18

Met Asp Trp Thr Trp Arg Ile Leu Phe Leu Val Ala Ala Ala Thr Gly
1               5                   10                  15

Thr His Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Glu Ile Ser Lys Ile Tyr Tyr Tyr Gly Ser Ser
        115                 120                 125

Tyr Glu Asn Gly Met Asp Tyr Trp Gly Gln Gly Thr Ser Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
```

-continued

```
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys Arg Gly Arg Lys
465                 470                 475                 480

Arg Arg Ser Gly Ser Gly Ala Thr Asn Phe Ser Leu Leu Lys Gln Ala
                485                 490                 495

Gly Asp Val Glu Glu Asn Pro Gly Pro Met Val Leu Gln Thr Gln Val
            500                 505                 510

Phe Ile Ser Leu Leu Leu Trp Ile Ser Gly Ala Tyr Gly Asn Ile Val
        515                 520                 525

Leu Thr Gln Ser Pro Ala Ser Leu Ala Val Ser Leu Gly Gln Arg Ala
    530                 535                 540

Thr Ile Ser Cys Arg Ala Ser Glu Ser Val Asp Ser Phe Gly Asn Ser
545                 550                 555                 560

Phe Met His Trp Phe Gln Gln Lys Pro Gly Gln Pro Pro Lys Leu Leu
                565                 570                 575

Ile Tyr Leu Ala Ser Asn Leu Glu Ser Gly Val Pro Ala Arg Phe Ser
            580                 585                 590

Gly Ser Gly Ser Arg Thr Asp Phe Thr Leu Thr Ile Asp Pro Val Glu
        595                 600                 605

Ala Asp Asp Ala Ala Thr Tyr Tyr Cys Gln Gln Asn Asn Glu Tyr Pro
    610                 615                 620

Tyr Thr Phe Gly Gly Gly Thr Lys Leu Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685
```

```
Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740


<210> SEQ ID NO 19
<211> LENGTH: 732
<212> TYPE: PRT
<213> ORGANISM: Artificial Sequence
<220> FEATURE:
<223> OTHER INFORMATION: Human anti-Zika (8A9F9)-IgG1: Human IgG heavy
      signal peptide-VH-CH1-Hinge Region-CH2 (with LALA variant at 4th
      and 5th residue)-CH3-custom Furin cleavage site-'GSG' Linker and
      P2A Peptide-human kappa light chain signal peptide-VL-CL (kappa)

<400> SEQUENCE: 19

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Ser Asp Gly Tyr Tyr Ser His Trp Gly Gln Gly Thr
        115                 120                 125

Ser Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285
```

-continued

```
Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Arg Gly Arg Lys Arg Arg Ser Gly Ser Gly Ala Thr Asn Phe Ser Leu
465                 470                 475                 480

Leu Lys Gln Ala Gly Asp Val Glu Glu Asn Pro Gly Pro Met Val Leu
                485                 490                 495

Gln Thr Gln Val Phe Ile Ser Leu Leu Leu Trp Ile Ser Gly Ala Tyr
            500                 505                 510

Gly Asp Val Val Met Thr Gln Ile Pro Leu Ser Leu Pro Val Ser Leu
        515                 520                 525

Gly Asp Gln Ala Ser Ile Ser Cys Arg Ser Ser Gln Ser Leu Val His
    530                 535                 540

Ser Asn Gly Asn Thr Tyr Leu His Trp Tyr Leu Gln Lys Pro Gly Gln
545                 550                 555                 560

Ser Pro Lys Leu Leu Ile Tyr Lys Val Ser Asn Arg Phe Ser Gly Val
                565                 570                 575

Pro Asp Arg Phe Ser Gly Ser Gly Ser Gly Thr Asp Phe Thr Leu Lys
            580                 585                 590

Ile Ser Arg Val Glu Ala Glu Asp Leu Gly Val Tyr Phe Cys Phe Gln
        595                 600                 605

Ser Thr His Val Pro Pro Thr Phe Gly Gly Gly Thr Lys Leu Glu Ile
    610                 615                 620

Lys Arg Thr Val Ala Ala Pro Ser Val Phe Ile Phe Pro Pro Ser Asp
625                 630                 635                 640

Glu Gln Leu Lys Ser Gly Thr Ala Ser Val Val Cys Leu Leu Asn Asn
                645                 650                 655

Phe Tyr Pro Arg Glu Ala Lys Val Gln Trp Lys Val Asp Asn Ala Leu
            660                 665                 670

Gln Ser Gly Asn Ser Gln Glu Ser Val Thr Glu Gln Asp Ser Lys Asp
        675                 680                 685

Ser Thr Tyr Ser Leu Ser Ser Thr Leu Thr Leu Ser Lys Ala Asp Tyr
    690                 695                 700
```

```
Glu Lys His Lys Val Tyr Ala Cys Glu Val Thr His Gln Gly Leu Ser
705                 710                 715                 720

Ser Pro Val Thr Lys Ser Phe Asn Arg Gly Glu Cys
                725                 730


<210> SEQ ID NO 20
<211> LENGTH: 731
<212> TYPE: PRT
<213> ORGANISM: Artificial Sequence
<220> FEATURE:
<223> OTHER INFORMATION: Human anti-Zika (3F12E9)-IgG1: Human IgG heavy
      signal peptide-VH-CH1-Hinge Region-CH2 (with LALA variant at 4th
      and 5th residue)-CH3-custom Furin cleavage site-'GSG' Linker and
      P2A Peptide-human kappa light chain signal peptide-VL-CL (kappa)

<400> SEQUENCE: 20

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Arg Tyr Gly Met Ser Trp Gly Arg Gln Thr Pro Asp Lys Arg Leu
    50                  55                  60

Glu Trp Val Ala Thr Ile Ser Ser Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Ser Trp Phe Ala Tyr Trp Gly Arg Gly Thr Leu
        115                 120                 125

Val Thr Val Ser Ala Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320
```

-continued

```
Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys Arg
    450                 455                 460

Gly Arg Lys Arg Arg Ser Gly Ser Gly Ala Thr Asn Phe Ser Leu Leu
465                 470                 475                 480

Lys Gln Ala Gly Asp Val Glu Glu Asn Pro Gly Pro Met Val Leu Gln
                485                 490                 495

Thr Gln Val Phe Ile Ser Leu Leu Leu Trp Ile Ser Gly Ala Tyr Gly
            500                 505                 510

Asp Val Val Met Thr Gln Thr Pro Leu Thr Leu Ser Val Thr Ile Gly
        515                 520                 525

Gln Pro Ala Ser Ile Ser Cys Lys Ser Ser Gln Ser Leu Leu Asp Ser
    530                 535                 540

Asp Gly Lys Thr Tyr Leu Asn Trp Leu Leu Gln Arg Pro Gly Gln Ser
545                 550                 555                 560

Pro Lys Arg Leu Ile Tyr Leu Val Ser Lys Leu Asp Ser Gly Val Pro
                565                 570                 575

Asp Arg Phe Thr Gly Ser Gly Ser Gly Thr Asp Phe Thr Leu Lys Ile
            580                 585                 590

Ser Arg Val Glu Ala Glu Asp Leu Gly Val Tyr Tyr Cys Trp Gln Gly
        595                 600                 605

Thr His Phe Pro His Thr Phe Gly Gly Gly Thr Lys Leu Glu Ile Lys
    610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
            660                 665                 670

Ser Gly Asn Ser Gln Glu Ser Val Thr Glu Gln Asp Ser Lys Asp Ser
        675                 680                 685

Thr Tyr Ser Leu Ser Ser Thr Leu Thr Leu Ser Lys Ala Asp Tyr Glu
    690                 695                 700

Lys His Lys Val Tyr Ala Cys Glu Val Thr His Gln Gly Leu Ser Ser
705                 710                 715                 720

Pro Val Thr Lys Ser Phe Asn Arg Gly Glu Cys
                725                 730
```

<210> SEQ ID NO 21
<211> LENGTH: 780
<212> TYPE: PRT
<213> ORGANISM: Artificial Sequence
<220> FEATURE:
<223> OTHER INFORMATION: Human anti-Zika (IC2A6)-IgG4: Human IgG heavy signal peptide-VH-CH1-Hinge Region-CH2-CH3-custom Furin cleavage site-'GSG' Linker and P2A Peptide-human kappa light chain signal peptide-VL-CL (kappa)

<400> SEQUENCE: 21

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Ser Asp Gly Tyr Tyr Ser His Trp Gly Gln Gly Thr
        115                 120                 125

Ser Val Thr Val Ser Ser Val Thr Gly Arg Phe Thr Ile Ser Arg Asp
    130                 135                 140

Asn Ala Lys Asn Thr Leu Tyr Leu Glu Met Ser Ser Leu Arg Ser Glu
145                 150                 155                 160

Asp Thr Ala Met Tyr Tyr Cys Ala Ser Asp Gly Tyr Tyr Ser His Trp
                165                 170                 175

Gly Gln Gly Thr Ser Val Thr Val Ser Ser Ala Ser Thr Lys Gly Pro
            180                 185                 190

Ser Val Phe Pro Leu Ala Pro Cys Ser Arg Ser Thr Ser Glu Ser Thr
        195                 200                 205

Ala Ala Leu Gly Cys Leu Val Lys Asp Tyr Phe Pro Glu Pro Val Thr
    210                 215                 220

Val Ser Trp Asn Ser Gly Ala Leu Thr Ser Gly Val His Thr Phe Pro
225                 230                 235                 240

Ala Val Leu Gln Ser Ser Gly Leu Tyr Ser Leu Ser Ser Val Val Thr
                245                 250                 255

Val Pro Ser Ser Ser Leu Gly Thr Lys Thr Tyr Thr Cys Asn Val Asp
            260                 265                 270

His Lys Pro Ser Asn Thr Lys Val Asp Lys Arg Val Ser Pro Asn Met
        275                 280                 285

Val Pro His Ala His His Ala Gln Ala Pro Glu Phe Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser Gln Glu Asp
                325                 330                 335

Pro Glu Val Gln Phe Asn Trp Tyr Val Asp Gly Val Glu Val His Asn
            340                 345                 350

Ala Lys Thr Lys Pro Arg Glu Glu Gln Phe Asn Ser Thr Tyr Arg Val
```

-continued

```
        355                 360                 365

Val Ser Val Leu Thr Val Leu His Gln Asp Trp Leu Asn Gly Lys Glu
    370                 375                 380

Tyr Lys Cys Lys Val Ser Asn Lys Gly Leu Pro Ser Ser Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Gln Glu Glu Met Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Arg Leu Thr Val Asp Lys
465                 470                 475                 480

Ser Arg Trp Gln Glu Gly Asn Val Phe Ser Cys Ser Val Met His Glu
                485                 490                 495

Ala Leu His Asn His Tyr Thr Gln Lys Ser Leu Ser Leu Ser Leu Gly
            500                 505                 510

Lys Arg Gly Arg Lys Arg Arg Ser Gly Ser Gly Ala Thr Asn Phe Ser
        515                 520                 525

Leu Leu Lys Gln Ala Gly Asp Val Glu Glu Asn Pro Gly Pro Met Val
    530                 535                 540

Leu Gln Thr Gln Val Phe Ile Ser Leu Leu Leu Trp Ile Ser Gly Ala
545                 550                 555                 560

Tyr Gly Asp Val Val Met Thr Gln Thr Pro Leu Ser Leu Pro Val Cys
                565                 570                 575

Leu Gly Asp Gln Ala Ser Ile Ser Cys Arg Ser Ser Gln Ser Leu Val
            580                 585                 590

His Ser Asn Gly Asn Thr Tyr Leu His Trp Tyr Leu Gln Lys Pro Gly
        595                 600                 605

Gln Ser Pro Lys Leu Leu Ile Tyr Lys Val Ser Asn Arg Phe Ser Gly
    610                 615                 620

Val Pro Asp Arg Phe Ser Gly Ser Gly Ser Gly Thr Asp Phe Thr Leu
625                 630                 635                 640

Lys Ile Ser Arg Val Glu Ala Glu Asp Leu Gly Val Tyr Phe Cys Phe
                645                 650                 655

Gln Ser Thr His Val Pro Pro Thr Phe Gly Gly Gly Thr Lys Leu Glu
            660                 665                 670

Ile Lys Thr Val Ala Ala Pro Ser Val Phe Ile Phe Pro Pro Ser Asp
        675                 680                 685

Glu Gln Leu Lys Ser Gly Thr Ala Ser Val Val Cys Leu Leu Asn Asn
    690                 695                 700

Phe Tyr Pro Arg Glu Ala Lys Val Gln Trp Lys Val Asp Asn Ala Leu
705                 710                 715                 720

Gln Ser Gly Asn Ser Gln Glu Ser Val Thr Glu Gln Asp Ser Lys Asp
                725                 730                 735

Ser Thr Tyr Ser Leu Ser Ser Thr Leu Thr Leu Ser Lys Ala Asp Tyr
            740                 745                 750

Glu Lys His Lys Val Tyr Ala Cys Glu Val Thr His Gln Gly Leu Ser
        755                 760                 765

Ser Pro Val Thr Lys Ser Phe Asn Arg Gly Glu Cys
    770                 775                 780
```

<210> SEQ ID NO 22
<211> LENGTH: 784
<212> TYPE: PRT
<213> ORGANISM: Artificial Sequence
<220> FEATURE:
<223> OTHER INFORMATION: Human anti-Zika (IC2A6)-IgG1: Human IgG heavy signal peptide-VH-CH1-Hinge Region-CH2-CH3-custom Furin cleavage site-'GSG' Linker and P2A Peptide-human kappa light chain signal peptide-VL-CL (kappa)

<400> SEQUENCE: 22

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Ser Asp Gly Tyr Tyr Ser His Trp Gly Gln Gly Thr
        115                 120                 125

Ser Val Thr Val Ser Ser Val Thr Gly Arg Phe Thr Ile Ser Arg Asp
    130                 135                 140

Asn Ala Lys Asn Thr Leu Tyr Leu Glu Met Ser Ser Leu Arg Ser Glu
145                 150                 155                 160

Asp Thr Ala Met Tyr Tyr Cys Ala Ser Asp Gly Tyr Tyr Ser His Trp
                165                 170                 175

Gly Gln Gly Thr Ser Val Thr Val Ser Ser Ala Ser Thr Lys Gly Pro
            180                 185                 190

Ser Val Phe Pro Leu Ala Pro Ser Ser Lys Ser Thr Ser Gly Gly Thr
        195                 200                 205

Ala Ala Leu Gly Cys Leu Val Lys Asp Tyr Phe Pro Glu Pro Val Thr
    210                 215                 220

Val Ser Trp Asn Ser Gly Ala Leu Thr Ser Gly Val His Thr Phe Pro
225                 230                 235                 240

Ala Val Leu Gln Ser Ser Gly Leu Tyr Ser Leu Ser Ser Val Val Thr
                245                 250                 255

Val Pro Ser Ser Ser Leu Gly Thr Gln Thr Tyr Ile Cys Asn Val Asn
            260                 265                 270

His Lys Pro Ser Asn Thr Lys Val Asp Lys Lys Val Glu Pro Lys Ser
        275                 280                 285

Cys Asp Lys Thr His Thr Cys Pro Pro Cys Pro Ala Pro Glu Leu Leu
    290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
            340                 345                 350
```

-continued

```
Val His Asn Ala Lys Thr Lys Pro Arg Glu Glu Gln Tyr Asn Ser Thr
        355                 360                 365

Tyr Arg Val Val Ser Val Leu Thr Val Leu His Gln Asp Trp Leu Asn
    370                 375                 380

Gly Lys Glu Tyr Lys Cys Lys Val Ser Asn Lys Ala Leu Pro Ala Pro
385                 390                 395                 400

Ile Glu Lys Thr Ile Ser Lys Ala Lys Gly Gln Pro Arg Glu Pro Gln
                405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
    450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys Arg Gly Arg Lys Arg Arg Ser Gly Ser Gly Ala Thr
        515                 520                 525

Asn Phe Ser Leu Leu Lys Gln Ala Gly Asp Val Glu Glu Asn Pro Gly
    530                 535                 540

Pro Met Val Leu Gln Thr Gln Val Phe Ile Ser Leu Leu Leu Trp Ile
545                 550                 555                 560

Ser Gly Ala Tyr Gly Asp Val Val Met Thr Gln Thr Pro Leu Ser Leu
                565                 570                 575

Pro Val Cys Leu Gly Asp Gln Ala Ser Ile Ser Cys Arg Ser Ser Gln
            580                 585                 590

Ser Leu Val His Ser Asn Gly Asn Thr Tyr Leu His Trp Tyr Leu Gln
        595                 600                 605

Lys Pro Gly Gln Ser Pro Lys Leu Leu Ile Tyr Lys Val Ser Asn Arg
    610                 615                 620

Phe Ser Gly Val Pro Asp Arg Phe Ser Gly Ser Gly Ser Gly Thr Asp
625                 630                 635                 640

Phe Thr Leu Lys Ile Ser Arg Val Glu Ala Glu Asp Leu Gly Val Tyr
                645                 650                 655

Phe Cys Phe Gln Ser Thr His Val Pro Pro Thr Phe Gly Gly Gly Thr
            660                 665                 670

Lys Leu Glu Ile Lys Arg Thr Val Ala Ala Pro Ser Val Phe Ile Phe
        675                 680                 685

Pro Pro Ser Asp Glu Gln Leu Lys Ser Gly Thr Ala Ser Val Val Cys
    690                 695                 700

Leu Leu Asn Asn Phe Tyr Pro Arg Glu Ala Lys Val Gln Trp Lys Val
705                 710                 715                 720

Asp Asn Ala Leu Gln Ser Gly Asn Ser Gln Glu Ser Val Thr Glu Gln
                725                 730                 735

Asp Ser Lys Asp Ser Thr Tyr Ser Leu Ser Ser Thr Leu Thr Leu Ser
            740                 745                 750

Lys Ala Asp Tyr Glu Lys His Lys Val Tyr Ala Cys Glu Val Thr His
        755                 760                 765
```

-continued

```
Gln Gly Leu Ser Ser Pro Val Thr Lys Ser Phe Asn Arg Gly Glu Cys
    770                 775                 780


<210> SEQ ID NO 23
<211> LENGTH: 702
<212> TYPE: PRT
<213> ORGANISM: Artificial Sequence
<220> FEATURE:
<223> OTHER INFORMATION: consensus Zika IgE Leader-prME

<400> SEQUENCE: 23

Met Asp Trp Thr Trp Ile Leu Phe Leu Val Ala Ala Ala Thr Arg Val
1               5                   10                  15

His Ser Gly Ile Ile Gly Leu Leu Leu Thr Thr Ala Met Ala Ala Glu
            20                  25                  30

Ile Thr Arg Arg Gly Ser Ala Tyr Tyr Met Tyr Leu Asp Arg Asn Asp
        35                  40                  45

Ala Gly Glu Ala Ile Ser Phe Pro Thr Thr Leu Gly Met Asn Lys Cys
    50                  55                  60

Tyr Ile Gln Ile Met Asp Leu Gly His Met Cys Asp Ala Thr Met Ser
65                  70                  75                  80

Tyr Glu Cys Pro Met Leu Asp Glu Gly Val Glu Pro Asp Asp Val Asp
                85                  90                  95

Cys Trp Cys Asn Thr Thr Ser Thr Trp Val Val Tyr Gly Thr Cys His
            100                 105                 110

His Lys Lys Gly Glu Ala Arg Arg Ser Arg Arg Ala Val Thr Leu Pro
        115                 120                 125

Ser His Ser Thr Arg Lys Leu Gln Thr Arg Ser Gln Thr Trp Leu Glu
    130                 135                 140

Ser Arg Glu Tyr Thr Lys His Leu Ile Arg Val Glu Asn Trp Ile Phe
145                 150                 155                 160

Arg Asn Pro Gly Phe Ala Leu Ala Ala Ala Ala Ile Ala Trp Leu Leu
                165                 170                 175

Gly Ser Ser Thr Ser Gln Lys Val Ile Tyr Leu Val Met Ile Leu Leu
            180                 185                 190

Ile Ala Pro Ala Tyr Ser Ile Arg Cys Ile Gly Val Ser Asn Arg Asp
        195                 200                 205

Phe Val Glu Gly Met Ser Gly Gly Thr Trp Val Asp Val Val Leu Glu
    210                 215                 220

His Gly Gly Cys Val Thr Val Met Ala Gln Asp Lys Pro Thr Val Asp
225                 230                 235                 240

Ile Glu Leu Val Thr Thr Thr Val Ser Asn Met Ala Glu Val Arg Ser
                245                 250                 255

Tyr Cys Tyr Glu Ala Ser Ile Ser Asp Met Ala Ser Asp Ser Arg Cys
            260                 265                 270

Pro Thr Gln Gly Glu Ala Tyr Leu Asp Lys Gln Ser Asp Thr Gln Tyr
        275                 280                 285

Val Cys Lys Arg Thr Leu Val Asp Arg Gly Trp Gly Asn Gly Cys Gly
    290                 295                 300

Leu Phe Gly Lys Gly Ser Leu Val Thr Cys Ala Lys Phe Thr Cys Ser
305                 310                 315                 320

Lys Lys Met Thr Gly Lys Ser Ile Gln Pro Glu Asn Leu Glu Tyr Arg
                325                 330                 335

Ile Met Leu Ser Val His Gly Ser Gln His Ser Gly Met Ile Val Asn
            340                 345                 350
```

-continued

```
Asp Ile Gly His Glu Thr Asp Glu Asn Arg Ala Lys Val Glu Val Thr
        355                 360                 365

Pro Asn Ser Pro Arg Ala Glu Ala Thr Leu Gly Gly Phe Gly Ser Leu
    370                 375                 380

Gly Leu Asp Cys Glu Pro Arg Thr Gly Leu Asp Phe Ser Asp Leu Tyr
385                 390                 395                 400

Tyr Leu Thr Met Asn Asn Lys His Trp Leu Val His Lys Glu Trp Phe
                405                 410                 415

His Asp Ile Pro Leu Pro Trp His Ala Gly Ala Asp Thr Gly Thr Pro
            420                 425                 430

His Trp Asn Asn Lys Glu Ala Leu Val Glu Phe Lys Asp Ala His Ala
        435                 440                 445

Lys Arg Gln Thr Val Val Val Leu Gly Ser Gln Glu Gly Ala Val His
    450                 455                 460

Thr Ala Leu Ala Gly Ala Leu Glu Ala Glu Met Asp Gly Ala Lys Gly
465                 470                 475                 480

Arg Leu Phe Ser Gly His Leu Lys Cys Arg Leu Lys Met Asp Lys Leu
                485                 490                 495

Arg Leu Lys Gly Val Ser Tyr Ser Leu Cys Thr Ala Ala Phe Thr Phe
            500                 505                 510

Thr Lys Val Pro Ala Glu Thr Leu His Gly Thr Val Thr Val Glu Val
        515                 520                 525

Gln Tyr Ala Gly Thr Asp Gly Pro Cys Lys Val Pro Ala Gln Met Ala
    530                 535                 540

Val Asp Met Gln Thr Leu Thr Pro Val Gly Arg Leu Ile Thr Ala Asn
545                 550                 555                 560

Pro Val Ile Thr Glu Ser Thr Glu Asn Ser Lys Met Met Leu Glu Leu
                565                 570                 575

Asp Pro Pro Phe Gly Asp Ser Tyr Ile Val Ile Gly Val Gly Asp Lys
            580                 585                 590

Lys Ile Thr His His Trp His Arg Ser Gly Ser Thr Ile Gly Lys Ala
        595                 600                 605

Phe Glu Ala Thr Val Arg Gly Ala Lys Arg Met Ala Val Leu Gly Asp
    610                 615                 620

Thr Ala Trp Asp Phe Gly Ser Val Gly Gly Val Phe Asn Ser Leu Gly
625                 630                 635                 640

Lys Gly Ile His Gln Ile Phe Gly Ala Ala Phe Lys Ser Leu Phe Gly
                645                 650                 655

Gly Met Ser Trp Phe Ser Gln Ile Leu Ile Gly Thr Leu Leu Val Trp
            660                 665                 670

Leu Gly Leu Asn Thr Lys Asn Gly Ser Ile Ser Leu Thr Cys Leu Ala
        675                 680                 685

Leu Gly Gly Val Met Ile Phe Leu Ser Thr Ala Val Ser Ala
    690                 695                 700
```

<210> SEQ ID NO 24
<211> LENGTH: 2112
<212> TYPE: DNA
<213> ORGANISM: Artificial Sequence
<220> FEATURE:
<223> OTHER INFORMATION: consensus Zika IgE Leader-prME (construct 1)

<400> SEQUENCE: 24

```
atggactgga cctggattct gtttctggtc gctgctgcta caagagtgca ttctgggatt      60

attggactgc tgctgactac tgccatggca gcagagatca ccaggagagg cagcgcctac     120
```

```
tatatgtacc tggaccggtc tgatgccggc aaggccatca gctttgccac cacactgggc    180
gtgaataagt gccacgtgca gatcatggac ctgggccaca tgtgcgatgc caccatgtcc    240
tacgagtgtc caatgctgga cgagggcgtg gagcccgacg atgtggattg ctggtgtaac    300
accacatcta catgggtggt gtatggcacc tgtcaccaca agaagggaga ggcacggcgc    360
agcaggagag cagtgacact gccctctcac agcaccagga agctgcagac aagaagccag    420
acctggctgg agtcccggga gtatacaaag cacctgatca aggtggagaa ctggatcttt    480
cgcaatccag gattcgcact ggtggcagtg gcaatcgcat ggctgctggg cagctccacc    540
tcccagaaag tgatctacct ggtcatgatc ctgctgatcg cccctgccta ttccatcagg    600
tgcatcggcg tgtctaatag agacttcgtg gagggcatgt ctggcggcac ctgggtggat    660
gtggtgctgg agcacggcgg atgcgtgaca gtgatggccc aggacaagcc aaccgtggat    720
atcgagctgg tgaccacaac cgtgagcaac atggccgagg tgaggtccta ctgctatgag    780
gcctccatct ctgacatggc cagcgattcc agatgtccca cccagggcga ggcctacctg    840
gacaagcagt ccgatacaca gtacgtgtgc aagcggaccc tggtggacag gggatgggga    900
aatggatgtg gcctgtttgg caagggctct ctggtgacat gcgccaagtt cacctgttct    960
aagaagatga ccggcaagag catccagccc gagaacctgg agtacaggat catgctgagc   1020
gtgcacggca gccagcactc cggcatgaca gtgaacgaca tcggctatga gaccgatgag   1080
aatagggcca aggtggaggt gacacctaac agcccaagag ccgaggccac cctgggcggc   1140
tttggctccc tgggactgga ctgcgagcct agaacaggcc tggacttctc cgatctgtac   1200
tatctgacca tgaacaataa gcactggctg gtgcacaagg agtggtttca cgacatccca   1260
ctgccatggc acgcaggagc agatacagga accccacact ggaacaataa ggaggccctg   1320
gtggagttca aggatgccca cgccaagcgc cagacagtgg tggtgctggg cagccaggag   1380
ggagcagtgc acaccgccct ggcaggcgcc ctggaggccg agatggacgg cgccaagggc   1440
aagctgtttt ccggccacct gaagtgccgg ctgaagatgg ataagctgcg cctgaagggc   1500
gtgtcttaca gcctgtgcac agccgccttc accttcacca aggtgcctgc cgagaccctg   1560
cacggcacag tgaccgtgga ggtgcagtat gccggcacag acggcccctg taagatccct   1620
gtgcagatgg ccgtggatat gcagacactg acccctgtgg gccggctgat caccgcaaat   1680
ccagtgatca cagagtccac cgagaactct aagatgatgc tggagctgga ccctcccttc   1740
ggcgacagct acatcgtgat cggcgtgggc gacaagaaga tcacacacca ctggcaccgc   1800
tccggctcta caatcggcaa ggccttcgag gcaaccgtgc ggggcgccaa gaggatggcc   1860
gtgctgggcg acaccgcatg ggattttggc tccgtgggcg gcgtgttcaa ctctctgggc   1920
aagggcatcc accagatctt cggcgccgcc tttaagtctc tgttcggcgg aatgtcttgg   1980
ttcagccaga tcctgatcgg cacactgctg gtgtggctgg gcctgaacac caagaatggc   2040
agcatctctc tgacttgtct ggccctggga ggcgtgatga ttttcctgtc cactgccgtg   2100
tctgcctgat aa                                                       2112
```

<210> SEQ ID NO 25
<211> LENGTH: 702
<212> TYPE: PRT
<213> ORGANISM: Artificial Sequence
<220> FEATURE:
<223> OTHER INFORMATION: consensus Zika IgE Leader-prME (construct 1)

<400> SEQUENCE: 25

-continued

```
Met Asp Trp Thr Trp Ile Leu Phe Leu Val Ala Ala Ala Thr Arg Val
1               5                   10                  15

His Ser Gly Ile Ile Gly Leu Leu Leu Thr Thr Ala Met Ala Ala Glu
            20                  25                  30

Ile Thr Arg Arg Gly Ser Ala Tyr Tyr Met Tyr Leu Asp Arg Ser Asp
        35                  40                  45

Ala Gly Lys Ala Ile Ser Phe Ala Thr Thr Leu Gly Val Asn Lys Cys
    50                  55                  60

His Val Gln Ile Met Asp Leu Gly His Met Cys Asp Ala Thr Met Ser
65                  70                  75                  80

Tyr Glu Cys Pro Met Leu Asp Glu Gly Val Glu Pro Asp Asp Val Asp
                85                  90                  95

Cys Trp Cys Asn Thr Thr Ser Thr Trp Val Val Tyr Gly Thr Cys His
            100                 105                 110

His Lys Lys Gly Glu Ala Arg Arg Ser Arg Arg Ala Val Thr Leu Pro
        115                 120                 125

Ser His Ser Thr Arg Lys Leu Gln Thr Arg Ser Gln Thr Trp Leu Glu
    130                 135                 140

Ser Arg Glu Tyr Thr Lys His Leu Ile Lys Val Glu Asn Trp Ile Phe
145                 150                 155                 160

Arg Asn Pro Gly Phe Ala Leu Val Ala Val Ala Ile Ala Trp Leu Leu
                165                 170                 175

Gly Ser Ser Thr Ser Gln Lys Val Ile Tyr Leu Val Met Ile Leu Leu
            180                 185                 190

Ile Ala Pro Ala Tyr Ser Ile Arg Cys Ile Gly Val Ser Asn Arg Asp
        195                 200                 205

Phe Val Glu Gly Met Ser Gly Gly Thr Trp Val Asp Val Val Leu Glu
    210                 215                 220

His Gly Gly Cys Val Thr Val Met Ala Gln Asp Lys Pro Thr Val Asp
225                 230                 235                 240

Ile Glu Leu Val Thr Thr Thr Val Ser Asn Met Ala Glu Val Arg Ser
                245                 250                 255

Tyr Cys Tyr Glu Ala Ser Ile Ser Asp Met Ala Ser Asp Ser Arg Cys
            260                 265                 270

Pro Thr Gln Gly Glu Ala Tyr Leu Asp Lys Gln Ser Asp Thr Gln Tyr
        275                 280                 285

Val Cys Lys Arg Thr Leu Val Asp Arg Gly Trp Gly Asn Gly Cys Gly
    290                 295                 300

Leu Phe Gly Lys Gly Ser Leu Val Thr Cys Ala Lys Phe Thr Cys Ser
305                 310                 315                 320

Lys Lys Met Thr Gly Lys Ser Ile Gln Pro Glu Asn Leu Glu Tyr Arg
                325                 330                 335

Ile Met Leu Ser Val His Gly Ser Gln His Ser Gly Met Thr Val Asn
            340                 345                 350

Asp Ile Gly Tyr Glu Thr Asp Glu Asn Arg Ala Lys Val Glu Val Thr
        355                 360                 365

Pro Asn Ser Pro Arg Ala Glu Ala Thr Leu Gly Gly Phe Gly Ser Leu
    370                 375                 380

Gly Leu Asp Cys Glu Pro Arg Thr Gly Leu Asp Phe Ser Asp Leu Tyr
385                 390                 395                 400

Tyr Leu Thr Met Asn Asn Lys His Trp Leu Val His Lys Glu Trp Phe
                405                 410                 415

His Asp Ile Pro Leu Pro Trp His Ala Gly Ala Asp Thr Gly Thr Pro
```

-continued

```
            420                 425                 430

His Trp Asn Asn Lys Glu Ala Leu Val Glu Phe Lys Asp Ala His Ala
        435                 440                 445

Lys Arg Gln Thr Val Val Val Leu Gly Ser Gln Glu Gly Ala Val His
    450                 455                 460

Thr Ala Leu Ala Gly Ala Leu Glu Ala Glu Met Asp Gly Ala Lys Gly
465                 470                 475                 480

Lys Leu Phe Ser Gly His Leu Lys Cys Arg Leu Lys Met Asp Lys Leu
                485                 490                 495

Arg Leu Lys Gly Val Ser Tyr Ser Leu Cys Thr Ala Ala Phe Thr Phe
            500                 505                 510

Thr Lys Val Pro Ala Glu Thr Leu His Gly Thr Val Thr Val Glu Val
        515                 520                 525

Gln Tyr Ala Gly Thr Asp Gly Pro Cys Lys Ile Pro Val Gln Met Ala
    530                 535                 540

Val Asp Met Gln Thr Leu Thr Pro Val Gly Arg Leu Ile Thr Ala Asn
545                 550                 555                 560

Pro Val Ile Thr Glu Ser Thr Glu Asn Ser Lys Met Met Leu Glu Leu
                565                 570                 575

Asp Pro Pro Phe Gly Asp Ser Tyr Ile Val Ile Gly Val Gly Asp Lys
            580                 585                 590

Lys Ile Thr His His Trp His Arg Ser Gly Ser Thr Ile Gly Lys Ala
        595                 600                 605

Phe Glu Ala Thr Val Arg Gly Ala Lys Arg Met Ala Val Leu Gly Asp
    610                 615                 620

Thr Ala Trp Asp Phe Gly Ser Val Gly Gly Val Phe Asn Ser Leu Gly
625                 630                 635                 640

Lys Gly Ile His Gln Ile Phe Gly Ala Ala Phe Lys Ser Leu Phe Gly
                645                 650                 655

Gly Met Ser Trp Phe Ser Gln Ile Leu Ile Gly Thr Leu Leu Val Trp
            660                 665                 670

Leu Gly Leu Asn Thr Lys Asn Gly Ser Ile Ser Leu Thr Cys Leu Ala
        675                 680                 685

Leu Gly Gly Val Met Ile Phe Leu Ser Thr Ala Val Ser Ala
    690                 695                 700
```

<210> SEQ ID NO 26
<211> LENGTH: 1119
<212> TYPE: DNA
<213> ORGANISM: Artificial Sequence
<220> FEATURE:
<223> OTHER INFORMATION: consensus Zika IgE Leader-NS1

<400> SEQUENCE: 26

```
atggactgga cttggattct gttcctggtg gctgccgcta caagagtgca tagcgtggga      60

tgcagcgtgg acttcagcaa gaaggagacc cgctgcggaa caggcgtgtt cgtgtacaac     120

gacgtggagg cttggagaga ccggtacaag taccaccccg atagccctag aagactggcc     180

gcagccgtga aacaggcttg ggaagaggga atttgcggca tcagcagcgt gtcccggatg     240

gagaacatca tgtggaagag cgtggagggc gagctgaacg ctatcctgga ggagaacggc     300

gtgcagctga cagtggtcgt gggatcagtg aagaacccca tgtggagagg ccctcagagg     360

ctgccagtgc cagtgaacga actgcctcac ggttggaagg cttggggcaa gagctacttc     420

gtgagggccg ccaagaccaa caacagcttc gtggtggacg gcgataccct caaggagtgt     480
```

```
cctctgaagc accgggcttg gaacagcttc ctggtggaag accacggctt tggcgtgttc     540

cacacaagcg tctggctgaa ggtccgcgaa gactacagcc tggagtgcga tccagcagtg     600

atcggcacag ccgtgaaggg aaaagaggcc gctcacagcg acctgggcta ttggatcgag     660

agcgagaaga acgacacttg gaggctgaag cgggcccacc tgatcgagat gaagacttgc     720

gagtggccca agagccacac tctgtggaca gacggcgtgg aagagagcga cctgatcatc     780

cctaagagcc tggccggacc tctgtctcat cacaacacca gggagggcta cagaacccag     840

gtgaagggac cttggcacag cgaagagctg gagatccgct tcgaggagtg tccaggaacc     900

aaggtgcacg tggaggagac ttgcggaacc agaggcccta gcctgagaag cacaacagcc     960

agcggacgcg tgatcgagga gtggtgttgt agggagtgca ccatgcctcc tctgagcttc    1020

agggccaagg acggttgttg gtacggcatg gagatcaggc ccagaaagga gccagagagc    1080

aacctcgtgc ggtctatggt gacagccgga agctgataa                          1119
```

```
<210> SEQ ID NO 27
<211> LENGTH: 371
<212> TYPE: PRT
<213> ORGANISM: Artificial Sequence
<220> FEATURE:
<223> OTHER INFORMATION: consensus Zika IgE Leader-NS1

<400> SEQUENCE: 27

Met Asp Trp Thr Trp Ile Leu Phe Leu Val Ala Ala Ala Thr Arg Val
1               5                   10                  15

His Ser Val Gly Cys Ser Val Asp Phe Ser Lys Lys Glu Thr Arg Cys
            20                  25                  30

Gly Thr Gly Val Phe Val Tyr Asn Asp Val Glu Ala Trp Arg Asp Arg
        35                  40                  45

Tyr Lys Tyr His Pro Asp Ser Pro Arg Arg Leu Ala Ala Ala Val Lys
    50                  55                  60

Gln Ala Trp Glu Glu Gly Ile Cys Gly Ile Ser Ser Val Ser Arg Met
65                  70                  75                  80

Glu Asn Ile Met Trp Lys Ser Val Glu Gly Glu Leu Asn Ala Ile Leu
                85                  90                  95

Glu Glu Asn Gly Val Gln Leu Thr Val Val Val Gly Ser Val Lys Asn
            100                 105                 110

Pro Met Trp Arg Gly Pro Gln Arg Leu Pro Val Pro Val Asn Glu Leu
        115                 120                 125

Pro His Gly Trp Lys Ala Trp Gly Lys Ser Tyr Phe Val Arg Ala Ala
    130                 135                 140

Lys Thr Asn Asn Ser Phe Val Val Asp Gly Asp Thr Leu Lys Glu Cys
145                 150                 155                 160

Pro Leu Lys His Arg Ala Trp Asn Ser Phe Leu Val Glu Asp His Gly
                165                 170                 175

Phe Gly Val Phe His Thr Ser Val Trp Leu Lys Val Arg Glu Asp Tyr
            180                 185                 190

Ser Leu Glu Cys Asp Pro Ala Val Ile Gly Thr Ala Val Lys Gly Lys
        195                 200                 205

Glu Ala Ala His Ser Asp Leu Gly Tyr Trp Ile Glu Ser Glu Lys Asn
    210                 215                 220

Asp Thr Trp Arg Leu Lys Arg Ala His Leu Ile Glu Met Lys Thr Cys
225                 230                 235                 240

Glu Trp Pro Lys Ser His Thr Leu Trp Thr Asp Gly Val Glu Glu Ser
                245                 250                 255
```

```
Asp Leu Ile Ile Pro Lys Ser Leu Ala Gly Pro Leu Ser His His Asn
            260                 265                 270

Thr Arg Glu Gly Tyr Arg Thr Gln Val Lys Gly Pro Trp His Ser Glu
        275                 280                 285

Glu Leu Glu Ile Arg Phe Glu Glu Cys Pro Gly Thr Lys Val His Val
    290                 295                 300

Glu Glu Thr Cys Gly Thr Arg Gly Pro Ser Leu Arg Ser Thr Thr Ala
305                 310                 315                 320

Ser Gly Arg Val Ile Glu Glu Trp Cys Cys Arg Glu Cys Thr Met Pro
                325                 330                 335

Pro Leu Ser Phe Arg Ala Lys Asp Gly Cys Trp Tyr Gly Met Glu Ile
            340                 345                 350

Arg Pro Arg Lys Glu Pro Glu Ser Asn Leu Val Arg Ser Met Val Thr
        355                 360                 365

Ala Gly Ser
    370


<210> SEQ ID NO 28
<211> LENGTH: 438
<212> TYPE: DNA
<213> ORGANISM: Artificial Sequence
<220> FEATURE:
<223> OTHER INFORMATION: consensus Zika IgE Leader-capsid

<400> SEQUENCE: 28

atggactgga cttggatcct gtttctggtg gccgccgcca caagagtgca tagcaagaac      60

cccaagaaga agagcggcgg cttcaggatc gtgaacatgc tgaagcgggg cgtggctaga     120

gtgaaccctc tgggaggcgg actgaagaga ctgccagcag gactgctcct gggacacgga     180

cctattcgca tggtgctggc catcctggct ttcctgaggt tcaccgccat caagcccagc     240

ctgggactga tcaaccgctg gggttcagtc ggcaagaagg aggccatgga gatcatcaag     300

aagttcaaga aggacctggc cgccatgctg aggatcatca acgcccggaa ggagcggaag     360

agaagaggag ccgacaccag catcggcatc atcggactgc tgctgacaac cgccatggct     420

gccgagatct gatgatga                                                   438


<210> SEQ ID NO 29
<211> LENGTH: 143
<212> TYPE: PRT
<213> ORGANISM: Artificial Sequence
<220> FEATURE:
<223> OTHER INFORMATION: consensus Zika IgE Leader-capsid

<400> SEQUENCE: 29

Met Asp Trp Thr Trp Ile Leu Phe Leu Val Ala Ala Ala Thr Arg Val
1               5                   10                  15

His Ser Lys Asn Pro Lys Lys Lys Ser Gly Gly Phe Arg Ile Val Asn
            20                  25                  30

Met Leu Lys Arg Gly Val Ala Arg Val Asn Pro Leu Gly Gly Gly Leu
        35                  40                  45

Lys Arg Leu Pro Ala Gly Leu Leu Leu Gly His Gly Pro Ile Arg Met
    50                  55                  60

Val Leu Ala Ile Leu Ala Phe Leu Arg Phe Thr Ala Ile Lys Pro Ser
65                  70                  75                  80

Leu Gly Leu Ile Asn Arg Trp Gly Ser Val Gly Lys Lys Glu Ala Met
                85                  90                  95
```

-continued

```
Glu Ile Ile Lys Lys Phe Lys Lys Asp Leu Ala Ala Met Leu Arg Ile
            100                 105                 110

Ile Asn Ala Arg Lys Glu Arg Lys Arg Arg Gly Ala Asp Thr Ser Ile
        115                 120                 125

Gly Ile Ile Gly Leu Leu Leu Thr Thr Ala Met Ala Ala Glu Ile
    130                 135                 140
```

<210> SEQ ID NO 30
<211> LENGTH: 2130
<212> TYPE: DNA
<213> ORGANISM: Artificial Sequence
<220> FEATURE:
<223> OTHER INFORMATION: Zika IgE Leader-prME MR766

<400> SEQUENCE: 30

```
atggactgga cttggattct gttcctggtg gctgccgcta caagagtgca ttcaggagcc      60

gacacctcta tcggcatcgt gggactgctg ctgaccacag ccatggccgc cgaaattacc     120

aggaggggca gcgcctacta catgtacctg gacagaagcg acgccggaaa agccatcagc     180

ttcgccacaa ccctgggcgt caacaagtgc cacgtgcaga tcatggacct gggccacatg     240

tgcgacgcca caatgagcta cgagtgccct atgctggacg agggagtgga accagacgac     300

gtcgactgtt ggtgcaacac cacctccact tgggtcgtgt acggcacttg ccaccacaag     360

aagggcgagg ccagaagaag cagaagagcc gtgaccctgc ctagccacag caccagaaag     420

ctgcagacca ggagccagac ttggctggaa agccgcgagt acaccaagca cctgatcaag     480

gtggagaatt ggatcttccg gaaccccggc ttcacactgg tggccgtggc aatcgcttgg     540

ctgctgggat ctagcaccag ccagaaagtg atctacctgg tcatgatcct gctgatcgcc     600

ccagcctaca gcatccgctg tatcggagtg agcaaccggg acttcgtgga gggaatgagc     660

ggaggaactt gggtggacgt ggtgctggaa cacggaggtt gcgtgacagt gatggctcag     720

gacaagccca ccgtggatat cgagctggtg accaccaccg tgtccaacat ggccgaagtg     780

cgcagctact gctacgaggc cagtatctcc gacatggcca gcgatagccg ctgtcctaca     840

cagggagagg cctatctgga caagcagagc gacacccagt acgtctgcaa gaggaccctc     900

gtggatagag gctggggaaa cggttgcgga ctgttcggaa agggcagcct cgtgacttgc     960

gccaagttca cttgcagcaa gaagatgacc ggcaagtcta tccagcccga gaacctggag    1020

taccggatca tgctgagcgt gcacggaagc cagcacagcg gcatgatcgt gaacgacgag    1080

ggatacgaga ccgacgagaa cagggccaag gtggaagtga cccctaacag ccctagagcc    1140

gaagccacac tgggaggatt tggcagcctg ggactggatt gcgagcctag aacaggcctg    1200

gacttcagcg acctgtacta cctgaccatg aacaacaagc attggctggt gcacaaggag    1260

tggttccacg acatccctct gccttggcac gcaggagccg atacaggcac acctcattgg    1320

aacaacaagg aggccctggt ggagttcaag gacgctcacg ccaagagaca gacagtggtg    1380

gtgctgggaa gccaggaagg agcagtgcat acagccctgg caggagctct ggaagcagaa    1440

atggacggcg ctaagggcag actgttcagc ggacacctca agtgccggct gaagatggac    1500

aagctgcggc tgaagggcgt gtcttacagc ctctgcaccg cagccttcac cttcaccaag    1560

gtgccagcag agacactgca cggaacagtg accgtggaag tgcagtacgc cggaacagac    1620

ggaccttgca aagtgccagc ccagatggca gtggacatgc agacactgac cccagtggga    1680

aggctgatca ccgctaaccc cgtcatcacc gagagcaccg agaacagcaa gatgatgctg    1740

gagctggacc ccccttcgg cgatagctac atcgtgatcg gcgtgggcga caagaagatc    1800
```

```
acccaccatt ggcacagaag cggcagcaca atcggcaagg ctttcgaggc caccgtgaga   1860

ggagctaaga gaatggccgt gctgggagac accgcttggg attttggcag cgtgggagga   1920

gtgttcaaca gcctgggcaa gggcatccac cagatcttcg gagccgcctt caagagcctg   1980

ttcggcggca tgtcttggtt cagccagatc ctgatcggaa cactcctcgt ctggctggga   2040

ctgaacacca agaacggcag catcagcctg acttgtctgg ccctgggagg cgtgatgatc   2100

ttcctgagca ccgccgtgtc cgcttgataa                                    2130


<210> SEQ ID NO 31
<211> LENGTH: 708
<212> TYPE: PRT
<213> ORGANISM: Artificial Sequence
<220> FEATURE:
<223> OTHER INFORMATION: Zika IgE Leader-prME MR766

<400> SEQUENCE: 31

Met Asp Trp Thr Trp Ile Leu Phe Leu Val Ala Ala Ala Thr Arg Val
1               5                   10                  15

His Ser Gly Ala Asp Thr Ser Ile Gly Ile Val Gly Leu Leu Leu Thr
            20                  25                  30

Thr Ala Met Ala Ala Glu Ile Thr Arg Arg Gly Ser Ala Tyr Tyr Met
        35                  40                  45

Tyr Leu Asp Arg Ser Asp Ala Gly Lys Ala Ile Ser Phe Ala Thr Thr
    50                  55                  60

Leu Gly Val Asn Lys Cys His Val Gln Ile Met Asp Leu Gly His Met
65                  70                  75                  80

Cys Asp Ala Thr Met Ser Tyr Glu Cys Pro Met Leu Asp Glu Gly Val
                85                  90                  95

Glu Pro Asp Asp Val Asp Cys Trp Cys Asn Thr Thr Ser Thr Trp Val
            100                 105                 110

Val Tyr Gly Thr Cys His His Lys Lys Gly Glu Ala Arg Arg Ser Arg
        115                 120                 125

Arg Ala Val Thr Leu Pro Ser His Ser Thr Arg Lys Leu Gln Thr Arg
    130                 135                 140

Ser Gln Thr Trp Leu Glu Ser Arg Glu Tyr Thr Lys His Leu Ile Lys
145                 150                 155                 160

Val Glu Asn Trp Ile Phe Arg Asn Pro Gly Phe Thr Leu Val Ala Val
                165                 170                 175

Ala Ile Ala Trp Leu Leu Gly Ser Ser Thr Ser Gln Lys Val Ile Tyr
            180                 185                 190

Leu Val Met Ile Leu Leu Ile Ala Pro Ala Tyr Ser Ile Arg Cys Ile
        195                 200                 205

Gly Val Ser Asn Arg Asp Phe Val Glu Gly Met Ser Gly Gly Thr Trp
    210                 215                 220

Val Asp Val Val Leu Glu His Gly Gly Cys Val Thr Val Met Ala Gln
225                 230                 235                 240

Asp Lys Pro Thr Val Asp Ile Glu Leu Val Thr Thr Thr Val Ser Asn
                245                 250                 255

Met Ala Glu Val Arg Ser Tyr Cys Tyr Glu Ala Ser Ile Ser Asp Met
            260                 265                 270

Ala Ser Asp Ser Arg Cys Pro Thr Gln Gly Glu Ala Tyr Leu Asp Lys
        275                 280                 285

Gln Ser Asp Thr Gln Tyr Val Cys Lys Arg Thr Leu Val Asp Arg Gly
    290                 295                 300
```

-continued

```
Trp Gly Asn Gly Cys Gly Leu Phe Gly Lys Gly Ser Leu Val Thr Cys
305                 310                 315                 320

Ala Lys Phe Thr Cys Ser Lys Lys Met Thr Gly Lys Ser Ile Gln Pro
                325                 330                 335

Glu Asn Leu Glu Tyr Arg Ile Met Leu Ser Val His Gly Ser Gln His
            340                 345                 350

Ser Gly Met Ile Val Asn Asp Glu Gly Tyr Glu Thr Asp Glu Asn Arg
        355                 360                 365

Ala Lys Val Glu Val Thr Pro Asn Ser Pro Arg Ala Glu Ala Thr Leu
    370                 375                 380

Gly Gly Phe Gly Ser Leu Gly Leu Asp Cys Glu Pro Arg Thr Gly Leu
385                 390                 395                 400

Asp Phe Ser Asp Leu Tyr Tyr Leu Thr Met Asn Asn Lys His Trp Leu
                405                 410                 415

Val His Lys Glu Trp Phe His Asp Ile Pro Leu Pro Trp His Ala Gly
            420                 425                 430

Ala Asp Thr Gly Thr Pro His Trp Asn Asn Lys Glu Ala Leu Val Glu
        435                 440                 445

Phe Lys Asp Ala His Ala Lys Arg Gln Thr Val Val Val Leu Gly Ser
    450                 455                 460

Gln Glu Gly Ala Val His Thr Ala Leu Ala Gly Ala Leu Glu Ala Glu
465                 470                 475                 480

Met Asp Gly Ala Lys Gly Arg Leu Phe Ser Gly His Leu Lys Cys Arg
                485                 490                 495

Leu Lys Met Asp Lys Leu Arg Leu Lys Gly Val Ser Tyr Ser Leu Cys
            500                 505                 510

Thr Ala Ala Phe Thr Phe Thr Lys Val Pro Ala Glu Thr Leu His Gly
        515                 520                 525

Thr Val Thr Val Glu Val Gln Tyr Ala Gly Thr Asp Gly Pro Cys Lys
    530                 535                 540

Val Pro Ala Gln Met Ala Val Asp Met Gln Thr Leu Thr Pro Val Gly
545                 550                 555                 560

Arg Leu Ile Thr Ala Asn Pro Val Ile Thr Glu Ser Thr Glu Asn Ser
                565                 570                 575

Lys Met Met Leu Glu Leu Asp Pro Pro Phe Gly Asp Ser Tyr Ile Val
            580                 585                 590

Ile Gly Val Gly Asp Lys Lys Ile Thr His His Trp His Arg Ser Gly
        595                 600                 605

Ser Thr Ile Gly Lys Ala Phe Glu Ala Thr Val Arg Gly Ala Lys Arg
    610                 615                 620

Met Ala Val Leu Gly Asp Thr Ala Trp Asp Phe Gly Ser Val Gly Gly
625                 630                 635                 640

Val Phe Asn Ser Leu Gly Lys Gly Ile His Gln Ile Phe Gly Ala Ala
                645                 650                 655

Phe Lys Ser Leu Phe Gly Gly Met Ser Trp Phe Ser Gln Ile Leu Ile
            660                 665                 670

Gly Thr Leu Leu Val Trp Leu Gly Leu Asn Thr Lys Asn Gly Ser Ile
        675                 680                 685

Ser Leu Thr Cys Leu Ala Leu Gly Gly Val Met Ile Phe Leu Ser Thr
    690                 695                 700

Ala Val Ser Ala
705
```

<210> SEQ ID NO 32
<211> LENGTH: 2130
<212> TYPE: DNA
<213> ORGANISM: Artificial Sequence
<220> FEATURE:
<223> OTHER INFORMATION: Zika IgE Leader-prME Brazil

<400> SEQUENCE: 32
atggactgga cttggattct gttcctggtg gctgccgcta caagagtgca ttcaggagcc 60
gacacatcag tgggcatcgt gggactgctg ctgacaacag ctatggccgc cgaagtgacc 120
agaagaggca gcgcctacta catgtacctg gaccggaacg acgccggaga ggccattagc 180
tttcctacca ccctgggcat gaacaagtgc tacatccaga tcatggacct gggccacatg 240
tgcgacgcta caatgagcta cgagtgcccc atgctggacg aaggagtgga gccagacgac 300
gtggattgtt ggtgcaacac cacctccact tgggtcgtgt acggcacctg tcaccacaaa 360
aagggcgaag ccaggagaag cagaagagcc gtgaccctgc ctagccactc taccaggaag 420
ctgcagacca ggagccagac ttggctggag agcagggagt acaccaagca cctgatccgc 480
gtggagaatt ggatcttcag aaaccccggc ttcgccctgg cagccgcagc aattgcttgg 540
ctgctgggat ctagcaccag ccagaaggtc atctacctgg tcatgatcct gctgatcgcc 600
cccgcttaca gcatccgctg tatcggcgtg tccaacaggg acttcgtgga gggcatgagc 660
ggaggaactt gggtggacgt ggtgctggaa cacggaggtt gtgtgaccgt gatggctcag 720
gacaagccta ccgtggacat cgagctggtg accacaaccg tgtccaacat ggccgaggtc 780
cgcagctatt gctacgaggc cagcatcagc gatatggcca gcgatagcag gtgtcccacc 840
cagggtgaag cttacctgga caagcagagc gacacccagt acgtgtgcaa gcggacactg 900
gtggatagag gctggggaaa cggttgcggc ctgtttggca agggaagcct ggtgacctgc 960
gccaagttcg catgcagcaa gaagatgacc ggcaagagca tccagcccga gaacctggag 1020
taccggatca tgctgagcgt gcacggatct cagcatagcg gaatgatcgt gaacgacacc 1080
ggccacgaga ccgacgaaaa cagggccaag gtggaaatca cccccaactc tcctagagcc 1140
gaggccacac tgggaggttt tggaagcctg ggcctggatt gcgagcctag aacaggcctg 1200
gacttcagcg acctgtacta cctgaccatg aacaacaagc attggctggt gcacaaggag 1260
tggttccacg acatccctct gccttggcac gcaggagcag atacaggaac cccccattgg 1320
aacaacaagg aggccctggt ggagttcaag gacgctcacg ccaagagaca gacagtggtg 1380
gtgctgggaa gccaggaagg agcagtgcac acagctctgg caggagctct ggaagccgaa 1440
atggacggag ccaagggcag actgtcctcc ggacacctca agtgccggct gaagatggac 1500
aagctgcggc tgaagggcgt gtcttatagc ctctgcacag ccgctttcac cttcaccaag 1560
atccccgcag agaccctgca cggaacagtg accgtggaag tgcagtacgc cggaacagac 1620
ggaccttgca aggtgccagc tcagatggca gtggacatgc agaccctgac cccagtggga 1680
agactgatca ccgctaaccc cgtcatcacc gagagcaccg agaacagcaa gatgatgctg 1740
gagctggacc cccccttcgg cgatagctac atcgtgatcg gcgtgggcga gaaaaagatc 1800
acccaccatt ggcacaggag cggcagcaca atcggcaagg cctttgaggc caccgtgaga 1860
ggagccaaga gaatggccgt gctgggagat accgcttggg atttcggcag cgtgggaggc 1920
gccctgaaca gcctgggcaa gggcattcac cagatcttcg gagccgcctt caagagcctg 1980
ttcggcggca tgtcttggtt cagccagatc ctgatcggca cactgctcat gtggctgggc 2040
ctgaacacca agaacggcag catcagcctg atgtgtctgg ctctgggagg cgtgctgatc 2100
ttcctgagca ccgctgtgtc cgcttgataa 2130

<210> SEQ ID NO 33
<211> LENGTH: 708
<212> TYPE: PRT
<213> ORGANISM: Artificial Sequence
<220> FEATURE:
<223> OTHER INFORMATION: Zika IgE Leader-prME Brazil

<400> SEQUENCE: 33

```
Met Asp Trp Thr Trp Ile Leu Phe Leu Val Ala Ala Ala Thr Arg Val
1               5                   10                  15

His Ser Gly Ala Asp Thr Ser Val Gly Ile Val Gly Leu Leu Leu Thr
            20                  25                  30

Thr Ala Met Ala Ala Glu Val Thr Arg Arg Gly Ser Ala Tyr Tyr Met
        35                  40                  45

Tyr Leu Asp Arg Asn Asp Ala Gly Glu Ala Ile Ser Phe Pro Thr Thr
    50                  55                  60

Leu Gly Met Asn Lys Cys Tyr Ile Gln Ile Met Asp Leu Gly His Met
65                  70                  75                  80

Cys Asp Ala Thr Met Ser Tyr Glu Cys Pro Met Leu Asp Glu Gly Val
                85                  90                  95

Glu Pro Asp Asp Val Asp Cys Trp Cys Asn Thr Thr Ser Thr Trp Val
            100                 105                 110

Val Tyr Gly Thr Cys His His Lys Lys Gly Glu Ala Arg Arg Ser Arg
        115                 120                 125

Arg Ala Val Thr Leu Pro Ser His Ser Thr Arg Lys Leu Gln Thr Arg
    130                 135                 140

Ser Gln Thr Trp Leu Glu Ser Arg Glu Tyr Thr Lys His Leu Ile Arg
145                 150                 155                 160

Val Glu Asn Trp Ile Phe Arg Asn Pro Gly Phe Ala Leu Ala Ala Ala
                165                 170                 175

Ala Ile Ala Trp Leu Leu Gly Ser Ser Thr Ser Gln Lys Val Ile Tyr
            180                 185                 190

Leu Val Met Ile Leu Leu Ile Ala Pro Ala Tyr Ser Ile Arg Cys Ile
        195                 200                 205

Gly Val Ser Asn Arg Asp Phe Val Glu Gly Met Ser Gly Gly Thr Trp
    210                 215                 220

Val Asp Val Val Leu Glu His Gly Gly Cys Val Thr Val Met Ala Gln
225                 230                 235                 240

Asp Lys Pro Thr Val Asp Ile Glu Leu Val Thr Thr Thr Val Ser Asn
                245                 250                 255

Met Ala Glu Val Arg Ser Tyr Cys Tyr Glu Ala Ser Ile Ser Asp Met
            260                 265                 270

Ala Ser Asp Ser Arg Cys Pro Thr Gln Gly Glu Ala Tyr Leu Asp Lys
        275                 280                 285

Gln Ser Asp Thr Gln Tyr Val Cys Lys Arg Thr Leu Val Asp Arg Gly
    290                 295                 300

Trp Gly Asn Gly Cys Gly Leu Phe Gly Lys Gly Ser Leu Val Thr Cys
305                 310                 315                 320

Ala Lys Phe Ala Cys Ser Lys Lys Met Thr Gly Lys Ser Ile Gln Pro
                325                 330                 335

Glu Asn Leu Glu Tyr Arg Ile Met Leu Ser Val His Gly Ser Gln His
            340                 345                 350

Ser Gly Met Ile Val Asn Asp Thr Gly His Glu Thr Asp Glu Asn Arg
```

```
        355                 360                 365

Ala Lys Val Glu Ile Thr Pro Asn Ser Pro Arg Ala Glu Ala Thr Leu
    370                 375                 380

Gly Gly Phe Gly Ser Leu Gly Leu Asp Cys Glu Pro Arg Thr Gly Leu
385                 390                 395                 400

Asp Phe Ser Asp Leu Tyr Tyr Leu Thr Met Asn Asn Lys His Trp Leu
                405                 410                 415

Val His Lys Glu Trp Phe His Asp Ile Pro Leu Pro Trp His Ala Gly
            420                 425                 430

Ala Asp Thr Gly Thr Pro His Trp Asn Asn Lys Glu Ala Leu Val Glu
        435                 440                 445

Phe Lys Asp Ala His Ala Lys Arg Gln Thr Val Val Val Leu Gly Ser
    450                 455                 460

Gln Glu Gly Ala Val His Thr Ala Leu Ala Gly Ala Leu Glu Ala Glu
465                 470                 475                 480

Met Asp Gly Ala Lys Gly Arg Leu Ser Ser Gly His Leu Lys Cys Arg
                485                 490                 495

Leu Lys Met Asp Lys Leu Arg Leu Lys Gly Val Ser Tyr Ser Leu Cys
            500                 505                 510

Thr Ala Ala Phe Thr Phe Thr Lys Ile Pro Ala Glu Thr Leu His Gly
        515                 520                 525

Thr Val Thr Val Glu Val Gln Tyr Ala Gly Thr Asp Gly Pro Cys Lys
    530                 535                 540

Val Pro Ala Gln Met Ala Val Asp Met Gln Thr Leu Thr Pro Val Gly
545                 550                 555                 560

Arg Leu Ile Thr Ala Asn Pro Val Ile Thr Glu Ser Thr Glu Asn Ser
                565                 570                 575

Lys Met Met Leu Glu Leu Asp Pro Pro Phe Gly Asp Ser Tyr Ile Val
            580                 585                 590

Ile Gly Val Gly Glu Lys Lys Ile Thr His His Trp His Arg Ser Gly
        595                 600                 605

Ser Thr Ile Gly Lys Ala Phe Glu Ala Thr Val Arg Gly Ala Lys Arg
    610                 615                 620

Met Ala Val Leu Gly Asp Thr Ala Trp Asp Phe Gly Ser Val Gly Gly
625                 630                 635                 640

Ala Leu Asn Ser Leu Gly Lys Gly Ile His Gln Ile Phe Gly Ala Ala
                645                 650                 655

Phe Lys Ser Leu Phe Gly Gly Met Ser Trp Phe Ser Gln Ile Leu Ile
            660                 665                 670

Gly Thr Leu Leu Met Trp Leu Gly Leu Asn Thr Lys Asn Gly Ser Ile
        675                 680                 685

Ser Leu Met Cys Leu Ala Leu Gly Gly Val Leu Ile Phe Leu Ser Thr
    690                 695                 700

Ala Val Ser Ala
705
```

<210> SEQ ID NO 34
<211> LENGTH: 1119
<212> TYPE: DNA
<213> ORGANISM: Artificial Sequence
<220> FEATURE:
<223> OTHER INFORMATION: consensus Zika IgE Leader-NS1 DNA (pGX7211)

<400> SEQUENCE: 34

```
atggactgga cctggattct gttcctggtg gcagcagcaa cacgggtgca ctccgtgggc      60
```

```
tgctctgtgg atttcagcaa gaaggagaca agatgtggca caggcgtgtt cgtgtacaac    120

gacgtggagg cctggaggga tcgctacaag tatcaccctg actctccacg gagactggca    180

gcagcagtga agcaggcatg ggaggagggc atctgcggca tcagctccgt gtcccggatg    240

gagaatatca tgtggaagtc tgtggagggc gagctgaacg ccatcctgga ggagaatgga    300

gtgcagctga ccgtggtggt gggcagcgtg aagaacccaa tgtggagggg accacagaga    360

ctgccagtgc cagtgaatga gctgccacac ggatggaagg catggggcaa gtcttatttc    420

gtgagggccg ccaagaccaa caatagcttt gtggtggacg gcgatacact gaaggagtgc    480

cccctgaagc accgcgcctg gaactccttt ctggtggagg atcacggctt cggcgtgttt    540

cacaccagcg tgtggctgaa ggtgagggag gactactccc tggagtgtga tcctgccgtg    600

atcggaacag cagtgaaggg caaggaggca gcacactctg acctgggcta ttggatcgag    660

agcgagaaga acgatacctg gaggctgaag cgcgcccacc tgatcgagat gaagacctgt    720

gagtggccaa agtcccacac cctgtggaca gacggcgtgg aggagtctga tctgatcatc    780

cctaagagcc tggccggccc actgtcccac cacaatacca gggagggcta ccgcacacag    840

gtgaagggcc cctggcactc cgaggagctg gagatccgct tcgaggagtg ccctggcacc    900

aaggtgcacg tggaggagac atgtggcaca cggggcccct ctctgagaag caccacagcc    960

agcggcagag tgatcgagga gtggtgctgt cgcgagtgca caatgccccc tctgtccttt   1020

cgggccaagg acggctgttg gtatggcatg gagatccggc ccagaaagga gcctgagtcc   1080

aatctggtga gatctatggt gaccgccggc agctgataa                         1119
```

<210> SEQ ID NO 35
<211> LENGTH: 435
<212> TYPE: DNA
<213> ORGANISM: Artificial Sequence
<220> FEATURE:
<223> OTHER INFORMATION: consensus Zika IgE Leader-capsid DNA (pGX7212)

<400> SEQUENCE: 35

```
atggactgga cctggattct gttcctggtg gcagcagcaa cacgggtgca cagcaagaac     60

cccaagaaga agagcggcgg cttccggatc gtgaacatgc tgaagcgggg cgtggccaga    120

gtgaatccac tgggcggcgg cctgaagcgg ctgcctgcag gcctgctgct gggccacggc    180

ccaatcagga tggtgctggc catcctggcc ttcctgcgct ttaccgccat caagccctct    240

ctgggcctga tcaacagatg gggcagcgtg ggcaagaagg aggccatgga gatcatcaag    300

aagttcaaga aggacctggc cgccatgctg cgcatcatca atgcaaggaa ggagaggaag    360

aggagaggcg ccgatacaag catcggcatc atcggcctgc tgctgaccac agcaatggca    420

gccgagatct gataa                                                     435
```

<210> SEQ ID NO 36
<211> LENGTH: 2130
<212> TYPE: DNA
<213> ORGANISM: Artificial Sequence
<220> FEATURE:
<223> OTHER INFORMATION: Zika IgE Leader-prME Brazil DNA (pGX7213)

<400> SEQUENCE: 36

```
atggactgga cctggattct gttcctggtg gcagcagcaa cacgggtgca cagcggagca     60

gatacctccg tgggaatcgt gggcctgctg ctgaccacag caatggcagc agaggtgacc    120

aggagaggct ctgcctacta tatgtacctg gacagaaatg atgccggcga ggccatcagc    180
```

```
ttccccacca cactgggcat gaacaagtgc tacatccaga tcatggacct gggccacatg    240
tgcgatgcca ccatgagcta tgagtgtcca atgctggacg agggcgtgga gcccgacgat    300
gtggattgct ggtgtaatac cacatccaca tgggtggtgt acggcacctg tcaccacaag    360
aagggagagg caaggcgctc tcggagagca gtgacactgc cttcccactc tacccggaag    420
ctgcagacaa gatctcagac ctggctggag agccgggagt atacaaagca cctgatccgg    480
gtggagaact ggatctttag aaatccagga ttcgcactgg cagcagcagc aatcgcctgg    540
ctgctgggca gctccacctc tcagaaagtg atctacctgg tcatgatcct gctgatcgcc    600
cctgcctatt ccatcaggtg catcggcgtg tctaatcgcg actttgtgga gggaatgtcc    660
ggcggcacct gggtggatgt ggtgctggag cacggcggat gcgtgacagt gatggcccag    720
gacaagccaa ccgtggatat cgagctggtg accacaaccg tgagcaacat ggccgaggtg    780
cggtcctact gctatgaggc cagcatctcc gacatggcct ctgatagcag atgtcccacc    840
cagggcgagg cctacctgga caagcagagc gatacacagt acgtgtgcaa gaggaccctg    900
gtggacaggg gatggggaaa tggatgtggc ctgtttggca agggctccct ggtgacatgc    960
gccaagttcg cctgttctaa gaagatgacc ggcaagagca tccagccaga gaacctggag   1020
taccggatca tgctgagcgt gcacggctcc cagcactctg gcatgatcgt gaacgacaca   1080
ggccacgaga cagatgagaa tagggccaag gtggagatca cacctaacag cccacgcgcc   1140
gaggccaccc tgggcggctt tggctccctg ggcctggact gcgagcctag aacaggcctg   1200
gacttctccg atctgtacta tctgaccatg aacaataagc actggctggt gcacaaggag   1260
tggtttcacg acatcccact gccatggcac gcaggagcag atacaggaac cccacactgg   1320
aacaataagg aggccctggt ggagttcaag gatgcccacg ccaagaggca gacagtggtg   1380
gtgctgggca gccaggaggg agcagtgcac accgccctgg caggcgccct ggaggccgag   1440
atggacggag caaagggccg cctgtctagc ggccacctga agtgccggct gaagatggat   1500
aagctgagac tgaagggcgt gtcctactct ctgtgcacag ccgccttcac cttcaccaag   1560
atccctgccg agacactgca cggcacagtg accgtggagg tgcagtatgc cggcacagac   1620
ggcccctgta aggtgcctgc ccagatggcc gtggatatgc agacactgac ccctgtgggc   1680
aggctgatca ccgccaatcc agtgatcaca gagtctaccg agaacagcaa gatgatgctg   1740
gagctggacc ctcccttcgg cgacagctat atcgtgatcg gcgtgggcga gaagaagatc   1800
acacaccact ggcaccgcag cggctccaca atcggcaagg cctttgaggc caccgtgagg   1860
ggcgccaaga ggatggccgt gctgggcgac accgcatggg atttcggctc cgtgggcggc   1920
gccctgaact ctctgggcaa gggcatccac cagatcttcg gcgccgcctt taagtccctg   1980
ttcggcggaa tgagctggtt ttcccagatc ctgatcggca cactgctgat gtggctgggc   2040
ctgaacacca agaatggctc tatcagcctg atgtgcctgg ccctgggcgg cgtgctgatc   2100
ttcctgtcca ccgccgtgtc tgcctgataa                                    2130
```

<210> SEQ ID NO 37
<211> LENGTH: 2130
<212> TYPE: DNA
<213> ORGANISM: Artificial Sequence
<220> FEATURE:
<223> OTHER INFORMATION: Zika IgE Leader-prME MR766 DNA (pGX7214)

<400> SEQUENCE: 37

```
atggactgga cctggattct gttcctggtg gcagcagcaa cacgggtgca ctccggagcc     60
gatacctcta tcggcatcgt gggcctgctg ctgaccacag caatggcagc agagatcacc    120
```

```
aggagaggca gcgcctacta tatgtacctg gacagatctg atgccggcaa ggccatcagc    180
ttcgccacca cactgggcgt gaataagtgc cacgtgcaga tcatggacct gggccacatg    240
tgcgatgcca ccatgtccta cgagtgtcca atgctggacg agggcgtgga gcccgacgat    300
gtggattgct ggtgtaacac cacatctaca tgggtggtgt atggcacctg tcaccacaag    360
aagggagagg caaggcgcag ccggagagca gtgacactgc cctctcacag cacccggaag    420
ctgcagacaa gaagccagac ctggctggag tccagggagt ataccaagca cctgatcaag    480
gtggagaact ggatctttcg caatcccggc ttcacactgg tggcagtggc aatcgcatgg    540
ctgctgggca gctccacctc tcagaaagtg atctacctgg tcatgatcct gctgatcgcc    600
cctgcctatt ccatccggtg catcggcgtg tctaatagag actttgtgga gggaatgtcc    660
ggcggcacct gggtggatgt ggtgctggag cacggcggat gcgtgacagt gatggcccag    720
gacaagccaa ccgtggatat cgagctggtg accacaaccg tgagcaacat ggccgaggtg    780
cggtcctact gctatgaggc ctccatctct gacatggcca gcgattccag atgtcccacc    840
cagggcgagg cctacctgga caagcagtcc gatacacagt acgtgtgcaa gaggaccctg    900
gtggacaggg gatggggaaa tggatgtggc ctgtttggca agggctctct ggtgacatgc    960
gccaagttca cctgttctaa gaagatgaca ggcaagagca tccagcccga gaacctggag   1020
taccggatca tgctgagcgt gcacggctct cagcacagcg gcatgatcgt gaacgacgag   1080
ggctatgaga cagatgagaa tcgggccaag gtggaggtga cacctaacag cccaagagcc   1140
gaggccaccc tgggcggctt tggctccctg ggcctggact gcgagcctag gacaggcctg   1200
gacttctccg atctgtacta tctgaccatg aacaataagc actggctggt gcacaaggag   1260
tggtttcacg acatcccact gccatggcac gcaggagcag atacaggaac cccacactgg   1320
aacaataagg aggccctggt ggagttcaag gatgcccacg ccaagaggca gacagtggtg   1380
gtgctgggca gccaggaggg agcagtgcac accgccctgg caggcgccct ggaggccgag   1440
atggacggag caaagggccg cctgttctcc ggccacctga agtgcaggct gaagatggat   1500
aagctgcgcc tgaagggcgt gtcttacagc ctgtgcacag ccgccttcac cttcaccaag   1560
gtgcctgccg agacactgca cggcacagtg accgtggagg tgcagtatgc cggcacagac   1620
ggcccctgta aggtgcctgc ccagatggcc gtggatatgc agacactgac ccctgtgggc   1680
aggctgatca ccgccaatcc agtgatcaca gagagcaccg agaactccaa gatgatgctg   1740
gagctggacc ctcccttcgg cgacagctac atcgtgatcg gcgtgggcga caagaagatc   1800
acacaccact ggcaccgctc cggctctaca atcggcaagg ccttcgaggc caccgtgagg   1860
ggcgccaaga ggatggccgt gctgggcgac accgcatggg attttggctc cgtgggcggc   1920
gtgttcaatt ctctgggcaa gggcatccac cagatcttcg gcgccgcctt taagagcctg   1980
ttcggcggaa tgtcctggtt ttctcagatc ctgatcggca cactgctggt gtggctgggc   2040
ctgaacacaa agaatggcag catctccctg acctgcctgg ccctgggcgg cgtgatgatc   2100
ttcctgtcta ccgccgtgag cgcctgataa                                    2130
```

<210> SEQ ID NO 38
<211> LENGTH: 2070
<212> TYPE: DNA
<213> ORGANISM: Artificial Sequence
<220> FEATURE:
<223> OTHER INFORMATION: Zika PreEnv (MR766) w/out capsid DNA (pGX7210)

<400> SEQUENCE: 38

-continued

```
atggactgga cttggattct gttcctggtg gctgccgcta caagagtgca ttcaattacc     60
aggaggggca gcgcctacta catgtacctg gacagaagcg acgccggaaa agccatcagc    120
ttcgccacaa ccctgggcgt caacaagtgc cacgtgcaga tcatggacct gggccacatg    180
tgcgacgcca caatgagcta cgagtgccct atgctggacg agggagtgga accagacgac    240
gtcgactgtt ggtgcaacac cacctccact tgggtcgtgt acggcacttg ccaccacaag    300
aagggcgagg ccagaagaag cagaagagcc gtgaccctgc ctagccacag caccagaaag    360
ctgcagacca ggagccagac ttggctggaa agccgcgagt acaccaagca cctgatcaag    420
gtggagaatt ggatcttccg gaaccccggc ttcacactgg tggccgtggc aatcgcttgg    480
ctgctgggat ctagcaccag ccagaaagtg atctacctgg tcatgatcct gctgatcgcc    540
ccagcctaca gcatccgctg tatcggagtg agcaaccggg acttcgtgga gggaatgagc    600
ggaggaactt gggtggacgt ggtgctggaa cacggaggtt gcgtgacagt gatggctcag    660
gacaagccca ccgtggatat cgagctggtg accaccaccg tgtccaacat ggccgaagtg    720
cgcagctact gctacgaggc cagtatctcc gacatggcca gcgatagccg ctgtcctaca    780
cagggagagg cctatctgga caagcagagc gacacccagt acgtctgcaa gaggaccctc    840
gtggatagag gctggggaaa cggttgcgga ctgttcggaa agggcagcct cgtgacttgc    900
gccaagttca cttgcagcaa gaagatgacc ggcaagtcta tccagcccga gaacctggag    960
taccggatca tgctgagcgt gcacggaagc cagcacagcg gcatgatcgt gaacgacgag   1020
ggatacgaga ccgacgagaa cagggccaag gtggaagtga cccctaacag ccctagagcc   1080
gaagccacac tgggaggatt tggcagcctg ggactggatt gcgagcctag aacaggcctg   1140
gacttcagcg acctgtacta cctgaccatg aacaacaagc attggctggt gcacaaggag   1200
tggttccacg acatccctct gccttggcac gcaggagccg atacaggcac acctcattgg   1260
aacaacaagg aggccctggt ggagttcaag gacgctcacg ccaagagaca gacagtggtg   1320
gtgctgggaa gccaggaagg agcagtgcat acagccctgg caggagctct ggaagcagaa   1380
atggacggcg ctaagggcag actgttcagc ggacacctca agtgccggct gaagatggac   1440
aagctgcggc tgaagggcgt gtcttacagc ctctgcaccg cagccttcac cttcaccaag   1500
gtgccagcag agacactgca cggaacagtg accgtggaag tgcagtacgc cggaacagac   1560
ggaccttgca aagtgccagc ccagatggca gtggacatgc agacactgac cccagtggga   1620
aggctgatca ccgctaaccc cgtcatcacc gagagcaccg agaacagcaa gatgatgctg   1680
gagctggacc ccccttcgg cgatagctac atcgtgatcg gcgtgggcga caagaagatc   1740
acccaccatt ggcacagaag cggcagcaca atcggcaagg ctttcgaggc caccgtgaga   1800
ggagctaaga gaatggccgt gctgggagac accgcttggg attttggcag cgtgggagga   1860
gtgttcaaca gcctgggcaa gggcatccac cagatcttcg gagccgcctt caagagcctg   1920
ttcggcggca tgtcttggtt cagccagatc ctgatcggaa cactcctcgt ctggctggga   1980
ctgaacacca agaacggcag catcagcctg acttgtctgg ccctgggagg cgtgatgatc   2040
ttcctgagca ccgccgtgtc cgcttgataa                                     2070
```

<210> SEQ ID NO 39
<211> LENGTH: 688
<212> TYPE: PRT
<213> ORGANISM: Artificial Sequence
<220> FEATURE:
<223> OTHER INFORMATION: Zika PreEnv (MR766) w/out capsid Protein
(pGX7210)

<400> SEQUENCE: 39

Met Asp Trp Thr Trp Ile Leu Phe Leu Val Ala Ala Ala Thr Arg Val
1 5 10 15

His Ser Ile Thr Arg Arg Gly Ser Ala Tyr Tyr Met Tyr Leu Asp Arg
20 25 30

Ser Asp Ala Gly Lys Ala Ile Ser Phe Ala Thr Thr Leu Gly Val Asn
35 40 45

Lys Cys His Val Gln Ile Met Asp Leu Gly His Met Cys Asp Ala Thr
50 55 60

Met Ser Tyr Glu Cys Pro Met Leu Asp Glu Gly Val Glu Pro Asp Asp
65 70 75 80

Val Asp Cys Trp Cys Asn Thr Thr Ser Thr Trp Val Val Tyr Gly Thr
85 90 95

Cys His His Lys Lys Gly Glu Ala Arg Arg Ser Arg Arg Ala Val Thr
100 105 110

Leu Pro Ser His Ser Thr Arg Lys Leu Gln Thr Arg Ser Gln Thr Trp
115 120 125

Leu Glu Ser Arg Glu Tyr Thr Lys His Leu Ile Lys Val Glu Asn Trp
130 135 140

Ile Phe Arg Asn Pro Gly Phe Thr Leu Val Ala Val Ala Ile Ala Trp
145 150 155 160

Leu Leu Gly Ser Ser Thr Ser Gln Lys Val Ile Tyr Leu Val Met Ile
165 170 175

Leu Leu Ile Ala Pro Ala Tyr Ser Ile Arg Cys Ile Gly Val Ser Asn
180 185 190

Arg Asp Phe Val Glu Gly Met Ser Gly Gly Thr Trp Val Asp Val Val
195 200 205

Leu Glu His Gly Gly Cys Val Thr Val Met Ala Gln Asp Lys Pro Thr
210 215 220

Val Asp Ile Glu Leu Val Thr Thr Thr Val Ser Asn Met Ala Glu Val
225 230 235 240

Arg Ser Tyr Cys Tyr Glu Ala Ser Ile Ser Asp Met Ala Ser Asp Ser
245 250 255

Arg Cys Pro Thr Gln Gly Glu Ala Tyr Leu Asp Lys Gln Ser Asp Thr
260 265 270

Gln Tyr Val Cys Lys Arg Thr Leu Val Asp Arg Gly Trp Gly Asn Gly
275 280 285

Cys Gly Leu Phe Gly Lys Gly Ser Leu Val Thr Cys Ala Lys Phe Thr
290 295 300

Cys Ser Lys Lys Met Thr Gly Lys Ser Ile Gln Pro Glu Asn Leu Glu
305 310 315 320

Tyr Arg Ile Met Leu Ser Val His Gly Ser Gln His Ser Gly Met Ile
325 330 335

Val Asn Asp Glu Gly Tyr Glu Thr Asp Glu Asn Arg Ala Lys Val Glu
340 345 350

Val Thr Pro Asn Ser Pro Arg Ala Glu Ala Thr Leu Gly Gly Phe Gly
355 360 365

Ser Leu Gly Leu Asp Cys Glu Pro Arg Thr Gly Leu Asp Phe Ser Asp
370 375 380

Leu Tyr Tyr Leu Thr Met Asn Asn Lys His Trp Leu Val His Lys Glu
385 390 395 400

Trp Phe His Asp Ile Pro Leu Pro Trp His Ala Gly Ala Asp Thr Gly
405 410 415

-continued

```
Thr Pro His Trp Asn Asn Lys Glu Ala Leu Val Glu Phe Lys Asp Ala
            420                 425                 430

His Ala Lys Arg Gln Thr Val Val Val Leu Gly Ser Gln Glu Gly Ala
        435                 440                 445

Val His Thr Ala Leu Ala Gly Ala Leu Glu Ala Glu Met Asp Gly Ala
    450                 455                 460

Lys Gly Arg Leu Phe Ser Gly His Leu Lys Cys Arg Leu Lys Met Asp
465                 470                 475                 480

Lys Leu Arg Leu Lys Gly Val Ser Tyr Ser Leu Cys Thr Ala Ala Phe
                485                 490                 495

Thr Phe Thr Lys Val Pro Ala Glu Thr Leu His Gly Thr Val Thr Val
            500                 505                 510

Glu Val Gln Tyr Ala Gly Thr Asp Gly Pro Cys Lys Val Pro Ala Gln
        515                 520                 525

Met Ala Val Asp Met Gln Thr Leu Thr Pro Val Gly Arg Leu Ile Thr
    530                 535                 540

Ala Asn Pro Val Ile Thr Glu Ser Thr Glu Asn Ser Lys Met Met Leu
545                 550                 555                 560

Glu Leu Asp Pro Pro Phe Gly Asp Ser Tyr Ile Val Ile Gly Val Gly
                565                 570                 575

Asp Lys Lys Ile Thr His His Trp His Arg Ser Gly Ser Thr Ile Gly
            580                 585                 590

Lys Ala Phe Glu Ala Thr Val Arg Gly Ala Lys Arg Met Ala Val Leu
        595                 600                 605

Gly Asp Thr Ala Trp Asp Phe Gly Ser Val Gly Gly Val Phe Asn Ser
    610                 615                 620

Leu Gly Lys Gly Ile His Gln Ile Phe Gly Ala Ala Phe Lys Ser Leu
625                 630                 635                 640

Phe Gly Gly Met Ser Trp Phe Ser Gln Ile Leu Ile Gly Thr Leu Leu
                645                 650                 655

Val Trp Leu Gly Leu Asn Thr Lys Asn Gly Ser Ile Ser Leu Thr Cys
            660                 665                 670

Leu Ala Leu Gly Gly Val Met Ile Phe Leu Ser Thr Ala Val Ser Ala
        675                 680                 685


<210> SEQ ID NO 40
<211> LENGTH: 16
<212> TYPE: PRT
<213> ORGANISM: Artificial Sequence
<220> FEATURE:
<223> OTHER INFORMATION: IgE Leader

<400> SEQUENCE: 40

Met Asp Trp Thr Trp Ile Leu Phe Leu Val Ala Ala Ala Thr Arg Val
1               5                   10                  15
```